US011078236B2

(12) United States Patent
Ratan et al.

(10) Patent No.: US 11,078,236 B2
(45) Date of Patent: Aug. 3, 2021

(54) SELENIUM-BASED THERAPIES

(71) Applicant: Burke Neurological Institute, White Plains, NY (US)

(72) Inventors: Rajiv R Ratan, Scarsdale, NY (US); Ishraq Alim, I, New York, NY (US); Saravanan Karuppagounder, White Plains, NY (US)

(73) Assignee: Burke Neurological Institute, White Plains, NY (US)

( * ) Notice: Subject to any disclaimer, the term of this patent is extended or adjusted under 35 U.S.C. 154(b) by 0 days.

(21) Appl. No.: 15/969,742

(22) Filed: May 2, 2018

(65) Prior Publication Data

US 2018/0327456 A1      Nov. 15, 2018

Related U.S. Application Data

(60) Provisional application No. 62/500,367, filed on May 2, 2017.

(51) Int. Cl.
| | | |
|---|---|---|
| *C07K 14/00* | (2006.01) | |
| *A61K 45/06* | (2006.01) | |
| *A61K 38/10* | (2006.01) | |
| *A61K 38/16* | (2006.01) | |
| *C07K 7/08* | (2006.01) | |
| *C07K 14/47* | (2006.01) | |
| *A61K 31/095* | (2006.01) | |
| *A61P 25/00* | (2006.01) | |

(52) U.S. Cl.
CPC .......... *C07K 14/001* (2013.01); *A61K 31/095* (2013.01); *A61K 38/10* (2013.01); *A61K 38/16* (2013.01); *A61K 45/06* (2013.01); *A61P 25/00* (2018.01); *C07K 7/08* (2013.01); *C07K 14/47* (2013.01); *C07K 2319/10* (2013.01)

(58) Field of Classification Search
None
See application file for complete search history.

(56) References Cited

U.S. PATENT DOCUMENTS 7,704,951 B2 *  4/2010  Hirashima ............... A61P 37/02
                                                            514/1.1
2003/0050243 A1 *  3/2003  Tymianski ............. A61K 38/08
                                                            514/8.3

FOREIGN PATENT DOCUMENTS

FR            2522359          * 11/2012  ............. A61K 38/44

OTHER PUBLICATIONS

Kornau et al., Science, 1995; 269: 1737-1740 (Year: 1995).*
Lim et al., JBC, 2002; 277: 21697-21711 (Year: 2002).*
Tagaki et al., J. Neurochem. 2000; 74: 169-178 (Year: 2000).*
Bassand et al., European Journal of Neuroscience, 1999; 11: 2031-2043 (Year: 1999).*
Bernhard HJ Juurlink; In: Inflammation and Stroke, Ed: G.Z. Feuerstein, Springer Basel AG, 2001, pp. pp. 299-312 (Year: 2001).*
Becker-Hapak et al., METHODS, 2001; 24: 247-256 (Year: 2001).*
Higuchi et al., PLoS ONE, 2010; 5: e9911 (Year: 2010).*
Burket al., FASEB J. 28, 3579-3588 (2014) (Year: 2014).*
Hirashima et al., Biol. Pharm. Bull. 26(6) 794-798 (2003) (Year: 2003).*

* cited by examiner

*Primary Examiner* — Christina M Borgeest
(74) *Attorney, Agent, or Firm* — Amster, Rothstein & Ebenstein LLP

(57) ABSTRACT

This invention relates to methods of administering compounds containing selenium, selenocysteine, or a selenocysteine peptide to treat, for example, conditions associated with selenium deficiency, or ferroptoptic, parthanototic, and endoplasmic reticulum stress, and/or cancer. The methods of treatment may activate or inhibit (via TFAP2C and Sp1 proteins) the adaptive homeostatic response of the selenome. The compounds may contain a targeting sequence that causes them to be delivered to specific organs and/or tissues. The compounds may be administered, for example, orally, intranasally, intravenously, or by a minimally invasive catheter or BrainPath.

3 Claims, 119 Drawing Sheets

Specification includes a Sequence Listing.

FIG. 1G(a)
FIG. 1H(a)
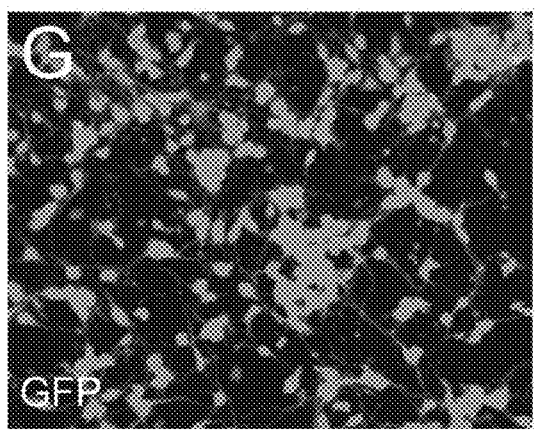
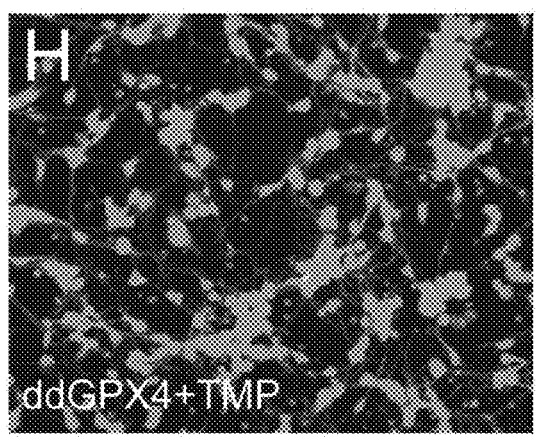
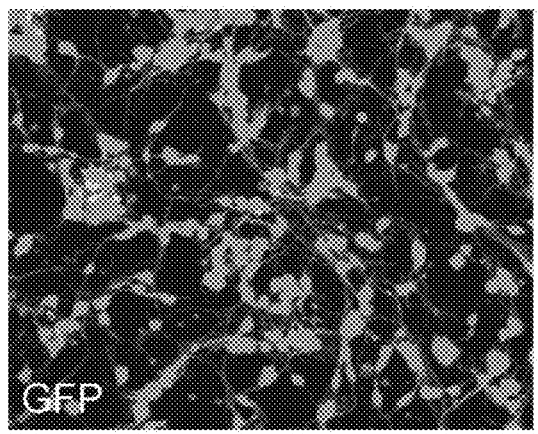
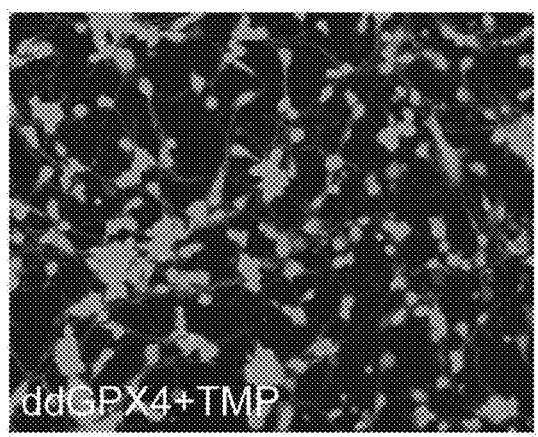
FIG. 1G(b)
FIG. 1H(b)

FIG. 1I(a)  FIG. 1J(a)
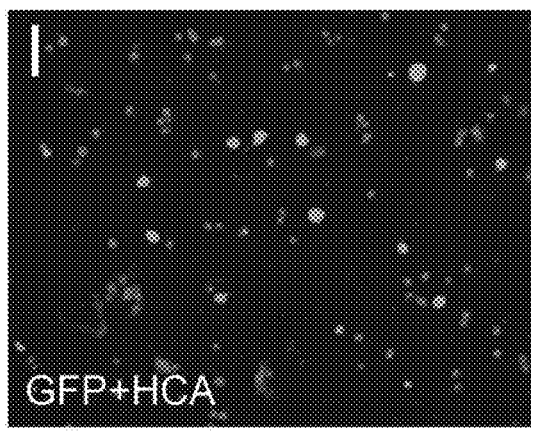
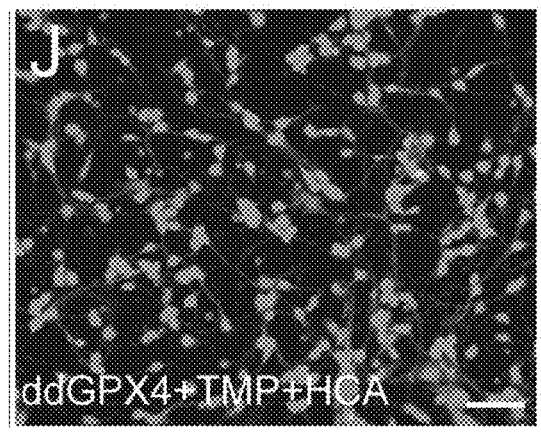
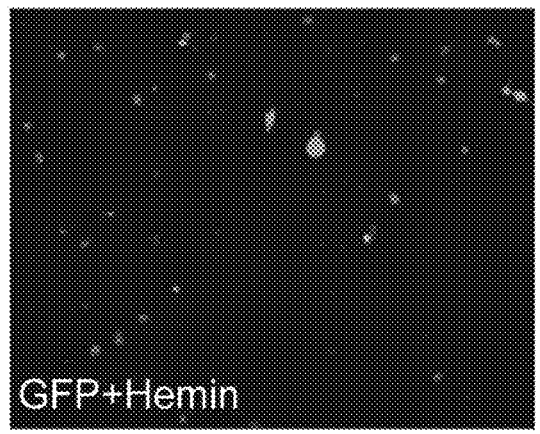
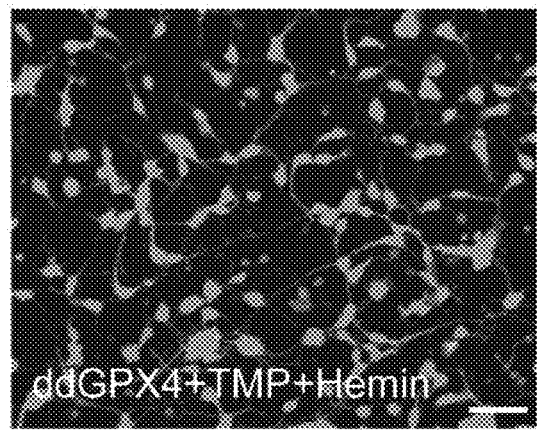
FIG. 1I(b)  FIG. 1J(a)

FIG. 2C  FIG. 2D
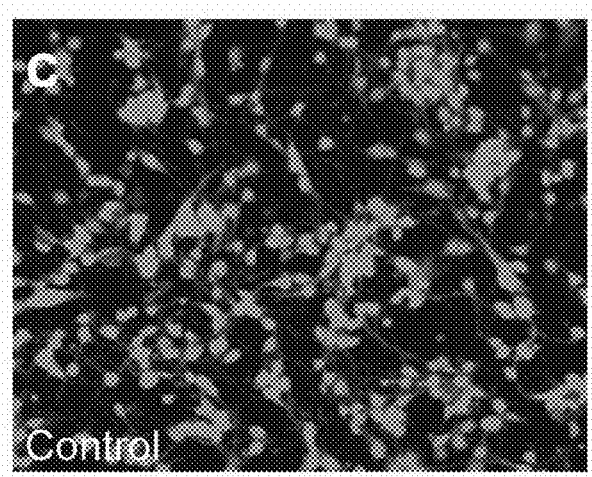 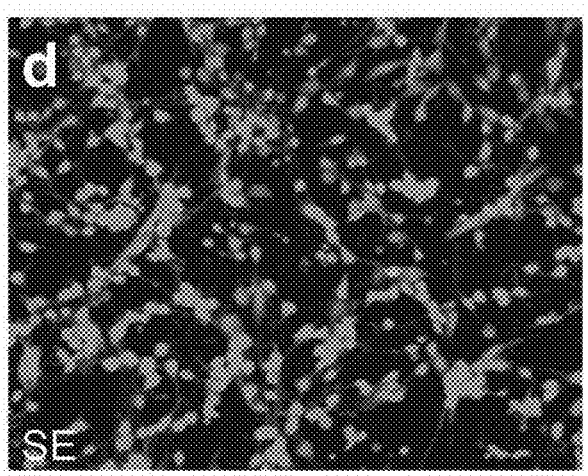
FIG. 2E  FIG. 2F
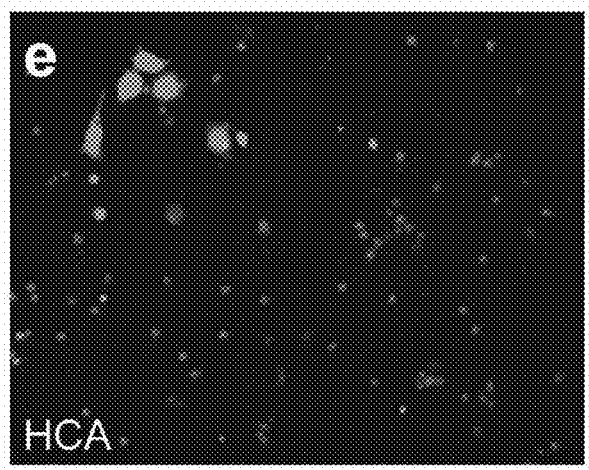 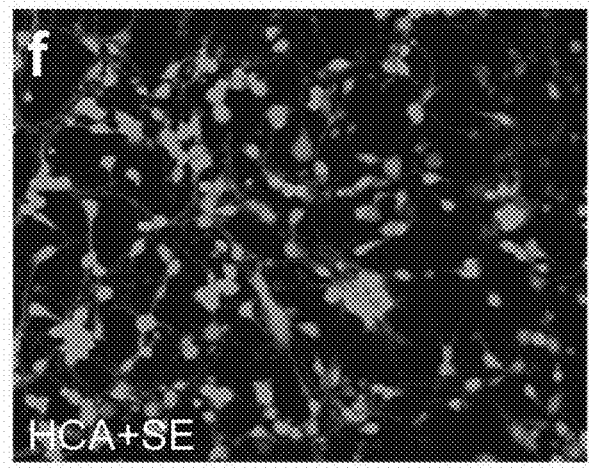
FIG. 2G  FIG. 2H
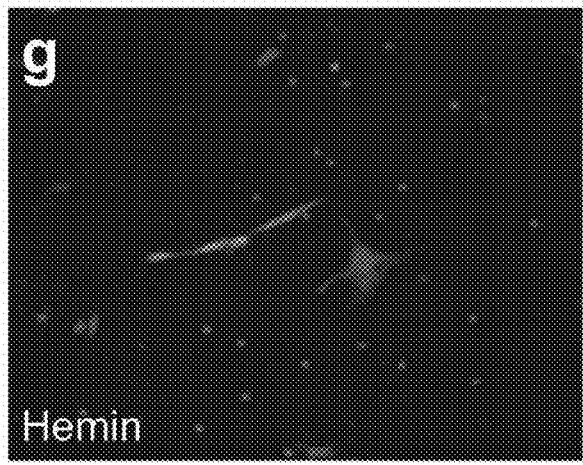 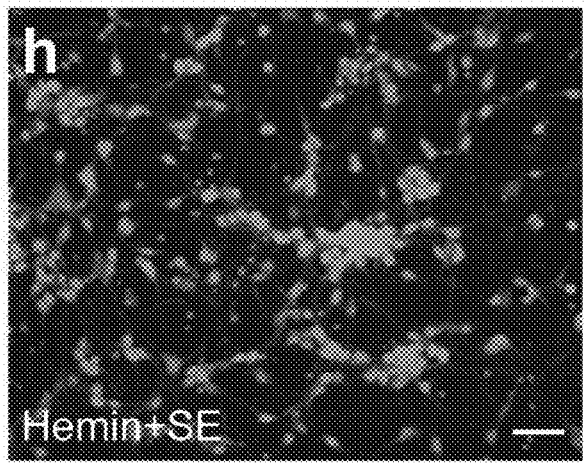

FIG. 3D     FIG. 3E     FIG. 3F
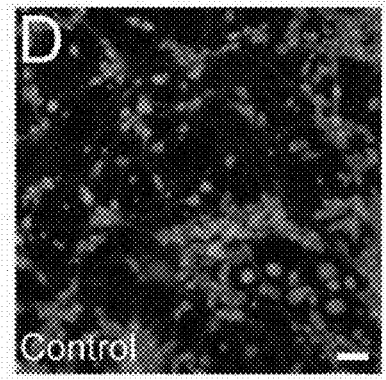 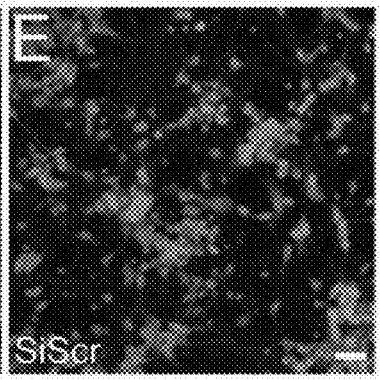 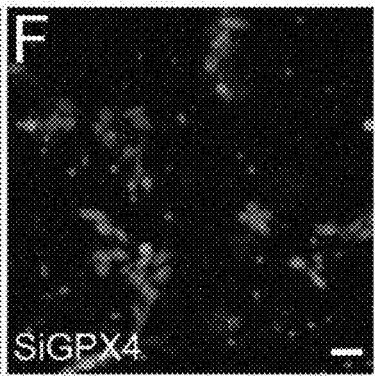
FIG. 3G     FIG. 3H     FIG. 3I
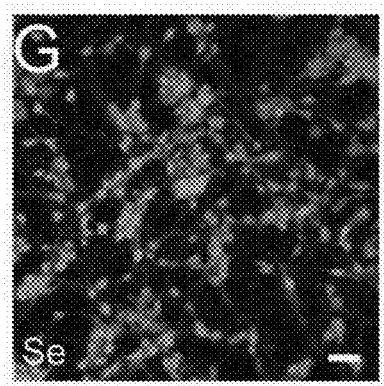 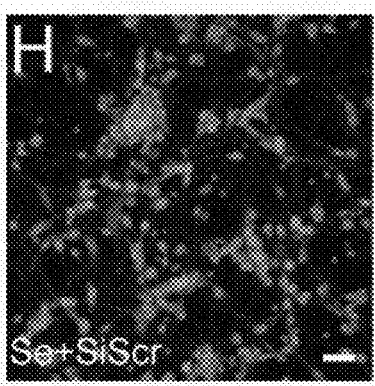 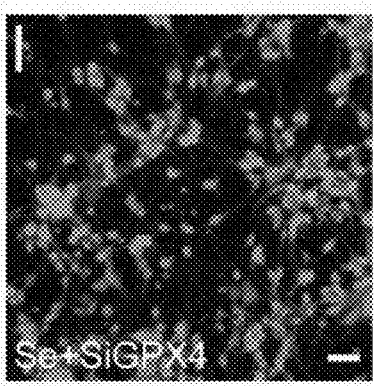
FIG. 3J     FIG. 3K     FIG. 3L
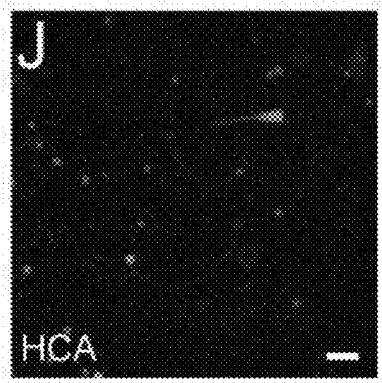 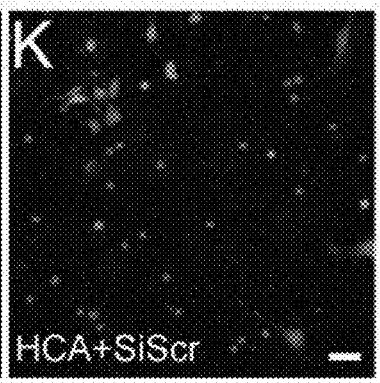 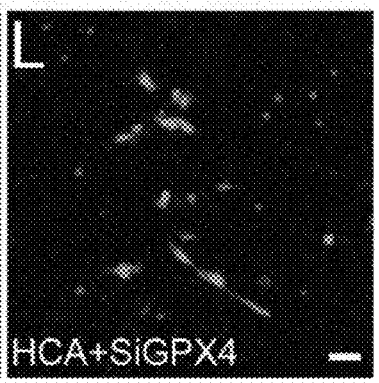

FIG. 3M
FIG. 3N
FIG. 3O
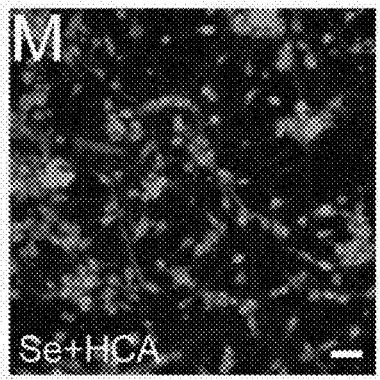
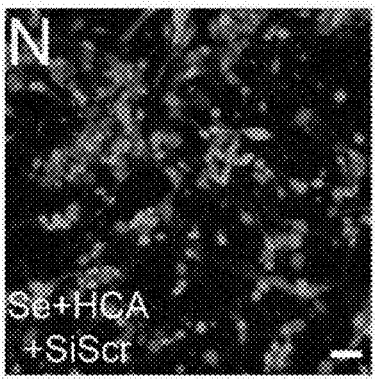
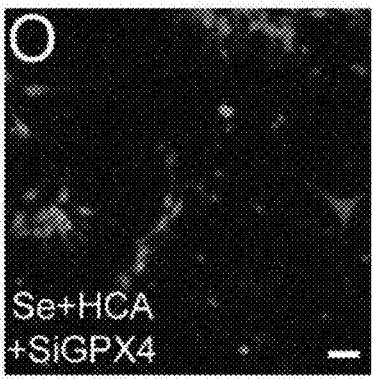
FIG. 3P
FIG. 3Q
FIG. 3R
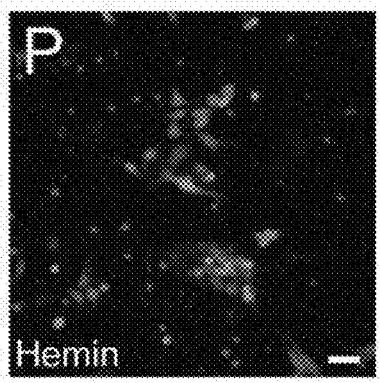
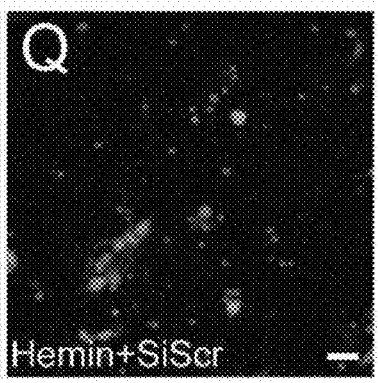
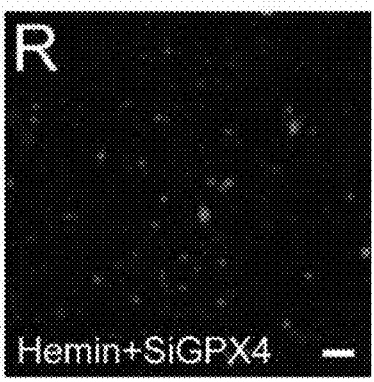
FIG. 3S
FIG. 3T
FIG. 3U
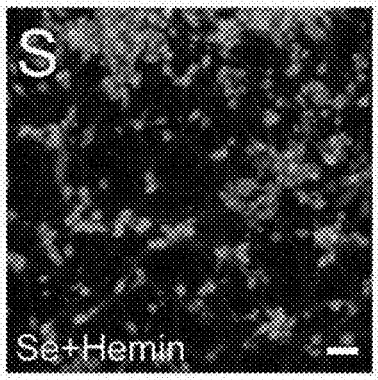
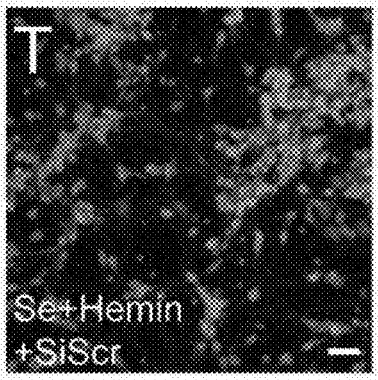
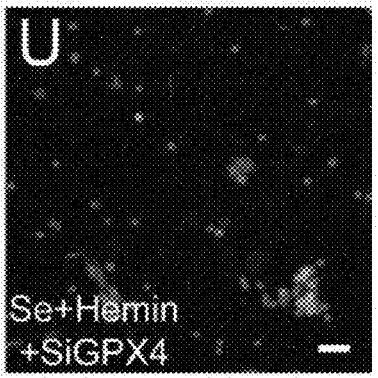

FIG. 11A FIG. 11B
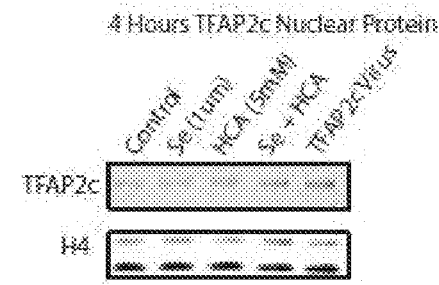
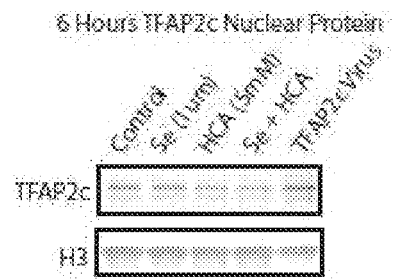
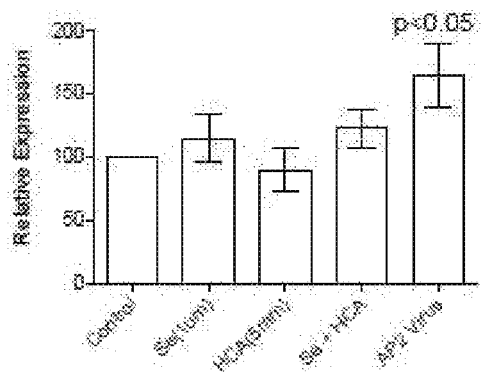
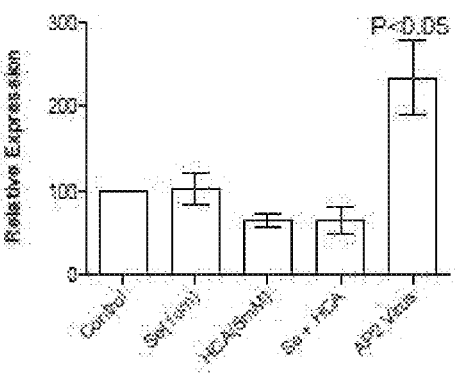
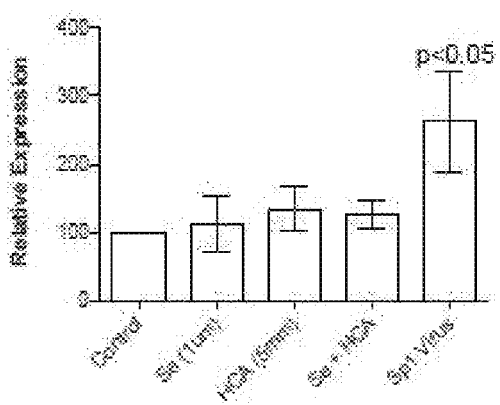
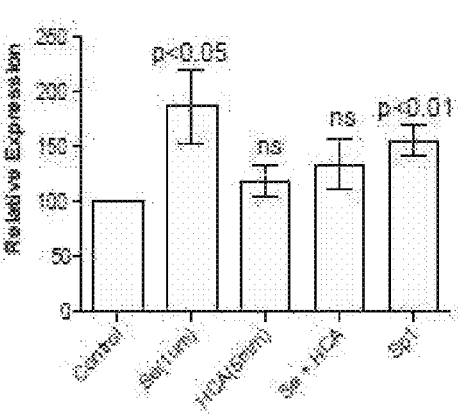
FIG. 11C FIG. 11D

FIG. 14A
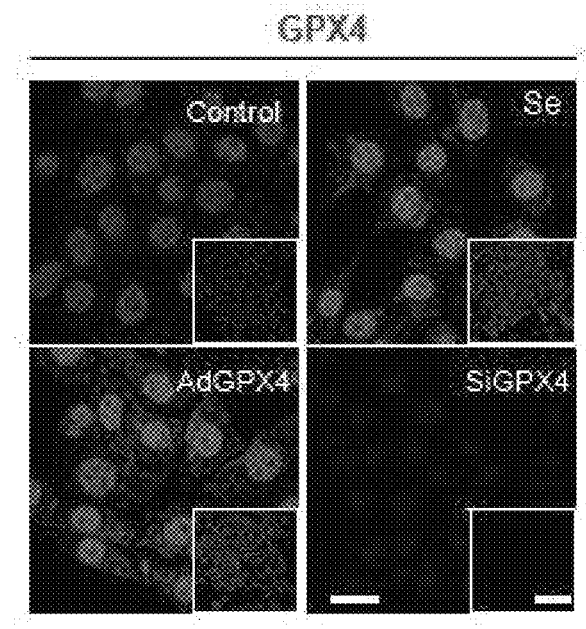
FIG. 14B
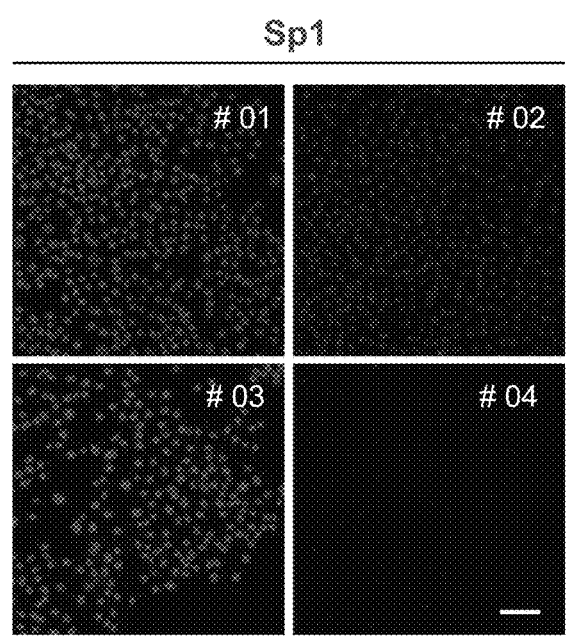
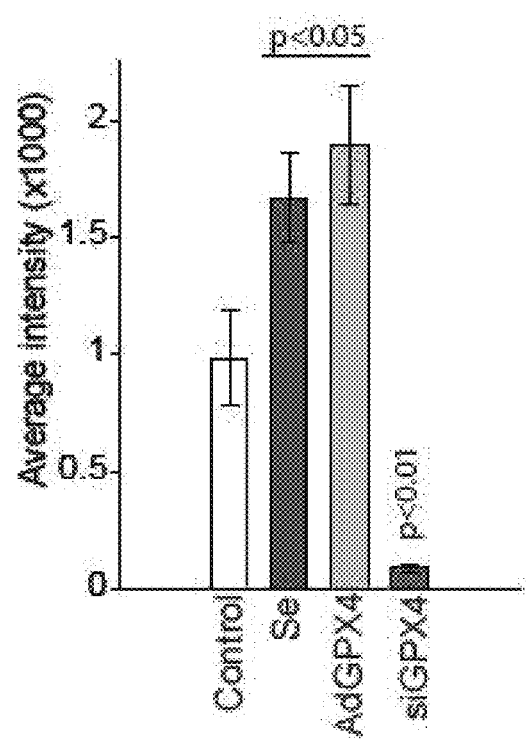
FIG. 14C
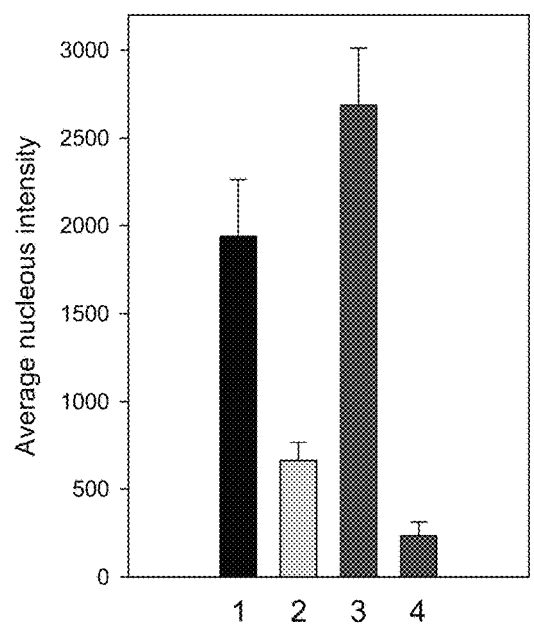
FIG. 14D FIG. 15
Sp1  NeuN  ToPro
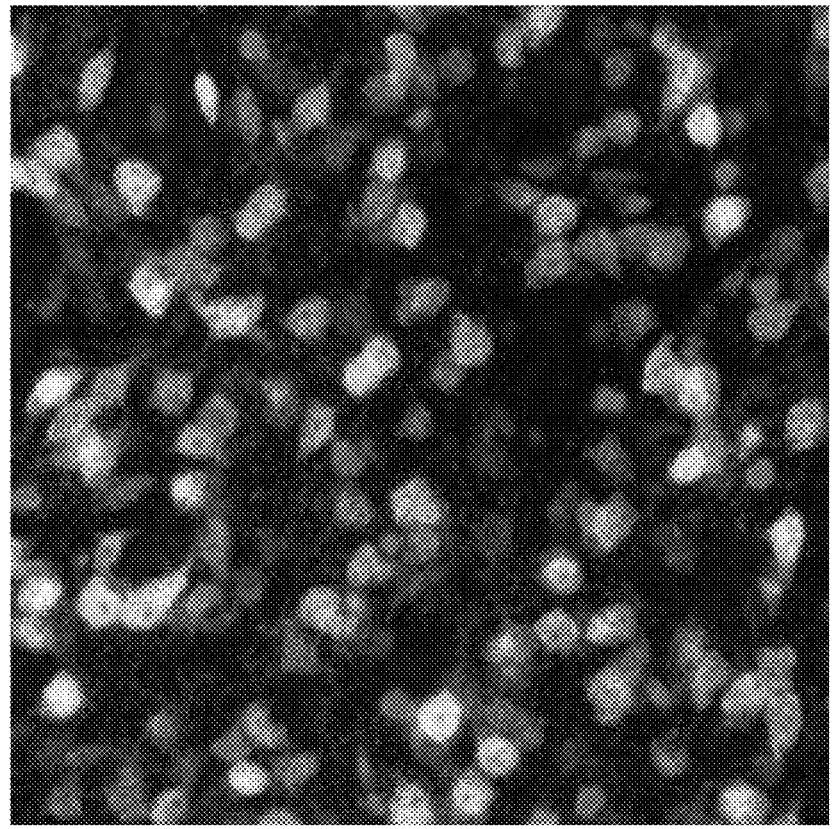
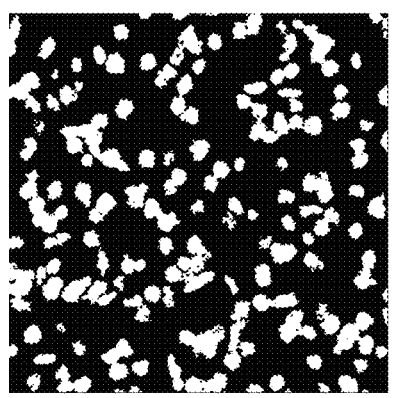 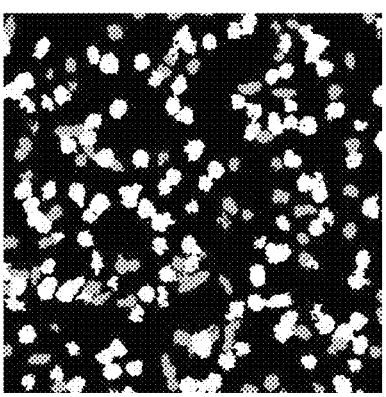 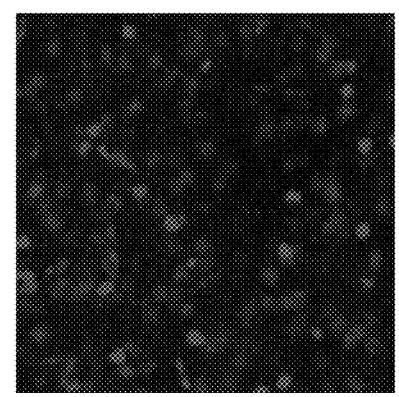

|  | Sa CTRL | Sa Stroke | Se CTRL | Se Stroke |
| --- | --- | --- | --- | --- |
| Number of cells | 2503 | 3123 | 3835 | 3853 |
| Average | 1023 | 1147 | 1152 | 1261 |
| SD | 21 | 35 | 23 | 27 |

FIG. 49
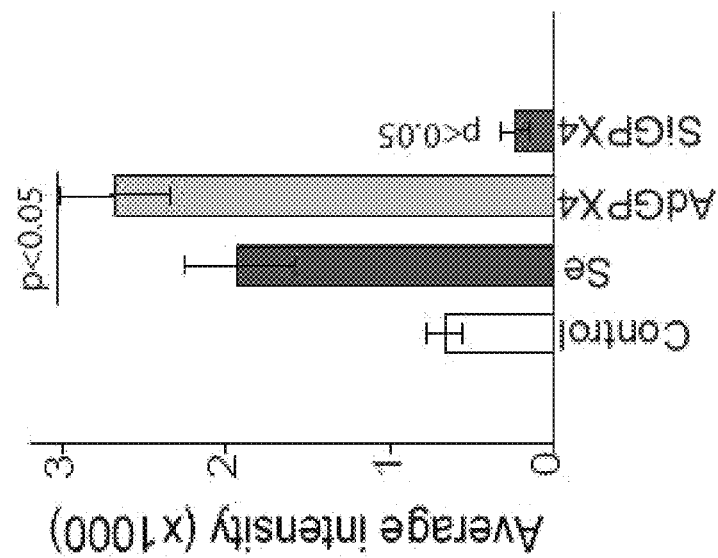
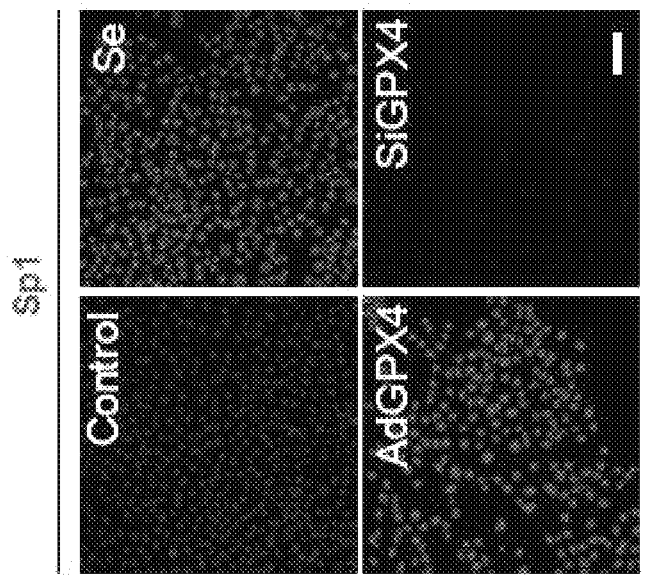

FIG. 56

| Turquoise | Genes |
|---|---|
| Regulation of dephosphorylation | Adora1, Dysfip1, Mki67ip, Nuak1, Pcdh11, Ppp2r2b, Ppp4r2, Ppp6r3, Sema4d, Sit1, Smad3, Spsb1, Tipr, Tsks, Zfyve1 |
| Energy coupled proton transport, against electrochemical gradient | Agtpbp1, Atp5a, Atp6v0a2, Atp6v0e, Atp6v1b1 |
| Regulation of defense to virus | 2010002M12Rik, Ccl5, Il15, Ifha, Taldp2 |
| Regulation of tyrosine phosphorylation of STAT protein | Cav1, Ccl5, Fgfr3, Il13, Il15, Pecam, Socs1 |
| Neuroprotection | Abce1, Atitoh1, Ccl5, Cnir1, Kit, Nmnat3, Tgfa, Tmx2 |
| Protein phosphatase regulator activity | Csnk2a1, Dysfip1, Ensa, Phactr3, Ppp1r8, Ppp2r2b, Ppp4r2 |
| Phosphatidylinositol binding | Akap2, Cyfip3, Inppl1, Pard3, Zfyve1 |
| Protein kinase A binding | Akap11, Akap13, Akap4, Pja2, Rvr2 |
| Leading edge membrane | Adora1, Apc2, Atf4, Clasp2, Fzd5, Itga8, Ptgrj, Robo1, Spata13, Synp2, Tln1 |

FIG. 58

| Color | Process | Genes |
|---|---|---|
| Brown | ATPase activity | Abca9, Abcf3, Atp2b4, Atp5f, Atp9b, Chd9, Ddx23, Ddx41, Dhx29, Ipo8, Katna1, Pex6, Rfc3, Xrcc6 |
| | Regulation of epithelial cell proliferation | Bnc1, Fgf10, Gas1, Kng1, Med1, Pold4, Tacr1 |
| | DNA replication | Chaf1a, Med1, Nfic, Orc3, Pold4, Rfc3, Rnaseh1 |
| | ATP metabolic process | Abca9, Atp2b4, Atp5f, Atp9b, Ipo8, Pex6, Rfc3, Slc25a13 |
| | Regulation of sequence specific DNA binding transcription factor activity | Bcl10, Gtf2a2, Kdm1a, Lrp5, Neurog1, Rnf11, Smarcb1, Tmeff1a |
| | Positive regulation of transcription from RNA polymerase II promoter | Arid2, Fgf10, Foxd2, Gtf2a2, Inhba, Kdm1a, Lrp5, Med1, Ncoa1, Neurog1, Nfic, Phox2a, Peo4f1, Rxrb, Smarcb1, Tbx20, Tead4, Xrcc6, Zfp292 |
| | Ribonucleoside triphosphate biosynthetic process | 1600029l14Rik, Atp2b4, Atp5f, Atp9b, Slc25a13 |
| | Transcription co-activator activity | Bcl10, Gtf2a2, Kdm1a, Med1, Ncoa1, Rxrb, Smarcb1, Taf10, Tbx20 |

SEQUENCE LISTING

```
<160> NUMBER OF SEQ ID NOS: 28

<210> SEQ ID NO 1
<211> LENGTH: 18
<212> TYPE: PRT
<213> ORGANISM: Artificial
<220> FEATURE:
<223> OTHER INFORMATION: sequence is synthesized
<220> FEATURE:
<221> NAME/KEY: SIGNAL
<222> LOCATION: (18)..(18)
<223> OTHER INFORMATION: CONH2

<400> SEQUENCE: 1

Tyr Gly Arg Lys Lys Arg Arg Gln Arg Arg Lys Cys Lys Cys Asn
1               5                   10                  15

Leu Asn

<210> SEQ ID NO 2
<211> LENGTH: 18
<212> TYPE: PRT
<213> ORGANISM: Artificial Sequence
<220> FEATURE:
<223> OTHER INFORMATION: Sequence is synthesized
<220> FEATURE:
<221> NAME/KEY: MISC_FEATURE
<222> LOCATION: (13)..(15)
<223> OTHER INFORMATION: Xaa=selenocysteine
<220> FEATURE:
<221> NAME/KEY: SIGNAL
<222> LOCATION: (18)..(18)
<223> OTHER INFORMATION: CONH2

<400> SEQUENCE: 2

Tyr Gly Arg Lys Lys Arg Arg Gln Arg Arg Lys Xaa Lys Xaa Asn
1               5                   10                  15

Leu Asn

<210> SEQ ID NO 3
<211> LENGTH: 15
<212> TYPE: PRT
<213> ORGANISM: Artificial Sequence
<220> FEATURE:
<223> OTHER INFORMATION: Sequence is synthesized
<220> FEATURE:
<221> NAME/KEY: MISC_FEATURE
<222> LOCATION: (14)..(14)
<223> OTHER INFORMATION: Xaa=Selenocysteine
<220> FEATURE:
<221> NAME/KEY: SIGNAL
<222> LOCATION: (15)..(15)
<223> OTHER INFORMATION: CONH2

<400> SEQUENCE: 3

Tyr Gly Arg Lys Lys Arg Arg Gln Arg Arg Gly Cys Xaa Gly
1               5                   10                  15

<210> SEQ ID NO 4
```

```
<211> LENGTH: 29
<212> TYPE: PRT
<213> ORGANISM: Artificial Sequence
<220> FEATURE:
<223> OTHER INFORMATION: Sequence is synthesized
<220> FEATURE:
<221> NAME/KEY: MISC_FEATURE
<222> LOCATION: (24)..(26)
<223> OTHER INFORMATION: Xaa=selenocysteine
<220> FEATURE:
<221> NAME/KEY: SIGNAL
<222> LOCATION: (29)..(29)
<223> OTHER INFORMATION: CONH2

<400> SEQUENCE: 4

Tyr Gly Arg Lys Lys Arg Arg Gln Arg Arg Pro Gln Lys Leu Ser
1               5                   10                  15

Ser Ile Glu Ser Asp Val Lys Xaa Lys Xaa Asn Leu Asn
            20                  25

<210> SEQ ID NO 5
<211> LENGTH: 26
<212> TYPE: PRT
<213> ORGANISM: Artificial Sequence
<220> FEATURE:
<223> OTHER INFORMATION: Sequence is synthesized
<220> FEATURE:
<221> NAME/KEY: MISC_FEATURE
<222> LOCATION: (25)..(25)
<223> OTHER INFORMATION: Xaa=selenocysteine
<220> FEATURE:
<221> NAME/KEY: SIGNAL
<222> LOCATION: (26)..(26)
<223> OTHER INFORMATION: CONH2

<400> SEQUENCE: 5

Tyr Gly Arg Lys Lys Arg Arg Gln Arg Arg Pro Gln Lys Leu Ser
1               5                   10                  15

Ser Ile Glu Ser Asp Val Gly Cys Xaa Gly
            20                  25

<210> SEQ ID NO 6
<211> LENGTH: 30
<212> TYPE: PRT
<213> ORGANISM: Artificial Sequence
<220> FEATURE:
<223> OTHER INFORMATION: Sequence is synthesized
<220> FEATURE:
<221> NAME/KEY: MISC_FEATURE
<222> LOCATION: (25)..(27)
<223> OTHER INFORMATION: Xaa=selenocysteine
<220> FEATURE:
<221> NAME/KEY: SIGNAL
<222> LOCATION: (30)..(30)
<223> OTHER INFORMATION: CONH2

<400> SEQUENCE: 6

Cys Ser Phe Asn Ser Tyr Glu Leu Gly Ser Leu Cys Tyr Gly Arg Lys
1               5                   10                  15

Lys Arg Arg Gln Arg Arg Arg Lys Xaa Lys Xaa Asn Leu Asn
            20                  25                  30

<210> SEQ ID NO 7
<211> LENGTH: 27
<212> TYPE: PRT
<213> ORGANISM: Artificial Sequence
<220> FEATURE:
<223> OTHER INFORMATION: Sequence is synthesized
<220> FEATURE:
<221> NAME/KEY: MISC_FEATURE
```

```
<222> LOCATION: (26)..(26)
<223> OTHER INFORMATION: Xaa=selenocysteine
<220> FEATURE:
<221> NAME/KEY: SIGNAL
<222> LOCATION: (27)..(27)
<223> OTHER INFORMATION: CONH2

<400> SEQUENCE: 7

Cys Ser Phe Asn Ser Tyr Glu Leu Gly Ser Leu Cys Tyr Gly Arg Lys
1               5                   10                  15

Lys Arg Arg Gln Arg Arg Arg Gly Cys Xaa Gly
            20                  25

<210> SEQ ID NO 8
<211> LENGTH: 42
<212> TYPE: PRT
<213> ORGANISM: Artificial Sequence
<220> FEATURE:
<223> OTHER INFORMATION: Sequence is synthesized
<220> FEATURE:
<221> NAME/KEY: MISC_FEATURE
<222> LOCATION: (37)..(39)
<223> OTHER INFORMATION: Xaa=selenocysteine

<400> SEQUENCE: 8

Gly Arg Lys Lys Arg Arg Gln Arg Arg Arg Cys Asp Met Ala Glu His
1               5                   10                  15

Met Glu Arg Leu Lys Ala Asn Asp Ser Leu Lys Leu Ser Gln Glu Tyr
            20                  25                  30

Glu Ser Ile Lys Xaa Lys Xaa Asn Leu Asn
        35                  40

<210> SEQ ID NO 9
<211> LENGTH: 39
<212> TYPE: PRT
<213> ORGANISM: Artificial Sequence
<220> FEATURE:
<223> OTHER INFORMATION: Sequence is synthesized
<220> FEATURE:
<221> NAME/KEY: MISC_FEATURE
<222> LOCATION: (38)..(38)
<223> OTHER INFORMATION: Xaa=selenocysteine

<400> SEQUENCE: 9

Gly Arg Lys Lys Arg Arg Gln Arg Arg Arg Cys Asp Met Ala Glu His
1               5                   10                  15

Met Glu Arg Leu Lys Ala Asn Asp Ser Leu Lys Leu Ser Gln Glu Tyr
            20                  25                  30

Glu Ser Ile Gly Cys Xaa Gly
        35

<210> SEQ ID NO 10
<211> LENGTH: 48
<212> TYPE: PRT
<213> ORGANISM: Artificial Sequence
<220> FEATURE:
<223> OTHER INFORMATION: Sequence is synthesized
<220> FEATURE:
<221> NAME/KEY: MISC_FEATURE
<222> LOCATION: (43)..(45)
<223> OTHER INFORMATION: Xaa=selenocysteine

<400> SEQUENCE: 10

Tyr Gly Arg Lys Lys Arg Arg Gln Arg Arg Tyr Tyr Gln Trp Asp
1               5                   10                  15

Lys Phe Ala Tyr Leu Tyr Asp Ser Asp Arg Gly Leu Ser Thr Leu Gln
```

```
                20                  25                  30

Ala Val Leu Asp Ser Ala Ala Glu Lys Lys Xaa Lys Xaa Asn Leu Asn
        35                  40                  45

<210> SEQ ID NO 11
<211> LENGTH: 45
<212> TYPE: PRT
<213> ORGANISM: Artificial Sequence
<220> FEATURE:
<223> OTHER INFORMATION: Sequence is synthesized
<220> FEATURE:
<221> NAME/KEY: MISC_FEATURE
<222> LOCATION: (44)..(44)
<223> OTHER INFORMATION: Xaa=selenocysteine

<400> SEQUENCE: 11

Tyr Gly Arg Lys Lys Arg Arg Gln Arg Arg Tyr Tyr Gln Trp Asp
1               5                   10                  15

Lys Phe Ala Tyr Leu Tyr Asp Ser Asp Arg Gly Leu Ser Thr Leu Gln
        20                  25                  30

Ala Val Leu Asp Ser Ala Ala Glu Lys Gly Cys Xaa Gly
        35                  40                  45

<210> SEQ ID NO 12
<211> LENGTH: 43
<212> TYPE: PRT
<213> ORGANISM: Artificial Sequence
<220> FEATURE:
<223> OTHER INFORMATION: Sequence is synthesized
<220> FEATURE:
<221> NAME/KEY: MISC_FEATURE
<222> LOCATION: (38)..(40)
<223> OTHER INFORMATION: Xaa=selenocysteine

<400> SEQUENCE: 12

Tyr Gly Arg Lys Lys Arg Arg Gln Arg Arg Lys Lys Glu Ala Phe
1               5                   10                  15

Trp Asp Arg Cys Leu Ser Val Ile Asn Leu Met Ser Ser Lys Met Leu
        20                  25                  30

Gln Ile Asn Ala Lys Xaa Lys Xaa Asn Leu Asn
        35                  40

<210> SEQ ID NO 13
<211> LENGTH: 40
<212> TYPE: PRT
<213> ORGANISM: Artificial Sequence
<220> FEATURE:
<223> OTHER INFORMATION: Sequence is synthesized
<220> FEATURE:
<221> NAME/KEY: MISC_FEATURE
<222> LOCATION: (39)..(39)
<223> OTHER INFORMATION: Xaa=selenocysteine

<400> SEQUENCE: 13

Tyr Gly Arg Lys Lys Arg Arg Gln Arg Arg Lys Lys Glu Ala Phe
1               5                   10                  15

Trp Asp Arg Cys Leu Ser Val Ile Asn Leu Met Ser Ser Lys Met Leu
        20                  25                  30

Gln Ile Asn Ala Gly Cys Xaa Gly
        35                  40

<210> SEQ ID NO 14
<211> LENGTH: 43
<212> TYPE: PRT
<213> ORGANISM: Artificial Sequence
```

```
<220> FEATURE:
<223> OTHER INFORMATION: Sequence is synthesized
<220> FEATURE:
<221> NAME/KEY: MISC_FEATURE
<222> LOCATION: (38)..(40)
<223> OTHER INFORMATION: Xaa=selenocysteine

<400> SEQUENCE: 14

Tyr Gly Arg Lys Lys Arg Arg Gln Arg Arg Lys Lys Asn Ala Phe
1               5                   10                  15

Tyr Glu Arg Ala Leu Ser Ile Ile Asn Leu Met Thr Ser Lys Met Val
                20                  25                  30

Gln Ile Asn Val Lys Xaa Lys Xaa Asn Leu Asn
        35                  40

<210> SEQ ID NO 15
<211> LENGTH: 40
<212> TYPE: PRT
<213> ORGANISM: Artificial Sequence
<220> FEATURE:
<223> OTHER INFORMATION: Sequence is synthesized
<220> FEATURE:
<221> NAME/KEY: MISC_FEATURE
<222> LOCATION: (39)..(39)
<223> OTHER INFORMATION: Xaa=selenocysteine

<400> SEQUENCE: 15

Tyr Gly Arg Lys Lys Arg Arg Gln Arg Arg Lys Lys Asn Ala Phe
1               5                   10                  15

Tyr Glu Arg Ala Leu Ser Ile Ile Asn Leu Met Thr Ser Lys Met Val
                20                  25                  30

Gln Ile Asn Val Gly Cys Xaa Gly
        35                  40

<210> SEQ ID NO 16
<211> LENGTH: 22
<212> TYPE: PRT
<213> ORGANISM: Artificial Sequence
<220> FEATURE:
<223> OTHER INFORMATION: Sequence is synthesized
<220> FEATURE:
<221> NAME/KEY: MISC_FEATURE
<222> LOCATION: (12)..(12)
<223> OTHER INFORMATION: Xaa=D-Arginine
<220> FEATURE:
<221> NAME/KEY: MOD_RES
<222> LOCATION: (13)..(13)
<223> OTHER INFORMATION: METHYLATION, 2',6'-dimethylTyr
<220> FEATURE:
<221> NAME/KEY: MISC_FEATURE
<222> LOCATION: (17)..(19)
<223> OTHER INFORMATION: Xaa=selenocysteine

<400> SEQUENCE: 16

Tyr Gly Arg Lys Lys Arg Arg Gln Arg Arg Xaa Tyr Lys Phe Lys
1               5                   10                  15

Xaa Lys Xaa Asn Leu Asn
            20

<210> SEQ ID NO 17
<211> LENGTH: 19
<212> TYPE: PRT
<213> ORGANISM: Artificial Sequence
<220> FEATURE:
<223> OTHER INFORMATION: Sequence is synthesized
<220> FEATURE:
<221> NAME/KEY: MISC_FEATURE
<222> LOCATION: (12)..(12)
```

```
<223> OTHER INFORMATION: Xaa=D-Arginine
<220> FEATURE:
<221> NAME/KEY: MOD_RES
<222> LOCATION: (13)..(13)
<223> OTHER INFORMATION: METHYLATION, 2',6'-dimethylTyr
<220> FEATURE:
<221> NAME/KEY: MISC_FEATURE
<222> LOCATION: (18)..(18)
<223> OTHER INFORMATION: Xaa=selenocysteine

<400> SEQUENCE: 17

Tyr Gly Arg Lys Lys Arg Arg Gln Arg Arg Xaa Tyr Lys Phe Gly
1               5                   10                  15

Cys Xaa Gly

<210> SEQ ID NO 18
<211> LENGTH: 22
<212> TYPE: PRT
<213> ORGANISM: Artificial Sequence
<220> FEATURE:
<223> OTHER INFORMATION: Sequence is synthesized
<220> FEATURE:
<221> NAME/KEY: MISC_FEATURE
<222> LOCATION: (12)..(12)
<223> OTHER INFORMATION: Xaa=D-Arginine
<220> FEATURE:
<221> NAME/KEY: MOD_RES
<222> LOCATION: (14)..(14)
<223> OTHER INFORMATION: METHYLATION, 2',6'-dimethylTyr

<400> SEQUENCE: 18

Tyr Gly Arg Lys Lys Arg Arg Gln Arg Arg Xaa Tyr Lys Phe Lys
1               5                   10                  15

Cys Lys Cys Asn Leu Asn
            20

<210> SEQ ID NO 19
<211> LENGTH: 45
<212> TYPE: PRT
<213> ORGANISM: Artificial Sequence
<220> FEATURE:
<223> OTHER INFORMATION: Sequence is synthesized
<220> FEATURE:
<221> NAME/KEY: MISC_FEATURE
<222> LOCATION: (40)..(42)
<223> OTHER INFORMATION: Xaa=selenocysteine

<400> SEQUENCE: 19

Tyr Gly Arg Lys Lys Arg Arg Gln Arg Arg Pro Ala Ala Lys Arg
1               5                   10                  15

Val Lys Leu Asp Pro Ala Ala Lys Arg Val Lys Leu Asp Pro Ala Ala
            20                  25                  30

Lys Arg Val Lys Leu Asp Lys Xaa Lys Xaa Asn Leu Asn
            35                  40                  45

<210> SEQ ID NO 20
<211> LENGTH: 42
<212> TYPE: PRT
<213> ORGANISM: Artificial Sequence
<220> FEATURE:
<223> OTHER INFORMATION: Sequence is synthesized
<220> FEATURE:
<221> NAME/KEY: MISC_FEATURE
<222> LOCATION: (41)..(41)
<223> OTHER INFORMATION: Xaa=selenocysteine

<400> SEQUENCE: 20

Tyr Gly Arg Lys Lys Arg Arg Gln Arg Arg Pro Ala Ala Lys Arg
```

```
                1               5                  10                 15
            Val Lys Leu Asp Pro Ala Ala Lys Arg Val Lys Leu Asp Pro Ala Ala
                        20                  25                  30

Lys Arg Val Lys Leu Asp Gly Cys Xaa Gly
                        35                  40

<210> SEQ ID NO 21
<211> LENGTH: 45
<212> TYPE: PRT
<213> ORGANISM: Artificial Sequence
<220> FEATURE:
<223> OTHER INFORMATION: Sequence is synthesized

<400> SEQUENCE: 21

Tyr Gly Arg Lys Lys Arg Arg Gln Arg Arg Pro Ala Ala Lys Arg
            1               5                   10                  15

Val Lys Leu Asp Pro Ala Ala Lys Arg Val Lys Leu Asp Pro Ala Ala
                        20                  25                  30

Lys Arg Val Lys Leu Asp Lys Cys Lys Cys Asn Leu Asn
                        35                  40                  45

<210> SEQ ID NO 22
<211> LENGTH: 21
<212> TYPE: DNA
<213> ORGANISM: MOUSE SP.

<400> SEQUENCE: 22
ctttgccccc tgtacaggca g                                              21

<210> SEQ ID NO 23
<211> LENGTH: 21
<212> TYPE: DNA
<213> ORGANISM: MOUSE SP.

<400> SEQUENCE: 23
tgttgccaca tgtccaagcc a                                              21

<210> SEQ ID NO 24
<211> LENGTH: 21
<212> TYPE: DNA
<213> ORGANISM: MOUSE SP.

<400> SEQUENCE: 24
cgagcccata ctgcccacat c                                              21

<210> SEQ ID NO 25
<211> LENGTH: 21
<212> TYPE: DNA
<213> ORGANISM: MOUSE SP.

<400> SEQUENCE: 25
gctgcccctg ggggtgggag c                                              21

<210> SEQ ID NO 26
<211> LENGTH: 21
<212> TYPE: DNA
<213> ORGANISM: MOUSE SP.

<400> SEQUENCE: 26
ctgggggtgg gagcccagga a                                              21

<210> SEQ ID NO 27
```

```
<211> LENGTH: 11
<212> TYPE: DNA
<213> ORGANISM: Mouse Sp.
<220> FEATURE:
<221> NAME/KEY: misc_feature
<222> LOCATION: (4)..(8)
<223> OTHER INFORMATION: n is a, c, g, or t

<400> SEQUENCE: 27
gccnnnnngg c                                                        11

<210> SEQ ID NO 28
<211> LENGTH: 6
<212> TYPE: PRT
<213> ORGANISM: Artificial Sequence
<220> FEATURE:
<223> OTHER INFORMATION: Sequence is synthesized
<220> FEATURE:
<221> NAME/KEY: MISC_FEATURE
<222> LOCATION: (1)..(1)
<223> OTHER INFORMATION: Xaa=selenocysteine
<220> FEATURE:
<221> NAME/KEY: MISC_FEATURE
<222> LOCATION: (3)..(3)
<223> OTHER INFORMATION: Xaa=selenocysteine

<400> SEQUENCE: 28

Xaa Lys Xaa Asn Leu Asn
1               5
```

SELENIUM-BASED THERAPIES

CROSS REFERENCE TO RELATED APPLICATION

This application claims the benefit of U.S. Provisional Application No. 62/500,367, filed May 2, 2017. The entire contents of that application are incorporated herein by reference.

REFERENCE TO AN ELECTRONIC SEQUENCE LISTING

The contents of the electronic sequence listing (Burke_ST25.txt; Size: 10,962 bytes; and Date of Creation: Jul. 23, 2018) is herein incorporated by reference in its entirety.

BACKGROUND OF THE INVENTION

Intracerebral hemorrhage (ICH; bleeding in the brain) is a stroke subtype observed in those with hypertension, diabetes, and arteriovenous malformations, and those on anticoagulants. Despite the high morbidity and mortality of ICH across the lifespan (See van Asch et al., Lancet Neurol. 9(2): p. 167-76 (2010)), there are no established treatments (See Keep et al., Lancet Neurol. 11(8): p. 720-731 (2012)). Therapeutic strategies to limit secondary damage after ICH are of intense interest (See Gurol et al., Curr. Atheroscler. Rep. 10(4): p. 324-331 (2008)). Secondary damage, including neuronal death, occurs hours and days following the initial bleed (See Brott et al., Stroke 28(1): p. 1-5 (1997)), and is attributable to a host of factors from lysed blood, such as rich hemoglobin and the oxidized form of iron-rich heme (See Huang et al., J Neurosurg 96(2): p. 287-93 (2002)). Recent studies demonstrate that secondary cell death in ICH is not the result of random destruction of macromolecules by iron-catalyzed oxidants, but rather by ferroptosis, a non-apoptotic, programmed cell death pathway (See Zille et al., Stroke 48(4): p. 1033-1043 (2017)). Ferroptosis is triggered by the enzymatic production of oxidant lipid species and can be inhibited by lipid peroxidation inhibitors such as vitamin E and ferrostatin (See Zille et al., Stroke 48(4): p. 1033-1043 (2017); Dixon et al., Cell 149(5): p. 1060-72(2012)). In addition to ICH, ferroptosis operates in erastin and p53-induced death of cancer cells (See Dixon et al., Cell 149(5): p. 1060-72 (2012); Jiang et al., Nature 520(7545): p. 57-62 (2015)), heat stress in plants (See Distefano et al., J Cell Biol 216(2): p. 463-476 (2017)), acute renal failure (See Friedmann Angeli et al., Nat Cell Biol 16(12): p. 1180-91 (2014)) and Parkinson's disease (See Do Van et al., Neurobiol Dis 94: p. 169-78 (2016)). Despite its broad relevance, our understanding of how cells adapt transcriptionally to ferroptosis-inducing stresses is unknown.

SUMMARY OF THE INVENTION

The present invention is based on the inventors' discovery that selenium drives a novel TFAP2C and Sp1-dependent, adaptive homeostatic response to ferroptosis, with implications for stroke and other conditions associated with oxidative stress, endoplasmic reticulum (ER) stress, non-ER induced apoptotic stress, and excitotoxic stress.

The invention provides a method of treating a condition associated with oxidative, ER, and/or excitotoxic stress in a subject in need thereof, and/or treating a subject at risk for a condition associated with oxidative, ER, and/or excitotoxic stress, comprising administering to the subject a therapeutically effective amount of a compound that comprises selenium or selenocysteine. In some embodiments, the compound is a peptide shown in Table 1 below. The compound may be administered, e.g., intranasally or intravenously. In a particular embodiment, the subject is a mammal, e.g., a human.

In some embodiments, administration of a selenium or selenocysteine-containing compound described herein according to a method of the invention inhibits ferroptosis. In some embodiments, the method increases expression of a selenium-containing antioxidant enzyme (which may be, for example, glutathione peroxidase 4 (GPX4), thioredoxin reductase 1 (TXNRD1), glutathione peroxidase 3 (GPX3), selenoprotein P (SelP or SPP1), or selenoprotein K (SelK)). In some embodiments, the method reduces excitotoxic death of neurons.

The methods described herein may be used to treat any condition associated with oxidative, ER, and/or excitotoxic stress. In some embodiments, the condition is a central nervous system (CNS) condition, such as, for example, stroke, intracebral hemorrhage, traumatic brain injury, spinal cord injury, a neurodegenerative condition (e.g., Alzheimer's disease, Parkinson's disease, Huntington's disease, multisystem atrophy, multiple sclerosis, amyolotrophic lateral sclerosis, cerebral ischemia, seizure disorders, schizophrenia, Friedreich's ataxia, progressive supranuclear palsy, prions, Down's syndrome, ataxia, tardive dyskinesia, or aging), or a neuropsychiatric disorder (e.g., schizophrenia, bipolar disorder, or depression). In some embodiments, the condition is a liver, kidney, or immune system condition. Any combination of the conditions described herein may also be treated using the methods of the invention.

The methods of the invention may comprise administering to the subject a combination of the compound that comprises selenium or selenocysteine and a further agent, such as a lipid peroxidation inhibitor (e.g., vitamin E or ferrostatin); an agent that induces transcriptional activation by TFAP2C, Sp1, or both; N-aceteylsteine (NAC), beta-carotene; or any combination of said agents. Any agent used to treat a condition associated with oxidative, ER, and/or excitotoxic stress is contemplated for the combination treatments of the invention.

The present invention also includes the use of a compound comprising selenium or selenocysteine (e.g., a selenocysteine peptide) for the manufacture of a medicament for treating a condition associated with oxidative, ER, and/or excitotoxic stress in a method described herein. In some embodiments, the medicament comprises a further agent as described herein.

The present invention also includes a compound comprising selenium or selenocysteine (e.g., a selenocysteine peptide) for use in treating a condition associated with oxidative, ER, and/or excitotoxic stress in a method described herein. In some embodiments, the compound comprising selenocysteine is administered with a further agent as described herein.

The present invention also provides a selenocysteine peptide as described herein, e.g., a selenocysteine peptide as shown in Table 1.

The present invention also provides a pharmaceutical composition comprising a compound comprising selenium or selenocysteine and a pharmaceutically acceptable excipient. In some embodiments, the compound comprising selenocysteine is a selenocysteine peptide as described herein (e.g., a selenocysteine peptide as shown in Table 1). The present invention further provides a compound that comprises selenium or selenocysteine for use in a treatment method described herein, wherein the compound may be, for example, a selenocysteine peptide as shown in Table 1. Also provided are use of a compound that comprises selenium or selenocysteine for the manufacture of a medicament used in a treatment method described herein, wherein the compound may be, for example, a selenocysteine peptide as shown in Table 1.

BRIEF DESCRIPTION OF THE FIGURES

A further understanding of the invention can be obtained by reference to embodiments set forth in the illustrations of the accompanying figures. Although the illustrated embodiments are merely exemplary of compounds and methods for carrying out the invention, both the organization and method of operation of the invention, in general, together with further objectives and advantages thereof, may be more easily understood by reference to the figures and the following description. However, the figures are not intended to limit the scope of this invention, which is set forth with particularity in the claims as appended hereto or as subsequently amended, but merely to clarify and exemplify the invention.

FIGS. 1G(a), 1G(b), 1H(a), 1H(b), 1I(a), 1I(b), 1J(a), and 1J(b) are photographs of live/dead imaging of cells overexpressing GFP (control) or GPX4 with destabilizing domain (ddGPX4) following hemin or HCA treatment. Scale bar=50 μm. GPX4 protein was stabilized by co-treating neurons with 10 μM of trimethoprim (TMP) (FIGS. 1H(a), 1H(b) 1J(a), and 1J(b)).

FIGS. 2C-2H are photographs from live/dead assays showing survival of neurons following hemin (80 μM) or HCA (5 mM) treatment with or without 1 μM of Se (n=3). All HCA survival measurements were taken at 24 h, all hemin measurements were taken at 16 h.

FIGS. 3D-3U are live/dead assay images assessing survival of control (non-transfected) and SiScr or SiGPX4 transfected cortical neurons untreated or treated with 1 μM Se, 5 mM HCA, 1 μM Se+5 mM HCA, 80 μM hemin, or 1 μM Se+80 μM hemin. Scale bar=50 μm.

FIG. 5N(b) is a graph showing hematoma volume in sham injected and collagenase injected ICH mice treated with saline or 2.5 μM SE for 24 hours. Samples were observed by light microscopy. The bottom graph shoes a quantification of hematoma size of the brain sections. Each square or triangle represents a sample (n=5).

FIGS. 11A-11D depict Western blots and graphs showing no significant change in Sp1 and TFAP2C protein expression from nuclear extracts at 4 and 6 hours post treatment with 5 mM HCA and/or 1 µM Se (though an increase in activity is seen) (n=4). Adenoviral overexpression is used as a positive control. Se is shown to increase Sp1 expression at 6 h.

FIGS. 14A-14D depict confocal images and graphs showing GPX4 and Sp1 in HT22 neurons (#01) after 8 hours of treatment with vehicle (#01); 1 µM Se (#02), adenoviral overexpression (AdGPX4, 60 MOI; #03); and siGPX4 (#04). Scale bar=25 µm; insert=200 µm; n=3.

FIG. 15 shows an overlay image of Sp1, Neun, and topro in a brain slice. Neun (neuronal marker) is used to determine Sp1 positive neurons.

FIG. 49 depicts immunofluorescent images (left) and a graph (right) showing intensity of Sp1 antibody staining (red) in HT22 cells treated with vehicle (control) or Se, overexpressing Sp1 (AdGPX4), or transduced with GPX4 siRNA (SiGPX4) (n=3).

FIG. 56 is a table showing gene ontology of specific genes significantly upregulated by Se treatment, based on supervised network analysis of GPX4 with exon 1a.

FIG. 58 is a table showing gene ontology of specific genes significantly downregulated by Se treatment, based on supervised network analysis of GPX4 with exon 1a.

FIG. 60 is depicts module eigengene and networks (Darkred) significantly upregulated by Se based on unsupervised WGCNA. ER stress and excitotoxicity related genes are highlighted in red (n=4).

FIG. 61 is a graph showing survival rates of control cells and cells treated with Se, ±tunicamycin (Tun), thapsigargin (Tg), or glutamate (Glu). Se protects against ER stress (induced by 3 µM tunicamycin or 1 µM thapsigargin) or glutamate-induced (100 µM) excitotoxicity in neurons (n=4).

FIG. 62A is a graph showing survival rates as determined by MTT assay of neurons overexpressing GFP (control) or GPX4 (AdGPX4) following 16 hours of treatment with 3 µM tunicamycin (n=4).

FIG. 62B is a graph showing survival rates by MTT assay of mature cortical neurons overexpressing GFP (control) or GPX4 via adenoviral infection following 24 h glutamate (100 µM; excitotoxicity) or erastin (1 µM; ferroptosis) treatment (n=4).

FIG. 63 is a Western blot (top) and a graph (bottom) showing GPX4 protein levels following no treatment or 8 hours of treatment with 5 mM HCA, 80 µM hemin, or 1 µM Se.

FIG. 64 is a schematic summary of major findings from the data presented herein.

Figure 64:
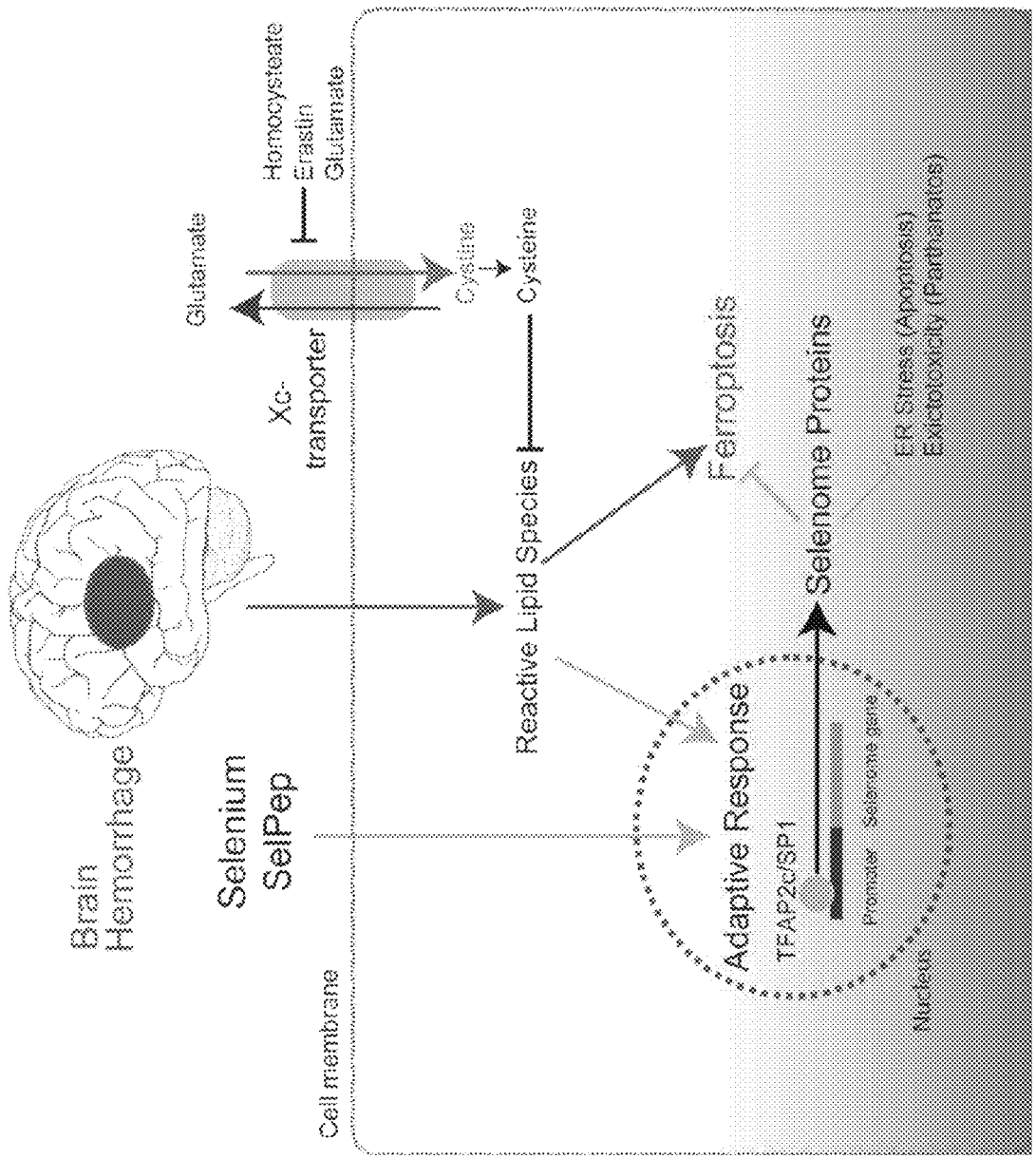
Figure 64A:
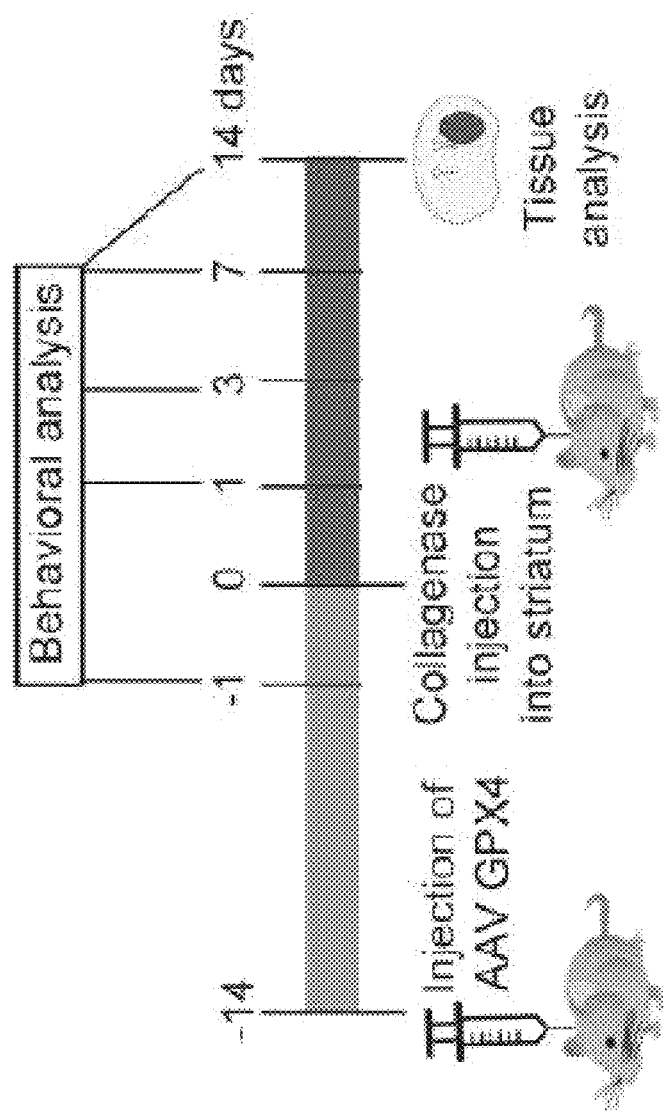

FIG. 64A shows a schematic of a procedure involving double injection of AAV8 GFP or GPX4 into striatum 14 days prior to collagenase induced ICH. Behavioral measurements were made prior to and 1, 3, 7, and 14 days after stroke.

Figure 64B:
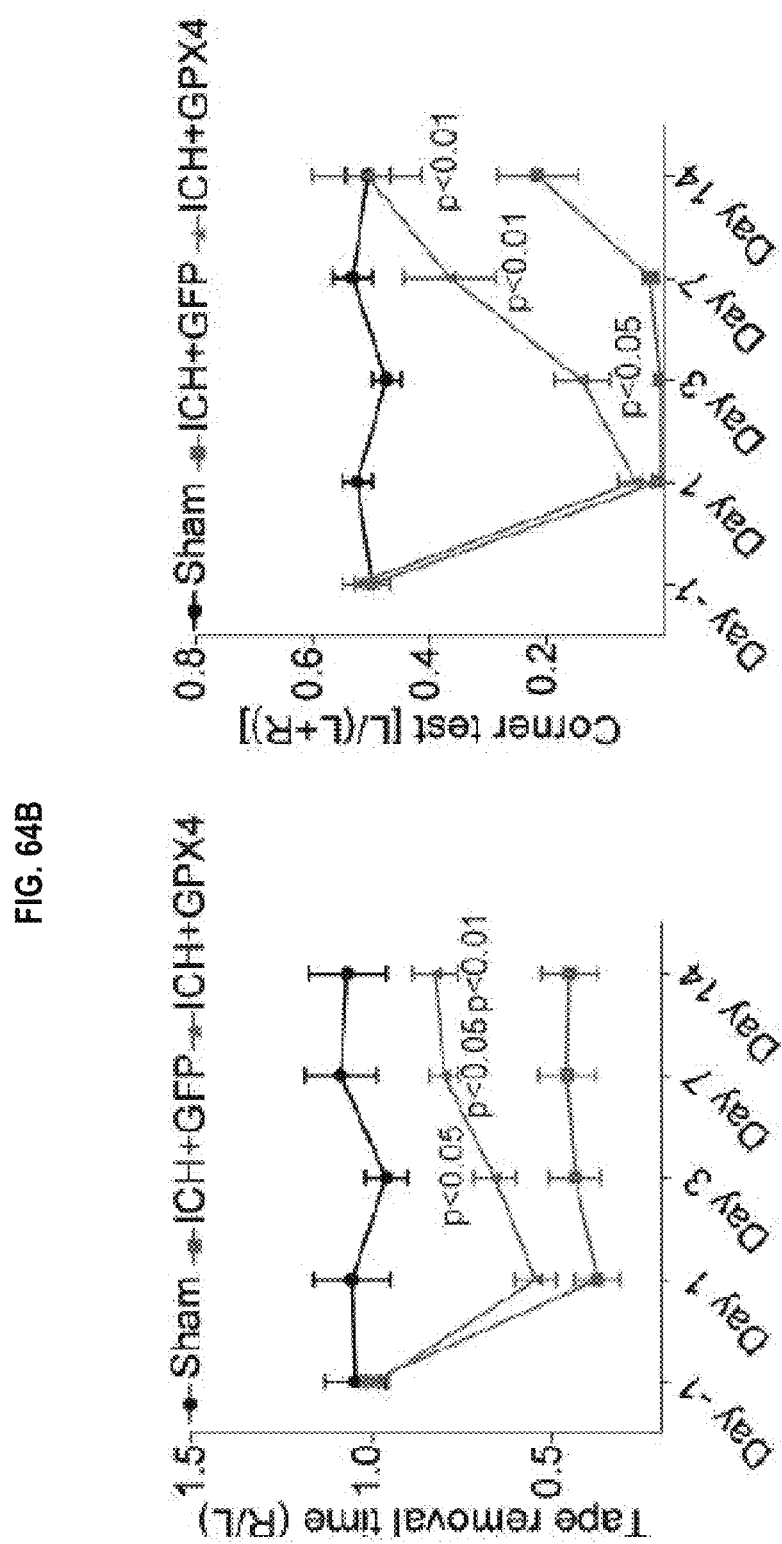

FIG. 64B shows behavior outcomes in sensory neglect task (n=12) and spatial neglect task (n=12) up to 14 days post-ICH in animals plus or minus overexpression of GPX4.

Figure 65A:
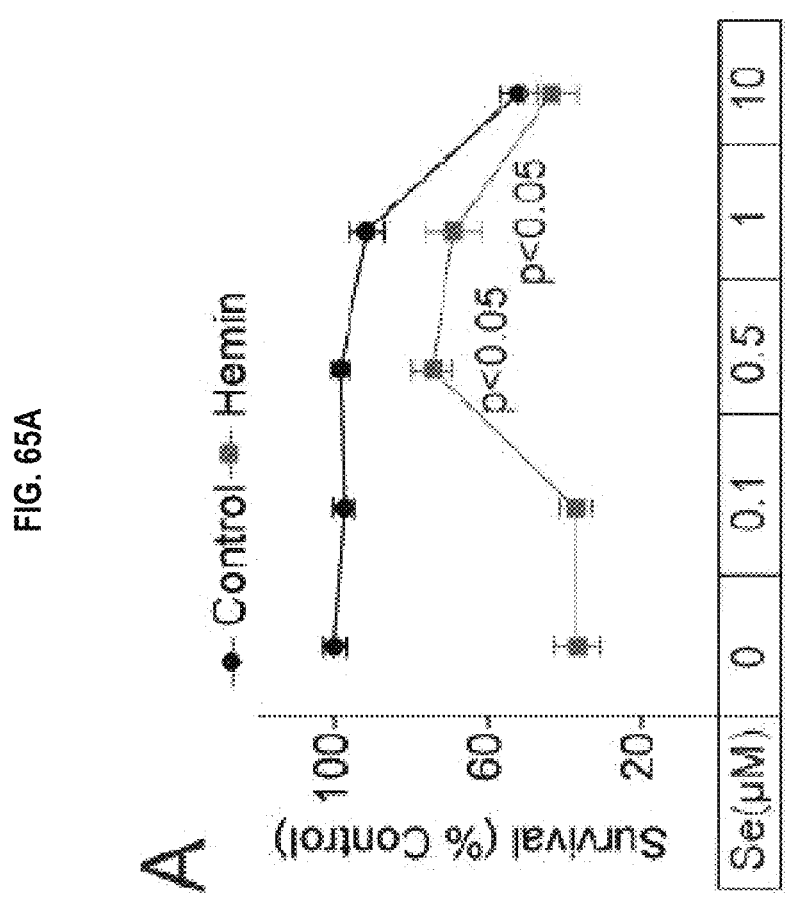

FIG. 65A shows viability of primary cortical neurons (MTT normalized to protein) 24 h following exposure to increasing concentrations of Se and hemin (80 µM; n=5)

Figure 65B:
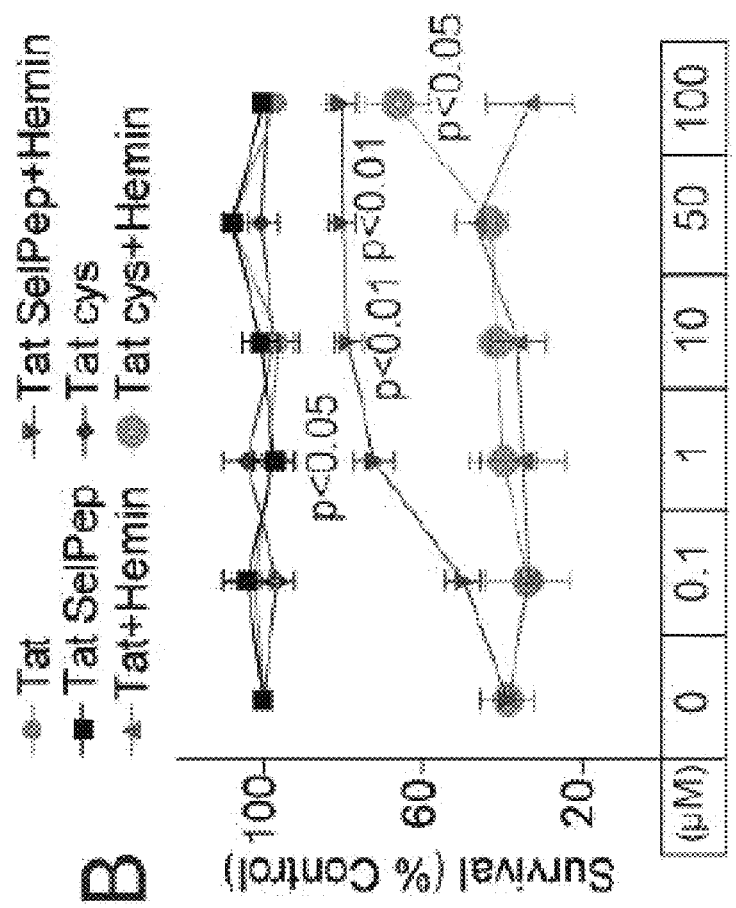
Figure 65C:
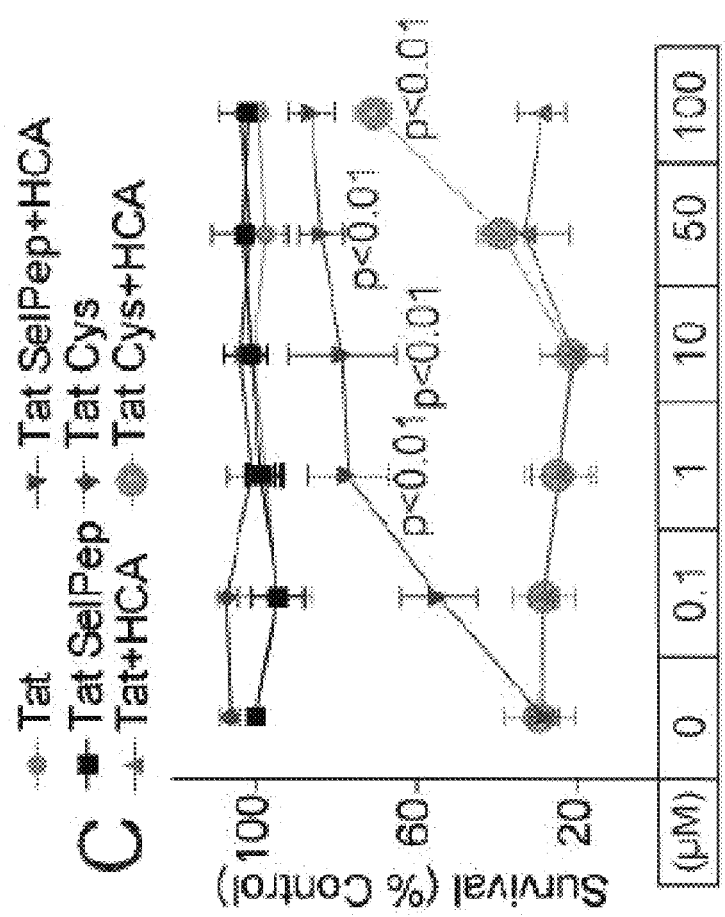

FIGS. 65B-65C show viability of primary cortical neurons following 16 h and 24 h of hemin (80 µM) and HCG (5 mM) respectively, with varying concentrations of Tat, Tat SelPep and Tat Cys (a Sec to Cys peptide variant).

Figure 65D:
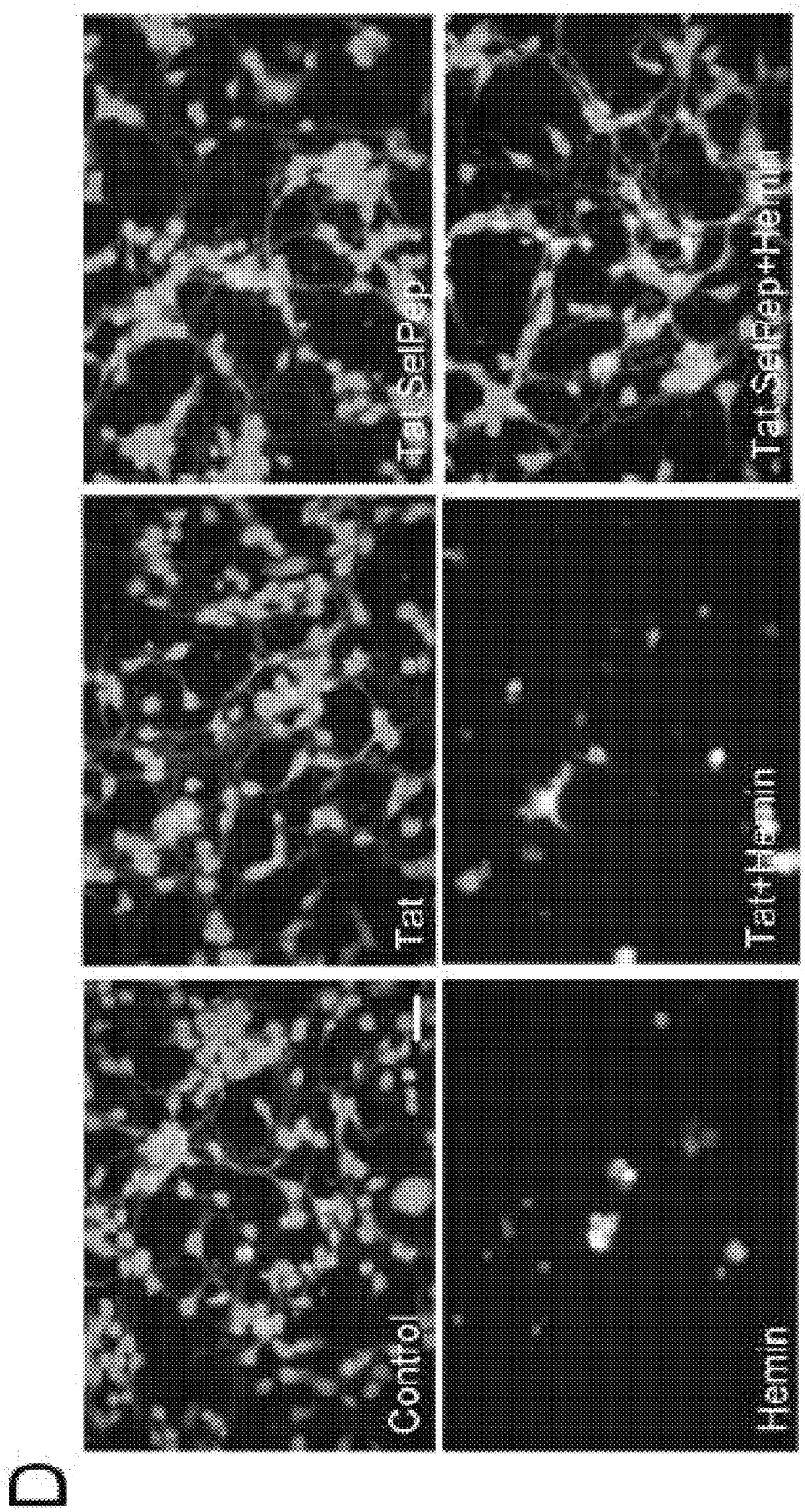

FIG. 65D shows a live (green)/dead (red) assay of primary cortical neurons following 16 h hemin (80 µM) treatment with or without Tat SelPep (1 µM; n=3). Scale bar, 50 µM.

Figure 65E:
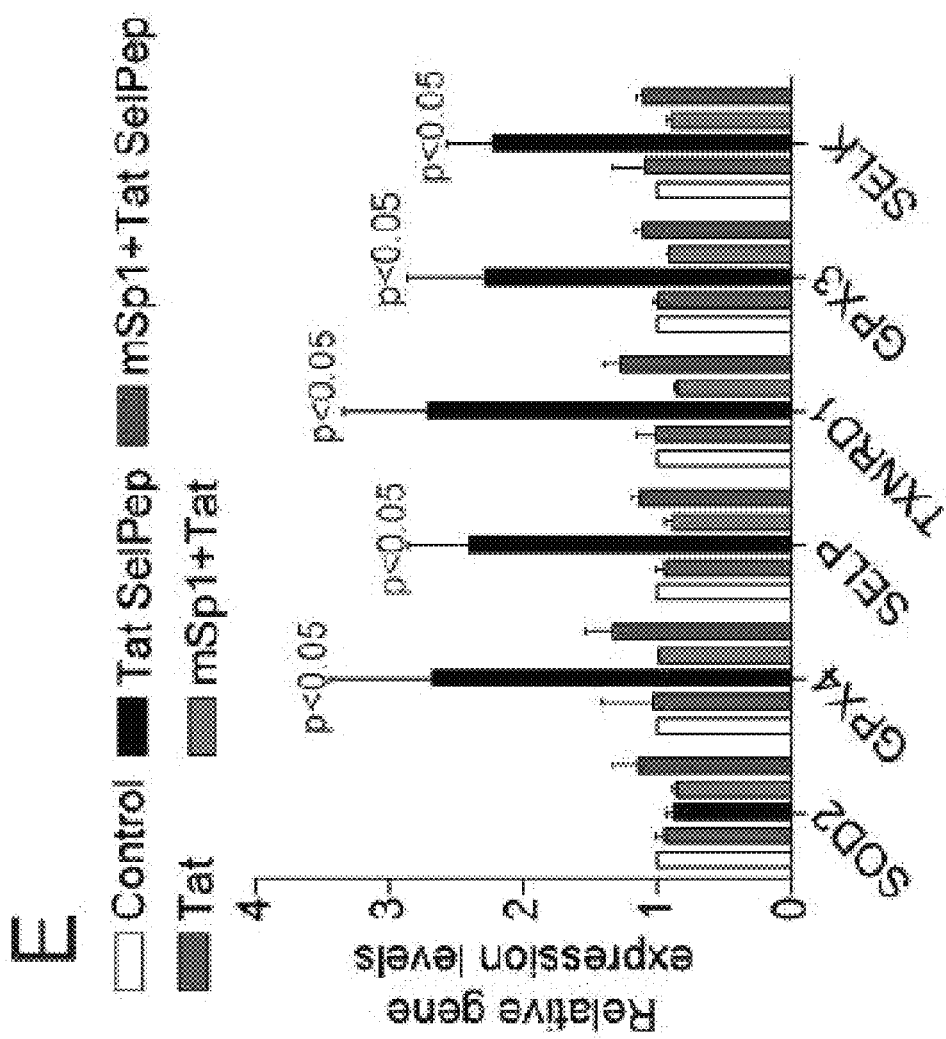

FIG. 65E shows results from qPCR of putative antioxidant genes from primary cortical neurons with or without overexpressing DNA binding mutant Sp1 (mSp1; GFP control virus), 6 h post-treatment with or without Tat/Tat SelPep (1 µM; n=5)

Figure 65F:
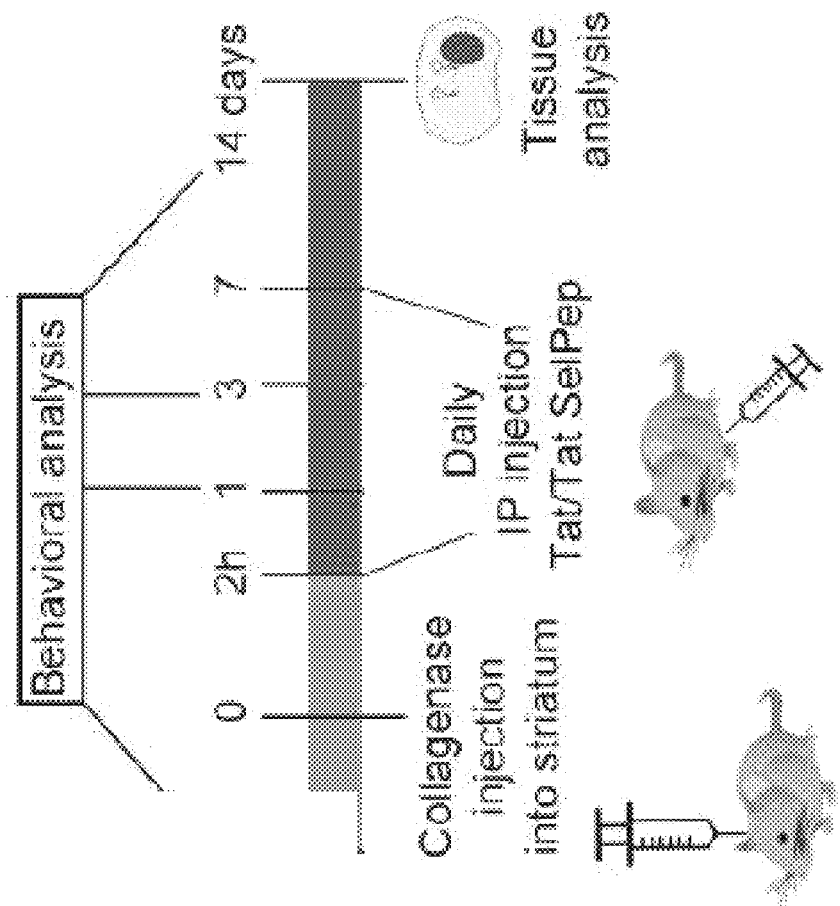

FIG. 65F shows a schematic of the procedure for data in FIG. 65(g-h). Collagenase-induced ICH followed at 2 h by intraperitoneal injection of Tat (12 µg/g) or Tat SelPep (12 µg/g) every day for 7 days post injury. Behavioral measurements were made prior to and 1, 3, 7, and 14 days after hemorrhagic stroke.

Figure 65G:
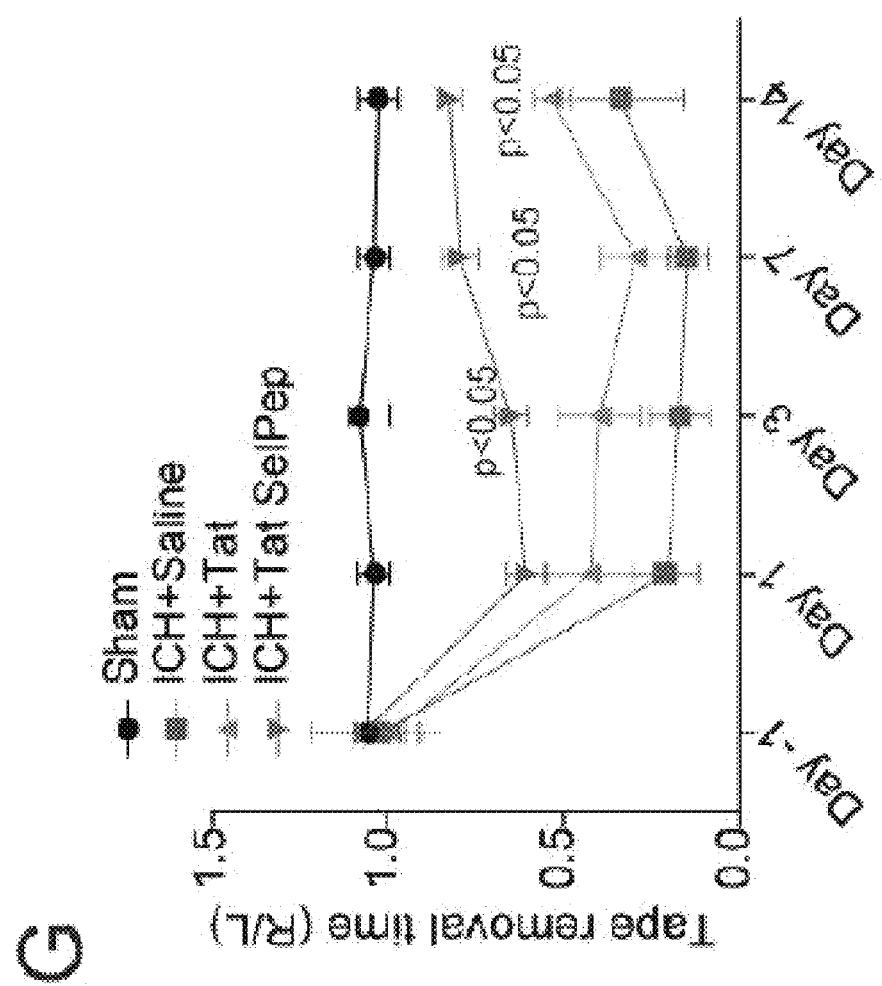
Figure 65H:
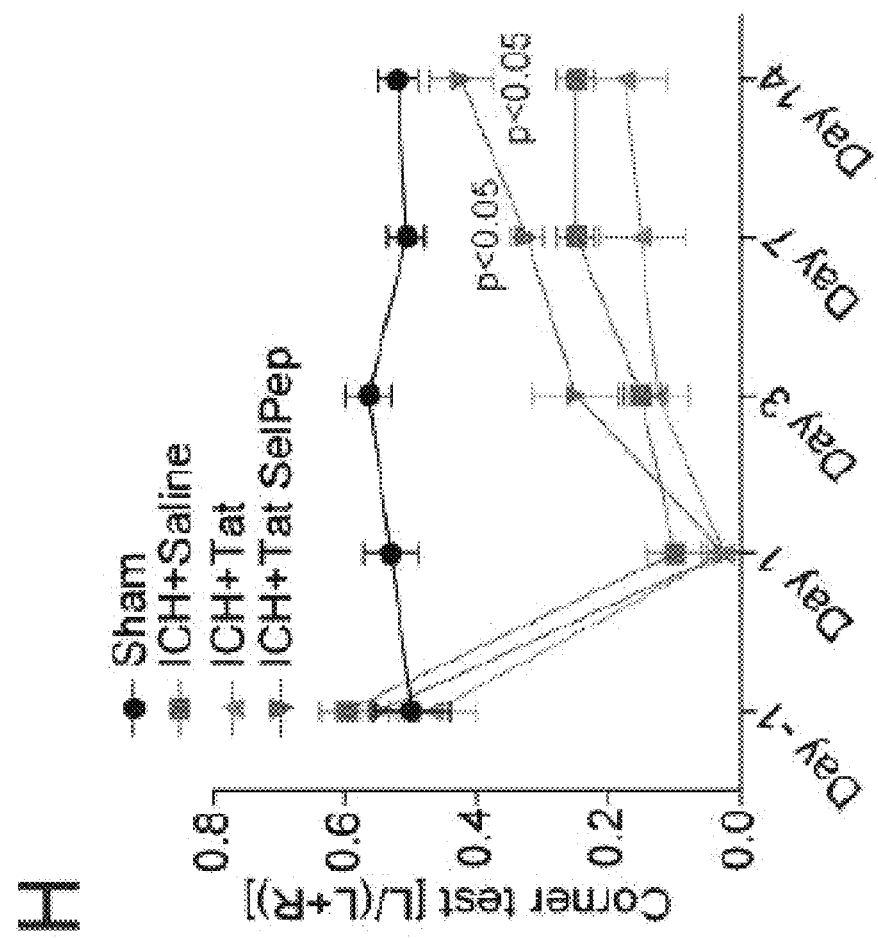

FIGS. 65G-65H show the behavioral outcomes in a sensory neglect task (n-12) and spatial neglect task (n=12) up to 14 days post-ICH in animals treated systemically with Tat or Tal SelPep.

Figure 65I:
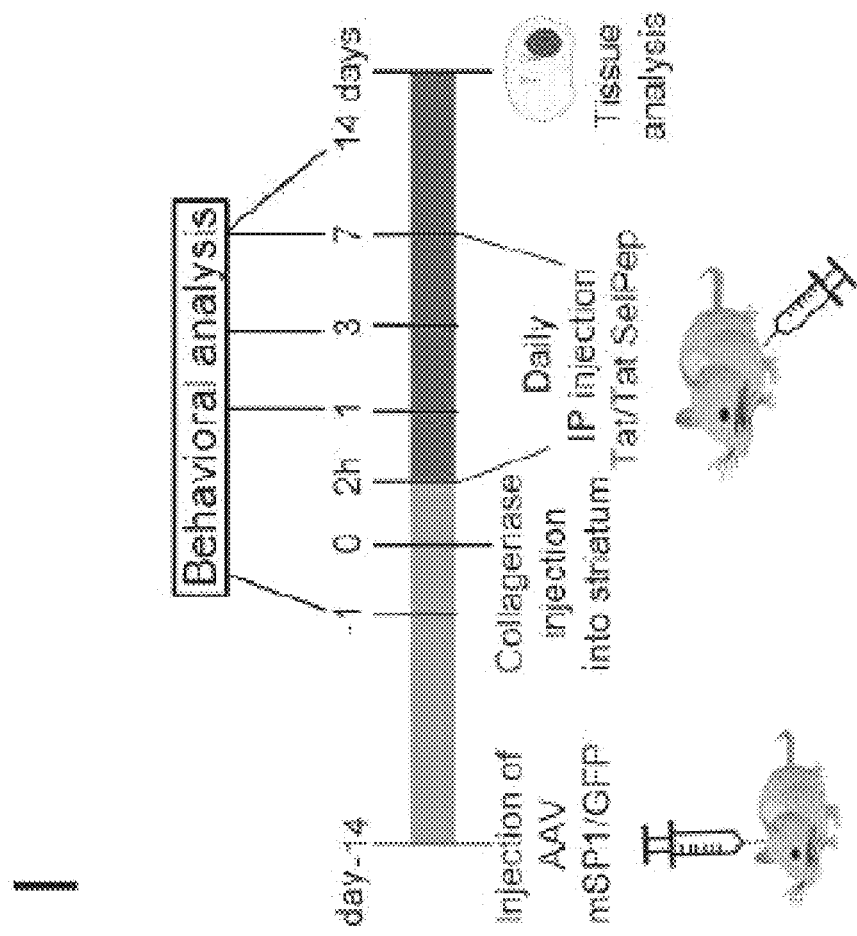

FIG. 65I shows a schematic of the procedure for data in FIG. 65(j-k). Double injection of AAV8-GFP or AAV8-DNA binding mutant Sp1 (AAV8-mSp1) into striatum 14 days prior to collagenase induced ICH. Intraperitoneal injection of Tat/Tat SelPep given 2 h (12 µg/g) post-ICH every day for 7 days post injury. Behavioural measurements were made prior to and 1, 3, 7 and 14 days after hemorrhagic stroke.

Figure 65J:
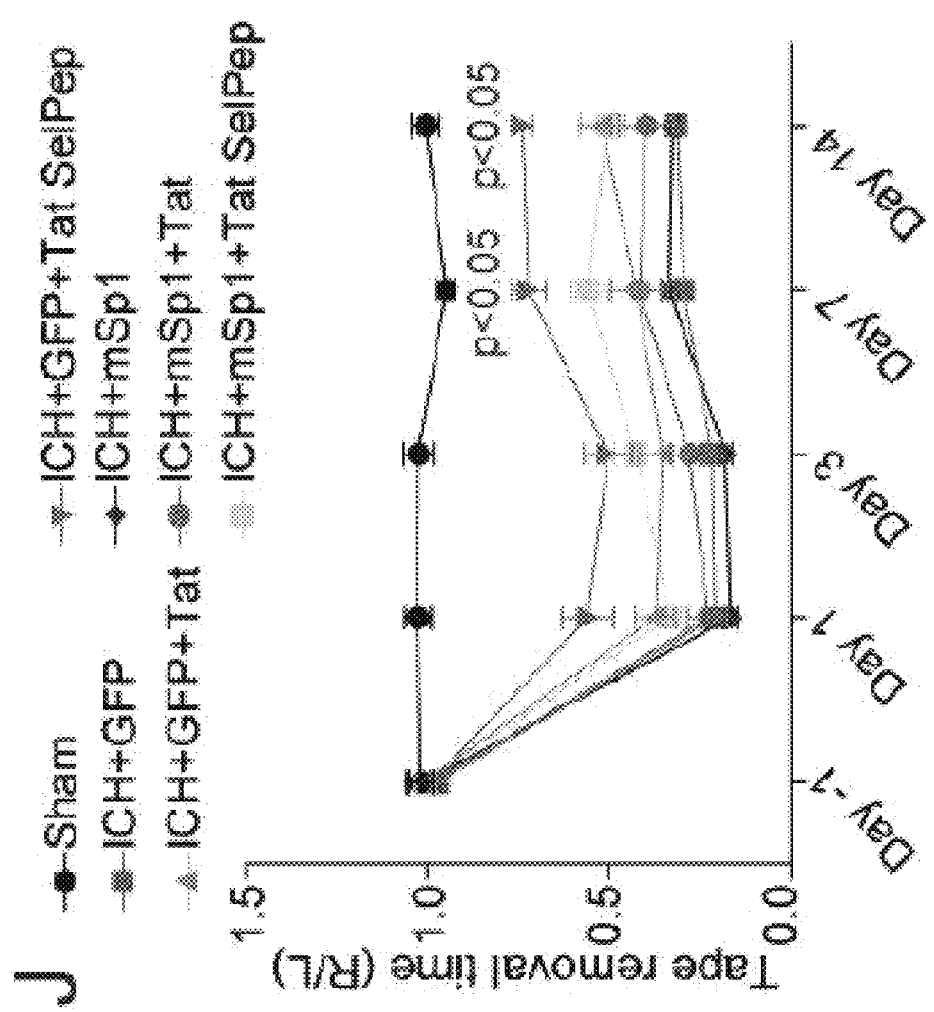
Figure 65K:
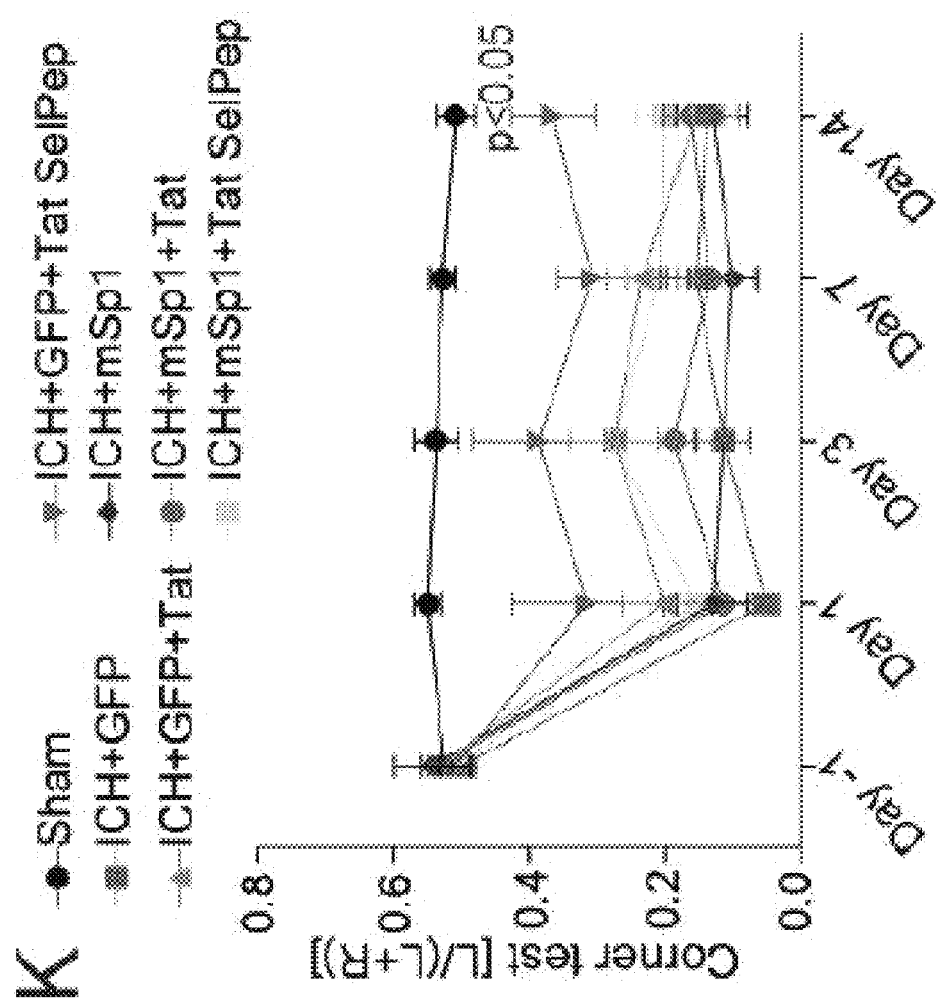

FIGS. 65J-65K show the behavior outcomes in sensory neglect task (n=16_ and spatial neglect task (n=16) 14 days post-ICH in animals with or without AAv8 overexpression of GFP or mSp1 systemically treated with Tat or Tat-SelPep. At day 14 post-stroke animals overexpressing mSp1 fail to demonstrate significant behavior improvements when treated with Tat SelPep.

Figure 66:
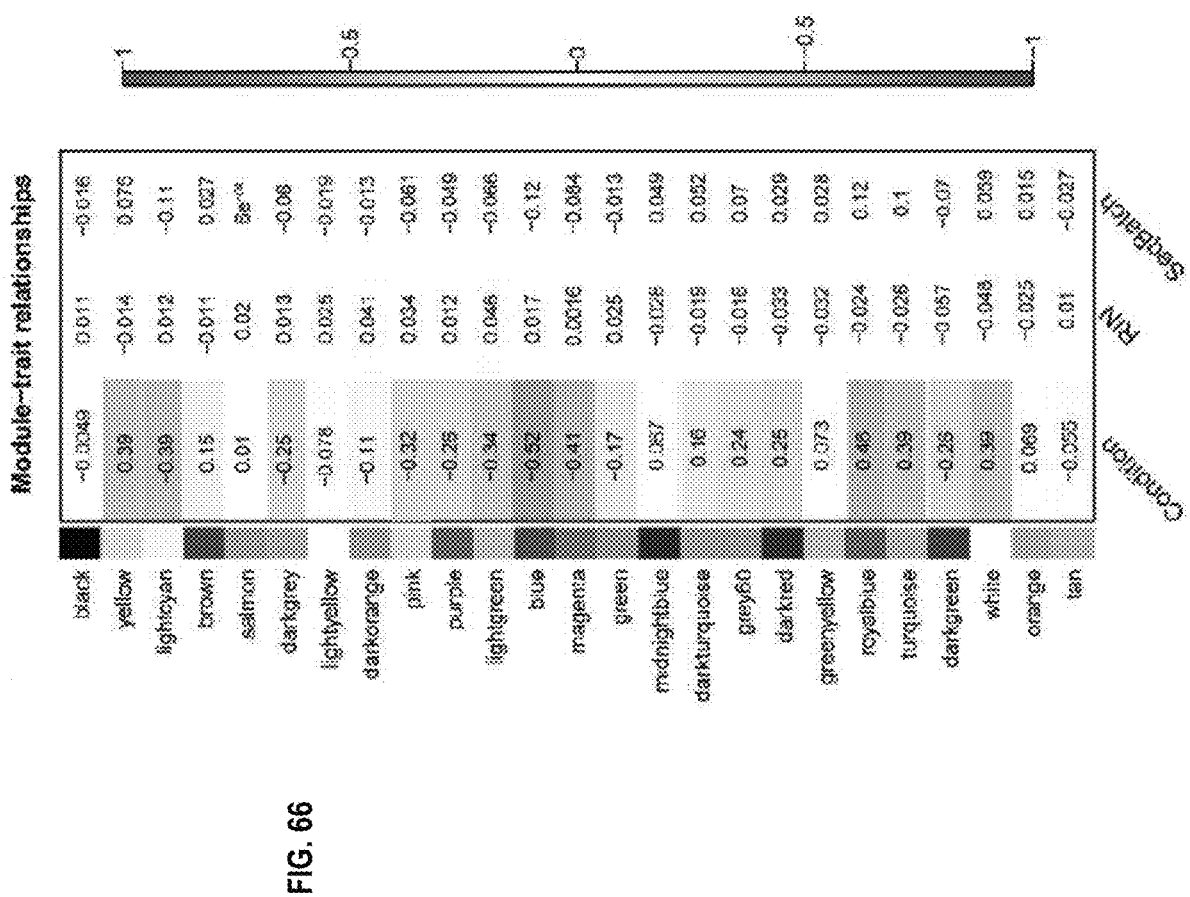

FIG. 66 shows a heatmap of module eigengene-traits upregulated and downregulated by 6 h Se treatment in cortical neurons based on unsupervised WGCNA analysis.

Figure 67:
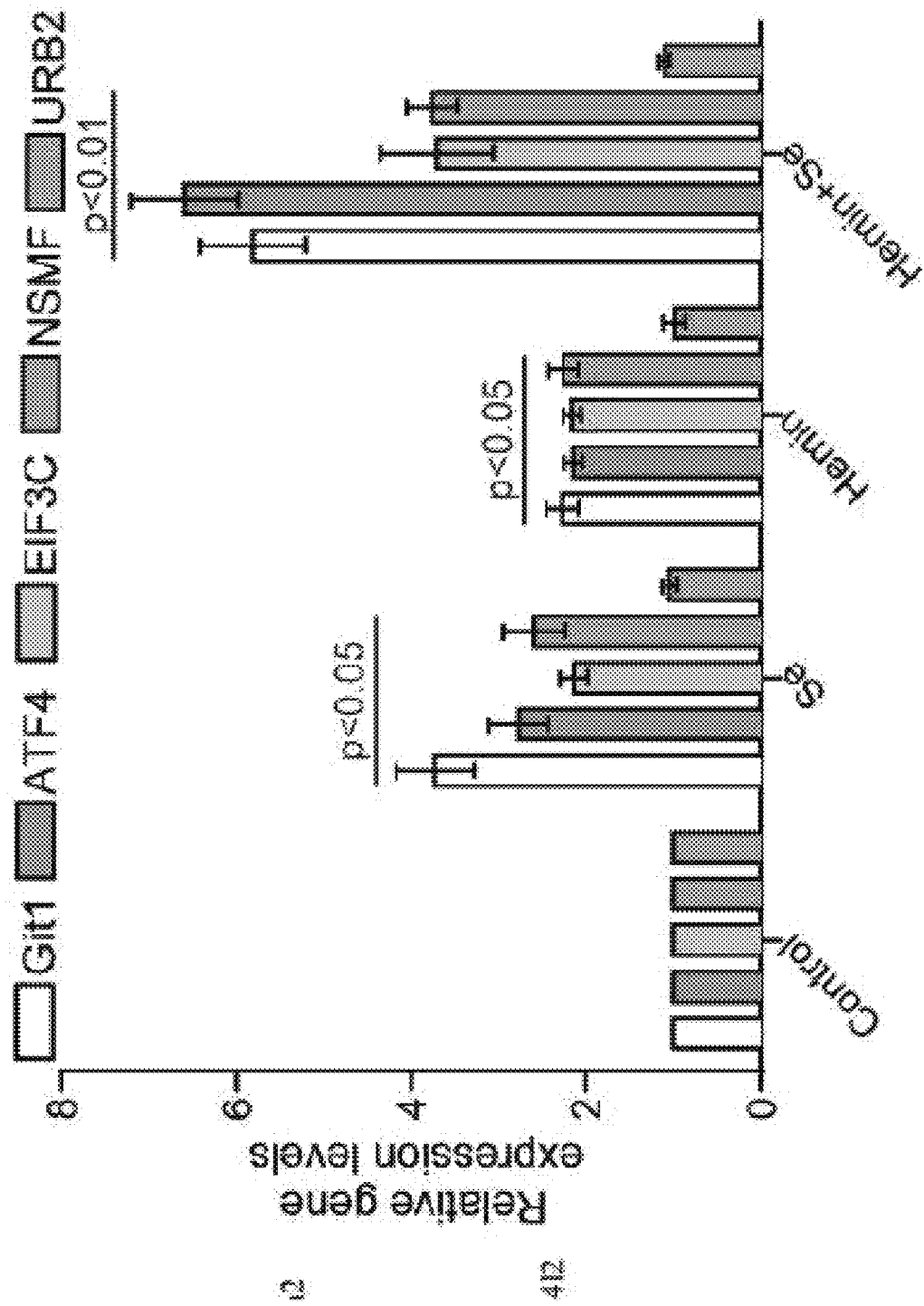

FIG. 67 shows validation of genes by qPCR potentially involved in ferroptosis, excitotoxcity (parthanatos) and ER stress (apoptosis) that are upregulated by 6 h Se (1 µM) in primary cortical neurons (n=4). URB2 is a negative control.

Figure 67A:
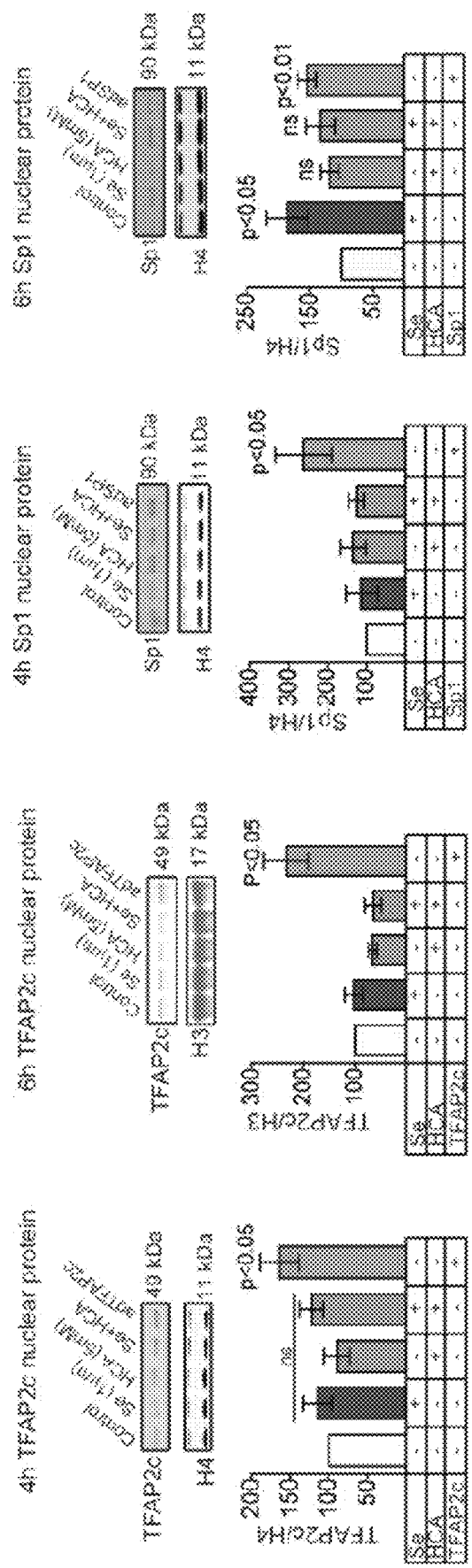

FIG. 67A shows western blots of Sp1 and TFAP2c from nuclear extracts of primary cortical neurons at 4 h and 6 h post HCA (5 mM) and/or Se (1 µM; n=4) exposure. Adenoviral overexpression of TFAP2c or Sp1 for 24 hours was used as positive control.

Figure 67B:
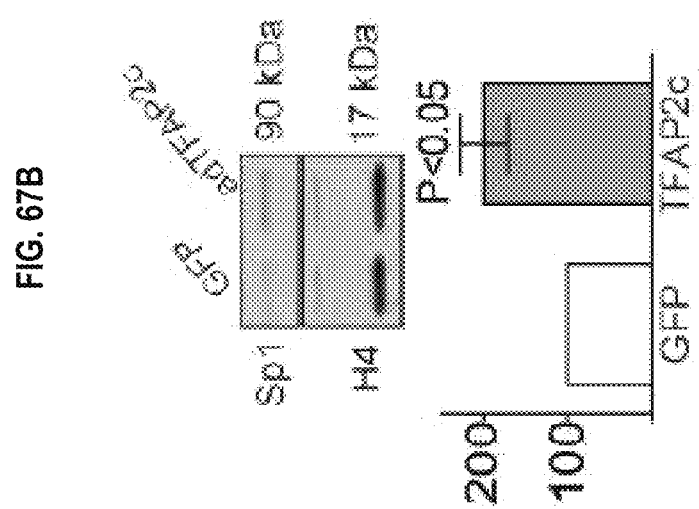

FIG. 67B shows a western blot of Sp1 expression in cortical neurons following 24 h adenoviral overexpression of GFP and TFAP2c (n=3).

Figures 68A, 68B, 68C, 68D, 68E:
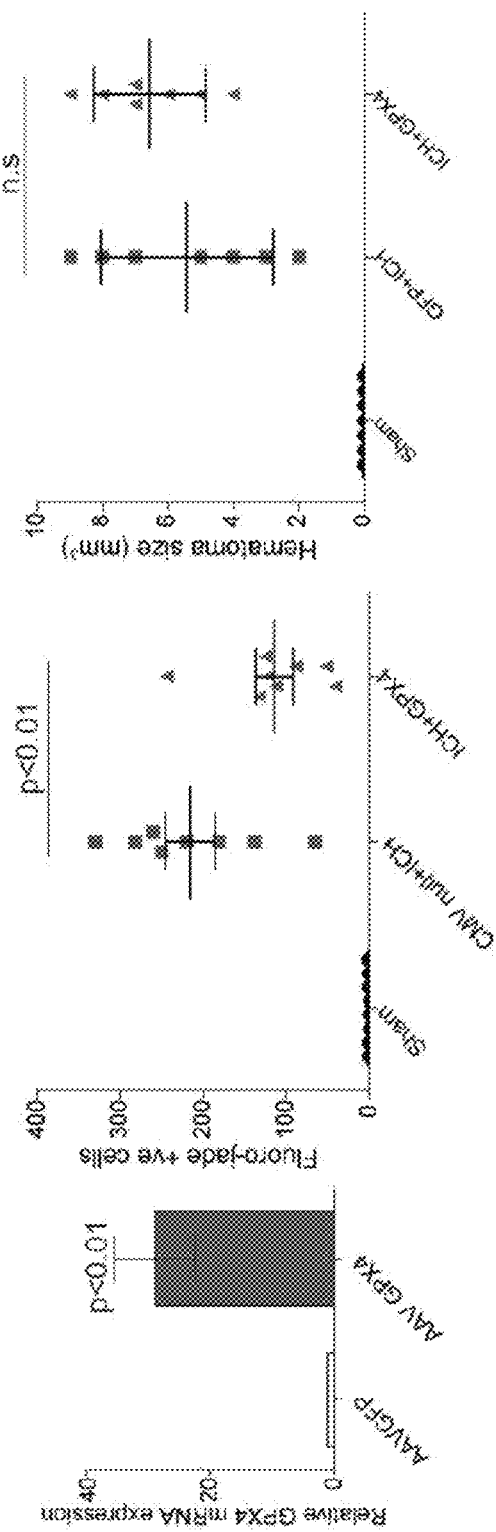

FIG. 68A shows mRNA expression by qPCR of GPX4 from mouse striatum collected 14 days after transduction with AAV8 GFP or GPX4 (n=4).

FIG. 68B shows the number of fluoro-jade positive cells in or near the hematoma at 14 days post ICH in mice infected with AAV8 CMV Null or AAv8-GPX4.

FIG. 68C is quantification of hematoma size after 24 h ICH in mice overexpressing AAV GFP or GPX4 in striatum and shows that GPX4 does not inhibit collagenase activity (n=7).

FIG. 68D-68E is a scatterplot of behavior outcomes in spatial neglect task (n=12) and sensory neglect task (n=12) up to 14 days post ICH in mice overexpressing GFP or GPX4 in striatum.

Figure 69A:
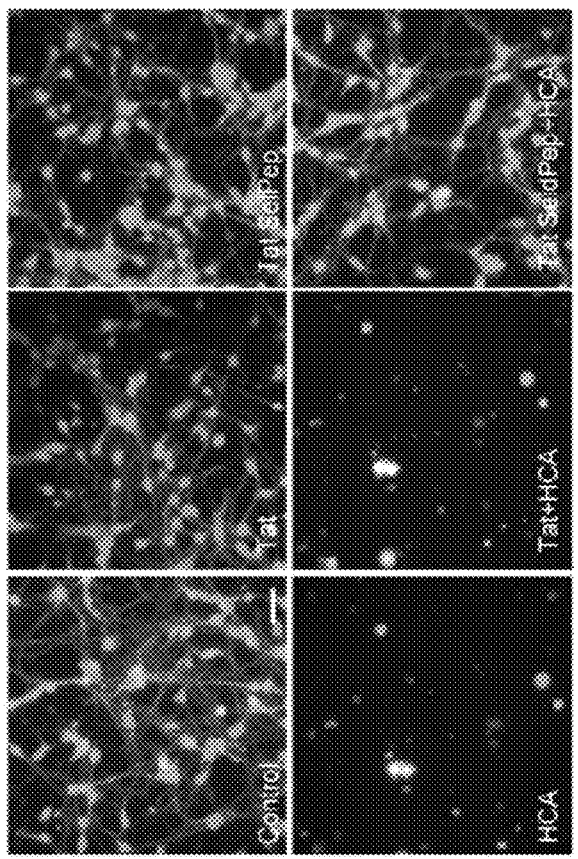

FIG. 69A shows a live (green)/dead (red) assay of primary cortical neurons following HCA (5 mM) treatment with or without 1 µM Tat SelPep (n=3). Scale bar, 75 µm.

Figure 69B:
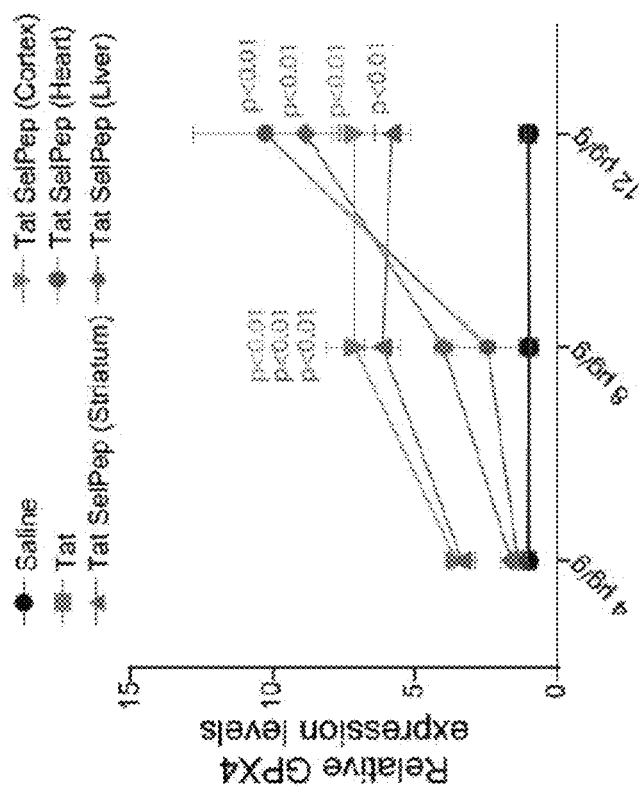

FIG. 69B quantifies GPX4 mRNA levels 24 h following IP injection of SelPep (4-12 µg/g; n=3) in the striatum, cortex, heart or liver.

Figure 69D:
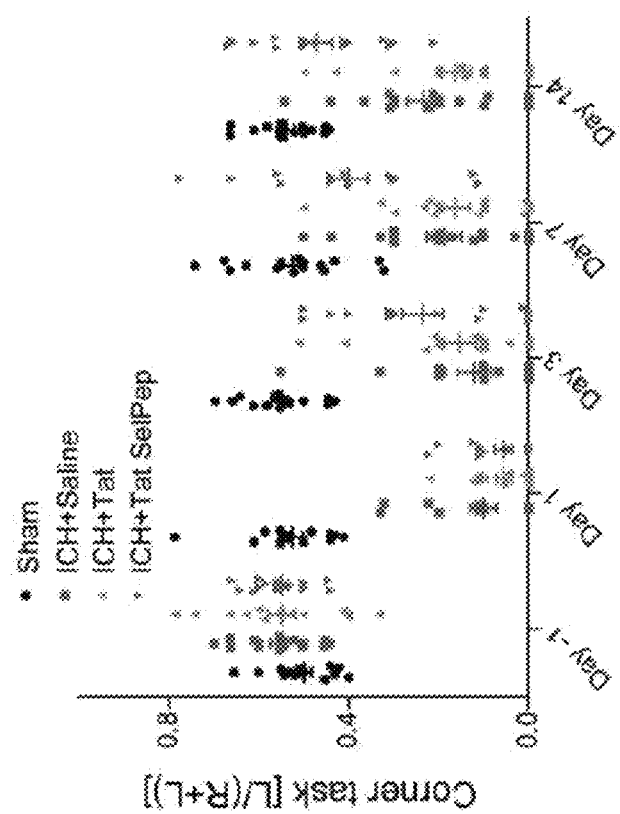
Figure 69C:
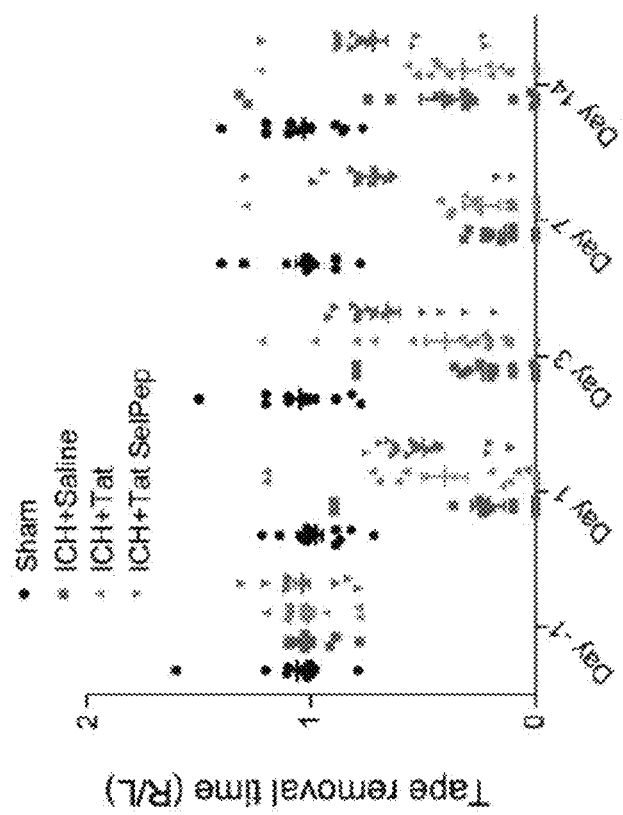

FIGS. 69C-69D show a scatterplot of behavioural outcomes in spatial neglect task (n=16) and sensory neglect task (n=16) for up to 14 days post ICH in mice given daily IP injections (for 7 days) of saline, Tat, or Tat SelPep (12 μg/g;n=12).

Figure 69F:
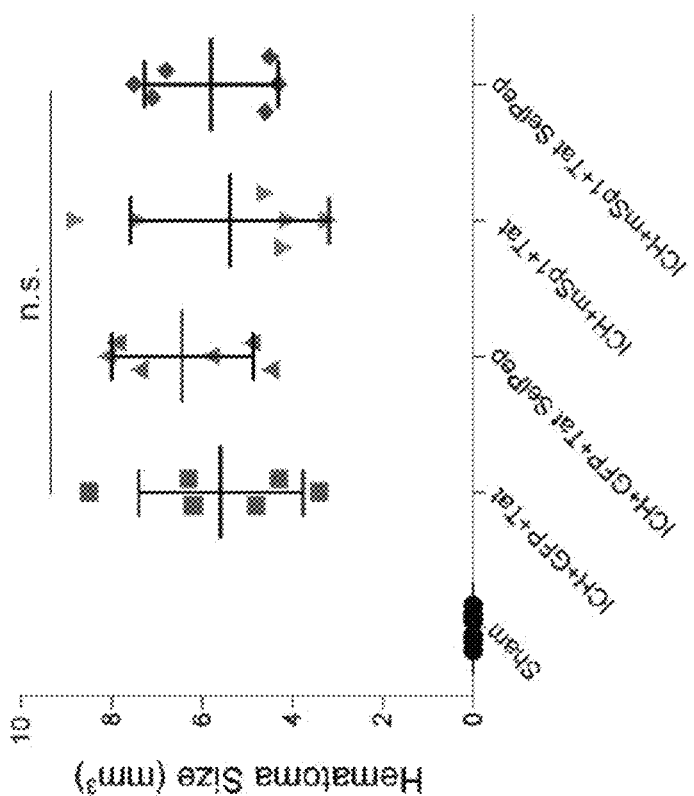
Figure 69E:
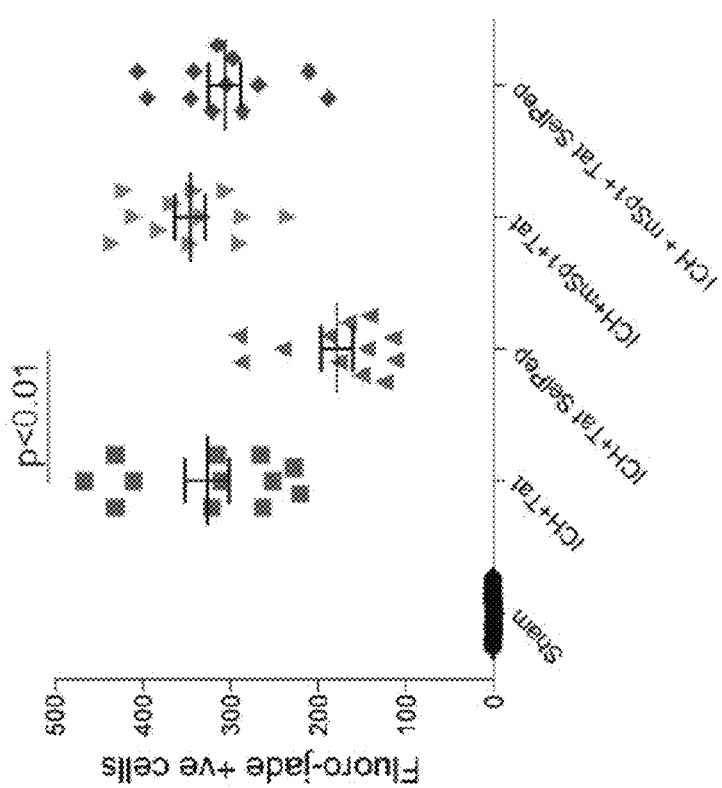

FIG. 69E is a quantification of fluro-jade positive cells near hematoma at 14 days post ICH in mice given daily injections of Tat or Tat-SelPep with overexpression of mSp1 or CMV Null in striatum by AAV8 transduction (12 μg/g; n=12).

FIG. 69F is a quantification of hematoma size 24 h after ICH in mice overexpressing GFP or mSp1 in striatum and given IP injection of Tat or Tat SelPep 2 h after ICH (n=6).

DETAILED DESCRIPTION OF THE INVENTION

The invention may be understood more readily by reference to the following detailed descriptions of embodiments of the invention. However, compounds, techniques, and operating structures in accordance with the invention may be embodied in a wide variety of forms and modes, some of which may be quite different from those in the disclosed embodiments. Also, the features and elements disclosed herein may be combined to form various combinations without exclusivity, unless expressly stated otherwise. Consequently, the specific structural and functional details disclosed herein are merely representative. Yet, in that regard, they are deemed to afford the best embodiments for purposes of disclosure and to provide a basis for the claims herein, which define the scope of the invention. It must be noted that, as used in the specification and the appended claims, the singular forms "a", "an", and "the" include plural referents unless the context clearly indicates otherwise.

Ferroptosis, a non-apoptotic form of programmed cell death, is dysregulated in cancer and neurological disorders, including intracerebral hemorrhage (ICH), a stroke subtype. It is also dysregulated in heat stress in plants. Ferroptotic death in ICH is triggered by oxidative stress in the absence of an adequate protective response; however the identity of a homeostatic transcriptional response to ferroptosis is unknown. Here we show that neurons adapt to ferroptotic stress by transcriptional induction of selenocysteine containing antioxidant enzymes, including the mitochondrial and nuclear forms of glutathione peroxidase 4 (GPX4). Addition of sodium selenite (Se) or selenocysteine peptides can augment this stress response to protect neurons or cancer cells from ferroptosis, excitotoxicity, or endoplasmic reticulum stress by driving a cassette of genes, the selenome. GPX4, a part of the selenome necessary for Se-induced protection, is regulated by coordinated activation of the transcriptional activators, TFAP2C and Sp1. Remarkably, a single dose of Se delivered into the brain drives GPX4 antioxidant expression, mediates neuroprotection and improves behavioral outcomes in a mouse model of ICH. Collectively, these findings suggest that pharmacological selenium supplementation drives adaptive, homeostatic transcription of the selenome. Pharmacological selenium thus may be effective not only as a treatment for the one in seven individuals worldwide with selenium deficiency, but also for treatment of stroke and other neurological conditions, including Parkinson's disease, Huntington's disease, and ALS, associated with ferroptotic neuronal loss where steady-state levels of selenium may be normal. These findings also have implications for cancer therapeutics.

The present invention provides a method for treating a condition associated with oxidative, ER, and/or excitotoxic stress in a subject in need thereof (e.g., a human subject), comprising administering to the subject a therapeutically effective amount of a compound that comprises selenium or selenocysteine.

"Treat", "treating" and "treatment" refer to a method of alleviating or abrogating a biological disorder and/or at least one of its attendant symptoms. As used herein, to "alleviate" a disease, disorder or condition means reducing the severity and/or occurrence frequency of the symptoms of the disease, disorder, or condition. Further, references herein to "treatment" include references to curative, palliative and prophylactic treatment.

"Therapeutically effective amount" refers to the amount of the therapeutic agent being administered that will relieve to some extent one or more of the symptoms of the disorder being treated. A therapeutically effective amount of an agent for halting or repairing neurodegeneration, for example, may result in reduced loss of neurons and/or their supporting cells (e.g., oligodendrocytes), enhancement of repair mechanisms, restored functionality, stimulated regeneration, glial reconstruction, or other clinical endpoints desired by healthcare professionals.

In some embodiments, the compound that comprises selenium or selenocysteine is a selenocysteine peptide. In some embodiments, the compound comprises a fragment of a selenoprotein. In certain embodiments, the selenoprotein is selenoprotein P. In certain embodiments, the compound comprises a peptide of at least two, at least three, at least four, at least five, at least six, at least seven, at least eight, at least nine, or at least ten amino acid residues from selenoprotein P. In a particular embodiment, the compound comprises a peptide or polypeptide comprising six amino acid residues from the N-terminus of selenoprotein P. The peptide or polypeptide may further comprise, e.g., a targeting sequence that targets the compound to a specific organ, tissue, or cell type, such as damaged neurons or neural tissue, liver, kidney, or the immune system, or to a specific subcellular location, such as the nucleus, mitochondria, cytoplasm, endoplasmic reticulum, lysosome, and cell membrane. In certain embodiments, the second sequence is selected from the group consisting of:

NA1-Tat NR2B9c
PTP-Sigma
GluR2-Gapdh inhibitor sequence
SDK-5 inhibitor sequence
SS31 sequence In certain embodiments, the compound is a selenocysteine peptide that has the amino acid sequence of a Sec (selenocysteine)-containing peptide as shown in Table 1 below.

TABLE 1

Peptide Sequences

| | Peptide Description | Sequence |
|---|---|---|
| 1 | Tat-cys SEQ ID NO: 1 | NH$_2$-YGRKKRRQRRR-Cys-containing-module-CONH$_2$ |

TABLE 1-continued

Peptide Sequences

| | Peptide Description | Sequence |
|---|---|---|
| 2 | Tat-sec<br>SEQ ID NO: 2<br>SEQ ID NO: 3 | $NH_2$-YGRKKRRQRRR-Sec-containing-module-$CONH_2$ |
| 3 | Tat-NA1-Sec<br>SEQ ID NO: 4<br>SEQ ID NO: 5 | NA1 (tat NR2b9c): $NH_2$-YGRKKRRQRRRPQKLSSIESDV-Sec-containing-module-$CONH_2$ |
| 4 | Tat-NA1scrambled-Sec<br>SEQ ID NO: 6<br>SEQ ID NO: 7 | NA1 (tat NR2b9c): $NH_2$-CSFNSYELGSLCYGRKKRRQRRR-Sec-containing-module-$CONH_2$ |
| 5 | Tat-PTP Sigma-Sec<br>SEQ ID NO: 8<br>SEQ ID NO: 9 | tat-PTP Sigma: $NH_2$-GRKKRRQRRRCDMAEHMERLKANDSLKLSQEYESI-Sec-containing-module-$NH_2$ |
| 6 | GLUR2-GAPDH inhibitor sec<br>SEQ ID NO: 10<br>SEQ ID NO: 11 | Tat-g-Gpep: $NH_2$-YGRKKRRQRRRYYQWDKFAYLYDSDRGLSTLQAVLDSAAEK-Sec-containing-module-$NH_2$ |
| 7 | P5 CDK5 inhibitor sec<br>SEQ ID NO: 12<br>SEQ ID NO: 13 | Tat-P5 wt: $NH_2$-YGRKKRRQRRRKKEAFWDRCLSVINLMSSKMLQINA-Sec-containing-module-$NH_2$ |
| 8 | P5 CDK5 inhibitor sec mut<br>SEQ ID NO: 14<br>SEQ ID NO: 15 | Tat-P5 mut: $NH_2$-YGRKKRRQRRRKKNAFYERALSIINLMTSKMVQINV-Sec-containing-module-$NH_2$ |
| 9 | SS31 sec<br>SEQ ID NO: 16<br>SEQ ID NO: 17 | Tat-ss31sec: $NH_2$-Y-G-R-K-K-R-R-Q-R-R-R-dR-DMT-K-F-Sec-containing-module-$NH_2$ |
| 10 | SS31 Cys<br>SEQ ID NO: 18 | Tat-ss31cys: $NH_2$-Y-G-R-K-K-R-R-Q-R-R-R-dR-DMT-K-F-Cys-containing-module-$NH_2$ |
| 11 | tat-3nls-sec<br>SEQ ID NO: 19<br>SEQ ID NO: 20 | Tat-3nls-sec: $NH_2$-YGRKKRRQRRRPAAKRVKLDPAAKRVKLDPAAKRVKLD-Sec-containing-module-$NH_2$ |
| 12 | tat-3nls-cys<br>SEQ ID NO: 21 | Tat-3nls-Cys: $NH_2$-YGRKKRRQRRRPAAKRVKLDPAAKRVKLDPAAKRVKLD-Cys-containing-module-$NH_2$ |

Cys-containing module = KCKCNLN
Sec-containing module (U = Sec) = KUKUNLN (or GCUG)

In some embodiments, the selenocysteine peptide has an amino acid sequence that is 90%, 91%, 92%, 93%, 94%, 95%, 96%, 97%, 98%, or 99% identical (i.e. analog) to the amino acid sequence of a Sec-containing polypeptide in Table 1 above.

The compound comprising selenium or selenocysteine may be administered alone or in combination with one or more other agents. In some embodiments, the compound may be co-administered or formulated with another agent for the treatment of a condition associated with oxidative stress. The agent may be selected from, for example, a lipid peroxidation inhibitor (e.g., vitamin E and its analogs or ferrostatin), an antioxidant (e.g., CoQ10), an agent that mediates transcriptional activation by TFAP2C, Sp1, or both, a translation inhibitor, a transcription inhibitor, an iron chelator, an ERK1/2 inhibitor, a RIPK inhibitor, and GPX4 (which may be virally overexpressed in the patient, for example) or a GPX4 mimetic. In certain embodiments, the agent is N-acetylcysteine (NAC), beta-carotene, adaptaquin, or necrostatin-1.

Any condition associated with oxidative, ER, and/or excitotoxic stress may benefit from treatment with the selenocysteine-containing compounds described herein. In some embodiments, the condition associated with oxidative, ER, and/or excitotoxic stress is a central nervous system (CNS) condition, such as stroke (e.g., intracerebral haemorrhage), subarachnoid hemorrhage, traumatic brain injury, spinal cord injury, a neurodegenerative condition (e.g., Alzheimer's disease, Parkinson's disease, Huntington's disease, multisystem atrophy, multiple sclerosis, amyotrophic lateral sclerosis, cerebral ischemia, seizure disorders, schizophrenia, Friedreich's ataxia, progressive supranuclear palsy, prions, Down's syndrome, ataxia, tardive dyskinesia, or aging), or a neuropsychiatric condition (e.g., schizophrenia, bipolar disorder, or depression).

In some embodiments, the condition associated with oxidative, ER, and/or excitotoxic stress is a liver, kidney, or immune system condition (e.g., hepatitis or chronic kidney disease).

The present invention additionally provides a method for treating a subject exhibiting, or at risk of, selenium deficiency, or having a condition associated with, causing, or resulting from selenium deficiency. The method includes administering to the subject a therapeutically effective amount of a compound comprising selenium or selenocysteine. The subject may be a human subject or an animal, such as a ruminant, a sheep, a goat, a pig, or a horse.

In humans, selenium deficiency may result if a daily intake of selenium is less than 54 µg, less than 40 µg, less than 30 µg, less than 20 µg, or less than 10 µg. In some embodiments, these daily intake levels apply to an adult, and may be scaled to a proportionately lower amount for a child by weight. Patients that may have or may be at risk of developing selenium deficiency include, e.g., patients who:
- have severely compromised intestinal function,
- are undergoing total parenteral nutrition,
- have had gastrointestinal bypass surgery,
- are of advanced age (e.g., over 90), and/or
- are dependent on food grown from selenium-deficient soil.

In animals, selenium deficiency is common in some regions, e.g., much of the northeastern and northwestern U.S. and adjacent Canada, and the southeastern U.S. Selenium-deficient animals may develop white muscle disease manifested by whitish appearance of striated muscle tissue due to bleaching by peroxides and hydroperoxides.

Selenium deficiency may lead to decreased immunity, and is associated with over 40 kinds of diseases, such as cancers (e.g., lung cancer, large bowel cancer, prostate cancer, rectal cancer, breast cancer, and leukocythemia), cardiovascular diseases, liver diseases, cataracts, pancreatic diseases, diabetes, Keshan disease, Kashin-Beck disease, white muscle disease, and reproductive system diseases. Additionally, since selenium is necessary for the conversion of the thyroid hormone thyroxine (T4) into its more active counterpart, triiodothyronine, selenium deficiency can cause symptoms of hypothyroidism, including extreme fatigue, mental slowing, goiter, cretinism, and recurrent miscarriage. Selenium deficiency may also cause muscle pains, skin dryness, and liver necrosis. Any of these conditions or symptoms may benefit from treatment with the selenium or selenocysteine-containing compounds described herein.

The present invention further provides compounds that deliver selenium or selenocysteine across the brain blood barrier. In some embodiments, the compounds are peptides or peptide mimetics that comprise selenocysteine. Examples of such peptides include, without limitation, the tat-derived peptides shown in Table 1. In some embodiments, the compound may be a brain delivery peptide derived from a molecule other than tat that crosses the blood brain barrier, including but not limited to larger molecules such as antibodies or antibody fragments (e.g., scFv, Fab, F(ab')2) that target the selenocysteine across the blood brain barrier, e.g., to a specific region in the brain.

The invention also provides a pharmaceutical composition comprising as an active ingredient a compound comprising selenocysteine for treating a condition associated with oxidative, ER, and/or excitotoxic stress. The pharmaceutical composition may also comprise one or more pharmaceutically acceptable excipients. The term "excipient" is used herein to describe any ingredient other than the selenium or selenocysteine-comprising compound(s) described herein. The choice of excipient(s) will to a large extent depend on factors such as the particular mode of administration, the effect of the excipient on solubility and stability, and the nature of the dosage form. As used herein, "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives, or buffers, which enhance the shelf life or effectiveness of the antibody.

Pharmaceutical compositions of the present invention and methods for their preparation will be readily apparent to those skilled in the art. Such compositions and methods for their preparation may be found, for example, in *Remington's Pharmaceutical Sciences,* 19th Edition (Mack Publishing Company, 1995). Pharmaceutical compositions are preferably manufactured under GMP (good manufacturing practices) conditions.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

Any method accepted in the art may suitably be employed for administering the selenium or selenocysteine-containing compounds described herein. The pharmaceutical compositions described herein are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, and intrasynovial injection or infusions; and kidney dialytic infusion techniques. Regional perfusion is also contemplated.

The selenium or selenocysteine-containing compounds can also be administered intranasally or by inhalation, typically in the form of a dry powder (either alone, as a mixture, or as a mixed component particle, for example, mixed with a suitable pharmaceutically acceptable excipient) from a dry powder inhaler; as an aerosol spray from a pressurised container, pump, spray, atomiser (preferably an atomiser using electrohydrodynamics to produce a fine mist), or nebuliser, with or without the use of a suitable propellant; or as nasal drops.

The pressurised container, pump, spray, atomizer, or nebuliser generally contains a solution or suspension of a compound and further comprises, for example, a suitable agent for dispersing, solubilising, or extending release of the compound, and may comprise a propellant(s) as solvent.

Prior to use in a dry powder or suspension formulation, the compound is generally micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules, blisters and cartridges for use in an inhaler or insufflator may be formulated to contain a powder mix of the compound, as well as, e.g., a suitable powder base and/or a performance modifier.

A suitable solution formulation for use in an atomiser using electrohydrodynamics to produce a fine mist may contain a suitable dose of the compound per actuation, and the actuation volume may for example vary from 1 µL to 100 µL.

Suitable flavours, such as menthol and levomenthol, or sweeteners, such as saccharin or saccharin sodium, may be added to those formulations intended for inhaled/intranasal administration.

Formulations for inhaled/intranasal administration may be formulated to be immediate and/or modified release. Modified release formulations include delayed-, sustained-, pulsed-, controlled-, targeted and programmed release.

In the case of dry powder inhalers and aerosols, the dosage unit may be determined by means of a valve which delivers a metered amount. Units in accordance with the invention are typically arranged to administer a metered dose or "puff" of a compound. The overall daily dose will typically be administered in a single dose or, more usually, as divided doses throughout the day.

The selenium or selenocysteine-containing compounds described herein may also be formulated for an oral route administration. Oral administration may involve swallowing, so that the compound enters the gastrointestinal tract, and/or buccal, lingual, or sublingual administration by which the compound enters the blood stream directly from the mouth.

In a particular embodiment, the selenium or selenocysteine-containing compounds are administered intravenously or intranasally.

It is understood that the selenium or selenocysteine-containing compounds may be used in a method of treatment as described herein, may be for use in a treatment as described herein, and/or may be for use in the manufacture of a medicament for a treatment as described herein.

Unless otherwise defined herein, scientific and technical terms used in connection with the present invention shall have the meanings that are commonly understood by those of ordinary skill in the art. Exemplary methods and materials are described below, although methods and materials similar or equivalent to those described herein can also be used in the practice or testing of the present invention. In case of conflict, the present specification, including definitions, will control.

Generally, nomenclature used in connection with, and techniques of, cell and tissue culture, molecular biology, immunology, microbiology, genetics, analytical chemistry, synthetic organic chemistry, medicinal and pharmaceutical chemistry, and protein and nucleic acid chemistry and hybridization described herein are those well-known and commonly used in the art. Enzymatic reactions and purification techniques are performed according to manufacturer's specifications, as commonly accomplished in the art or as described herein.

Further, unless otherwise required by context, singular terms shall include pluralities and plural terms shall include the singular. Throughout this specification and embodiments, the words "have" and "comprise," or variations such as "has," "having," "comprises," or "comprising," will be understood to imply the inclusion of a stated integer or group of integers but not the exclusion of any other integer or group of integers.

All publications and other references mentioned herein are incorporated by reference in their entirety. Although a number of documents are cited herein, this citation does not constitute an admission that any of these documents forms part of the common general knowledge in the art.

In order that this invention may be better understood, the following examples are set forth. These examples are for purposes of illustration only and are not to be construed as limiting the scope of the invention in any manner.

EXAMPLES

Materials and Methods
Collagenase-Induced Mouse Model of ICH

Male C57BL/6 mice (8 to 10 weeks of age; Charles River) were anesthetized with isoflurane (2 to 5%) and placed on a stereotaxic frame. During the procedure, the animal's body temperature was maintained at 37° C. with a homeothermic blanket. With a nanomite syringe pump (Harvard Apparatus) and a Hamilton syringe, 1 ml of collagenase (0.075 IU; Sigma) was infused into the right striatum at a flow rate of 0.120 ml/min. Relative to the bregma point, the stereotaxic coordinates of the injection were as follows: lateral, −0.20; anteroposterior, 0.62; and dorsoventral, −0.40. In control animals, 1 ml of saline was infused. The treatment group received sodium selenite (1-5 µM) 2 hours after collagenase infusion directly into the ventricals. The control groups received vehicle (saline) alone. The animals were randomized to sham or ICH groups. The identity of the mice that received vehicle or Se was masked to surgeons who performed the ICH. The identity was revealed after the data collected. Proper postoperative care was taken until the animals recovered completely.

Behavioral Analysis

The corner task assessed the integrated sensorimotor function in both stimulation of vibrissae (sensory neglect) and rearing (motor response) (See Schallert et al., Neuropharmacology 39(5): p. 777-87 (2000)). Mice were placed between two cardboard pieces forming a corner with a 30° angle. While maintaining the 30° angle, the boards were gradually moved toward the mouse until the mouse approached the corner, reared upward, and turned 180° to face the open end. The direction (left or right) in which the mouse turned around was recorded for each trial. Ten trials were performed for each mouse. The adhesive tape removal task in mice was performed as previously described. Briefly, adhesive tape was placed on the planter region of the forward paw (right and left) of mice. The time from which the tape was applied to when the mouse successfully removed it was recorded for each paw. A maximum of 300 s for each paw was allowed.

Quantitative Real-Time PCR

Total RNA was prepared using the NucleoSpin RNA II kit (MACHEREYNAGEL) according to the manufacturer's protocol. Duplex real-time PCR reactions were performed with gene expression assays using 6-carboxyfluorescein-labeled probes (Applied Biosystems) for antioxidant enzymes. All expression levels were normalized to β-actin gene expression levels, which were determined with a VIC-labeled probe (Applied Biosystems). All experiments were performed using a Quant 6 Real-Time PCR System (Applied Biosystems).

Primary Cortical Neuronal Cultures

Primary cortical neurons were obtained from either embryonic (E15) CD1 mice or embryonic (E17) Sprague-Dawley rats. Briefly, cortices were dissected, homogenized, and plated in minimum essential medium containing 10% fetal bovine serum (FBS), 5% horse serum, and 1% penicillin/streptomycin in 96-well plates, 6-well plates, or 10-cm dishes. Neurons were maintained at 37° C. with 5% $CO_2$. All experiments were started at 24 hours after plating.

Cultured Cell Lines

HT22 murine hippocampal cells were cultured at 37° C. with 5% CO2 in Dulbecco's modified Eagle's medium (DMEM), 10% FBS, and puromycin (4 mg/ml; Sigma). HT1080 were cultured at 37° C. in DMEM, 10% FBS, 10% non essential amino acids and puromycin (4 mg/ml; Sigma).

In Vitro ICH Model

Cell death was induced in primary cortical neurons and hippocampal HT22 cells by treatment with hemin (10 to 250 mM; Sigma). For the neuroprotection studies, cells were treated with 80 µM hemin in the presence of sodium selenite (Sigma) diluted in water. Cell viability was analyzed 16 hours after treatment. Cells were rinsed with warm phosphate-buffered saline (PBS) and assessed by MTT assay. The fidelity of MTT assays in measuring viability was verified by calcein-AM/ethidium homodimer-1 staining (Live/Dead assay, Molecular Probes) following the manufacturer's instructions.

In Vitro Model of Oxidative Stress-Induced Neuronal Death

Primary cortical neurons and HT22 cells were exposed to 5 mM HCA (glutamate structural analog) to induce oxidative stress-induced cell death, and sodium selenite (Sigma) was applied in media. 24 hours after treatment with HCA, the cells were rinsed with warm PBS, and cell viability was assessed by MTT assay (Life Technologies) and calcein-AM/ethidium homodimer-1 staining (Live/Dead assay, Molecular Probes).

Chromatin Immunoprecipitation

The ChIP assays were performed with the EZ-Magna ChIP assay kit (Millipore) following the manufacturer's instructions. Briefly, primary cortical cells were cross-linked with 1% formaldehyde at 37° C. for 7 min and then sonicated using the Bioruptor (Diagenode). Genomic targets were immunoprecipitated with 5 mg of rabbit Sp1 or TFAP2C antibody. Quantitation of immunoprecipitated genomic DNA regions was performed with real-time PCR using the SYBR Green Master Mix (Applied Biosystems) on a 7500 Real-Time PCR System (Applied Bio systems) with primers specific to the promoter region of GPX4.

Promoter Bashing

A −1 to −4000 bp promoter region of GPX4 promoter region bound to luciferase reporter was developed (by Viraquest) and, using restriction enzymes (New England Biosciences), was cut and ligated to allow for various sizes of the promoter region bound to the luciferase. Mutations in the promoter region were developed by synthesizing mutated promoter regions and ligating those regions to the luciferase.

Viral Transfection

Primary cortical neurons or HT22 cells were transduced with adenovirus (containing a CMV promoter followed by a ddGPX4, Sp1, mut Sp1 or TFAP2C gene (developed by Viraquest)) by replacing media with warm HBSS with 50 MOI of adenovirus for 1 hour. After, HBSS with virus was replaced with warm media and cells were tested 12 h after transduction.

siRNA

Knock down of GPX4 was achieved by using lipofectamine RNAimax (Thermo-Fisher) to transfect primary cortical neurons with specific siRNA against GPX4. Three different sequences of siRNA were used separately to validate target specificity as opposed to sequence specificity. Knockdown was validated by mRNA and protein. 50 µM of NAC, which has no effect on GPX4 mRNA levels, was used to ensure survival of siGPX4 transfected cells so protein and mRNA could be collected.

Immunocytochemistry

For immunocytochemical experiments in the brain, three control mice with induced unilateral stroke and three selenium-treated mice with induced unilateral stroke were perfusion fixed with 4% PFA in PBS for 15 min. The brains were isolated and postfixed for 1 h in 4% PFA. After cryoprotection in a sucrose gradient, brain sections were cut at 30 µm.

Free-floating brain sections were blocked for 1 h in a PBS solution containing 3% bovine serum (Sigma), and 0.5% Triton X-100 (Biorad). Primary antibodies were diluted in the same solution and applied for 12 h, followed by incubation for 1 h with the appropriate secondary antibody, conjugated to Alexa 488 (1:1000; green fluorescence, Molecular Probes) or Alexa 568 (1:1000; red fluorescence, Molecular Probes). For nuclear labeling, ToPro was added to the mixture (1:15000, far red fluorescence, Invitrogen, T3605). In multi-labeling experiments, sections were incubated in a mixture of primary antibodies, followed by a mixture of secondary antibodies. Primary antibody treatment was performed at 4° C. and secondary antibody treatment was performed at room temperature. After staining, the sections were flat mounted on a slide and coverslipped using Vectashield mounting medium (H-1000, Vector Laboratories). The coverslip was sealed in place with nail polish.

The primary antibodies used in this study were the following: rabbit anti-GPX4 (1:800, LSBio, Cat# LS-C482326), rabbit anti-Sp1 (1:300, EMD Millipore, Cat#07-645), mouse anti-TFAP2C (1:300, Santa Cruz, Cat# SC12762), mouse anti-NeuN (1:1000, EMD Millipore, Cat# MAB377), and rabbit anti-NeuN (Cell Signaling; Cat#).

The samples for the different conditions were processed together with the same concentrations of mixtures of primary antibodies (for target and neuronal marker) and imaged under Nikon Eclipse Ti-U confocal microscope using a 20× water objective (0.75 N.A.) and 60× oil objective (1.4 N.A.). All sections were imaged under identical acquisition conditions, including: laser intensity, photomultiplier amplification, and Z-stack step size. All images were processed and analyzed using ImageJ software. Treatment conditions were masked during imaging and treatments were only revealed after completion of analysis.

Peptides

Peptides were chemically synthesized from C-terminus to N-terminus by amide bonds by either Dr. Robert Hondal, PhD (University of Vermont) or Bachem. The selenocysteine sequence was added to the C-terminus of the tat or targeting peptides and purified at >90%. Peptides were dissolved in water or saline prior to treatment in vivo or in vitro.

Statistics

GraphPad Prism 6 and Microsoft Excel 2016 were used for all statistical analyses. We evaluated normality by the Kolomogorov-Smirnov test and variance by homogeneity using the Levene test. For normally distributed data with homogeneous variance, we used student t-test if 2 groups were compared or one-way analysis of variance (ANOVA) followed by the Bonferroni post hoc test if two independent variables were compared. For not normally distributed results and or non homogeneous variance, we used the Kruskal-Wallis test followed by Dunn's post-hoc test. Data is shown with mean±SEM.

Figure 1A:
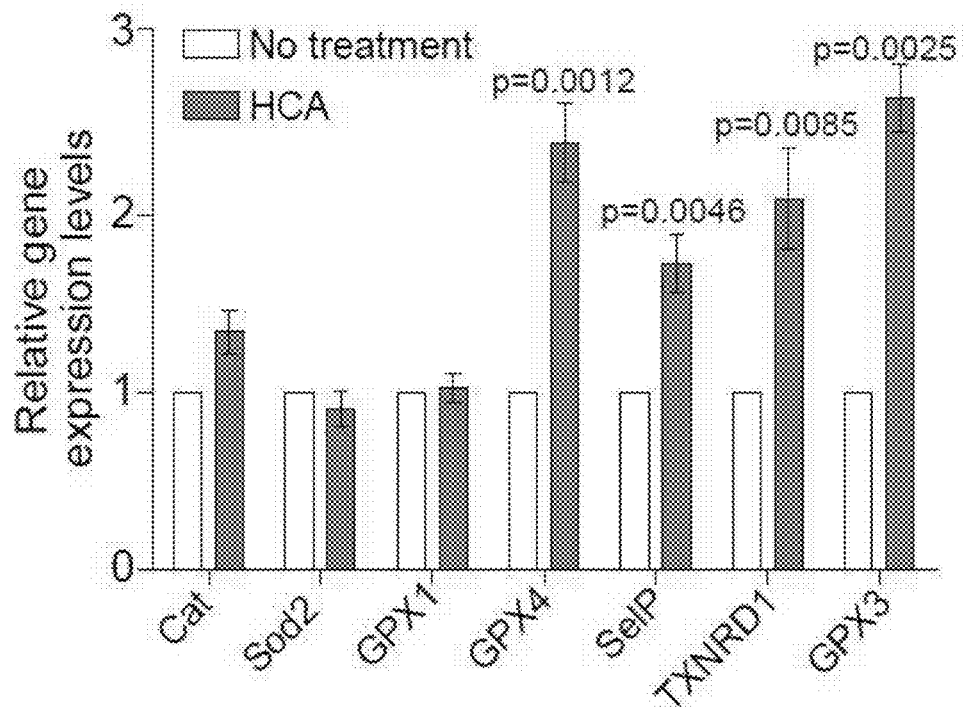
FIG. 1A is a graph of quantitative PCR (qPCR) results showing relative expression levels of indicated genes in primary cortical neurons not treated or treated with 5 mM HCA for 6 hours (n=5).
Figure 1B:
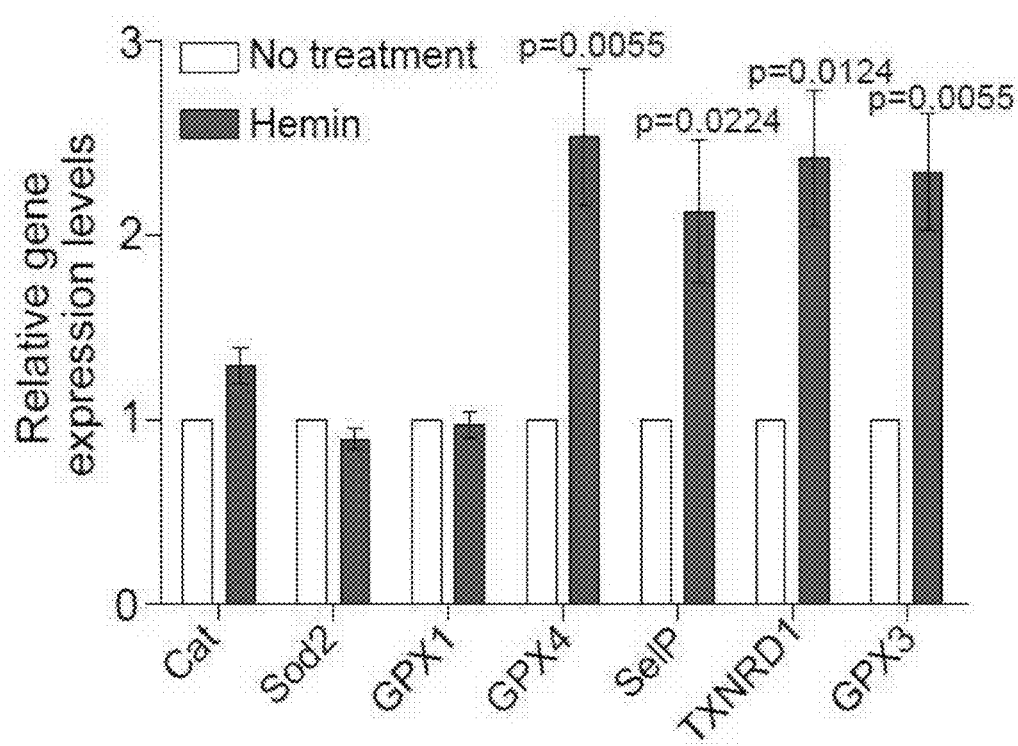
FIG. 1B is a graph of qPCR results showing relative expression levels of indicated genes in neurons not treated or treated with 80 μM hemin for 6 hours (n=5).
Figure 1C:
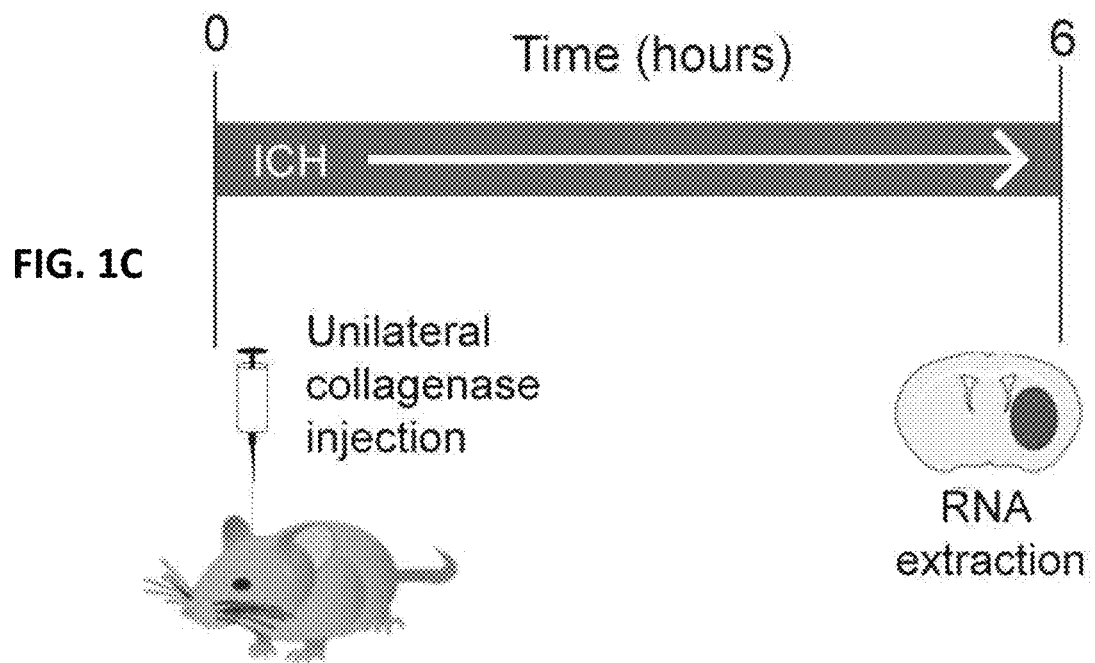
FIG. 1C is a schematic of experimental design for determining RNA levels of selected genes in mice with ICH induced by collagenase injection into the striatum.
Figure 1D:
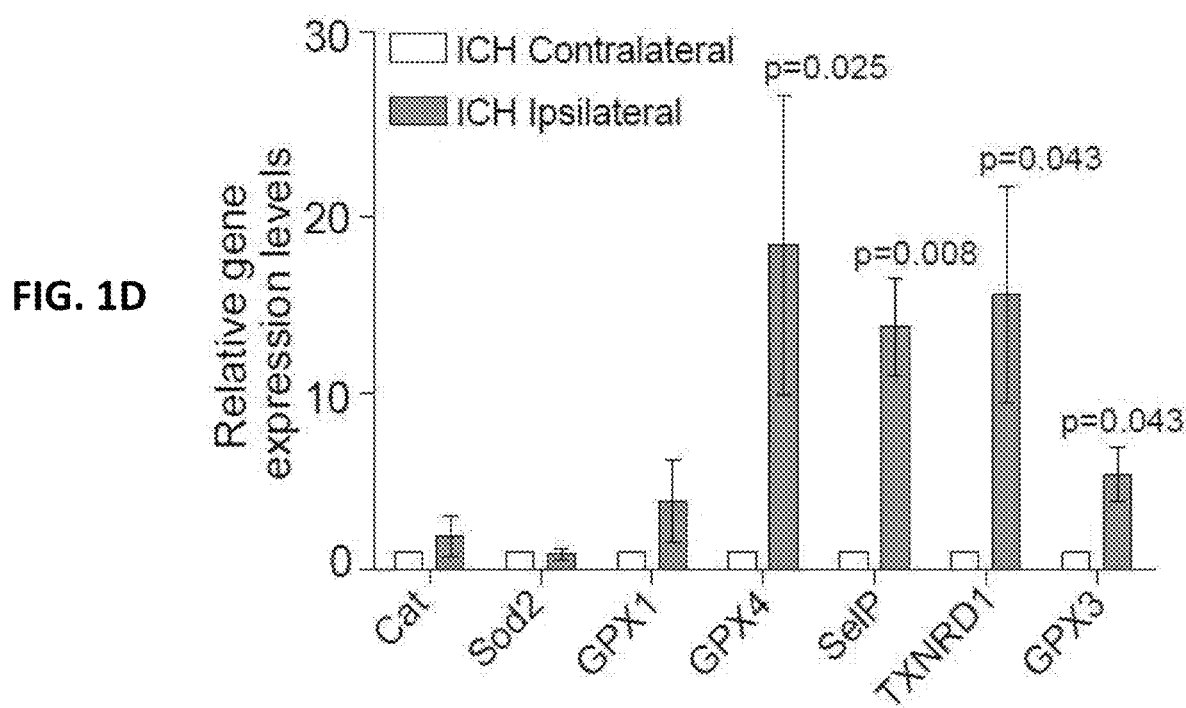
FIG. 1D is a graph of qPCR results showing relative mRNA expression levels of indicated genes in ICH mouse whole striatum collected 6 hours after unilateral collagenase injection (n=4).
Figure 1E:
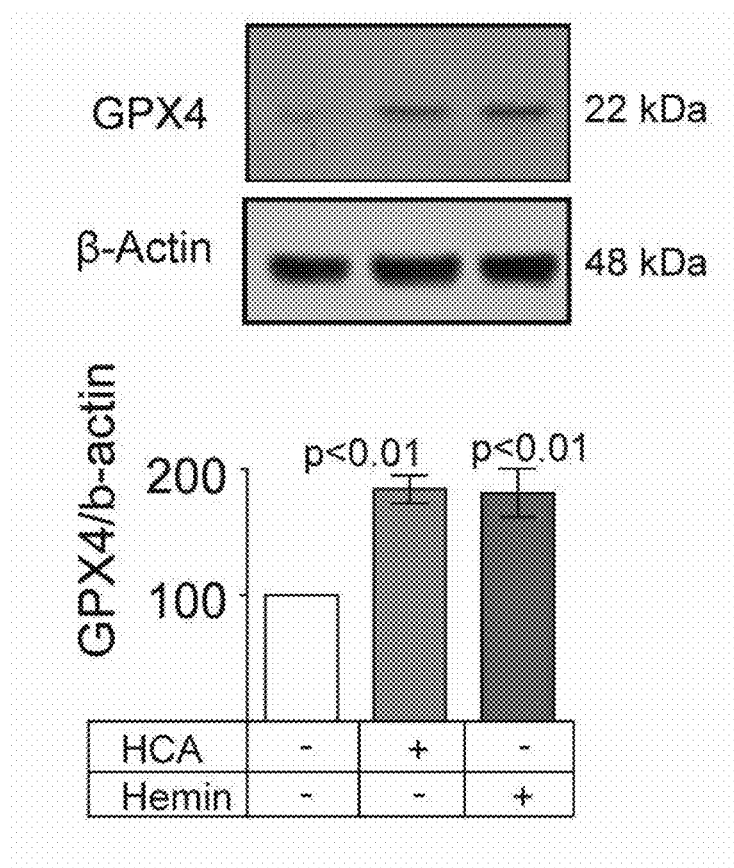
FIG. 1E is a Western blot and a graphic quantification base on the Western blot of GPX4 expression following 8 hours of no treatment, 5 mM HCA and 80 μM Hemin normalized to β-actin (n=4) in primary cortical neuronal cultures.
Figure 1F:
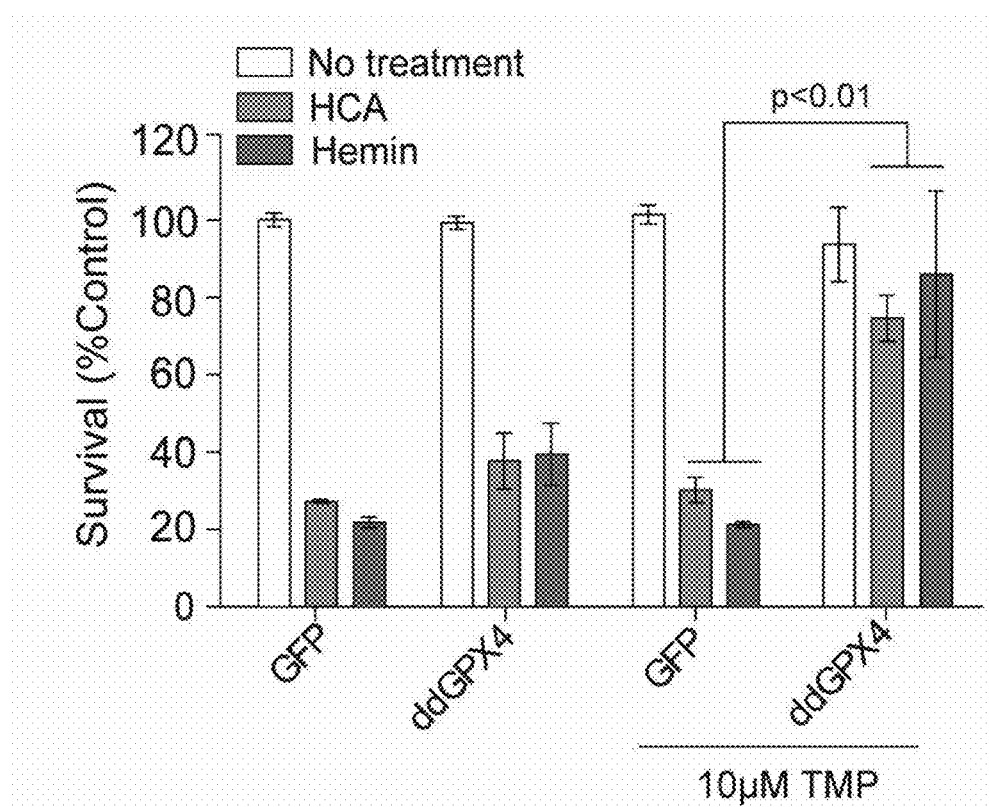
FIG. 1F is a graph showing percentages of survival determined by normalized measurement of MTT in cells overexpressing GFP (control) or GPX4 with destabilizing domain (ddGPX4) in the absence or presence of 10 μM of trimethoprim (TMP) stabilizing ddGPX4 (n=5).

Example 1: Ferroptotic Stresses and ICH Drive a Frustrated Adaptive Response Involving Selenoproteins FIGS. 1A-1J demonstrate that ferroptosis increases mRNA expression of selenoproteins. To identify the transcriptional adaptive response to ICH, we monitored mRNA levels for antioxidant enzymes in primary neurons using a classical glutamate-induced ferroptosis paradigm (See Dixon et al., Cell 149(5): p. 1060-72 (2012), and Ratan et al., Journal of Neurochemistry 62:376-379 (1994)) and an in vitro model of ICH (See Zille et al., Stroke 48(4):1033-1043 (2017)). Unexpectedly, the expression of canonical antioxidant enzymes, such as cytosolic or mitochondrial SOD or catalase, were not induced in either paradigm. Rather, within 6 hours of toxin exposure, both model systems induced the expression of several selenium-containing antioxidant enzymes, including glutathione peroxidase 4 (GPX4), thioredoxin reductase 1 (TXNRD1), glutathione peroxidase 3 (GPX3) and selenoprotein P (SelP or SPP1) (FIGS. 1A, 1B, and 1E). In addition, the expression of these selenoenzymes was induced in the striatum ipsilateral to ICH in an in vivo mouse ICH model system (FIGS. 1C and 1D), a paradigm with features of ferroptosis (See Zille et al., supra).

Figure 7A:
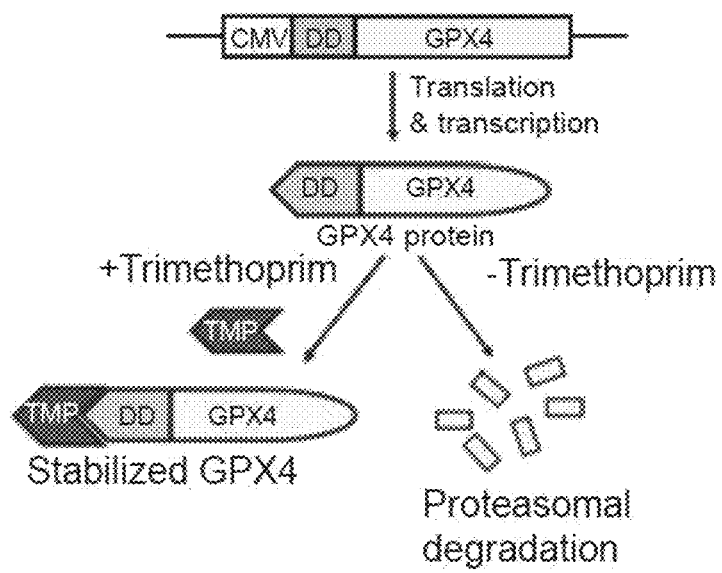
FIG. 7A is a schematic of neurons transduced with ddGPX4 with CMB promoter, showing that GPX4 bound to a wandless destabilization domain undergoes proteasomal degradation unless stabilized with trimethoprim (TMP).
Figure 7B:
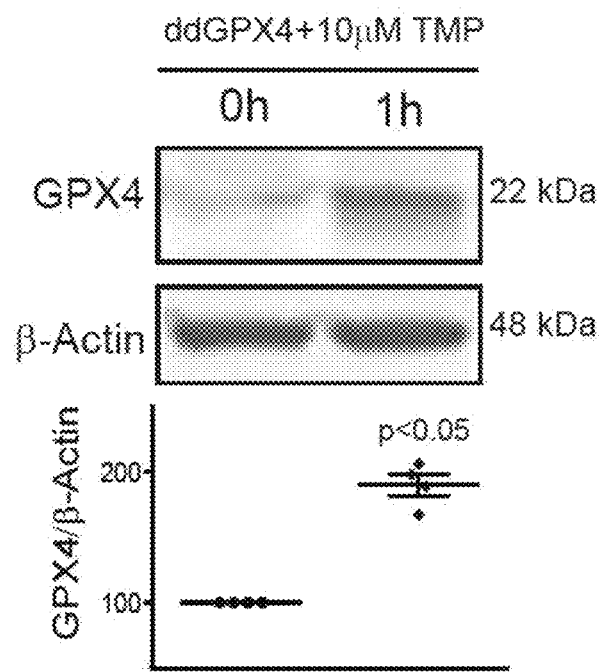
FIG. 7B is a Western blot showing that stabilization of GPX4 with trimethoprim occurs within 1 hour of 10 µM TMP treatment (n=3).
Figure 7C:
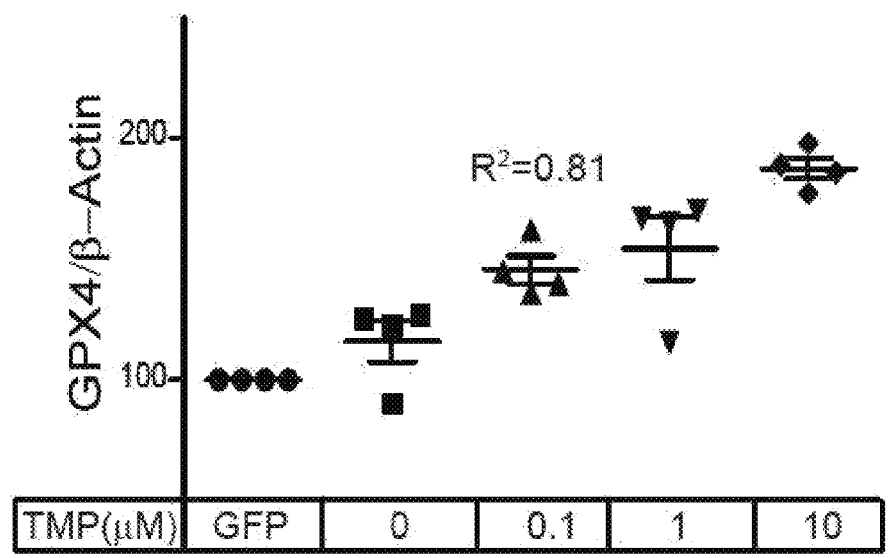
FIG. 7C is a graph showing a dose dependent increase in stabilization of GPX4 following 6 h of trimethoprim treatment as measured by Western blot (n=4).
Figure 7D:
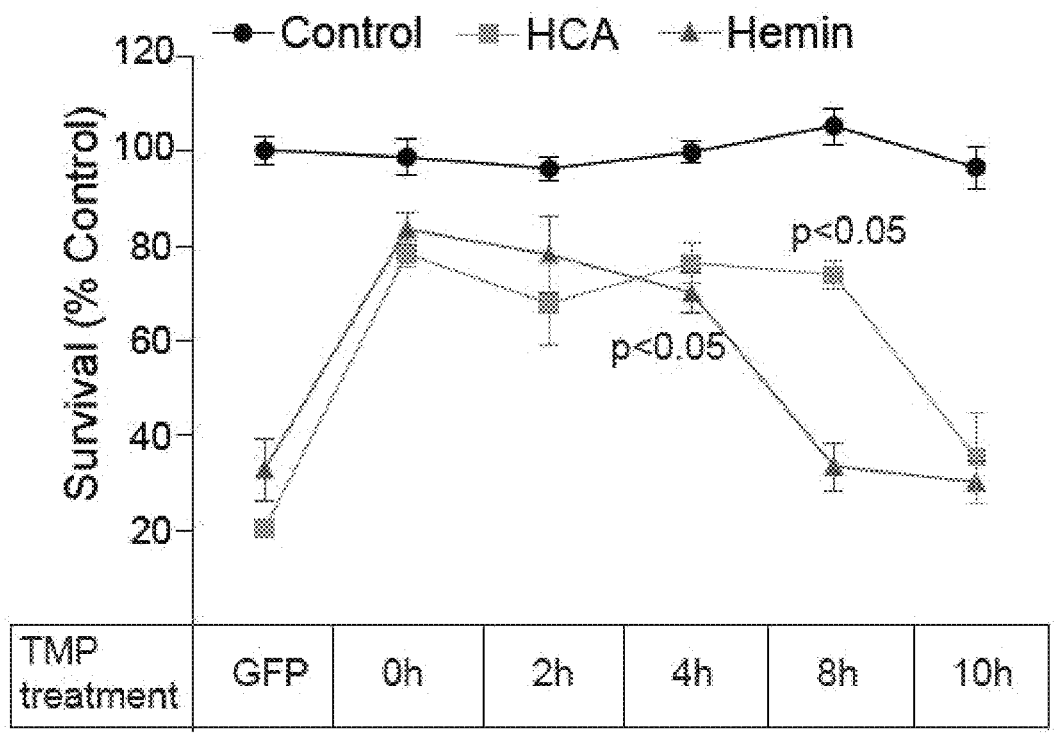
FIG. 7D is a graph of survival rates as measured by MTT assay of ddGPX4 overexpressing neurons with addition of 10 µM TMP following hemin (80 µM) or HCA (5 mM) treatment (n=5).
Figure 8A:
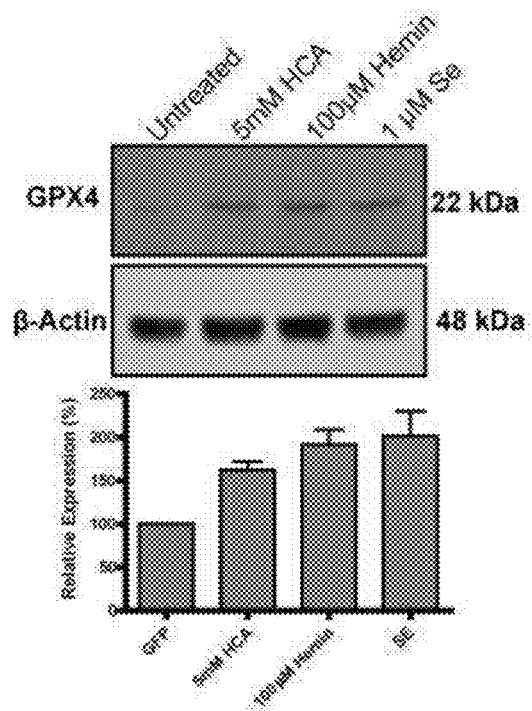
FIG. 8A is a Western blot (upper) and a graph (lower) showing that selenite, HCA and hemin increase GPX4 protein levels.
Figure 8B:
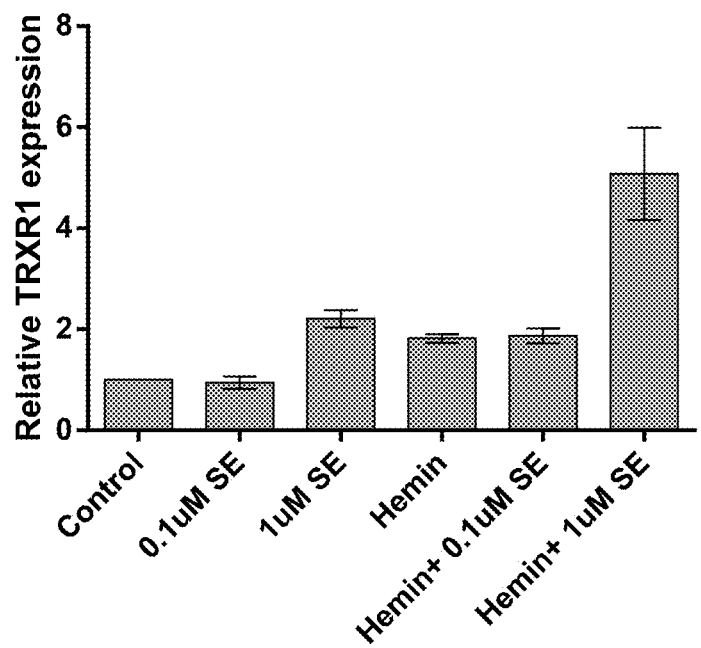
FIG. 8B is a graph showing relative increase in TRXR1 expression as measured by quantitative PCR in primary cortical neurons upon treatment with SE, hemin, or both SE and hemin.
Figure 8C:
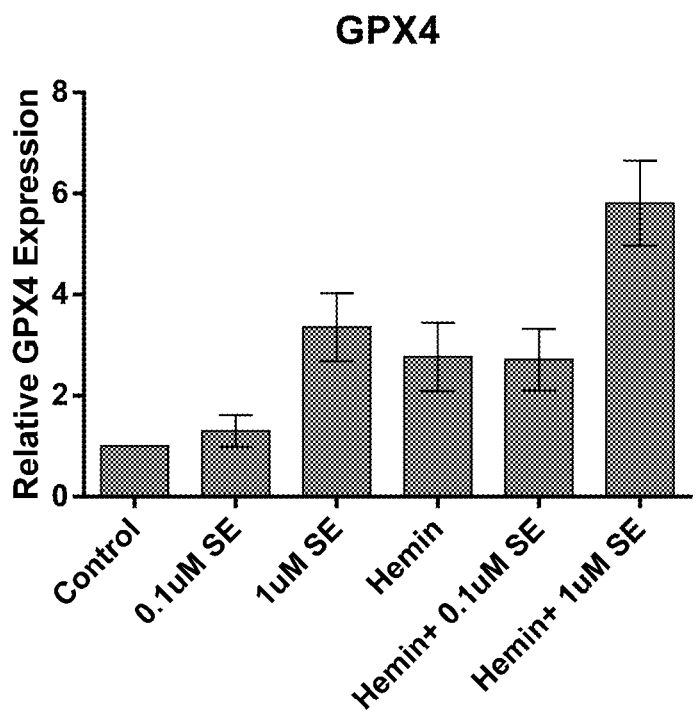
FIG. 8C is a graph showing relative increase in GPX4 expression as measured by quantitative PCR in primary cortical neurons upon treatment with SE, hemin, or both SE and hemin.
Figure 8D:
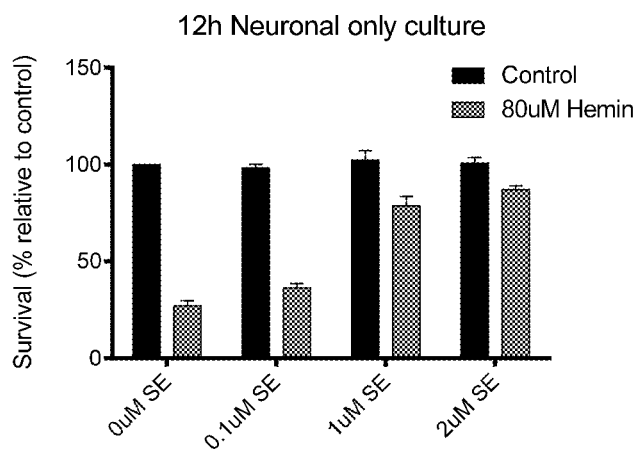
FIG. 8D. is a graph showing that neuronal only cultures are protected against treatment with 80 µM hemin by 1 µM Se (n=3).
Figure 9A:
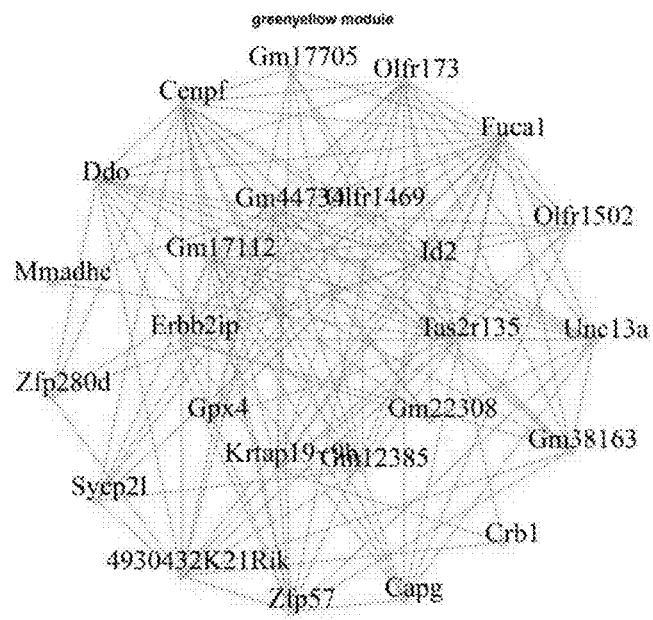
FIGS. 9A-9C show modules enriched with proteins most significantly downregulated by Se.
Figure 9B:
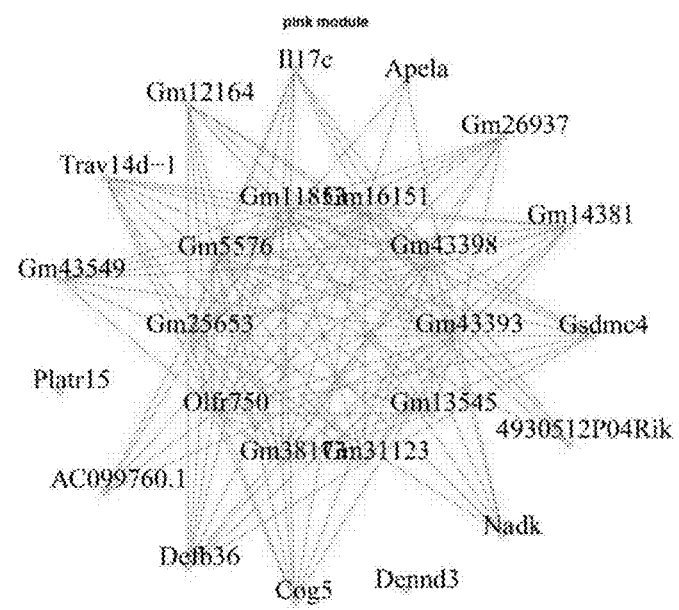
Figure 9C:
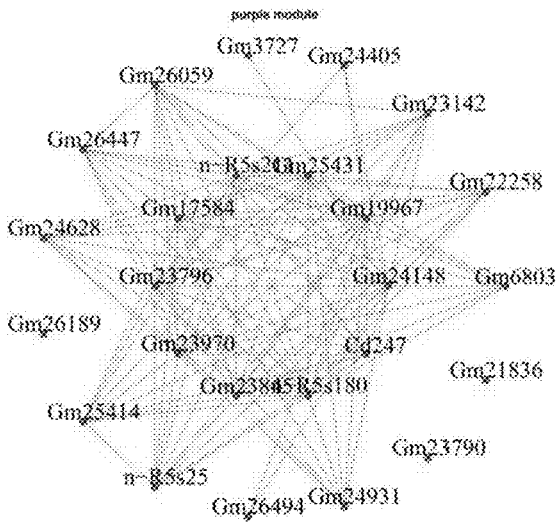
Figure 10A:
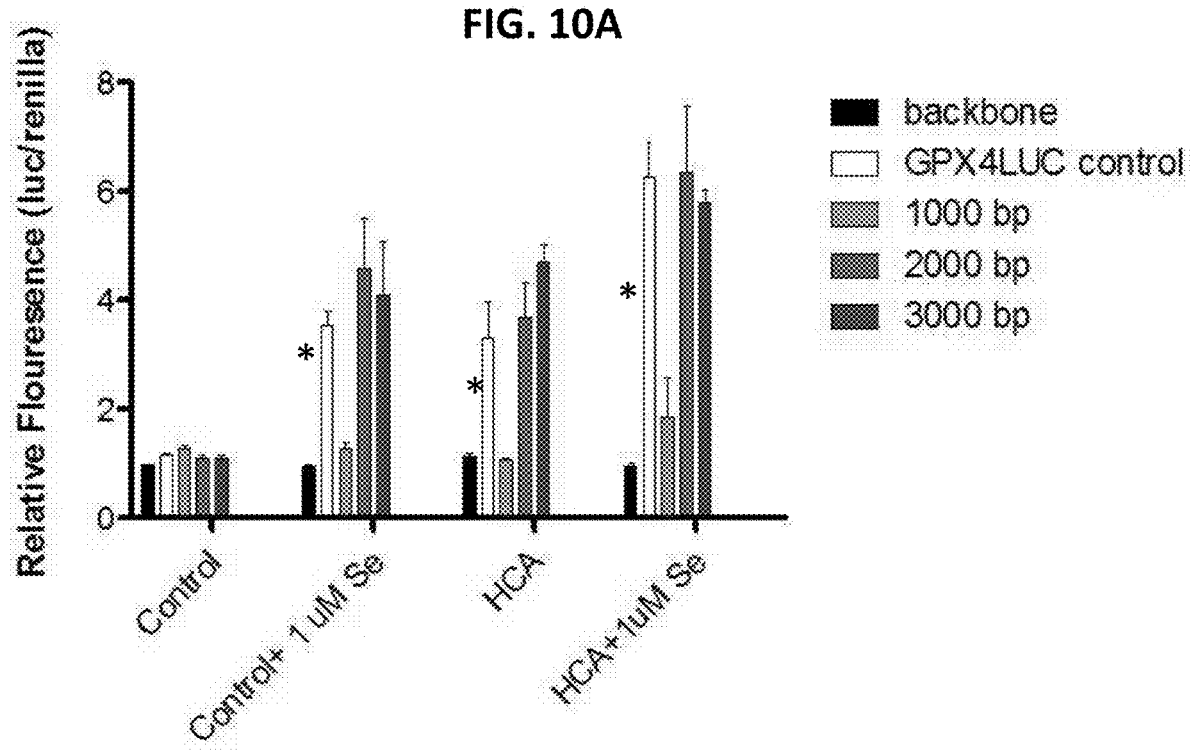
FIG. 10A is a graph showing GPX4 promoter reporter bashing with HCA and Se.
Figure 10B:
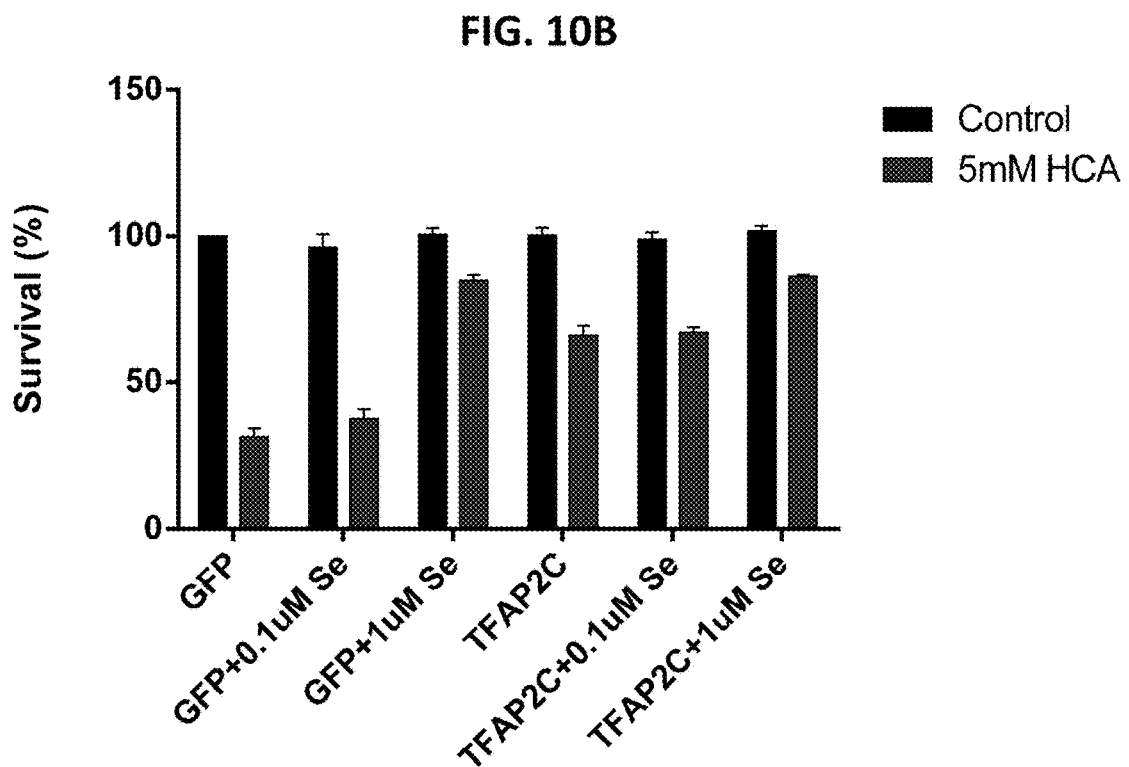
FIG. 10B is a graph showing that overexpression of TFAP2C is protective in HCA induced ferroptosis.
Figure 12A:
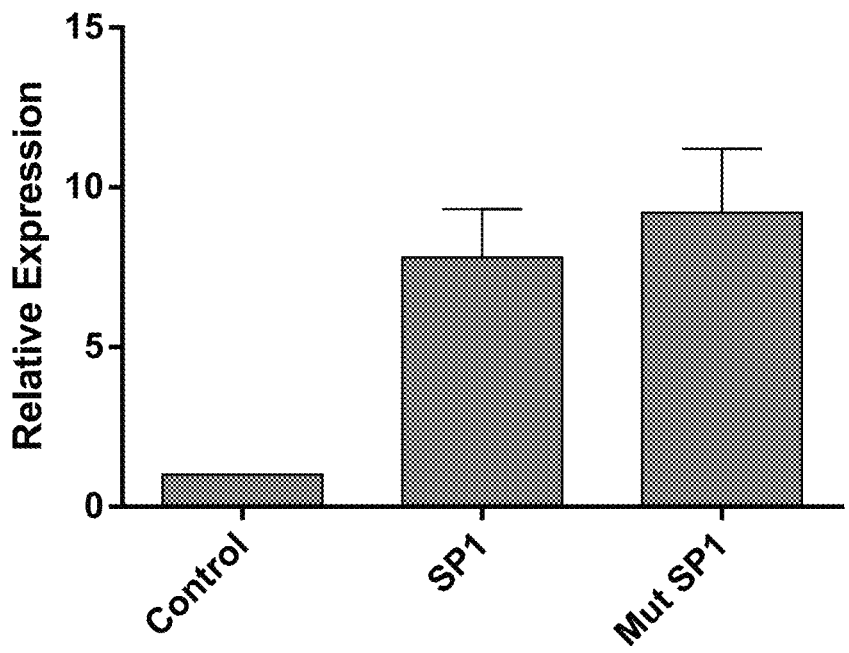
FIGS. 12A and 12B is a graph showing validation of an Sp1 binding mutant (MutSp1; exon 6 contains the binding domain).
Figure 12B:
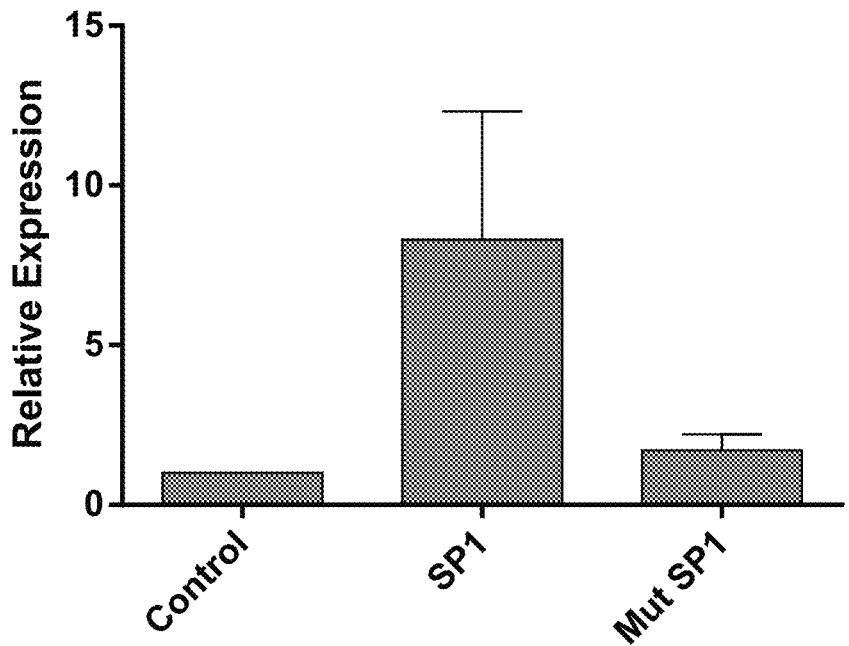
Figure 13A:
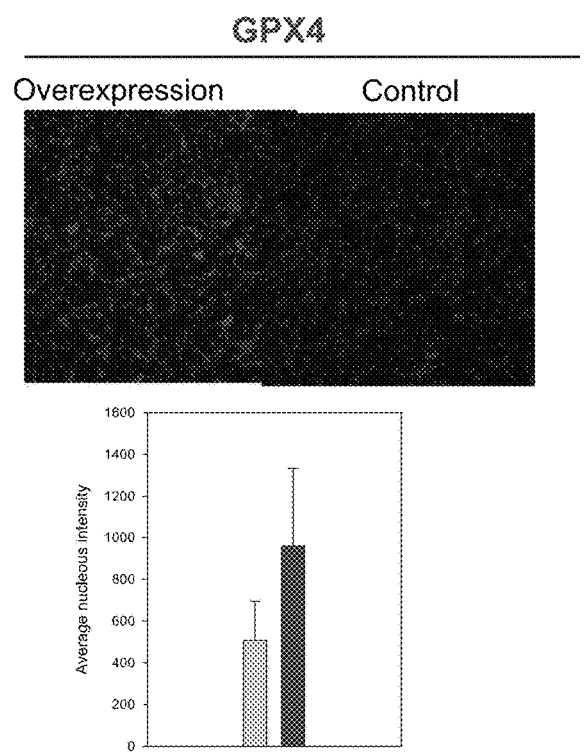
FIGS. 13A and 13B depict confocal images and graphs showing the effect on neurons of treatment with GPX4 and Sp1 overexpression constructs.
Figure 13B:
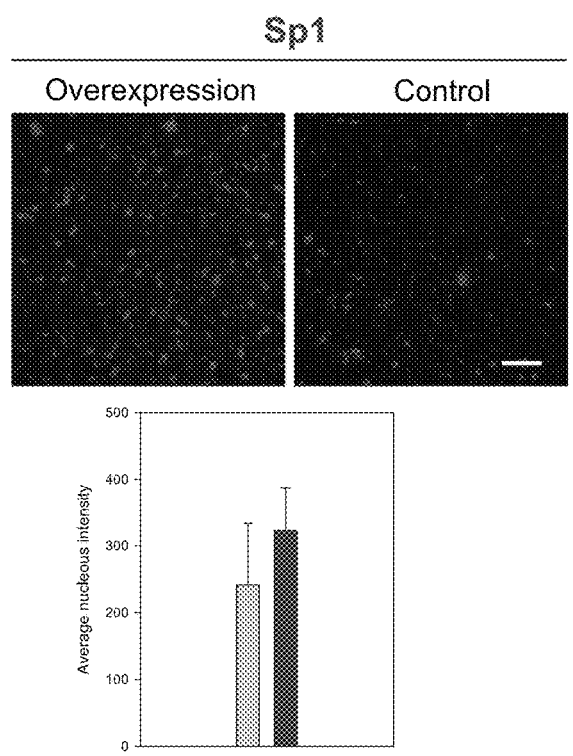
Figure 16A:
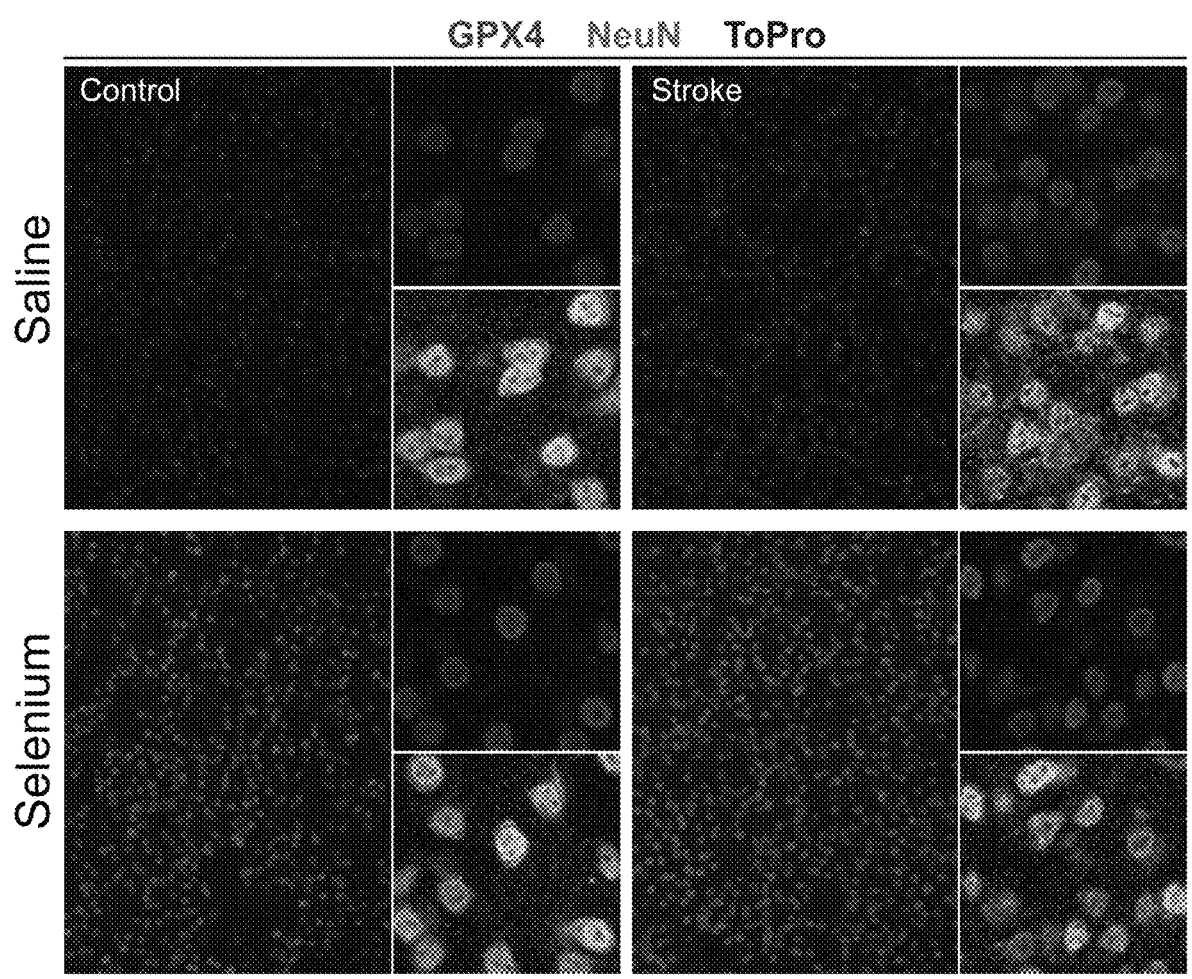
FIG. 16A depicts confocal images showing GPX4 expression in neurons following ICH and single 2.5 µM ICV Se treatment, 7 days post treatment.
Figures 16B, 16C:
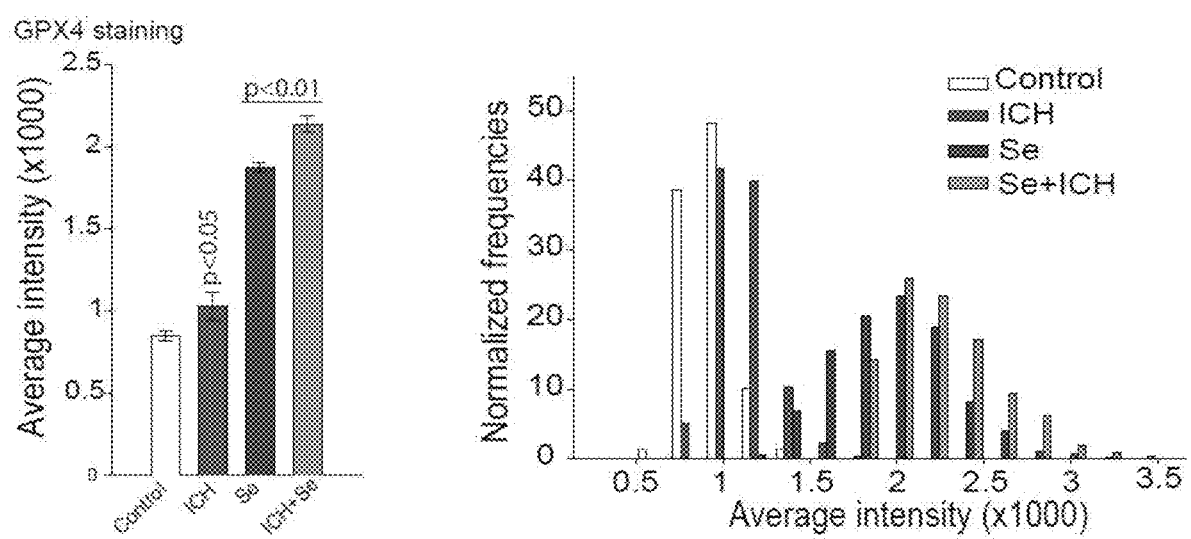
FIG. 16B depicts graphs showing GPX4 expression in neurons following ICH and single 2.5 µM ICV Se treatment, 7 days post treatment.
FIG. 16C depicts a table showing GPX4 expression in neurons following ICH and single 2.5 µM ICV Se treatment, 7 days post treatment.
Figure 17A:
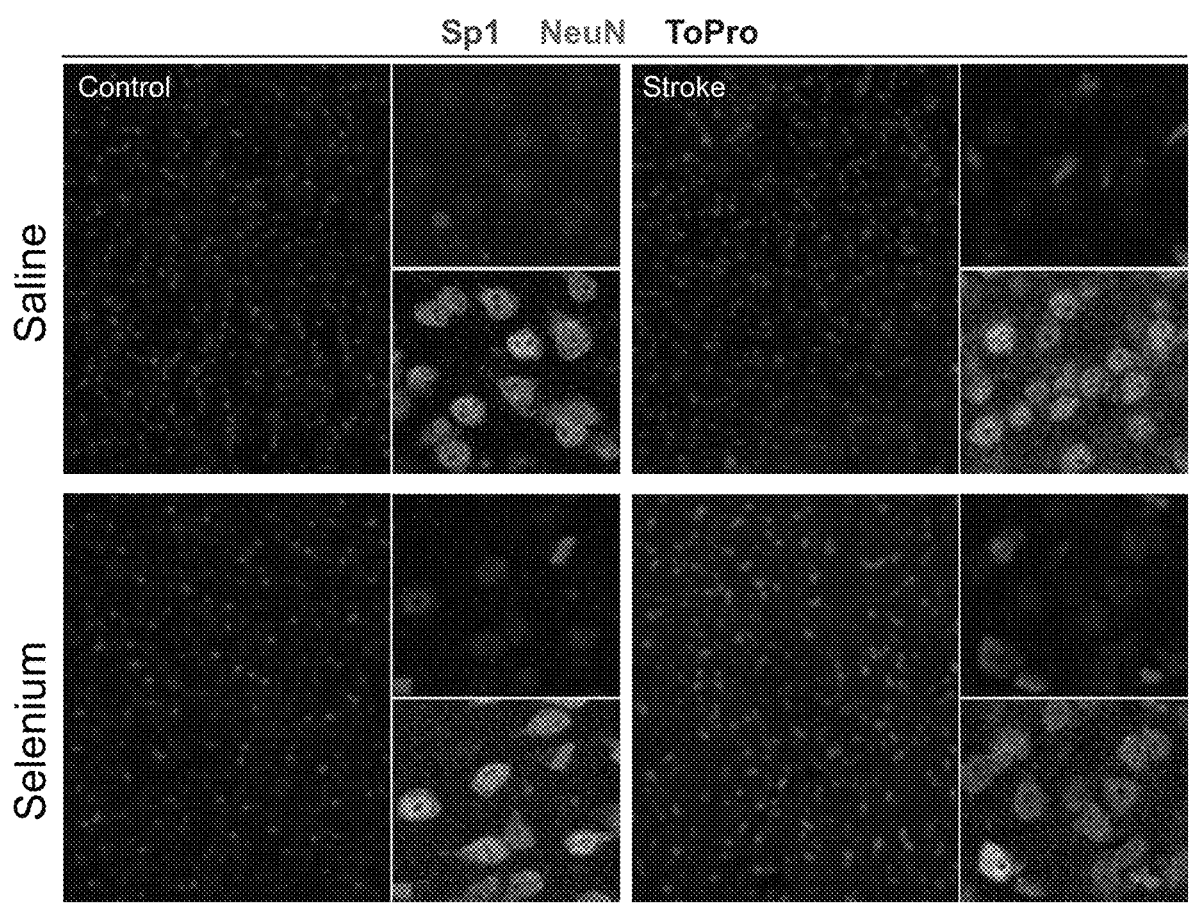
FIG. 17A depicts confocal images showing Sp1 expression in neurons following ICH and single 2.5 µM ICV Se treatment, 7 days post treatment.
Figures 17B, 17C:
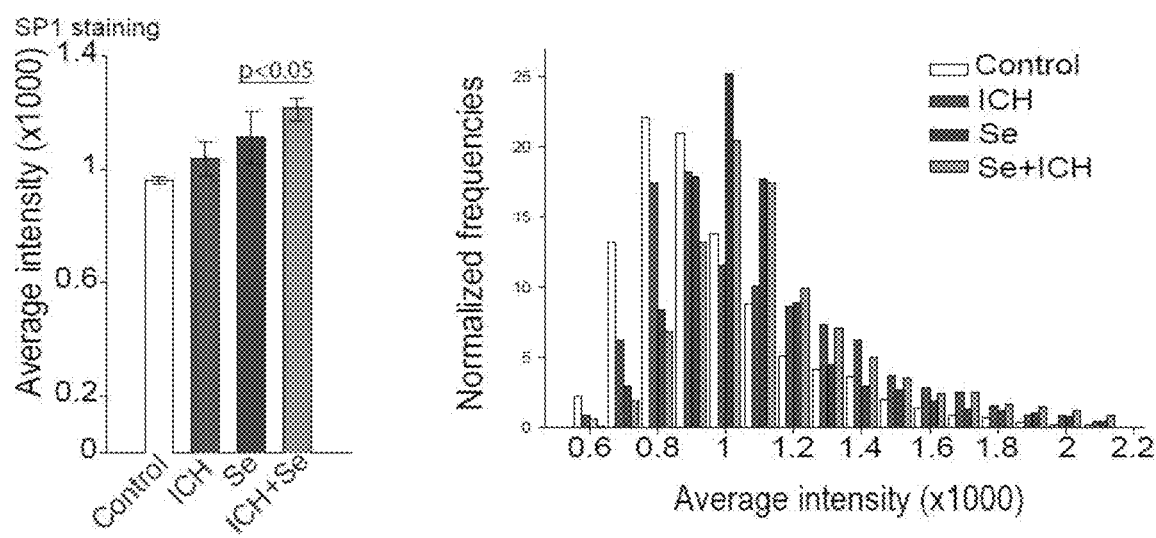
FIG. 17B depicts graphs showing Sp1 expression in neurons following ICH and single 2.5 µM ICV Se treatment, 7 days post treatment.
FIG. 17C depicts a table showing Sp1 expression in neurons following ICH and single 2.5 µM ICV Se treatment, 7 days post treatment.
Figure 18:
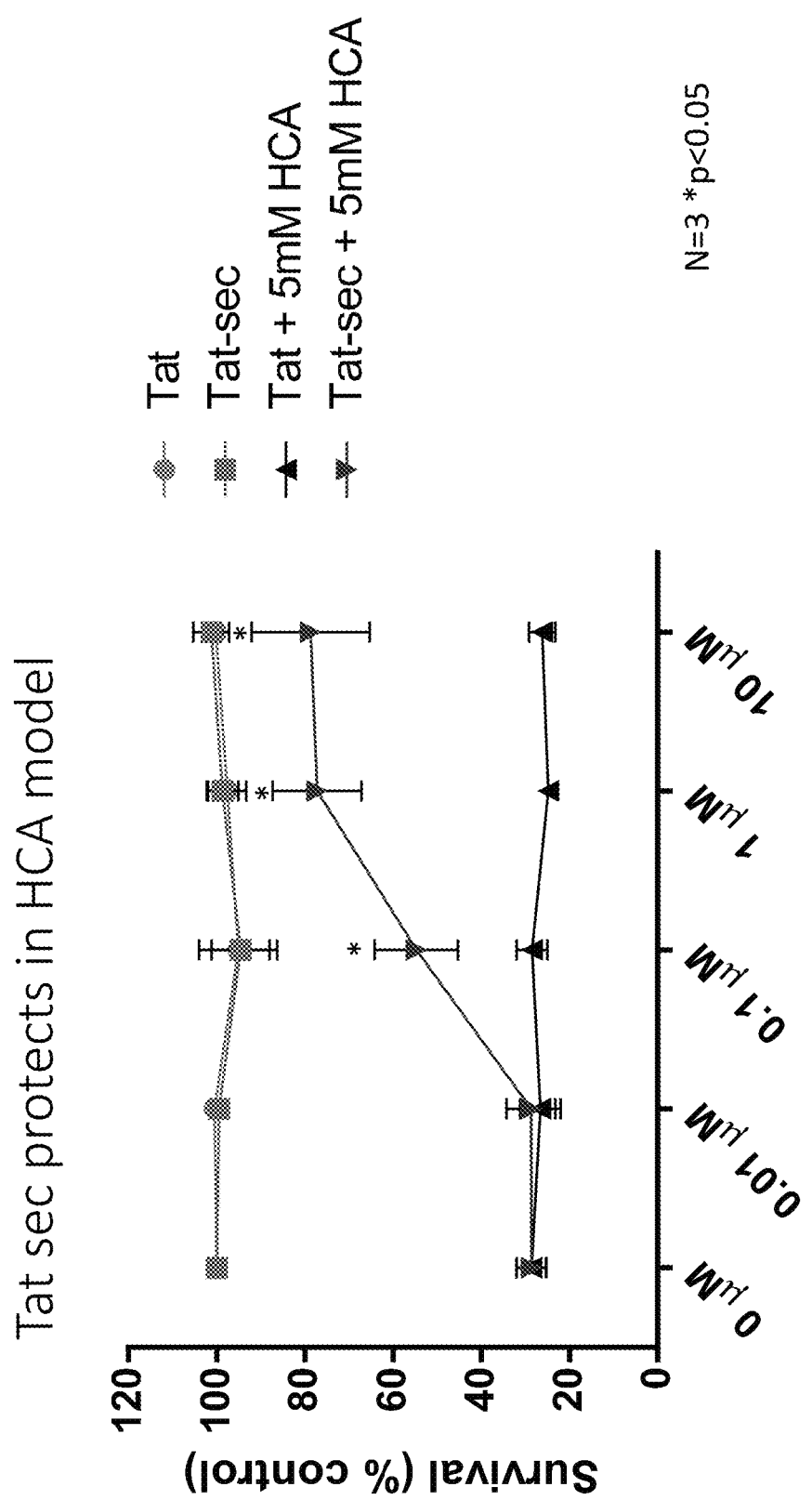
FIG. 18 is a graph showing the results of an MTT (3-(4,5-dimethylthiazol-2-yl)-2,5-diphenyltetrazolium bromide) survival assay in cortical neuronal cultures with dose response of tat peptides (selenocysteine) following treatment with homocysteate (5 mM HCA). Survival was determined 24 h after treatment.
Figure 19:
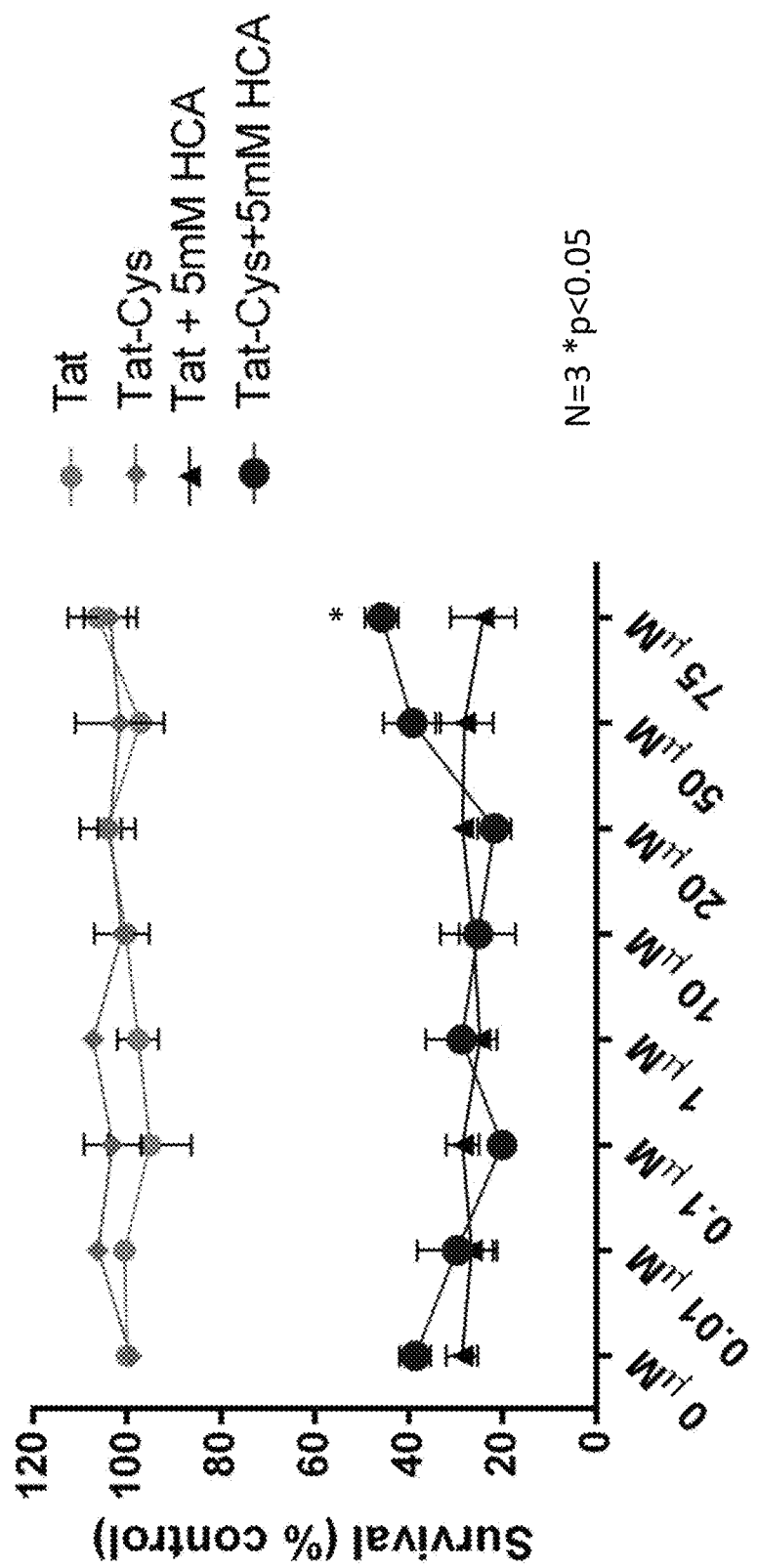
FIG. 19 is a graph showing the results of an MTT (3-(4,5-dimethylthiazol-2-yl)-2,5-diphenyltetrazolium bromide) survival assay in cortical neuronal cultures with dose response of tat peptides (cysteine) following treatment with homocysteate (5 mM HCA). Survival was determined 24 h after treatment.
Figure 20:
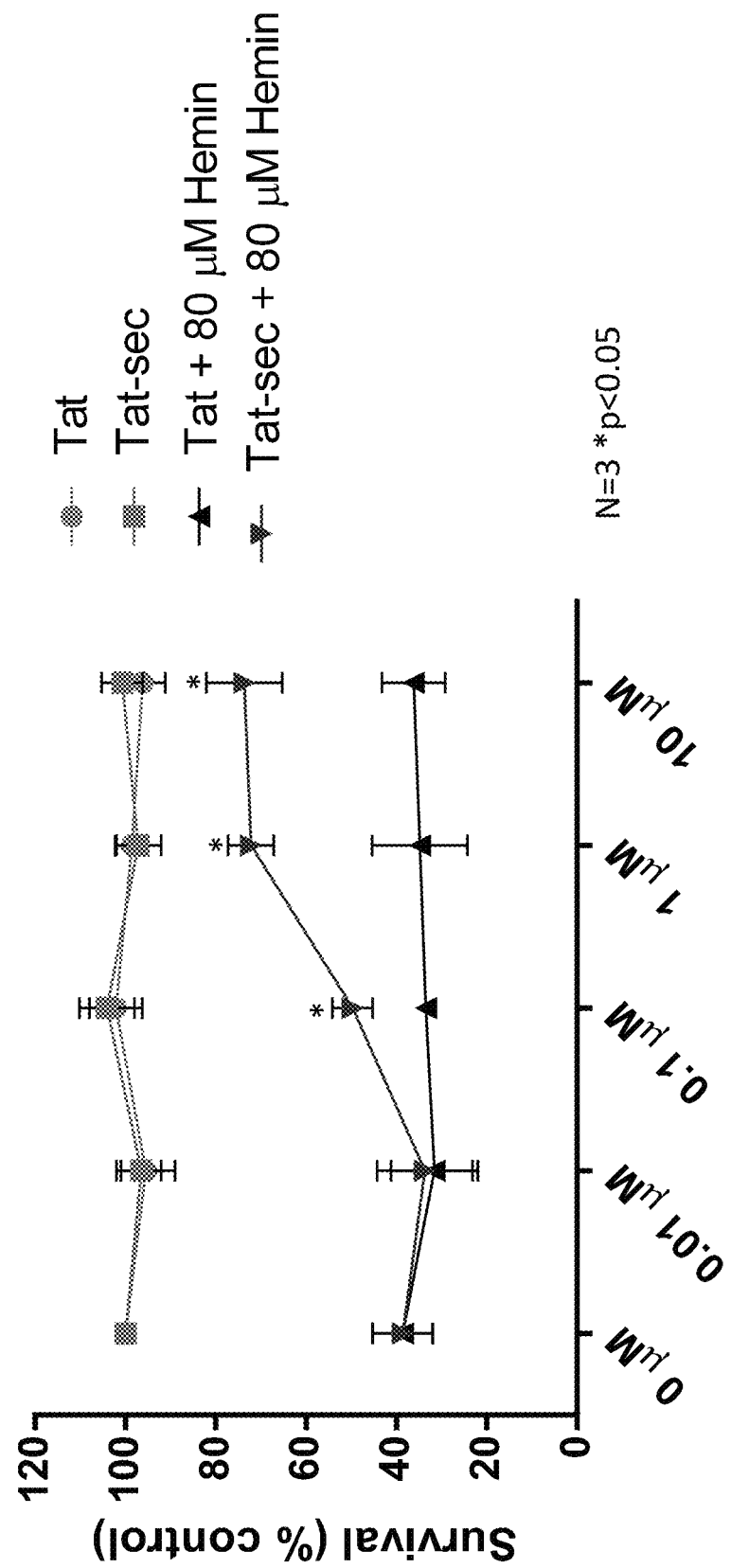
FIG. 20 is a graph showing the results of an MTT (3-(4,5-dimethylthiazol-2-yl)-2,5-diphenyltetrazolium bromide) survival assay in cortical neuronal cultures with dose response of tat peptides (selenocysteine) following treatment with hemin (80 µM), a component of hemoglobin. Survival was measured 16 h after treatment.
Figure 21:
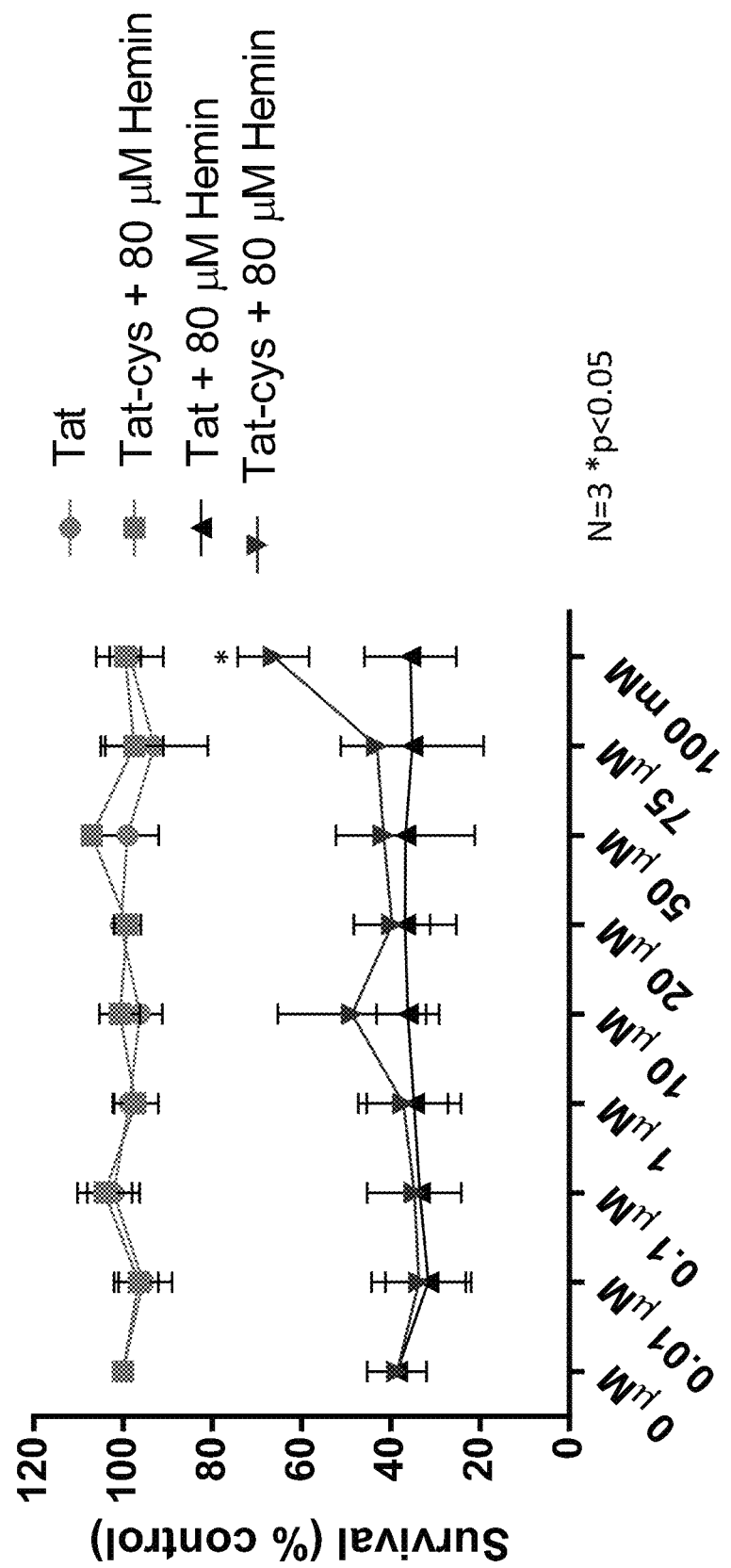
FIG. 21 is a graph showing the results of an MTT (3-(4,5-dimethylthiazol-2-yl)-2,5-diphenyltetrazolium bromide) survival assay in cortical neuronal cultures with dose response of tat peptides (cysteine) following treatment with hemin (80 µM), a component of hemoglobin. Survival was measured 16 h after treatment.
Figure 22:
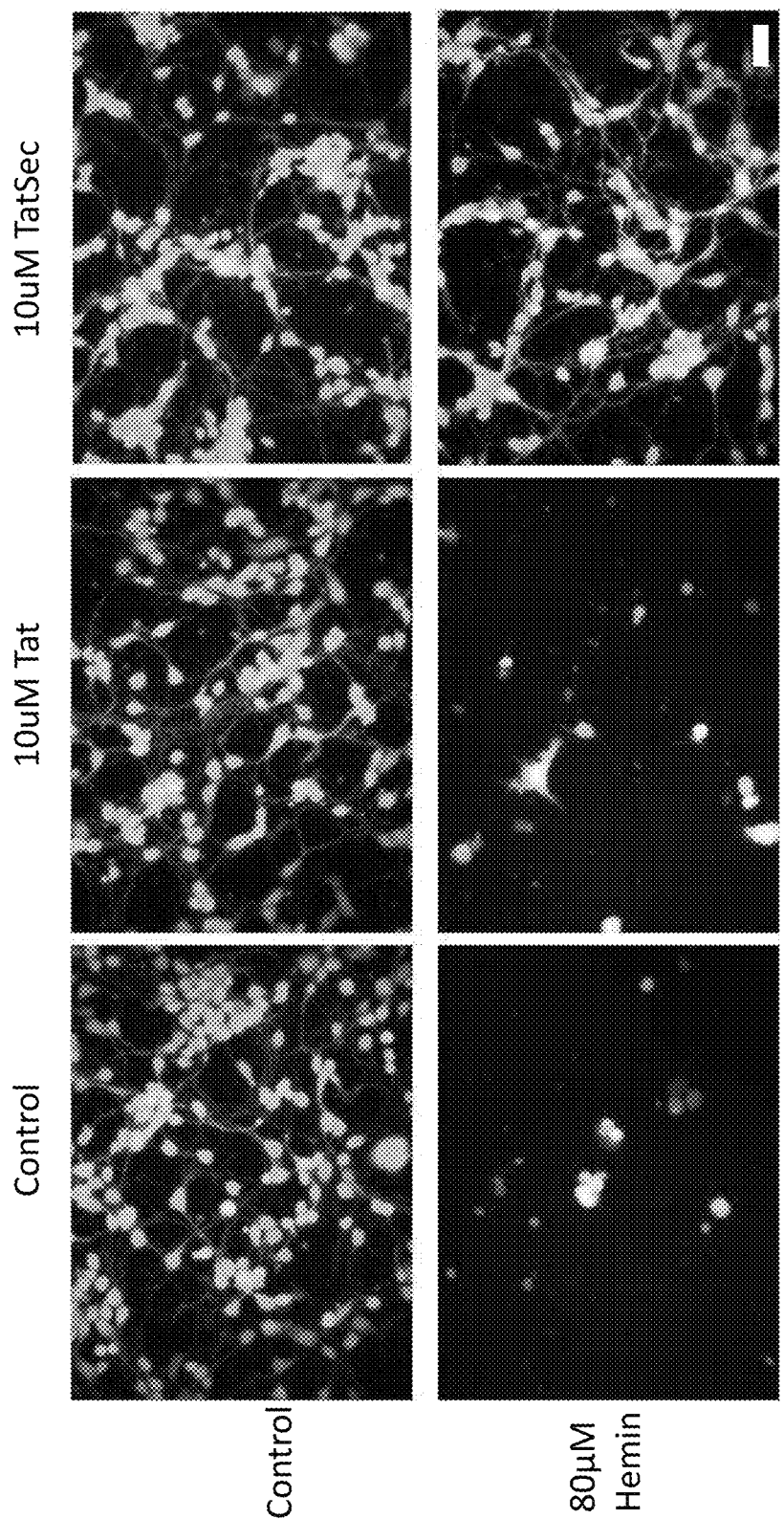
FIG. 22 shows confocal images of Live (calcien AM, green)/Dead (ethidium homodimer, red) staining of a cortical neuronal culture following 16 h of co-treatment with hemin (80 µM). Scale bar 50 µm.
Figure 23:
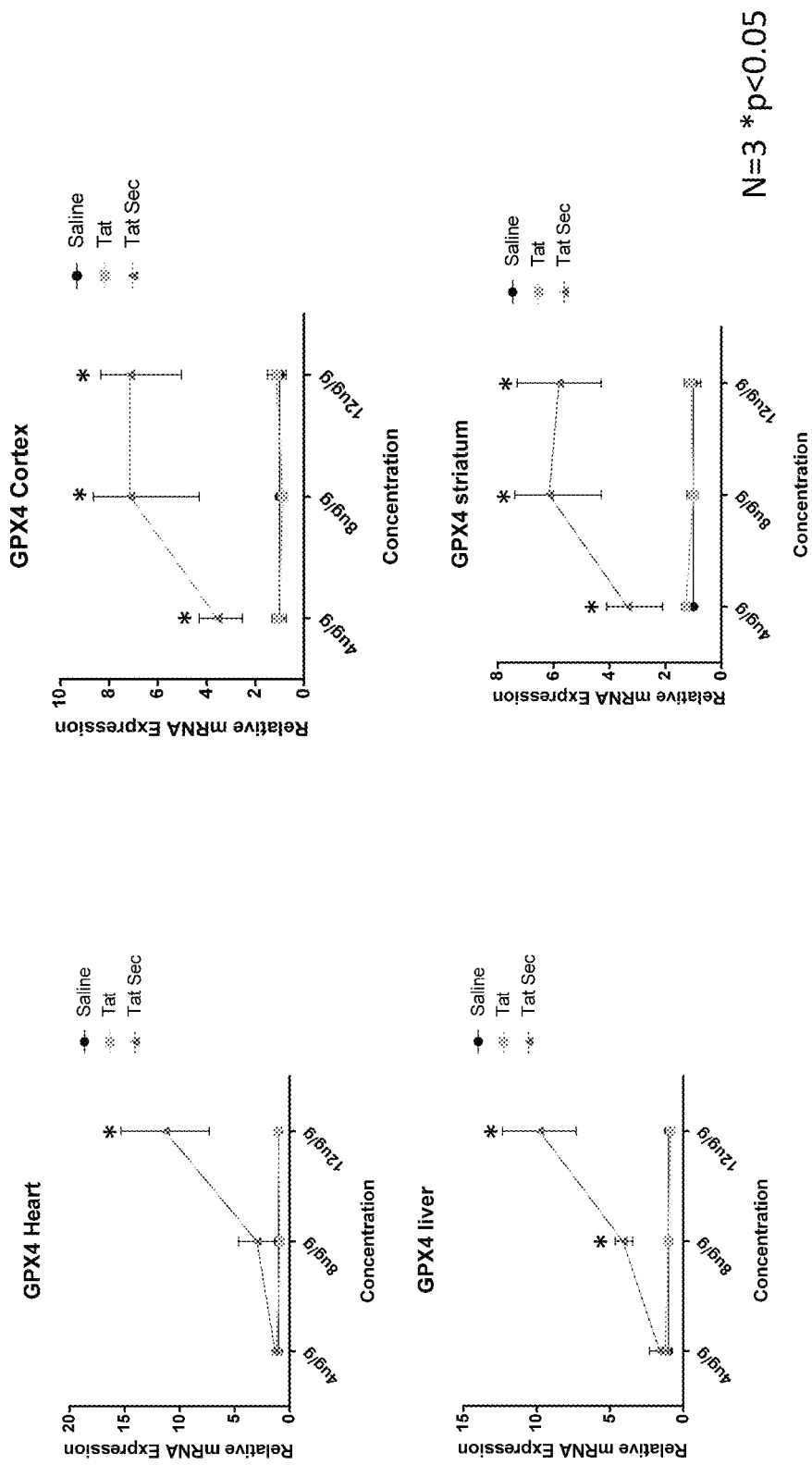
FIG. 23 shows graphs of quantitative rtPCR studies measuring relative GPX4 mRNA in various organs from mouse 24 h after intraperitoneal injection of tat peptides at various concentrations. Tat peptides were dissolved in saline and dosage was based on the weight of the mouse.
Figure 24:
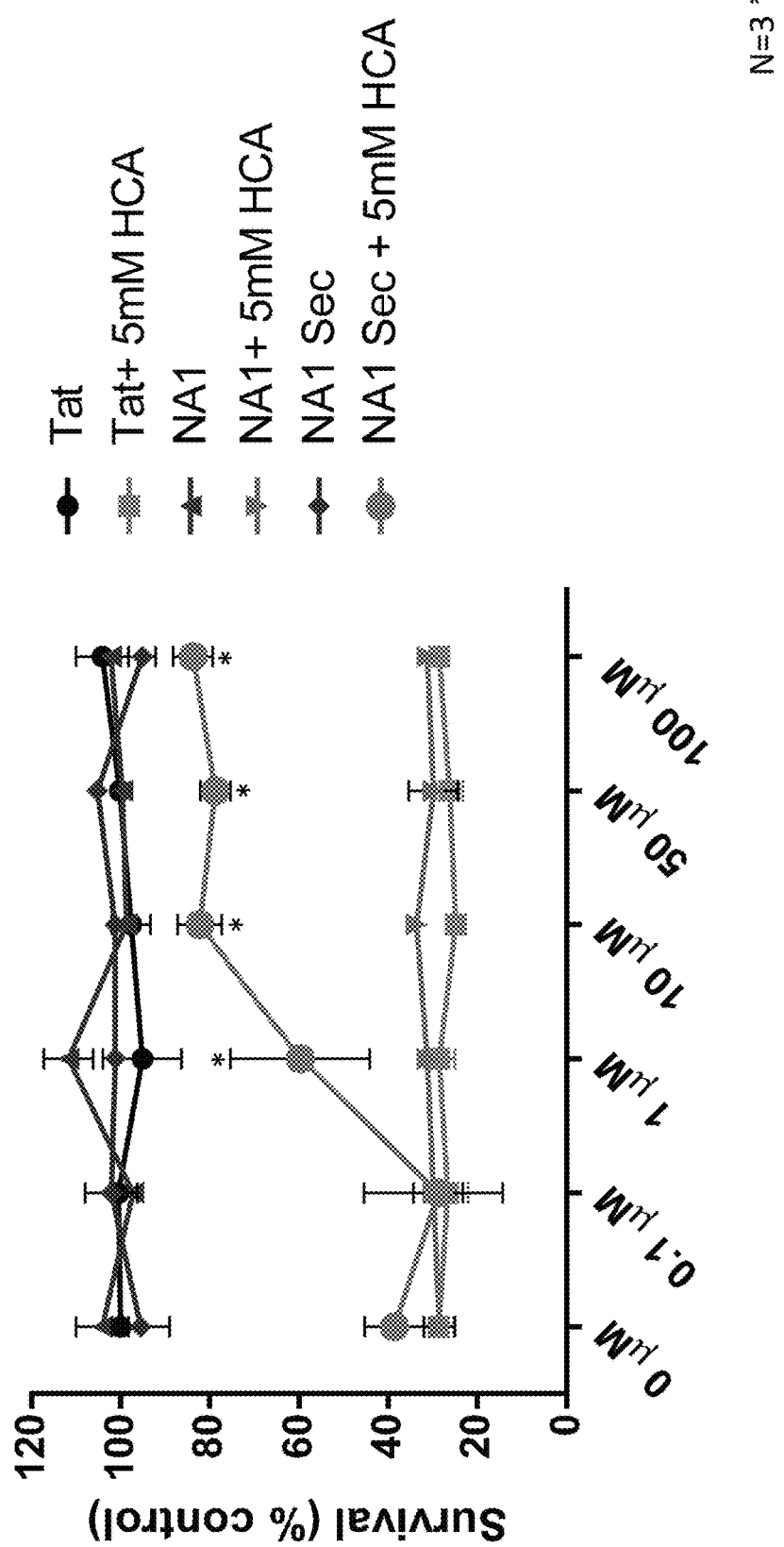
FIG. 24 is a graph showing the results of an MTT (3-(4,5-dimethylthiazol-2-yl)-2,5-diphenyltetrazolium bromide) survival assay in cortical neuronal cultures with dose response of tat peptides (selenocysteine) following treatment with homocysteate (5 mM HCA). Survival was measured 24 h after treatment. Na1 sec is a neuron directed selenocysteine peptide with tat-Na1 and selenocysteine component. Tat allows crossing of the blood brain barrier, NA1 binds specifically to NMDA receptors in neurons, and sec is selenocysteine.
Figure 25:
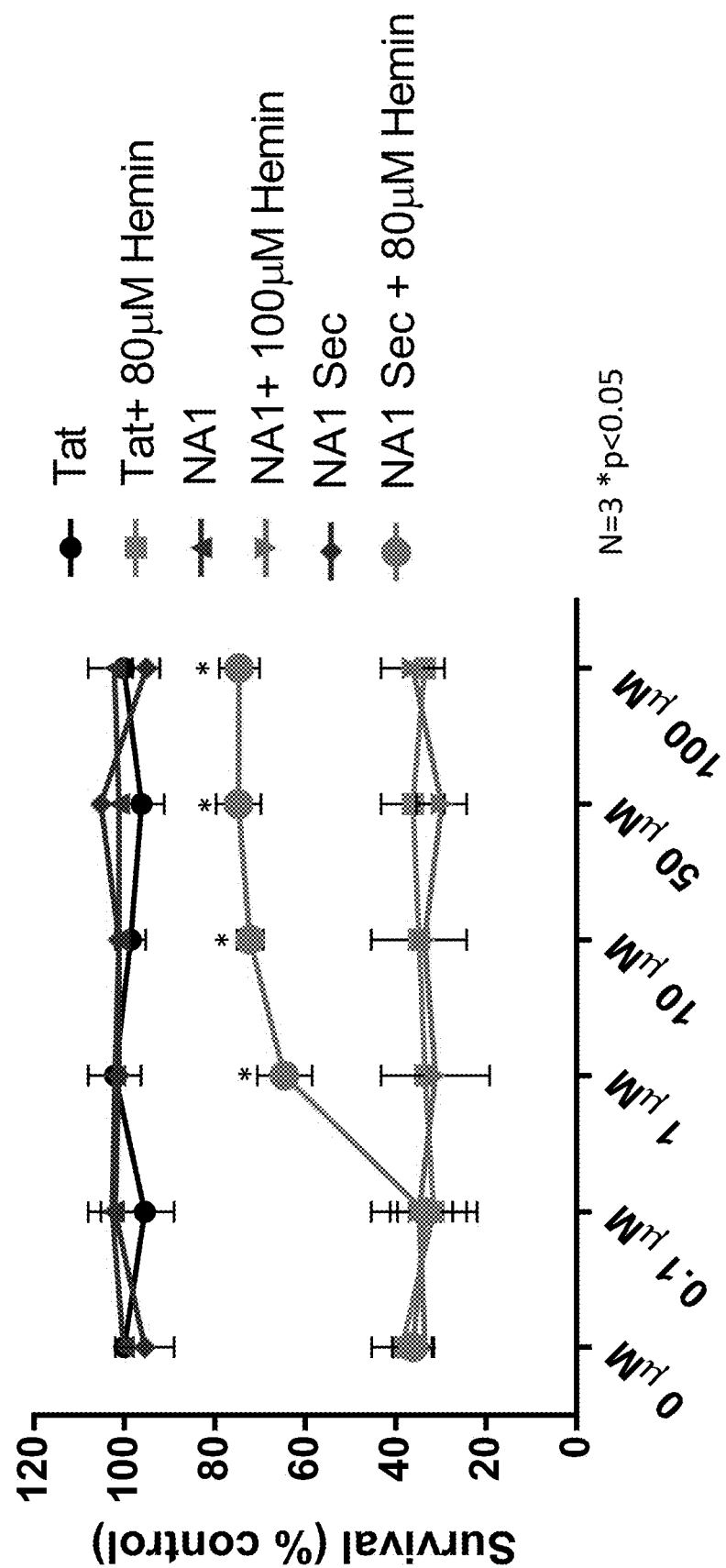
FIG. 25 is a graph showing the results of an MTT (3-(4,5-dimethylthiazol-2-yl)-2,5-diphenyltetrazolium bromide) survival assay in cortical neuronal cultures with dose response of tat peptides following treatment with hemin (80 µM). Survival was measured 16 h after treatment.
Figure 26:
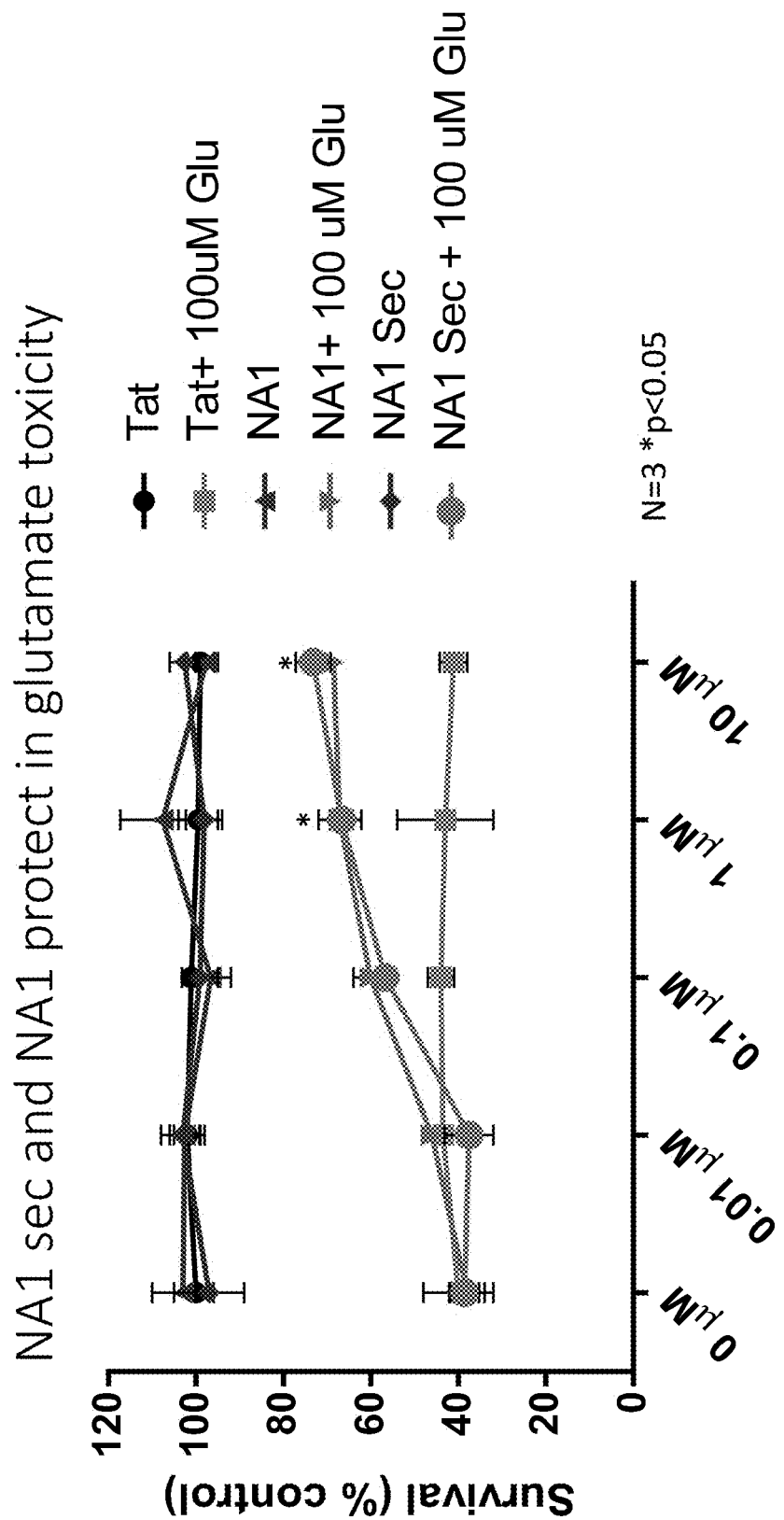
FIG. 26 is a graph showing the results of an MTT (3-(4,5-dimethylthiazol-2-yl)-2,5-diphenyltetrazolium bromide) survival assay in mature cortical neuronal cultures (grown for 2 weeks and allowed NMDA receptor maturation) with dose response of tat peptides following treatment with glutamate (100 µM). Survival was measured 24 h after treatment.
Figure 27:
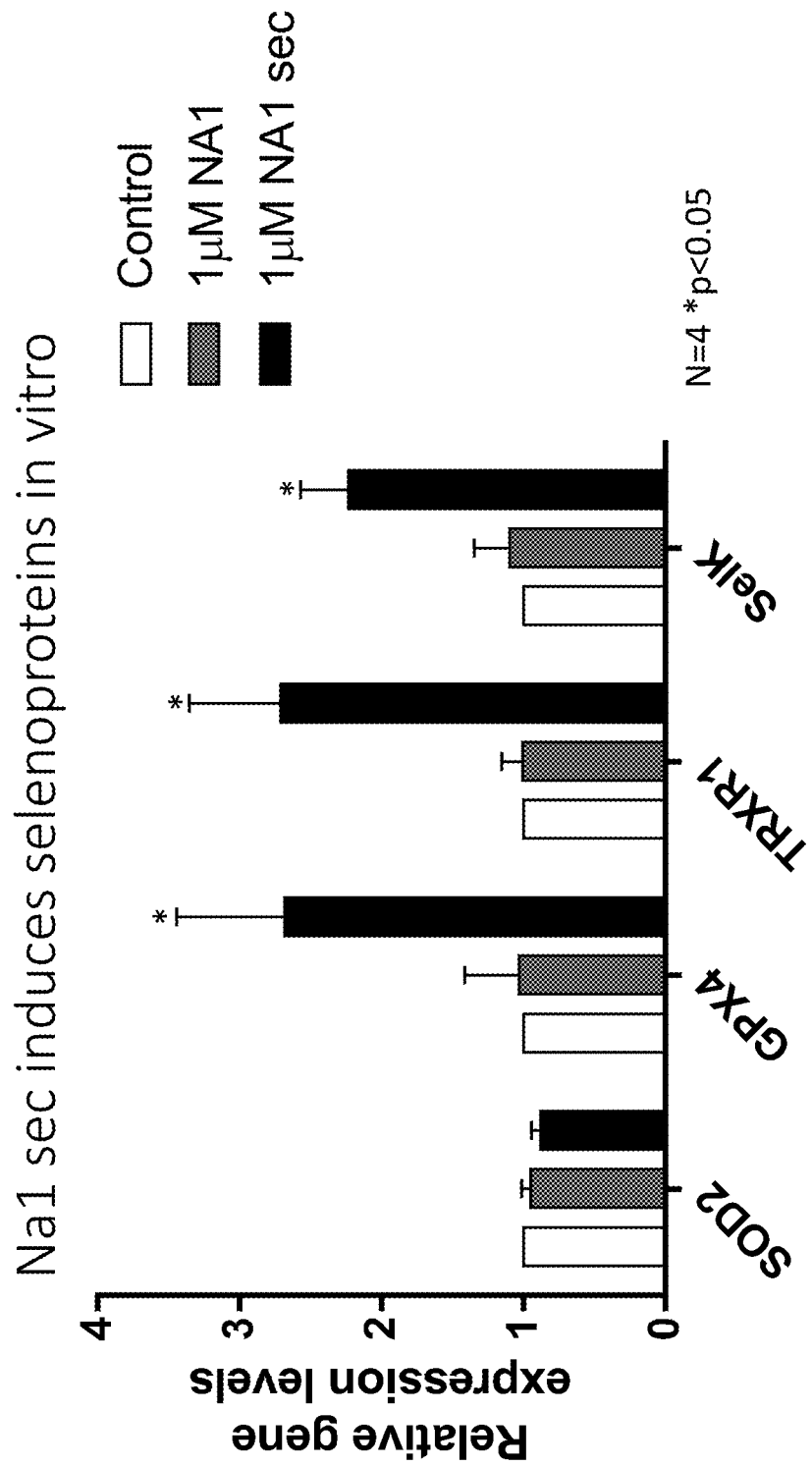
FIG. 27 is a graph of a quantitative rtPCR study measuring relative selenoprotein mRNA levels following treatment with NA1 and NA1 sec in primary cortical neurons. mRNA was collected 4 hours post treatment with the peptides.
Figure 28:
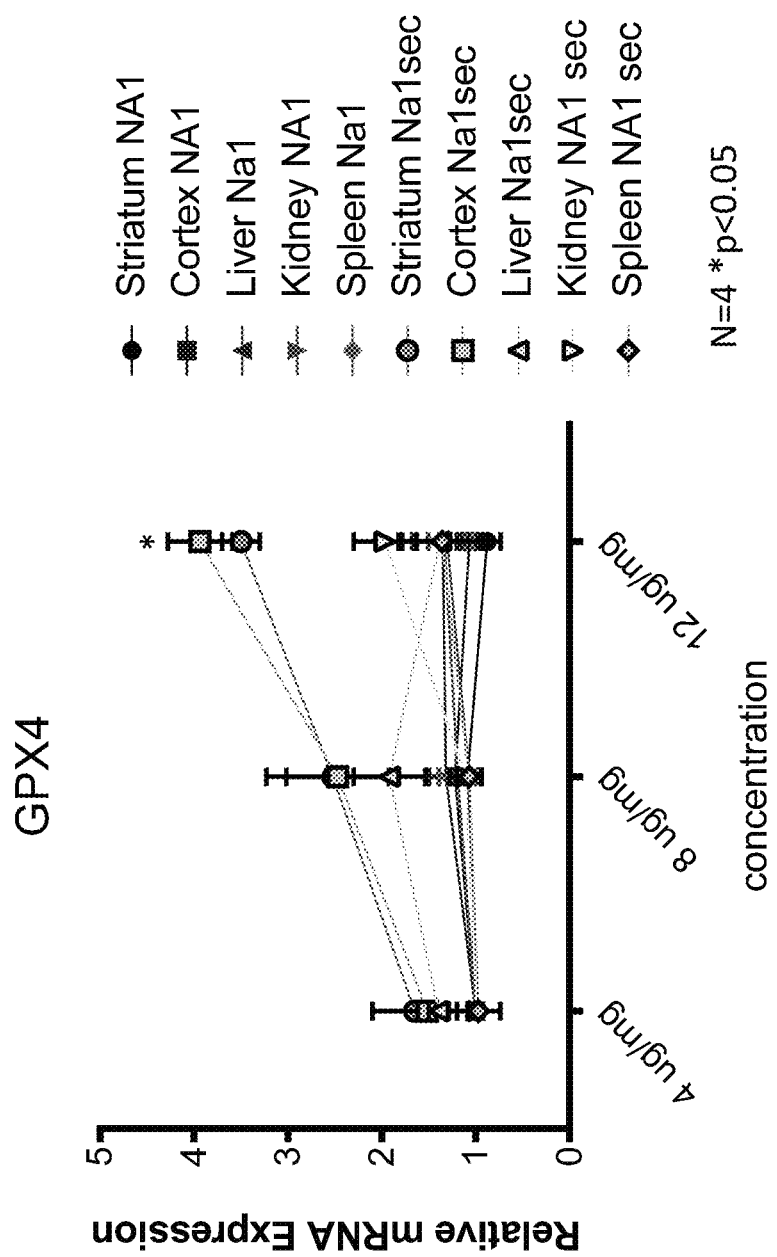
FIG. 28 is a graph of a quantitative rtPCR study measuring relative GPX4 mRNA in various organs from mouse 24 h after intraperitoneal injection of NA1 alone and NA1 sec peptides at various concentrations. All peptides were dissolved in saline and dosage was based on the weight of the mouse.
Figure 29:
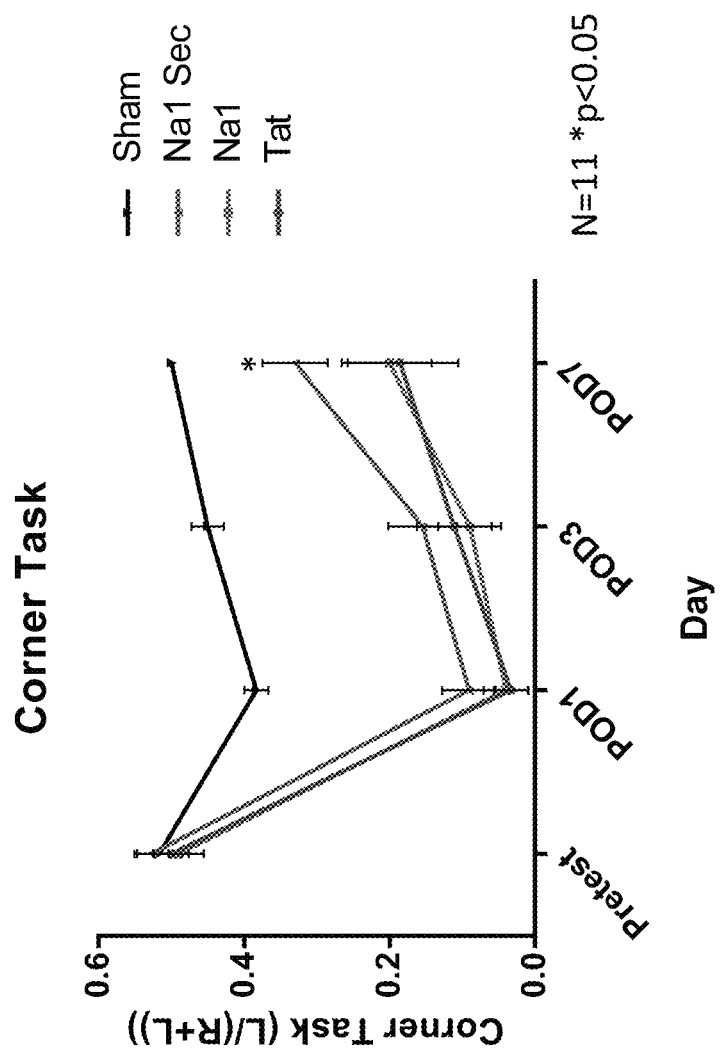
FIG. 29 is a graph showing the results of a spatial neglect (corner task) task study in mouse following ICH measured 1 day before and 1, 3 and 7 days post operation day. ICH was induced by collagenase injection into the striatum of the mouse, followed by intraperitoneal injection of tat, NA1, or NA1-sec alone. NA1-sec treatment is shown to provide significant improvement 7 days post treatment compared to tat and NA1.
Figure 30:
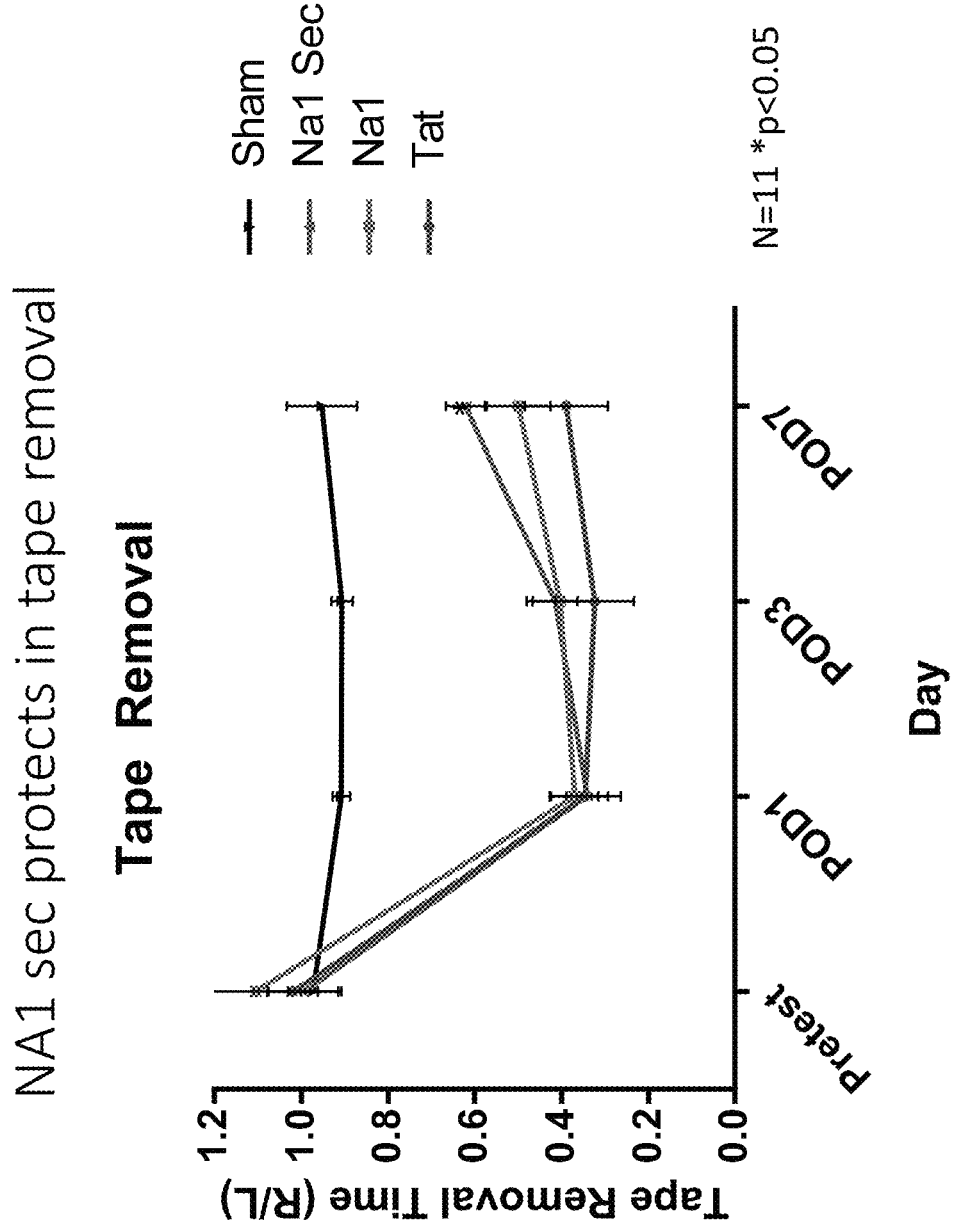
FIG. 30 is a graph showing the results of a sensory neglect (tape removal task) task study in mouse following ICH measured 1 day before and 1, 3 and 7 days post operation day. ICH was induced by collagenase injection into the striatum of the mouse, followed by intraperitoneal injection of tat, NA1, or NA1-sec alone. NA1-sec is shown to provide significant improvement compared to tat but not compared to NA1. NA1 is not shown to provide significant improvement compared to tat.
Figure 31:
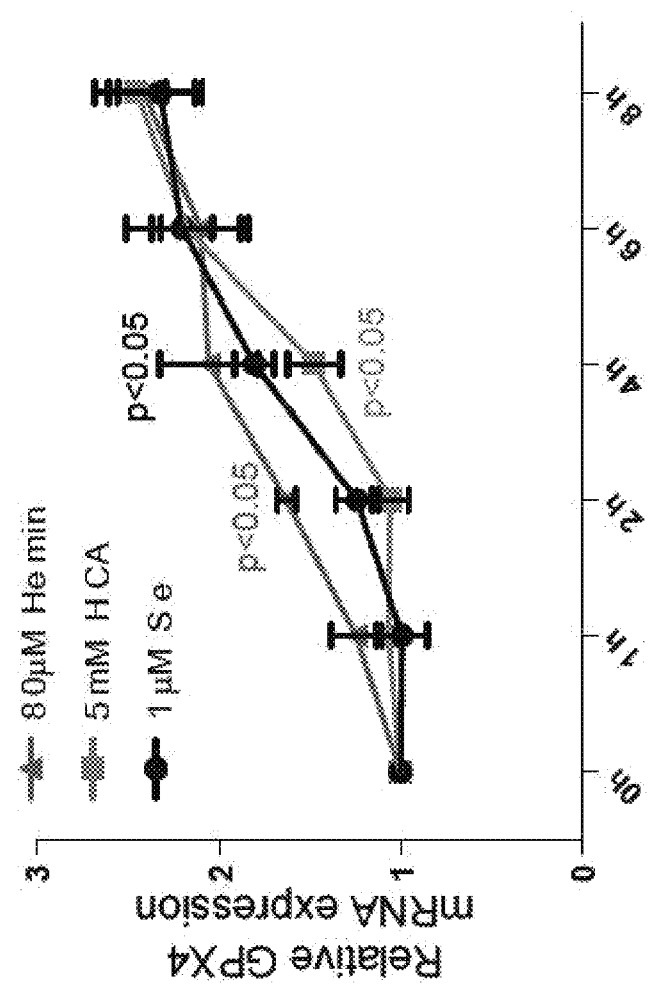
FIG. 31 is a graph showing a quantitative PCR time course of GPX4 mRNA in cortical neurons post-treatment with 80 μM hemin, 5 mM HCA, or 1 μM Se, with time of significant increase indicated (n=3).

As cell death occurs extensively in all of the paradigms examined, in vitro and in vivo, the induction of selenoprotein gene expression in our model systems could be either a frustrated adaptive response to prevent cell death or part of a meaningful program to execute cell death. To distinguish between these possibilities, we manipulated GPX4 levels, since this enzyme can neutralize oxidized lipids and inhibit ferroptosis in cancer cells (See Yang et al., Cell 156(1-2): 317-31 (2014)). In a characterized model of neuronal ferroptosis (See Zille et al., supra, and Dixon et al., supra), GPX4 message and protein induction is observed within 4-8 hours after toxin addition (FIGS. 1A-1E and 31). To establish whether this induced expression was protective, we utilized a previously described strategy for reversibly destabilizing proteins (See Iwamoto et al., Chem Biol 17(9): 981-8 (2010)). In this system, neurons expressed a destabilized form of GPX4 (ddGPX4) at a low steady state until trimethoprim (TMP, 10 □M) was added to rapidly stabilize GPX4 protein levels (within 1 hour; FIGS. 7A-7C). TMP-mediated stabilization of GPX4 protected neurons when added up to 4 or 8 hours after hemin or HCA addition, respectively. By contrast, neither the addition of TMP alone nor ddGPX4 expression without TMP had a protective effect (FIGS. 1F-1J). These studies show that GPX4 induction is part of an adaptive response within neurons to ferroptosis-inducing stresses, and increasing GPX4 levels is sufficient to augment this adaptive response to protect neurons from ferroptosis after exposure to hemin.

Example 2: Se Drives a Protective Transcriptional Response Involving GPX4

Figure 2A:
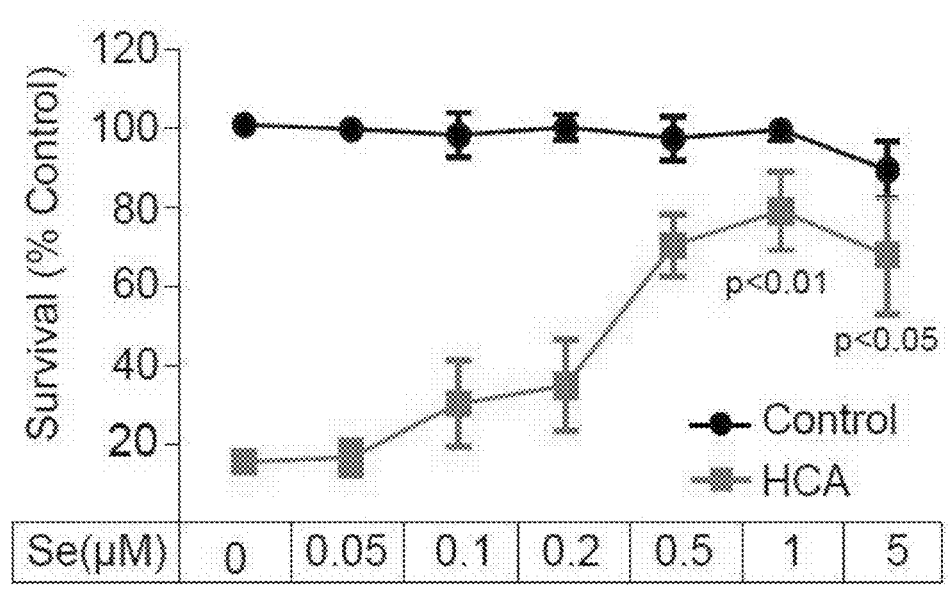
FIG. 2A is a graph showing percentages of survival of neurons 24 h following 5 mM HCA treatment and dose response of sodium selenite (Se) determined by MTT measurement (n=5). All HCA survival measurements were taken at 24 h, all hemin measurements were taken at 16 h.
Figure 2B:
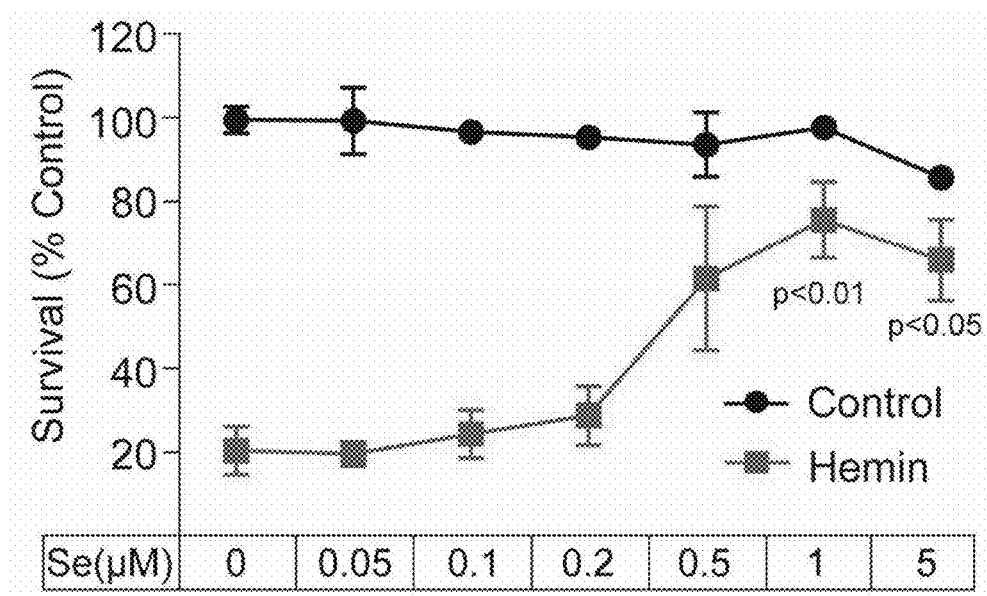
FIG. 2B is a graph showing percentages of survival of neurons following 16 h of 80 μM hemin treatment and dose response of sodium selenite (Se) determined by MTT measurement (n=5). All HCA survival measurements were taken at 24 h, all hemin measurements were taken at 16 h.
Figure 2I:
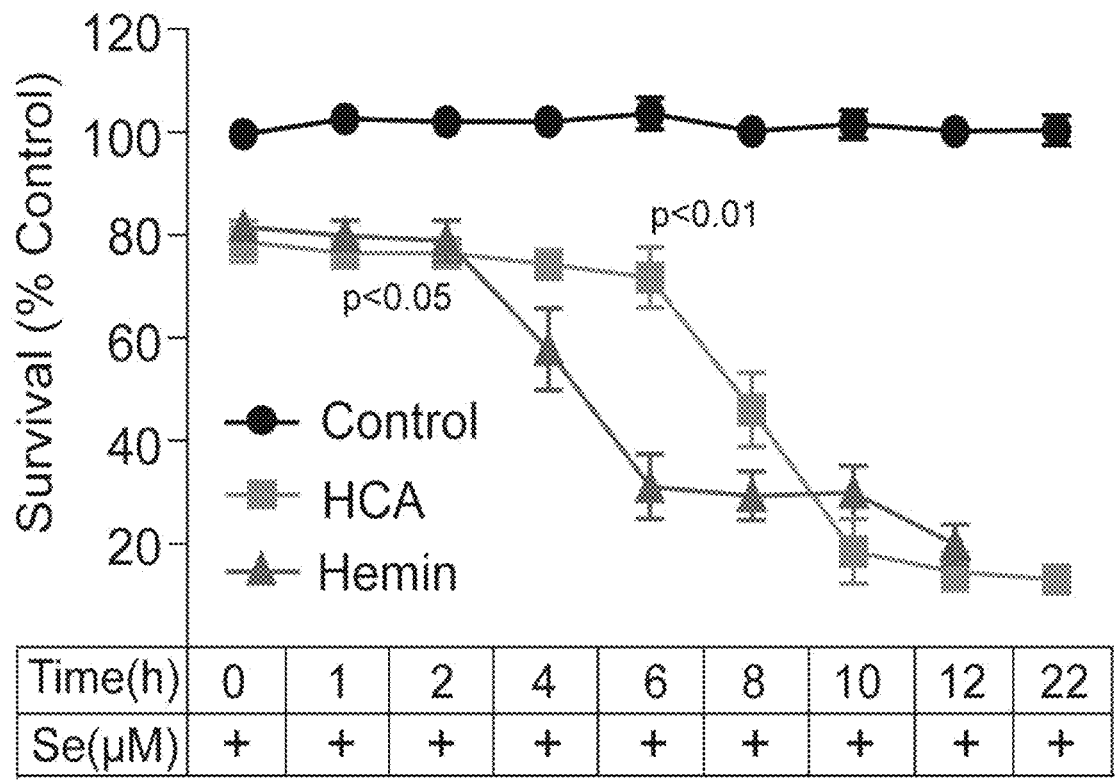
FIG. 2I is a graph showing percentages of survival of neurons treated with hemin or HCA followed by treatment with 1 μM Se (n=4). Time indicates hours after ferroptosis stress when neurons were treated with Se. All HCA survival measurements were taken at 24 h, all hemin measurements were taken at 16 h.
Figure 2J:
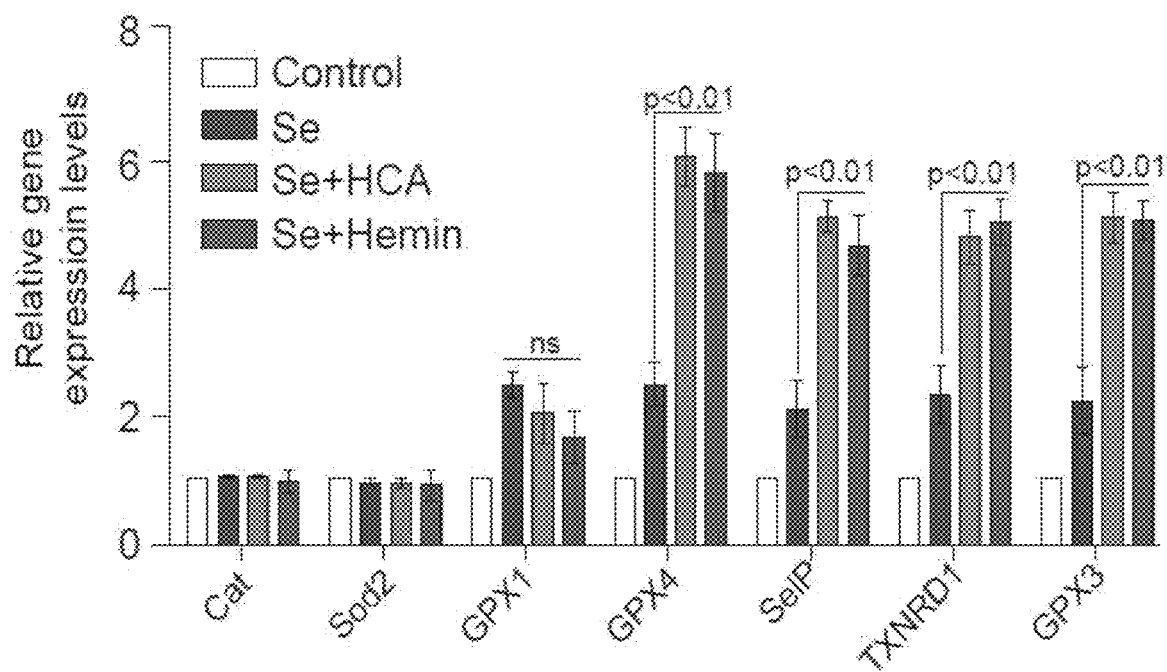
FIG. 2J is a graph of quantitative PCR results showing relative gene expression levels of antioxidant enzymes in neurons at 6 h post treatment with combined Se and HCA or hemin (n=5). All HCA survival measurements were taken at 24 h, all hemin measurements were taken at 16 h.
Figure 2K:
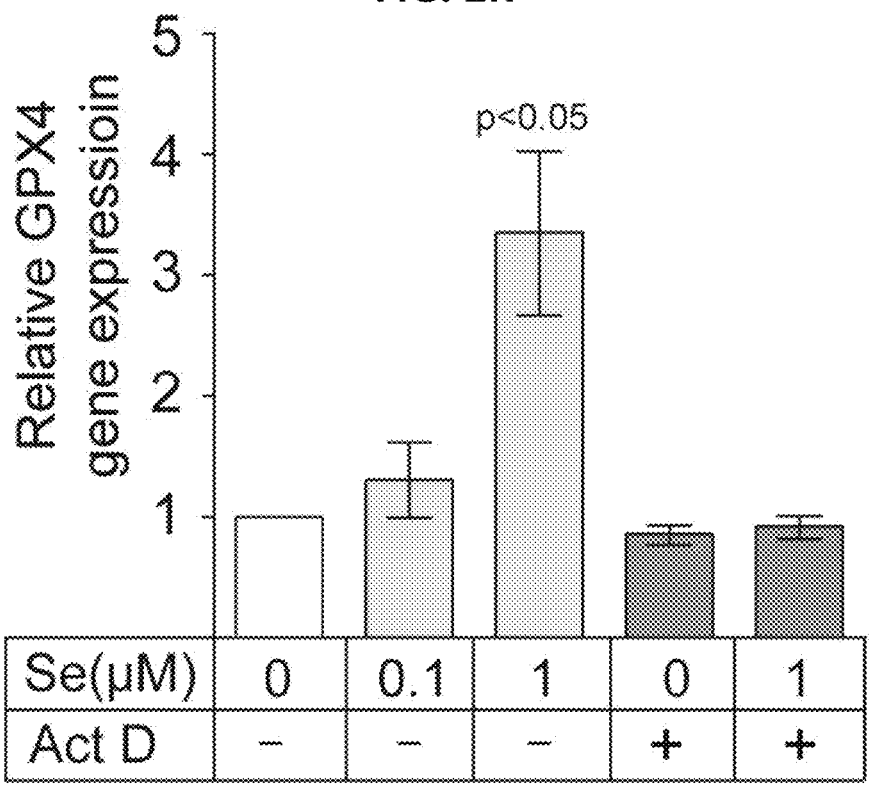
FIG. 2K is a graph of quantitative PCR results showing that transcription inhibitor actinomycin-D inhibited Se-dependent increase in GPX4 mRNA (n=4). All HCA survival measurements were taken at 24 h, all hemin measurements were taken at 16 h.
Figure 2L:
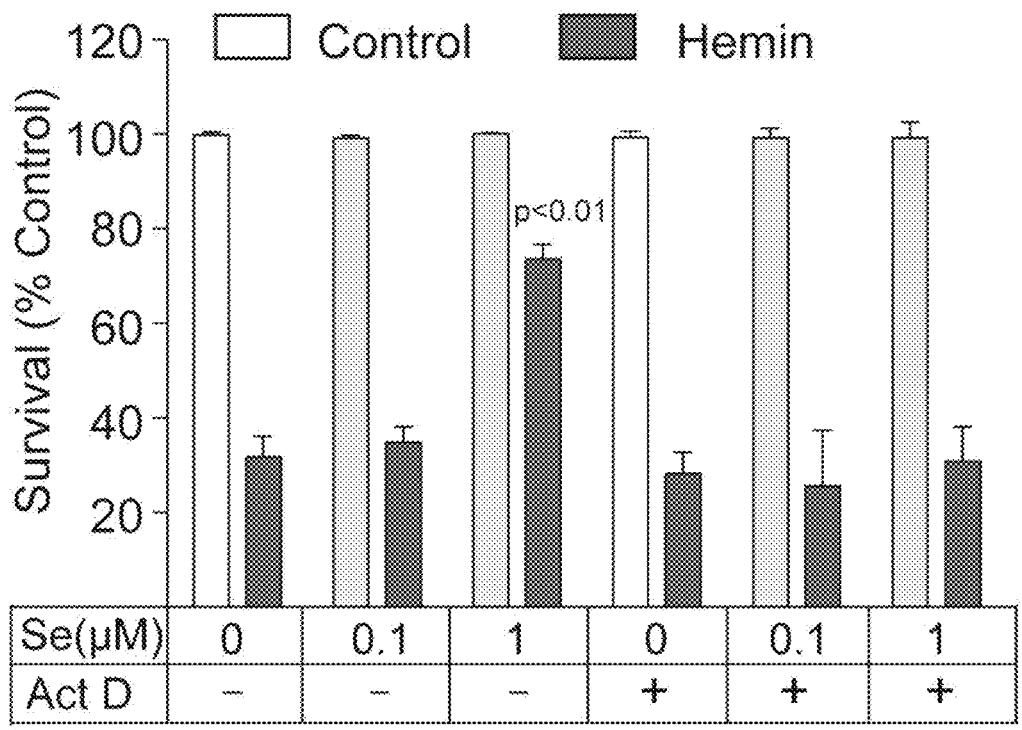
FIG. 2L is a graph showing that transcription inhibitor actinomycin-D abolished protection against hemin toxicity induced by Se, as determined by MTT measurement (n=3). All HCA survival measurements were taken at 24 h, all hemin measurements were taken at 16 h.
Figure 2M:
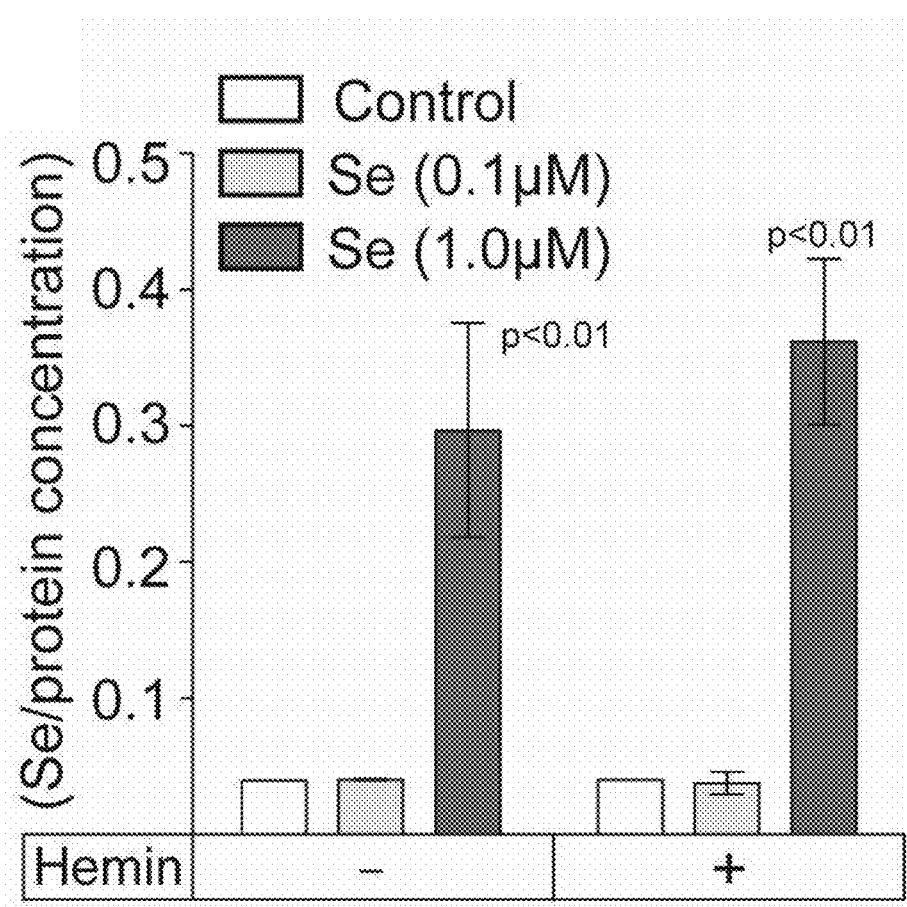
FIG. 2M is a graph showing inductively coupled mass spectrometry (ICP-MS) measurement of selenium levels normalized to protein concentration in cortical neurons treated with 80 μM hemin and/or Se.
Figure 32:
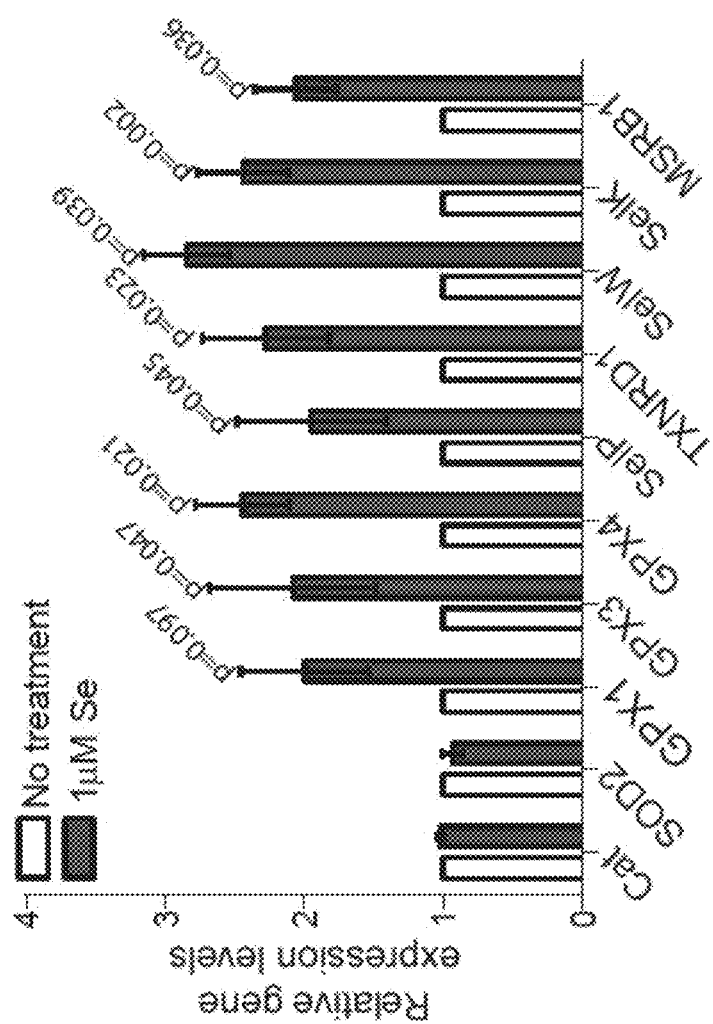
FIG. 32 is a graph showing quantitative PCR measurements of selenoproteins from neurons treated ±Se (1 μM) for six hours (n=4).
Figure 33:
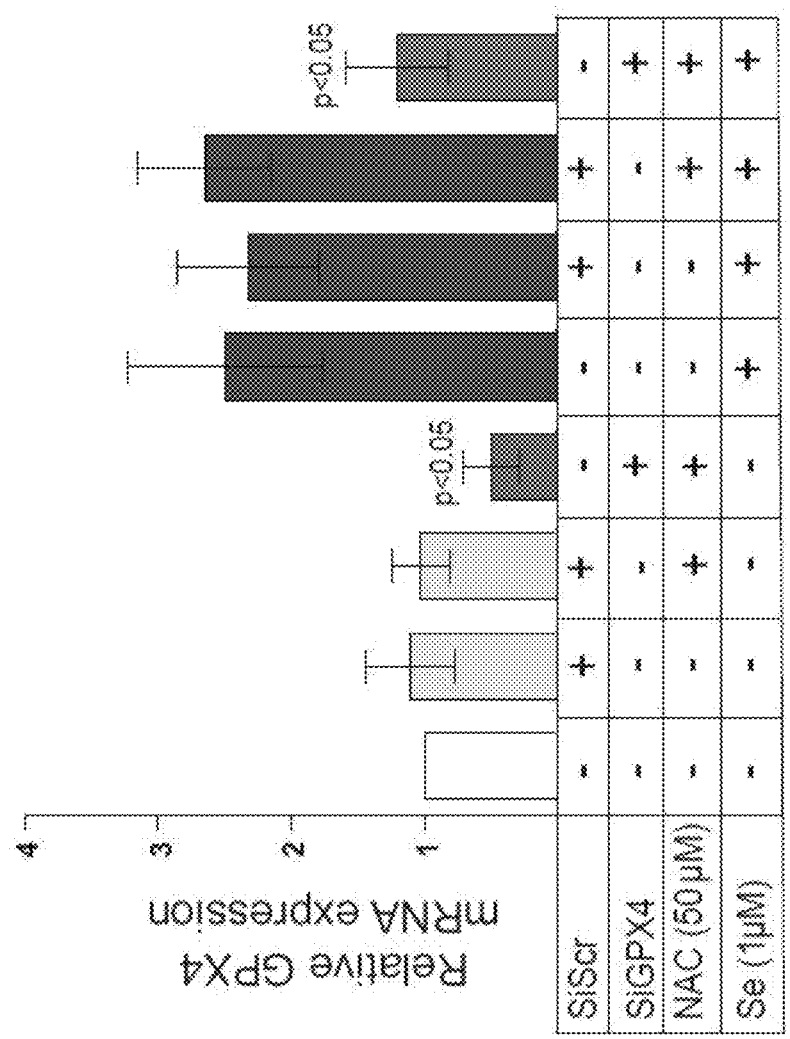
FIG. 33 is a graph showing quantitative PCR measurements of GPX4 from neurons transduced with siGPX4 targeted to sequences in exons 5-6 or with a scrambled sequence (SiScr), with or without NAC (50 μM) and/or Se (1 μM) treatment (n=3). 50 μM NAC treatment prevents cell death due to GPX4 molecular depletion.
Figure 34:
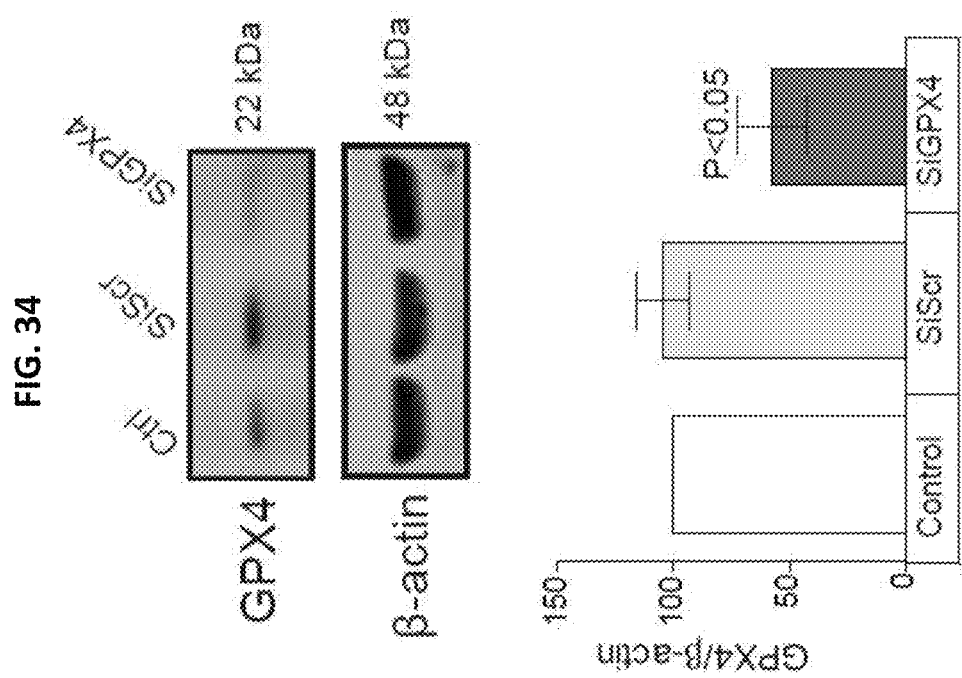
FIG. 34 depicts a Western blot image (top) and a graph (bottom) showing GPX4 levels in control neurons or neurons transduced with siGPX4 targeted to sequences in exons 5-6 or with a scrambled sequence (SiScr) (n=3).
Figure 35:
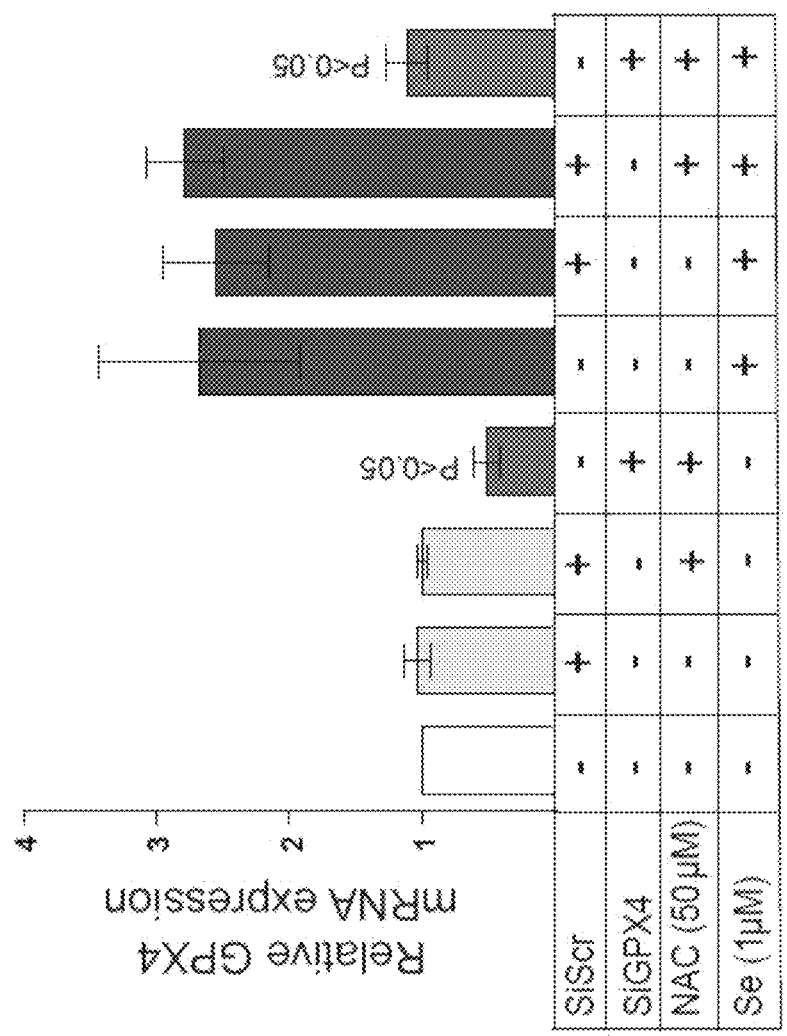
FIG. 35 is a graph showing quantitative PCR measurements of GPX4 from neurons transduced with siGPX4 targeted to exon 4 or with a scrambled sequence (Sicr), with or without NAC (50 μM) and/or Se (1 μM) treatment (n=3).
Figure 36:
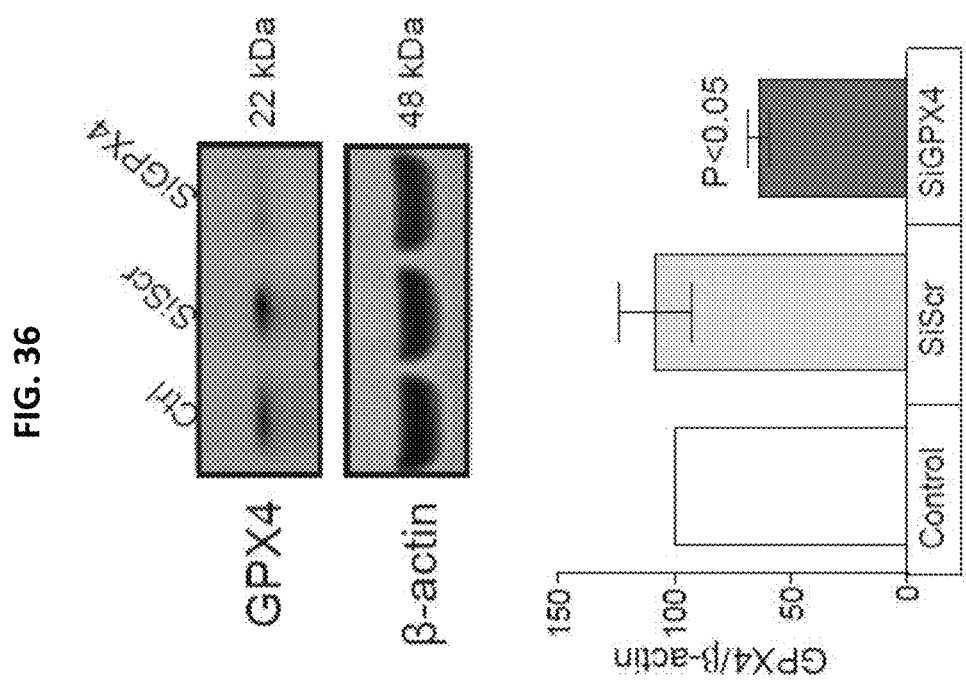
FIG. 36 depicts a Western blot image (top) and a graph (bottom) showing GPX4 levels in control neurons or neurons transduced with siGPX4 targeted to exon 4 or with a scrambled sequence (SiScr) (n=3).
Figure 37:
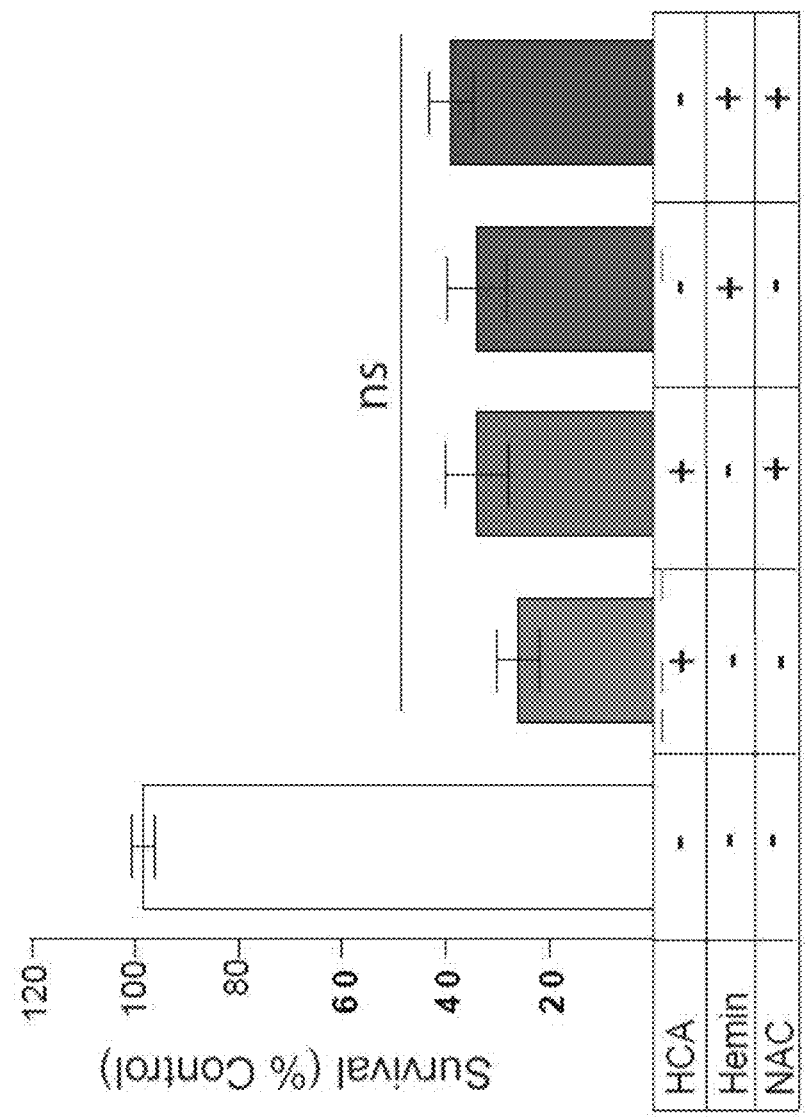
FIG. 37 is a graph showing survival rates as determined by MTT assay of cells co-treated with 50 μM NAC and 5 mM HCA for 24 hours or 80 μM hemin for 16 hours (n=3).
Figure 38:
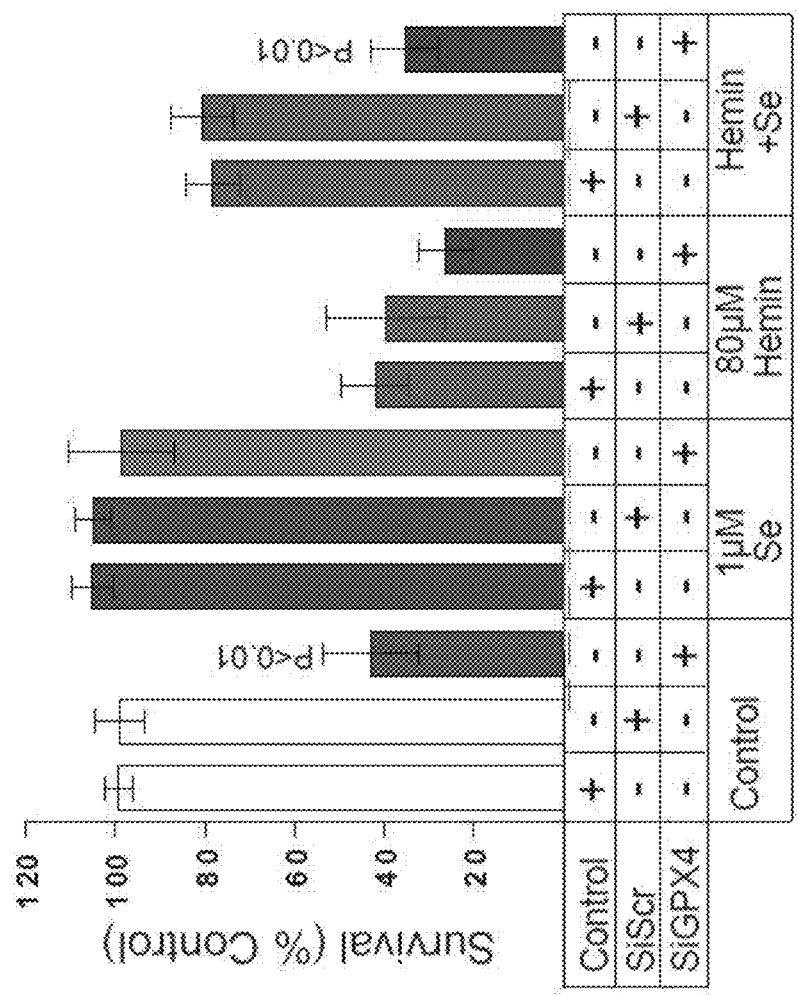
FIG. 38 is a graph showing survival rates as determined by MTT assay of control cells or cells transduced with siGPX4 targeting exons 5-6, or with a scrambled sequence (SiScr), following treatment with 80 μM hemin for 16 hours ±1 μM Se (n=3).
Figure 39:
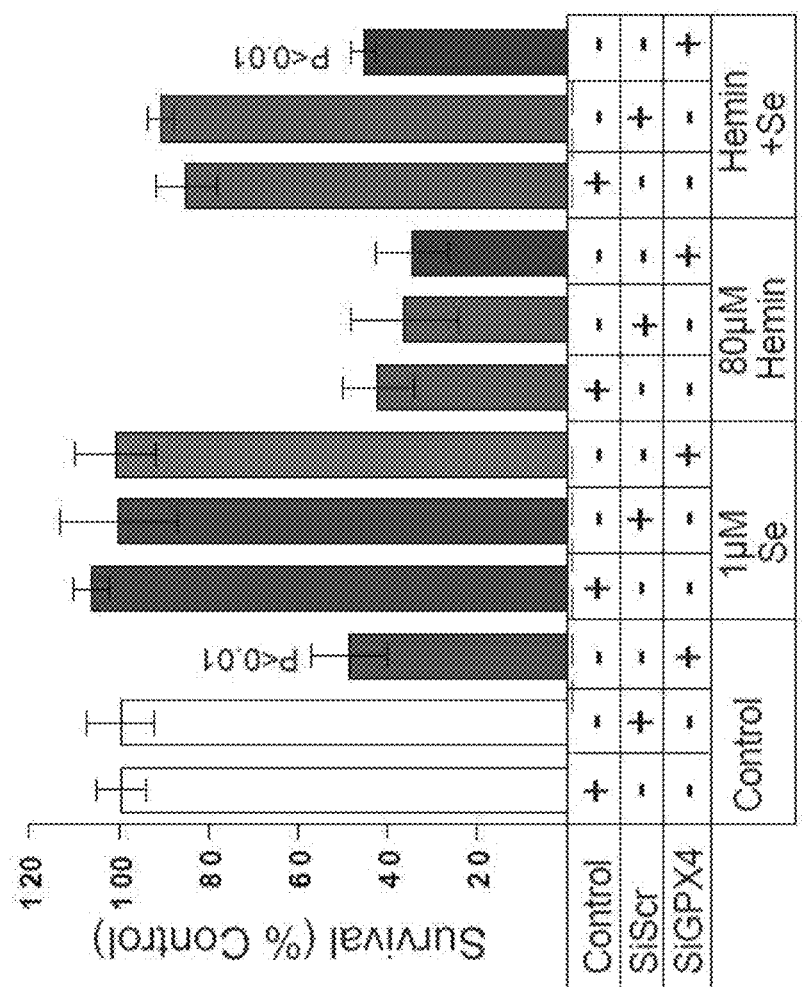
FIG. 39 is a graph showing survival rates as determined by MTT assay of control cells or cells transduced with siGPX4 targeting exon 4, or with a scrambled sequence (SiScr), following treatment with 80 μM hemin for 16 hours ±1 μM Se (n=3).

FIGS. 2A-2M demonstrate that sodium selenite (Se) treatment protects neurons from ferroptosis. Selenium is an essential micronutrient required for synthesis of selenocysteine, which is a critical feature of GPX4 and other selenoenzymes since it provides greater resistance to oxidative inactivation than enzymes that contain cysteine alone (See Snider et al., Biochemistry 52(32): 5472-81 (2013)). Sodium selenite ($SeO_3^{-2}$, hereafter referred to as Se) is used frequently to deliver selenium to cells in culture. Selenite is taken up into the cell, and is used to load selenocysteine cotranslationally (See Turanov et al., Adv Nutr 2(2): 122-8 (2011) and Turanov et al., Science 323259-261 (2009)). Accordingly, we tested whether Se treatment could provide neuroprotection. We found that Se dose-dependently inhibited ferroptosis induced by hemin or HCA, and like GPX4, Se could be added after toxin exposure and still manifest its protective effect (FIGS. 2A-2I, FIG. 1J). Unexpectedly, Se treatment also increased transcription of several selenoprotein genes, including GPX4 (FIG. 2J, FIG. 32). Moreover, the transcription inhibitor actinomycin-D abrogated protection from hemin-induced ferroptosis by Se (FIGS. 2K and 2L). Together, these findings indicate that Se can augment an adaptive transcriptional response to neuronal ferroptotic stresses and prevent death.

Figure 3A:
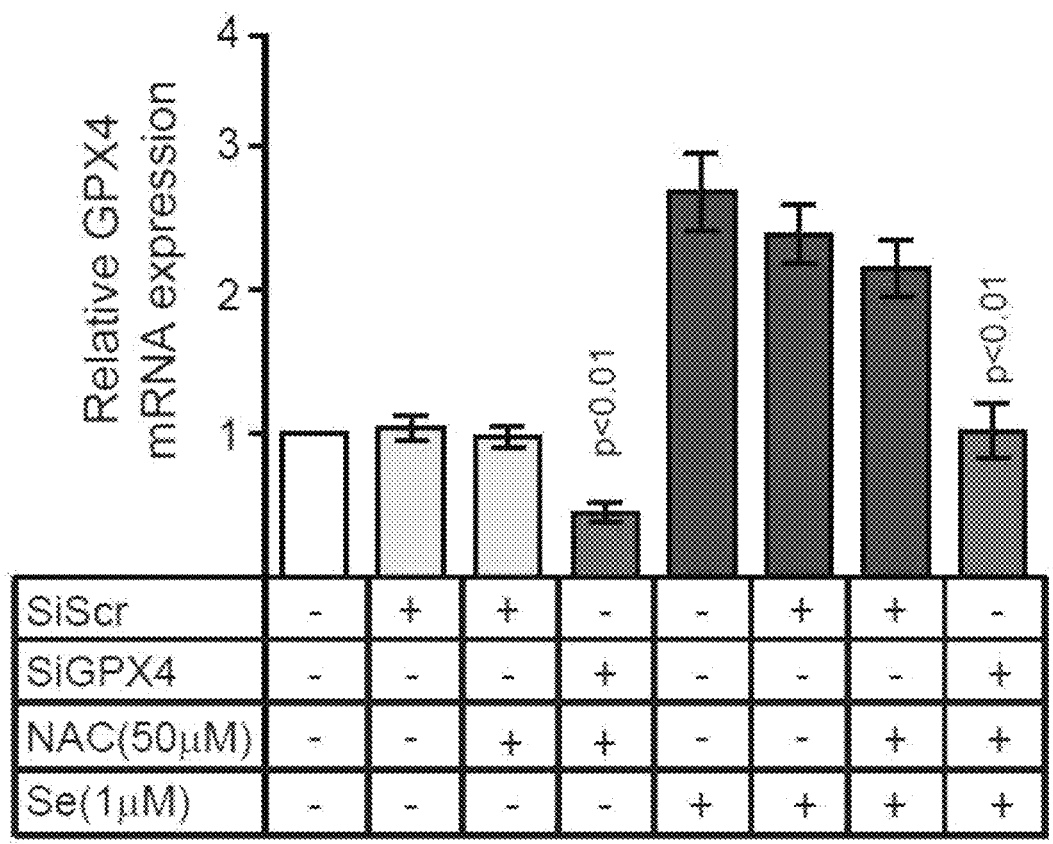
FIG. 3A is a graph showing relative GPX4 mRNA expression levels measured by quantitative PCR in neurons treated with 50 μM NAC, 1 μM Se, or both 50 μM NAC and 1 □μM Se following transfection with control scrambled siRNA (SiScr) or SiGPX4 to knockdown GPX4 (n=4).
Figure 3B:
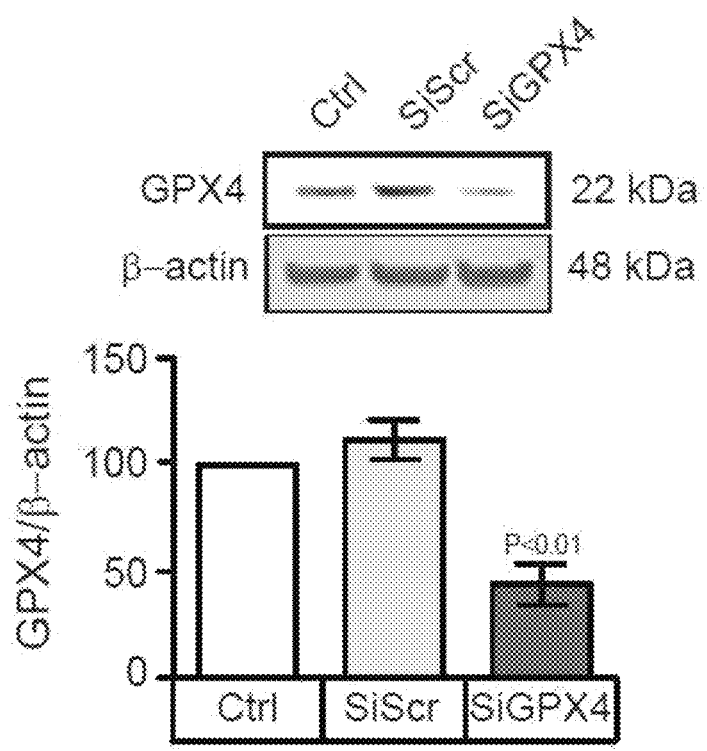
FIG. 3B is a Western blot showing GPX4 and β-actin protein levels in control (non-transfected) and SiScr or SiGPX4 transfected neurons treated with 50 μM NAC (top), and a graph quantifying the GPX4 protein levels normalized to the β-actin protein levels from the Western blot (n=3). 50 mM NAC treatment prevents cell death due to GPX4 knockdown.
Figure 3C:
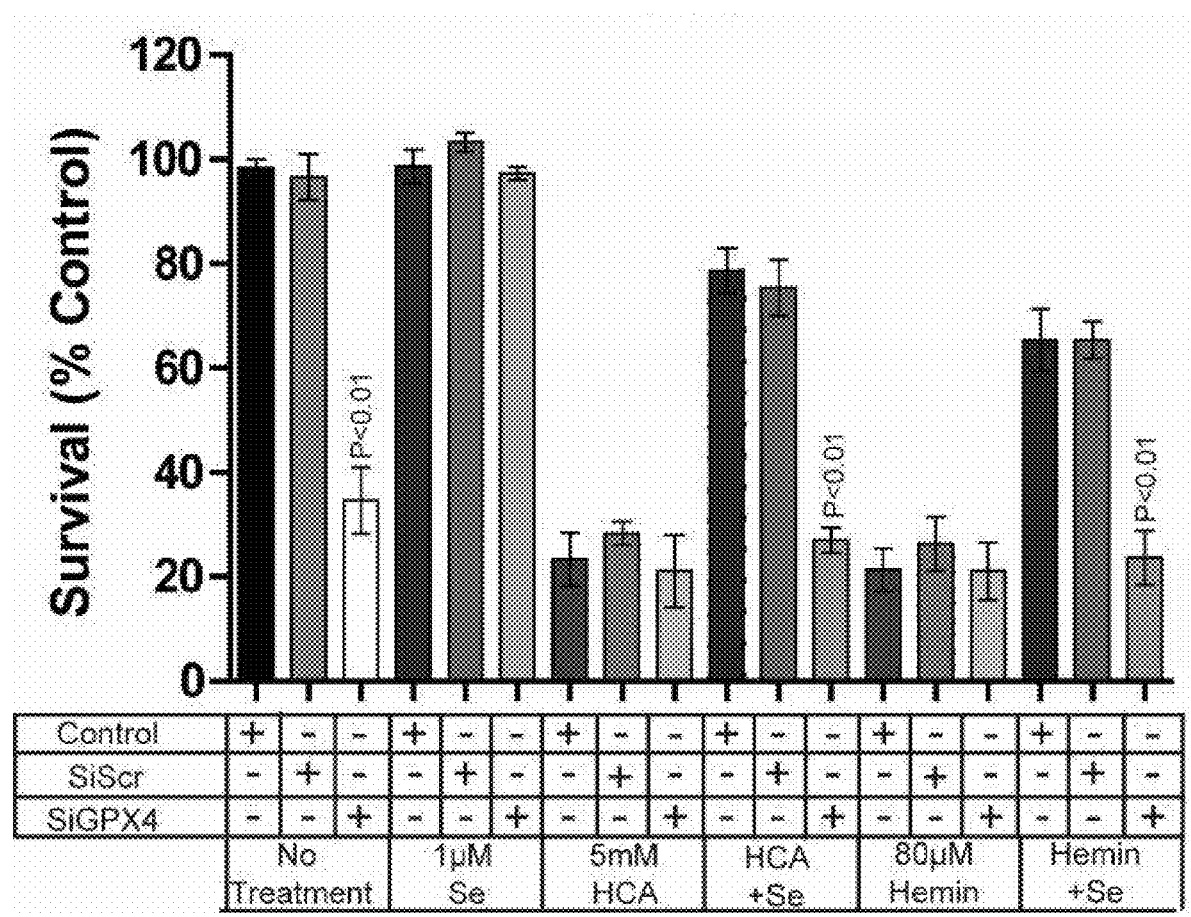
FIG. 3C is a graph showing the survival rates measured by MTT assay in control (non-transfected) and SiScr or SiGPX4 transfected cortical neurons untreated or treated with 1 μM Se, 5 mM HCA, 5 mM HCA+1 μM Se, 80 μM hemin, or 80 μM hemin+1 μM Se.

FIGS. 3A-3U demonstrate that knockdown of GPX4 inhibits protection by Se. To address whether transcriptional induction of GPX4 is necessary for the protective effects of Se, we reduced expression of GPX4 in neurons using siRNAs targeting three distinct GPX4 exons in separate experiments (FIGS. 3A, 3B, 33-36). Since reducing GPX4 expression levels alone leads to neuronal cell death within 12-16 hours (FIGS. 3C and 3F), cultures were supplemented with 50 µM of N-acetylcysteine (NAC), a versatile antioxidant, to maintain survival in the absence of GPX4. This concentration of NAC protected GPX4-deficient neurons without affecting GPX4 expression or sensitivity to hemin-induced or HCA-induced ferroptosis (FIGS. 3A, 33, 35, and 37). Exposure of cultured neurons to hemin and HCA resulted in cell death, whereas co-treatment with Se protected against ferroptosis except in cells where GPX4 levels were reduced (FIGS. 3C-3U, 38, and 39). These results demonstrated that GPX4 expression is necessary for Se-dependent protection against hemin and HCA-induced ferroptosis.

Example 3: Se Drives the Transcriptional Activators TFAP2C and Sp1 to Upregulate GPX4

Figure 4A:
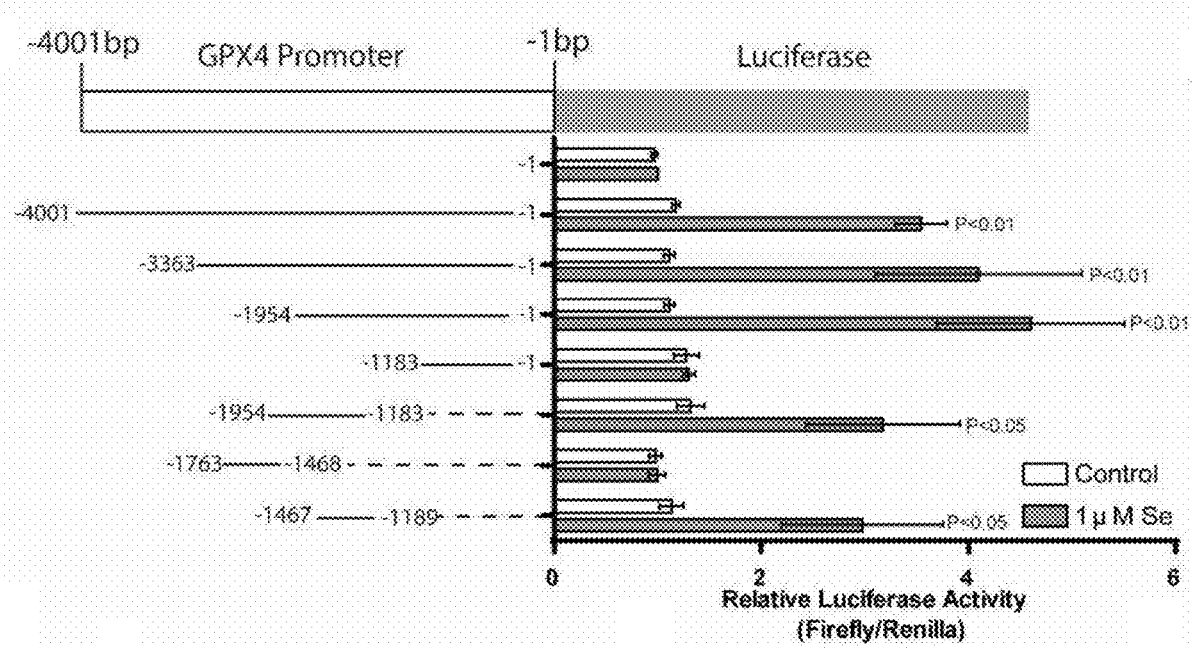
FIG. 4A is a graph showing various GPX4 promoter-luciferase reporter constructs and reporter assay results from neurons transfected with the indicated reporter constructs and untreated or treated with 1 μM Se (n=4). The reporter assay identified the promoter region of −1467 to −1189 bp as a selenite-dependent transcription factor binding site. All promoter reporter experiments were conducted in HT22 neuroblasts.
Figure 4B:
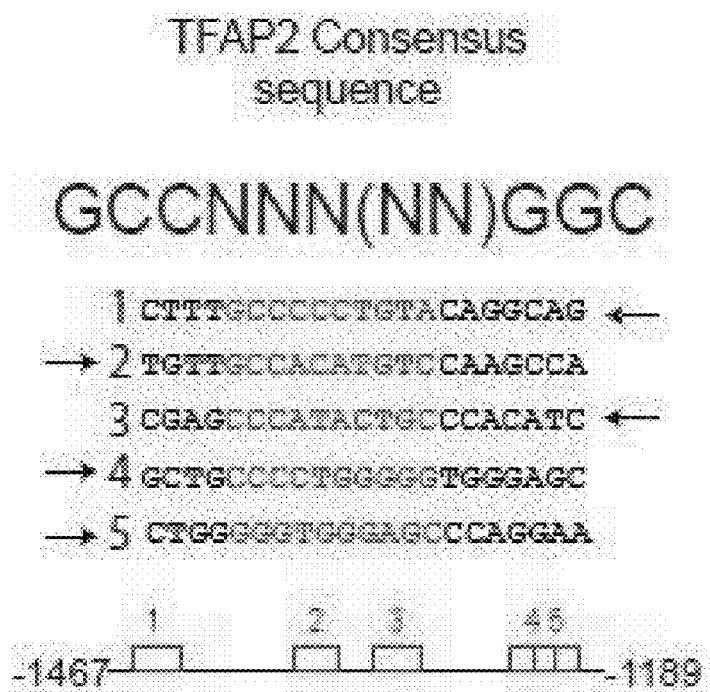
FIG. 4B indicates 5 TFAP2C and Sp1 binding sites in the GPX4 promoter region of −1467 to −1189 bp. (Top to bottom are SEQ ID NOS. 27, 22, 23, 24, 25 and 26, respectively) All promoter reporter experiments were conducted in HT22 neuroblasts.
Figure 4C:
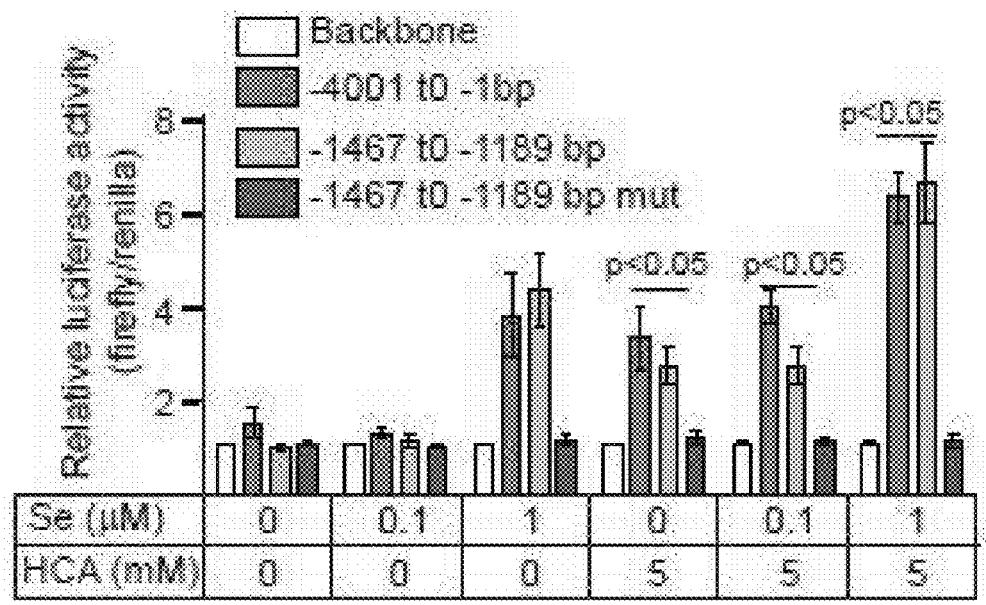
FIG. 4C is a graph showing GPX4 promoter-luciferase reporter assay results in neurons transfected with the vector (backbone) or the indicated GPX4 promoter-luciferase reporter constructs, and untreated or treated with Se, HCA, or Se+HCA (n=4). The results indicate that mutation of the top 3 homology sites for Sp1/TFAP2C resulted in abolishment of Se and HCA dependent transcription. The first, fourth, and fifth binding sites were mutated by converting GC to AT. All promoter reporter experiments were conducted in HT22 neuroblasts.
Figure 4D:
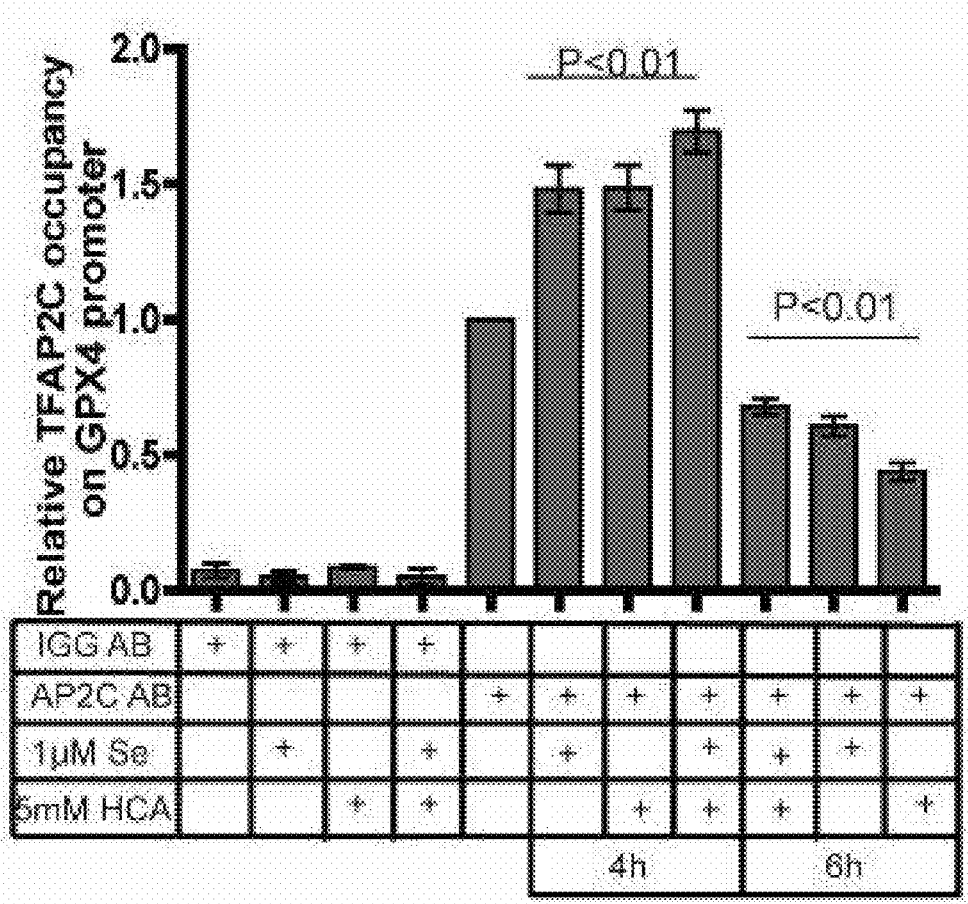
FIG. 4D is a graph of chromatin immunoprecipitation (chIP) results showing that HCA or Se treatment resulted in a transient increase in TFAP2C binding to the GPX4 promoter at 4 h post treatment (n=4).
Figure 4E:
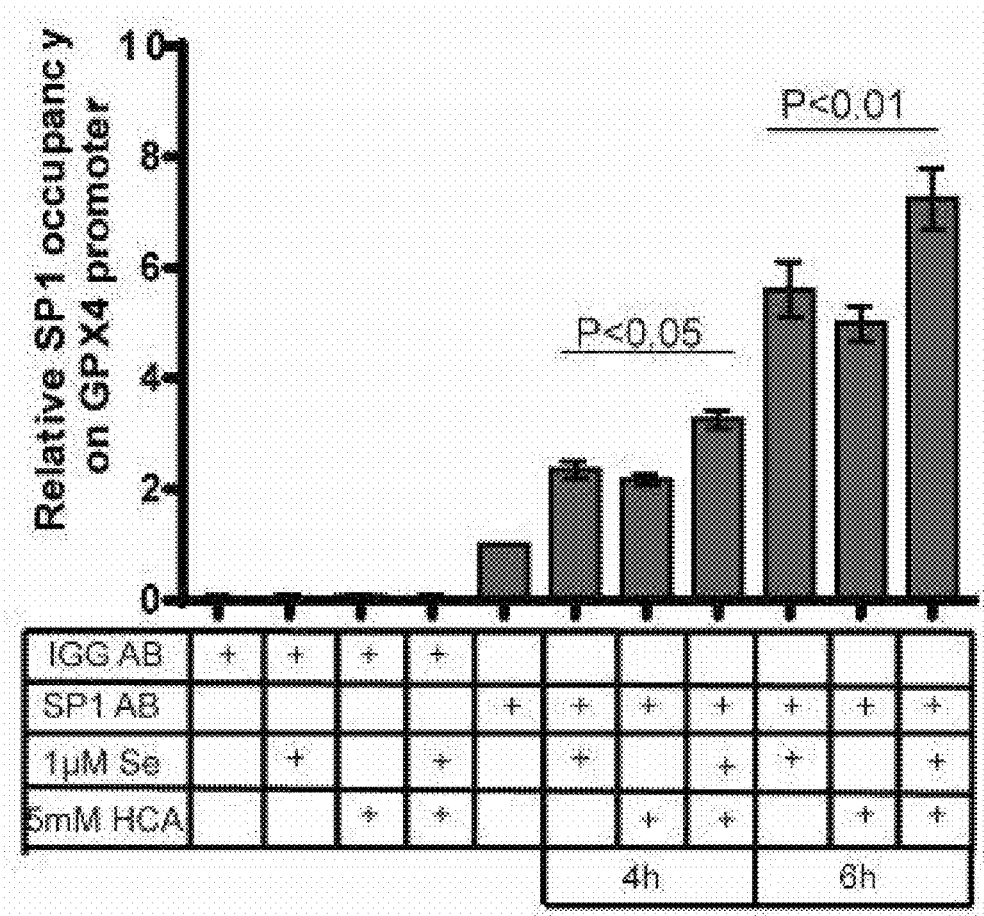
FIG. 4E is a graph of chromatin immunoprecipitation (chIP) results showing that HCA, Se, or HCA+Se treatment resulted in sustained occupancy of Sp1 at the GPX4 promoter region for up to 6 hours (n=4).
Figure 4F:
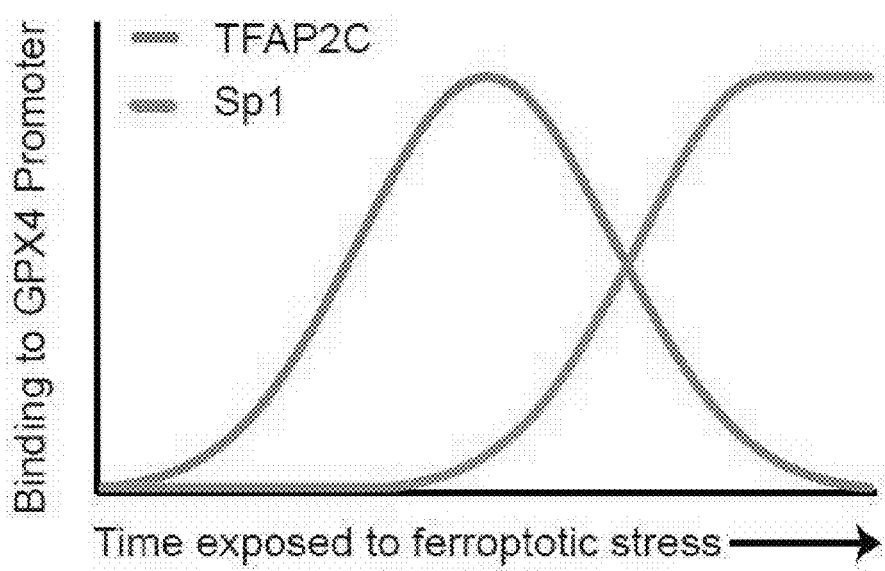
FIG. 4F is a graph illustrating the time course of TFAP2C and Sp1 occupancy at the GPX4 promoter during ferroptotic stress.
Figure 4G:
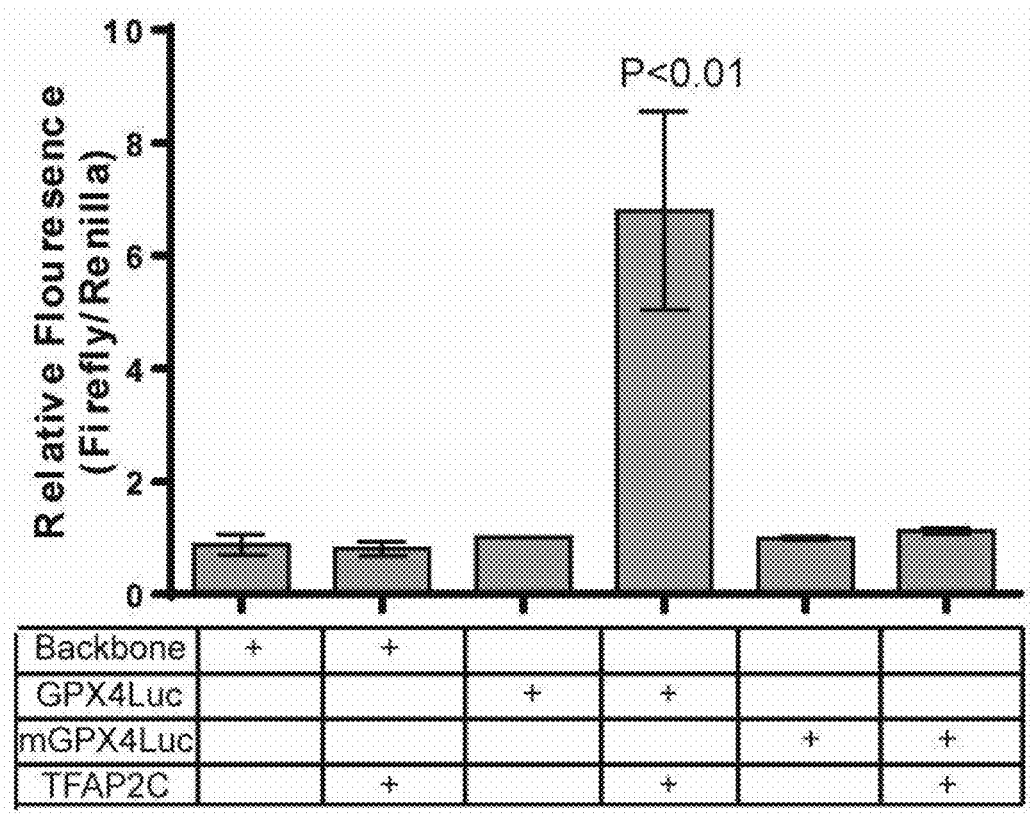
FIG. 4G is a graph showing wild type and mutant (m) GPX4 promoter luciferase reporter activity in cells overexpressing TFAP2C as compared to cells without TFAP2C overexpression (n=4). All promoter reporter experiments were conducted in HT22 neuroblasts.
Figure 4H:
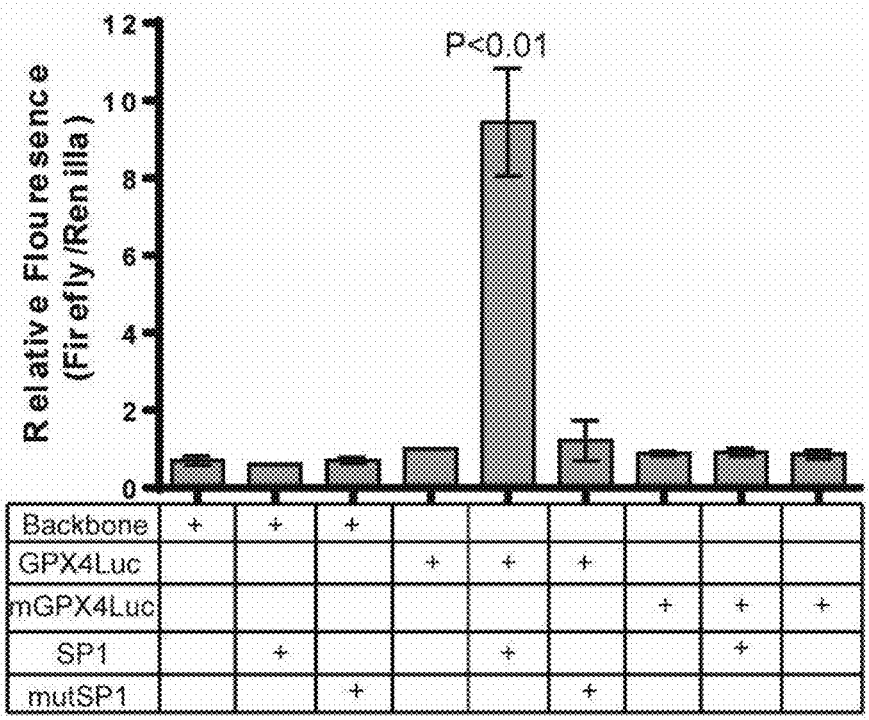
FIG. 4H is a graph showing wild type and mutant (m) GPX4 promoter luciferase reporter activity in cells overexpressing Sp1 as compared to cells without Sp1 overexpression and cells overexpressing binding mutant Sp1, which lacks a DNA binding domain in exon 5 (n=4). All promoter reporter experiments were conducted in HT22 neuroblasts.
Figure 4I:
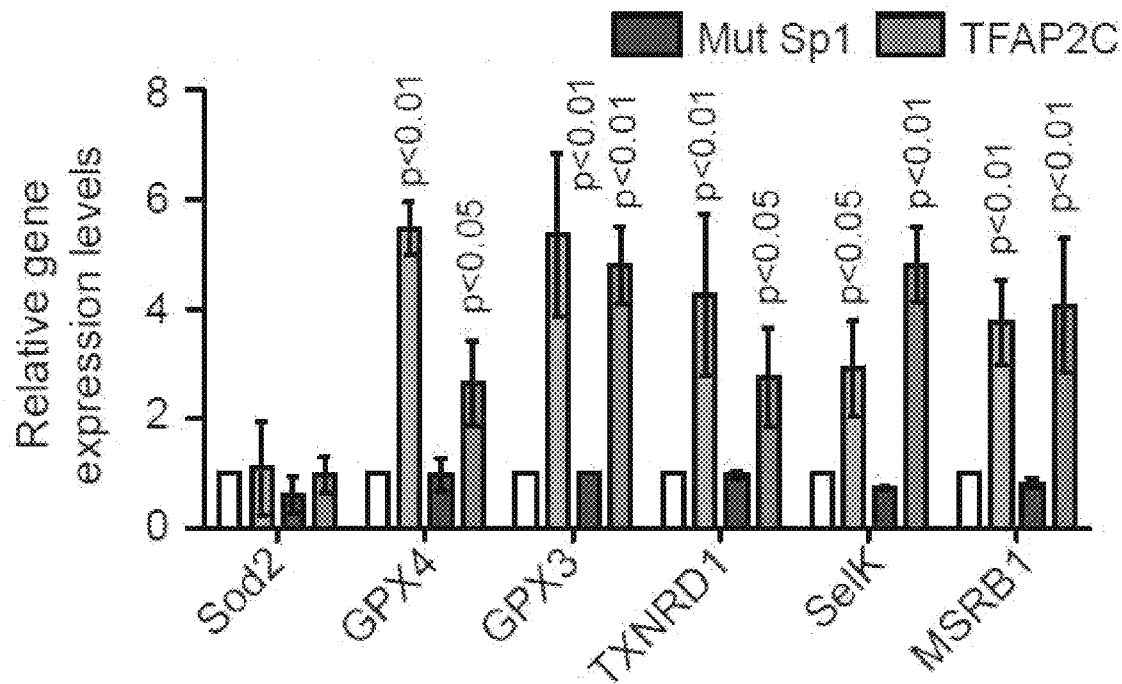
FIG. 4I is a graph of quantitative PCR results showing relative expression levels of antioxidant protein genes in control cells and cells overexpressing Sp1, binding mutant Sp1 and TFAP2C (n=5).
Figure 4J:
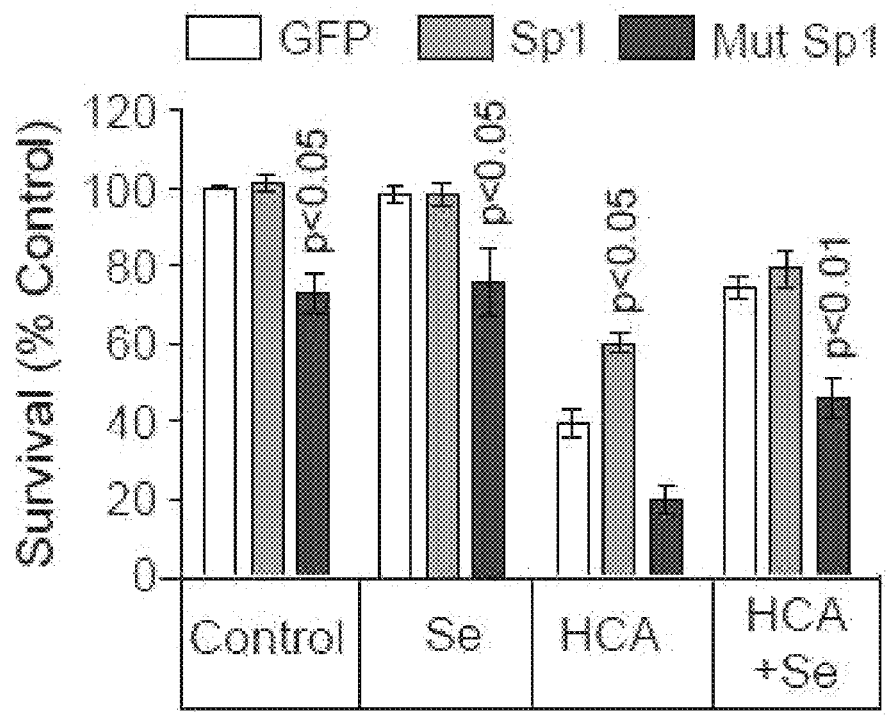
FIG. 4J is a graph of survival rates determined by MTT survival assay of control cortical neurons or neurons overexpressing Sp1 or binding mutant Sp1 that were untreated or treated with 5 mM HCA, 1 μM Se, or 1 μM Se+5 mM HCA, following 24 hours (n=4). The results demonstrate that Sp1 overexpression protected neurons from HCA, while binding mut Sp1 abolished protection from Se.
Figure 4K:
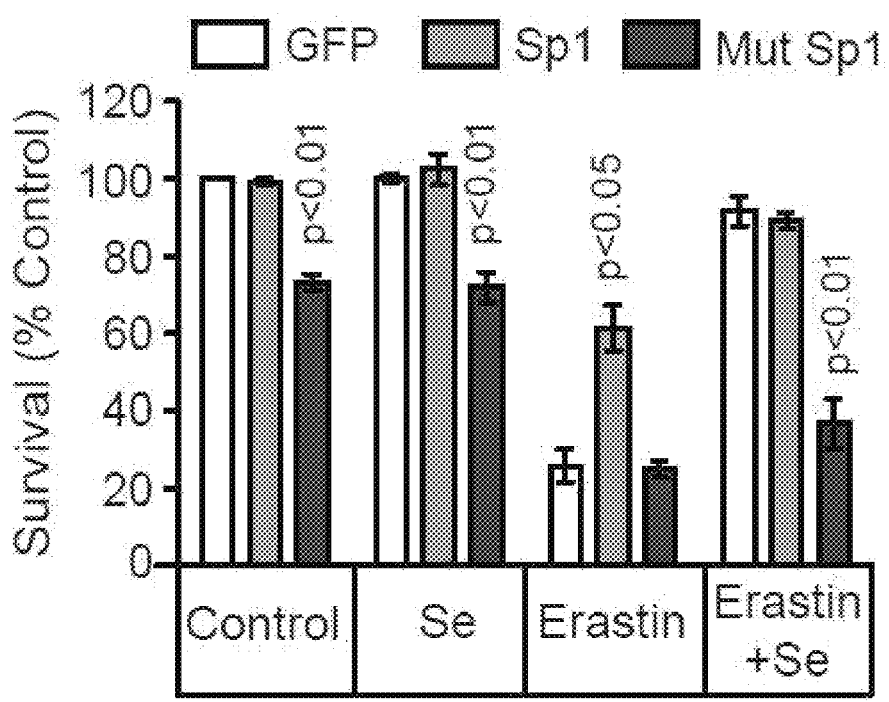
FIG. 4K is a graph of survival rates determined by MTT survival assay of control HT1080 neurons or neurons overexpressing Sp1 or binding mutant Sp1 that were untreated or treated with 1 μM erastin, 1 μM Se, or 1 μM erastin+1 μM Se, following 24 hours (n=4).
Figure 40:
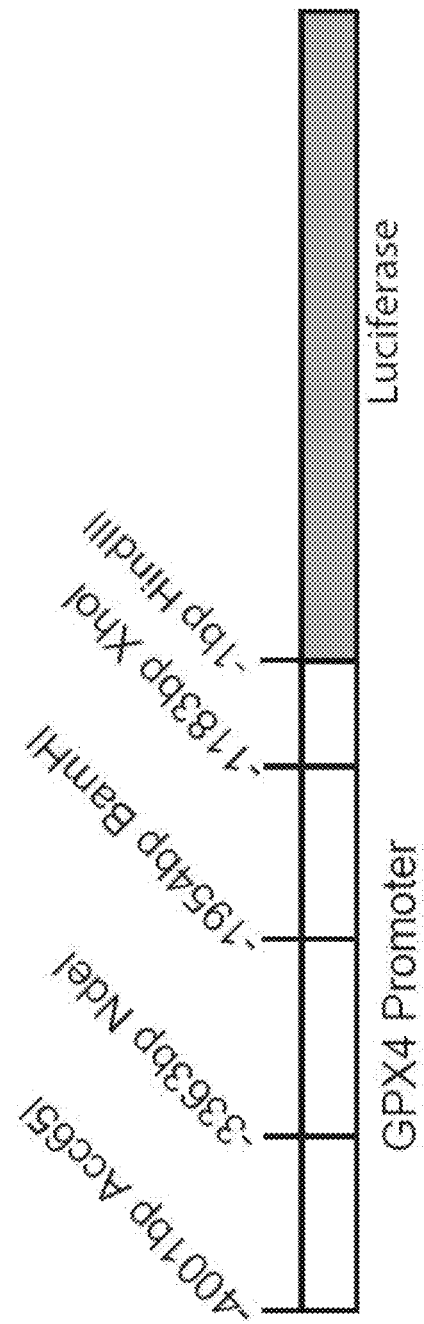
FIG. 40 is a restriction map depicting restriction enzyme sites for the GPX4 promoter reporter.
Figure 41:
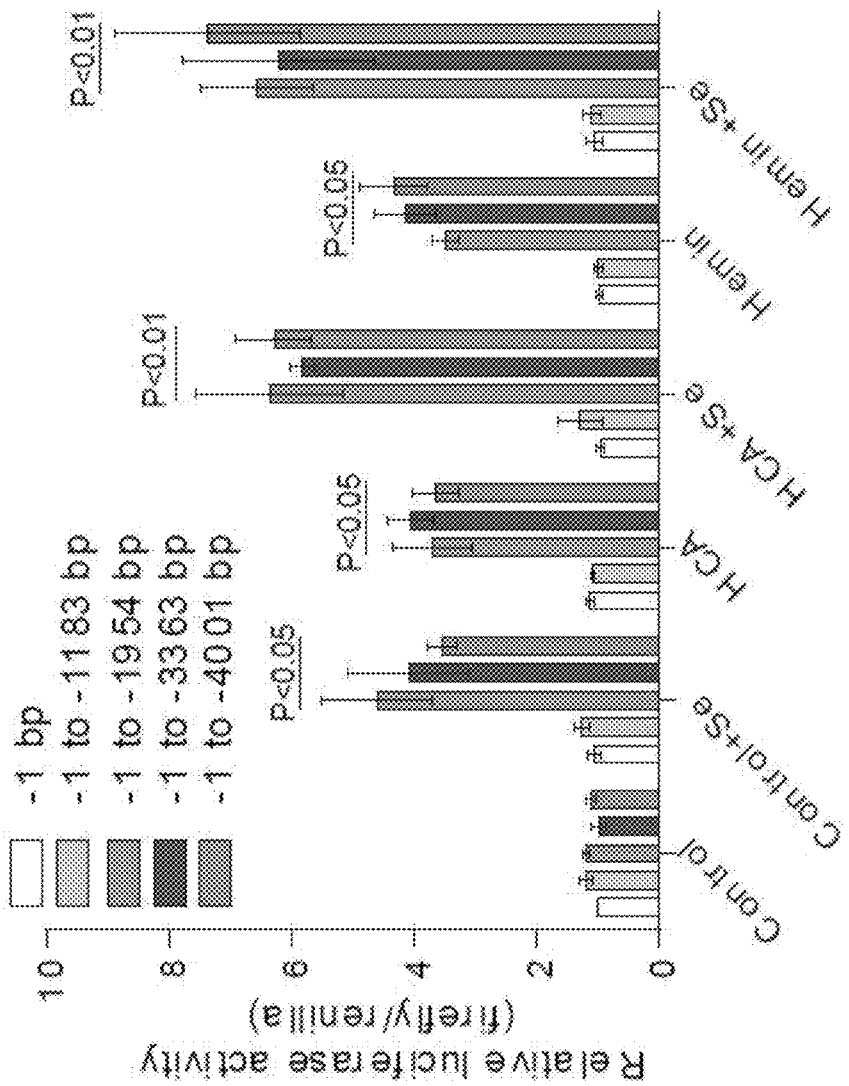
FIG. 41 is a graph showing luciferase activity from various truncated forms of the GPX4 promoter reporter in response to no treatment or six hours of treatment with 5 mM HCA or 80 μM hemin, ±1 μM Se (n=5).
Figure 42:
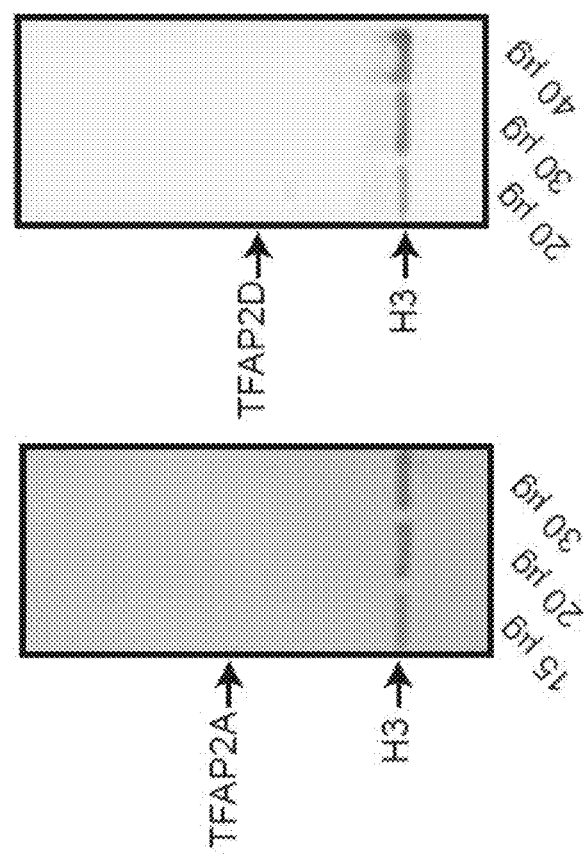
FIG. 42 is a pair of Western blots showing the dynamic range of TFAP2A (left) and TFAP2D (right) in neurons, with arrows pointing at the expected band site, which are not expressed at protein level (n=3).
Figure 43:
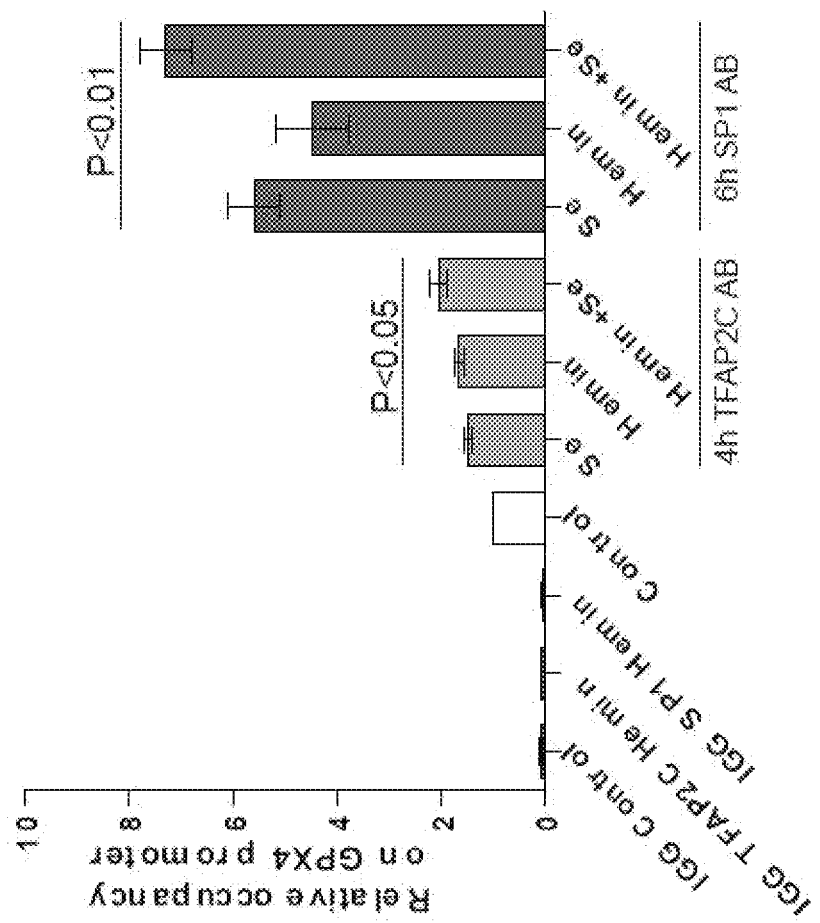
FIG. 43 is a graph showing chromatin immunoprecipitation (ChIP) results for the GPX4 promoter measuring binding of TFAP2C at 4 h and Sp1 at 6 h, without treatment or post-treatment with 80 μM hemin ±1 μM Se (n=3).
Figure 44B:
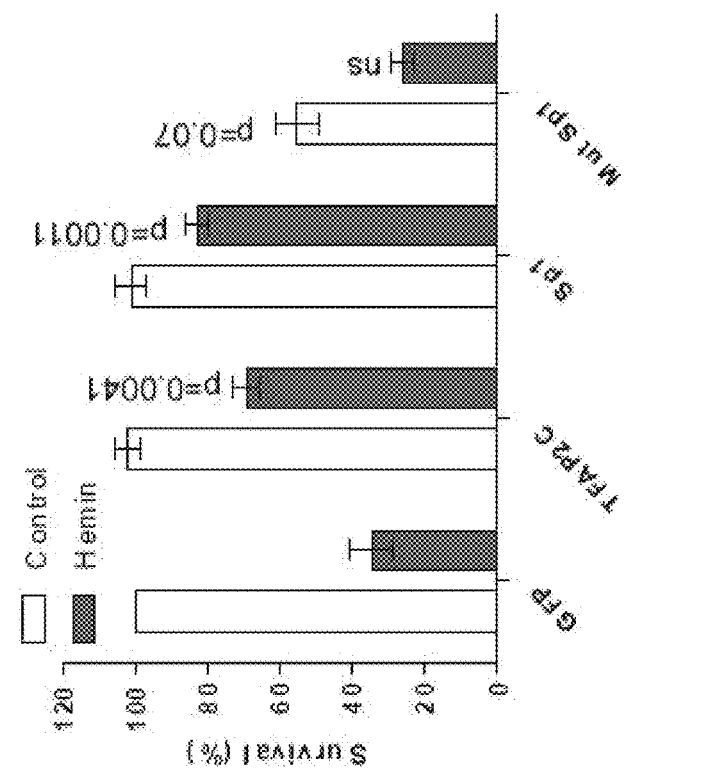
FIG. 44B is a graph showing survival rates as determined by MTT assay of neurons overexpressing GFP, TFAP2C, Sp1, or binding mutant Sp1 (Mut Sp1), following no treatment (control) or 16 hours of treatment with 80 μM hemin (n=4).
Figure 44A:
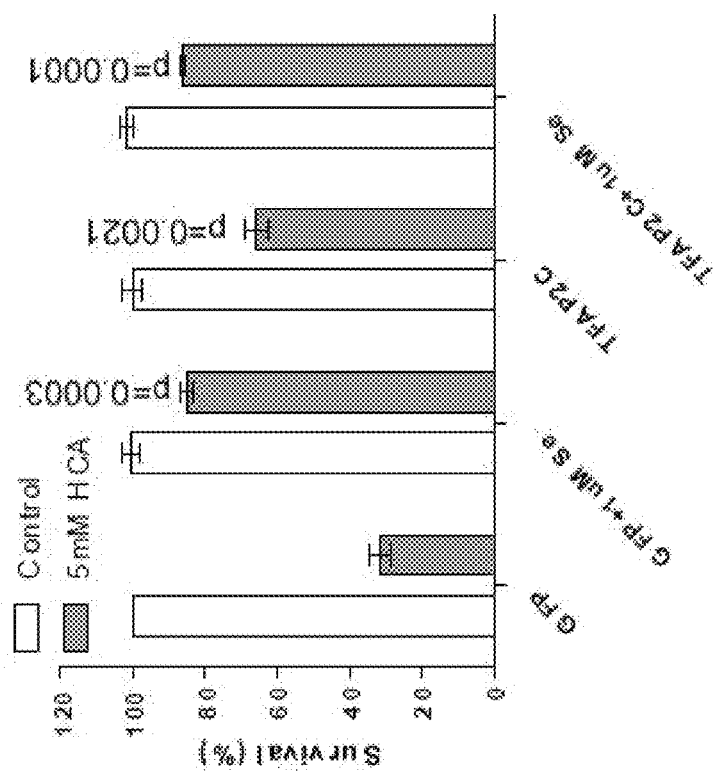
FIG. 44A is a graph showing survival rates as determined by MTT assay of neurons overexpressing TFAP2C, following no treatment (control) or 24 hours of treatment with 5 mM HCA (n=4). Neurons overexpressing TFAP2C show protection following HCA treatment.
Figure 45:
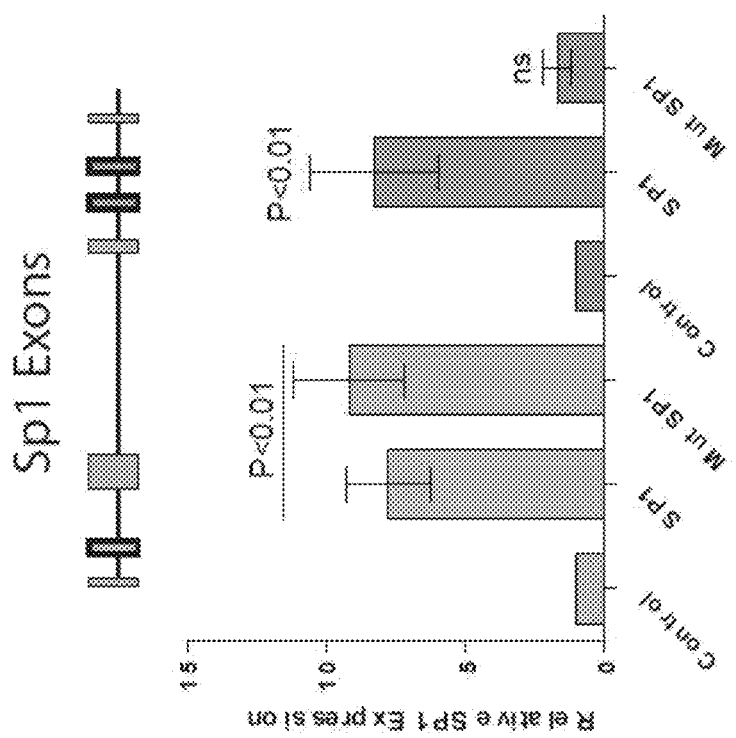
FIG. 45 depicts a schematic showing the exons of SP1 (top) and a graph (bottom) measuring SP1 expression levels in control cells or cells overexpressing SP1 or binding mutant SP1 (Mut Sp1) (n=4).
Figure 46:
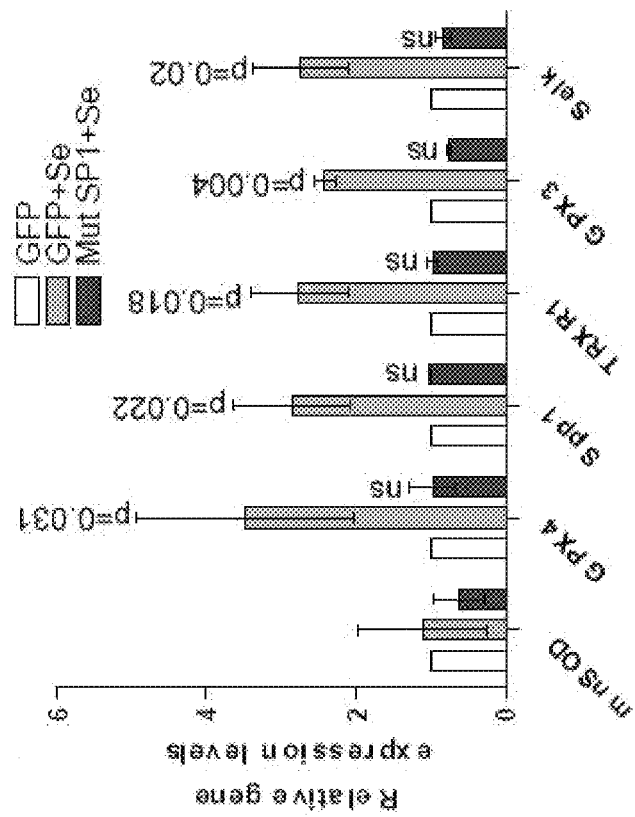
FIG. 46 is a graph showing quantitative PCR measurements of antioxidant genes from neurons overexpressing GFP or binding mutant SP1 (Mut Sp1) ±6 hours of treatment with 1 μM Se (n=3).
Figure 47:
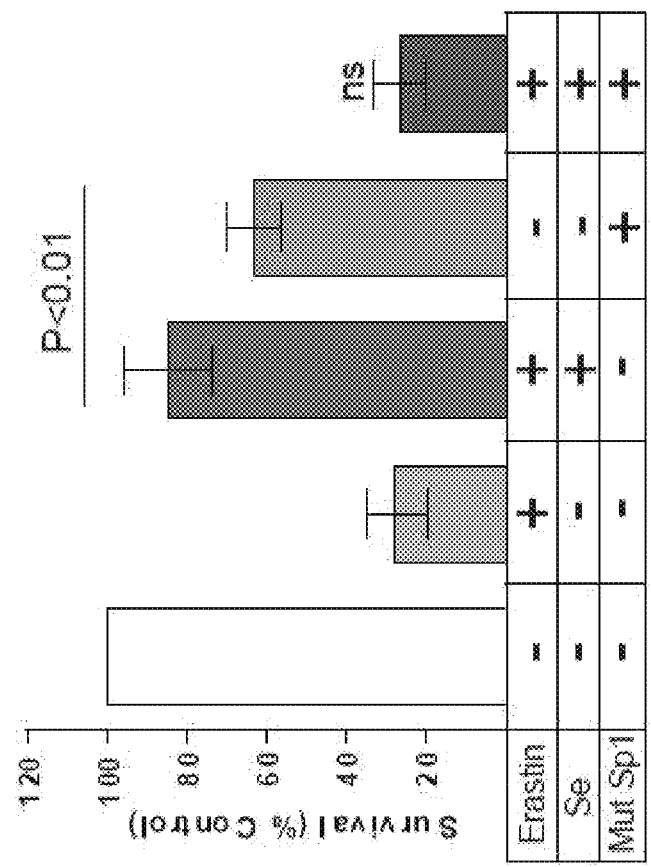
FIG. 47 is a graph showing survival rates as determined by MTT assay of neurons overexpressing GFP (control) or binding mutant SP1 (Mut Sp1) following no treatment or 24 hours of treatment with 5 μM erastin ±1 μM Se (n=4).
Figure 48B:
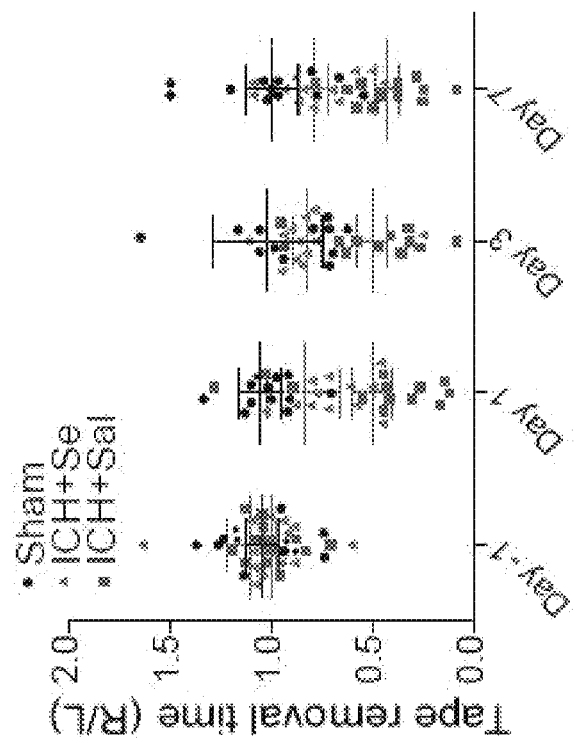
FIG. 48B is a scatterplot of behavioral outcomes in the sensory neglect task for up to seven days post ICH ±2.5 μM ICV injection of Se (n=12).
Figure 48A:
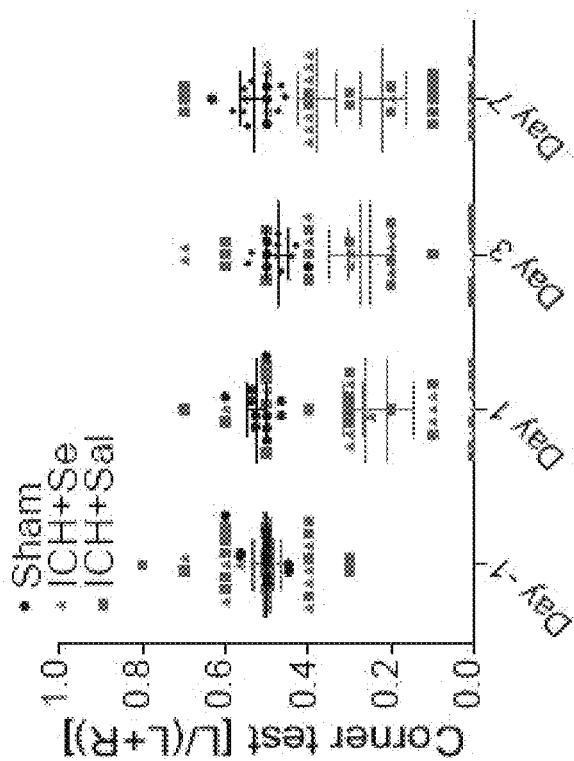
FIG. 48A is a scatterplot of behavioral outcomes in the spatial neglect task for up to seven days post ICH ±2.5 μM ICV injection of Se (n=12).

FIGS. 4A-4K demonstrate that selenite drives transcriptional activators TFAP2C and Sp1. Since the data establish a link between Se-induced GPX4 transcription and protection from neuronal ferroptosis, we examined the GPX4 promoter and upstream region to better understand how transcription of GPX4 (and other genes in the protective selenome) are induced by Se. Transcription assays using a transiently transfected reporter construct containing the 4 kb region upstream from the GPX4 translation start site showed significant induction of GPX4 promoter activity in neurons exposed to protective Se concentrations. Targeted deletions of this upstream region revealed that the −1189 bp and −1467 bp sub-region was critical for Se-induced promoter activity (FIGS. 4A, 40, and 41). Analysis of this critical sub-region identified five motifs with similarity to Transcription Factor AP-2 family binding sites (5'-GCCNNN (NN)GGC-3'; (SEQ ID NO:27), FIG. 4B) (where sequences 1 to 5 are SEQ ID NOS:22, 23, 24, 25 and 26, respectively) (See Williamson et al., Genomics 35(1):262-4 (1996)). Mutation of three of these motifs blocked Se-induced GPX4 promoter activity (FIG. 4C). The TFAP-2 family is highly conserved in mice and humans and is represented by five isoforms (TFAP2A-E) (See Eckert et al., Genome Biol 6(13): 246 (2005)). Since TFAP2C was the only isoform we detected in mouse primary neurons (FIG. 11 (panels A and B), FIG. 42, FIG. 67A, and FIG. 67B), we focused on this isoform. Chromatin immunoprecipitation (ChIP) assays showed that Se exposure significantly increased TFAP2C occupancy on the Se-responsive region of GPX4 (FIGS. 4D and 43). This binding to the upstream region was significantly stronger at 4 vs. 6 hours post-Se treatment (FIG. 4D). Since GPX4 expression levels are elevated longer than 4 hours following Se exposure, additional transcription factors likely sustain the activation of GPX4 transcription. TFAP2C binding overlaps with Sp1 in other gene promoters (See Orso et al., BMC Genomics 11: 355 (2010); Yang et al., J Biol Chem 270(15): 8514-20 (1995)), and our lab previously showed that Sp1 DNA binding is significantly induced by ferroptotic oxidative stress (See Ryu et al., J Neurosci 23(9): 3597-606 (2003)). Thus, we examined whether Se exposure induced Sp1 binding to the Se-responsive region of the GPX4 upstream region. ChIP studies showed that Se exposure induced the Sp1 occupancy of this region, but unlike TFAP2C, this occupancy was significantly greater at 6 vs 4 hours post Se treatment (FIGS. 4E and 4F, 11 (panels C and D), and 43). To confirm that the Se-responsive region of GPX4 could mediate TFAP2C and Sp1 dependent regulation, human TFAP2C or Sp1 were overexpressed with either a wild-type GPX4 reporter or a mutant reporter lacking the TFAP2C binding sites. These studies showed that TFAP2C and Sp1 activated only wild-type reporter, which suggests that TFAP2C and Sp1 act via the same DNA binding site(s) (FIGS. 4G and 4H). In addition, over-expression of TFAP2C or Sp1 drove mRNA expression for several ferroptotic-stress response genes and protected neurons from hemin or HCA-induced ferroptosis (FIGS. 4I, 4J, 44A, and 44B). By contrast, overexpression of a mutant Sp1 protein with a zinc-finger DNA binding domain deletion (FIG. 45) did not induce expression of ferroptotic-stress response genes or provide protection from HCA (FIGS. 4I, 4J, 44A, 44B, and 46). Overexpression of the mutant Sp1 protein also reduced protection mediated by Se treatment in primary neurons or HT1080 fibrosarcoma cells (FIGS. 4J, 4K, and 47). Together, these findings indicate that Se provides protection from ferroptosis, at least in part, by activating gene expression regulated by TFAP2C and Sp1.

Figure 5A:
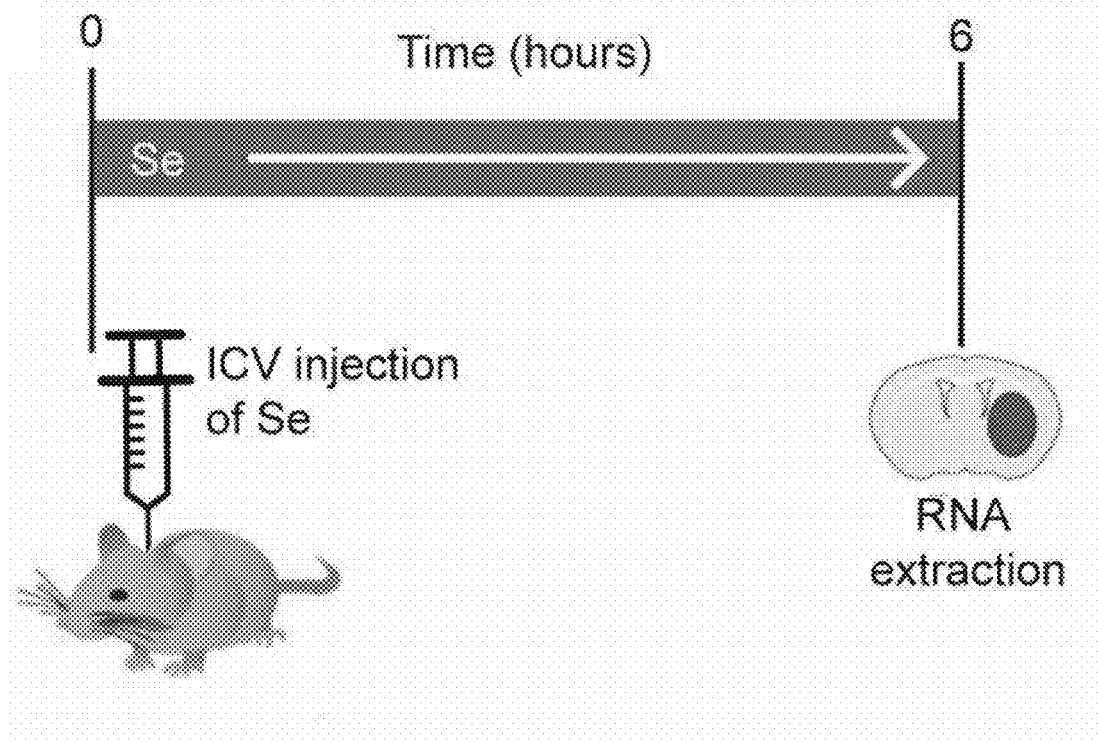
FIG. 5A is a schematic showing ICV injection of dose dependent Se (1-5 μM) and collection of striatum 6 hours later to extract RNA for quantitative PCR.
Figure 5B:
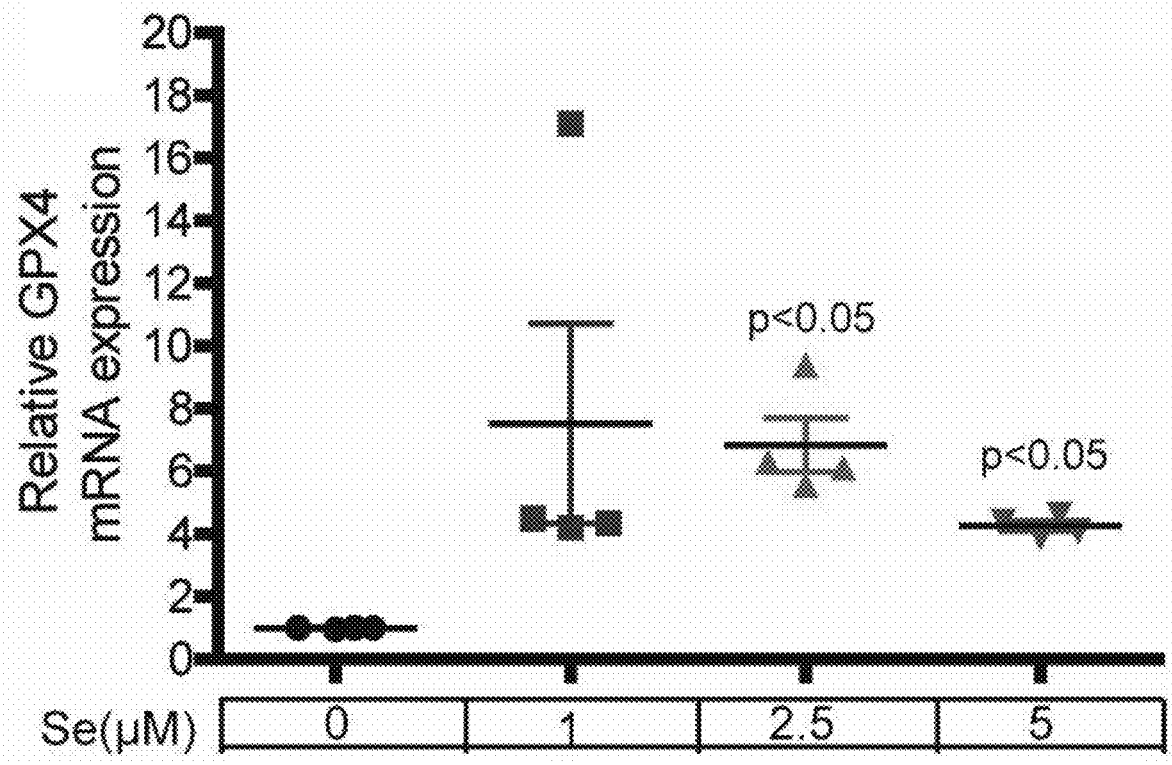
FIG. 5B is a graph showing relative GPX4 mRNA levels in whole striatum according to the study design of FIG. 5A. The results indicate that there was a significant increase in GPX4 mRNA with 2.5 μM of Se by ICV injection (n=4).
Figure 5C:
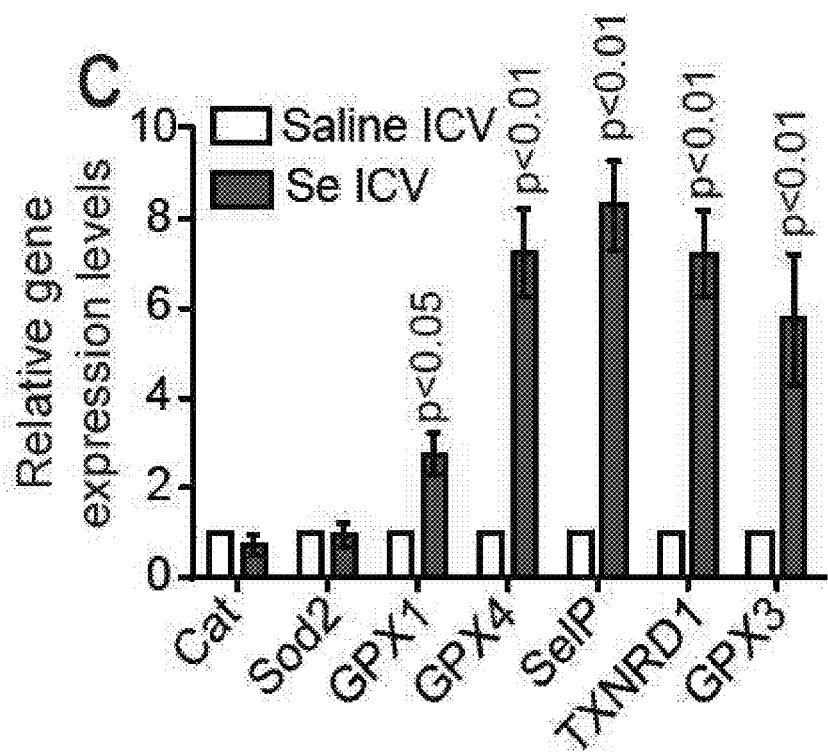
FIG. 5C is a graph showing relative mRNA levels of indicated genes in whole striatum according to the study design of FIG. 5A. The results indicate that there was a significant increase in mRNA levels of other selenoprotein genes besides GPX4 with 2.5 μM of Se by ICV injection (n=4).
Figure 5D:
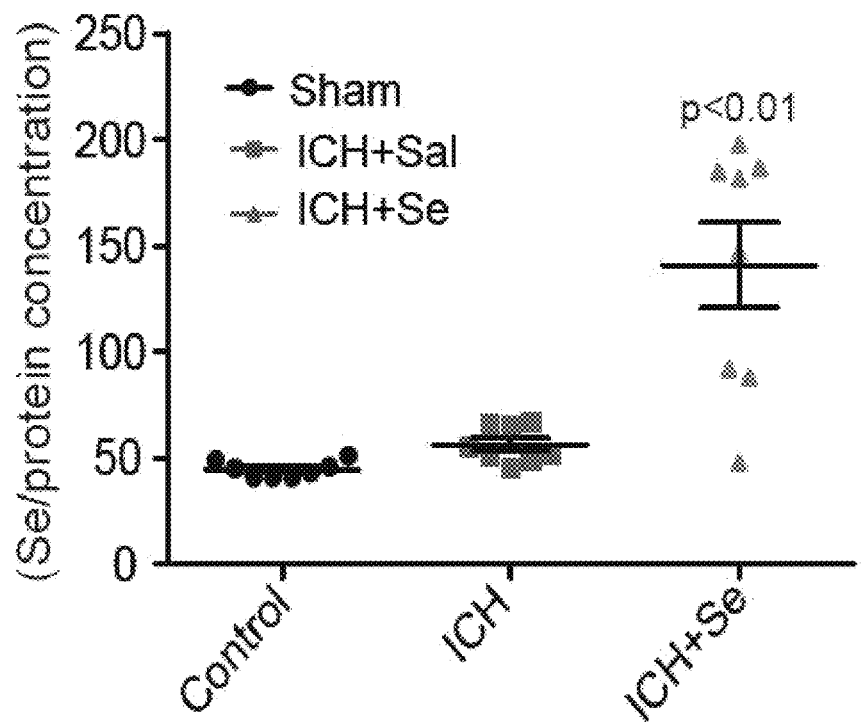
FIG. 5D is a graph showing inductively coupled mass spectrometry (ICP-MS) measurement of selenium levels normalized to protein concentration following ICH and ICH+2.5 μM Se in striatum at 24 h post treatment (n=8).
Figure 5E:
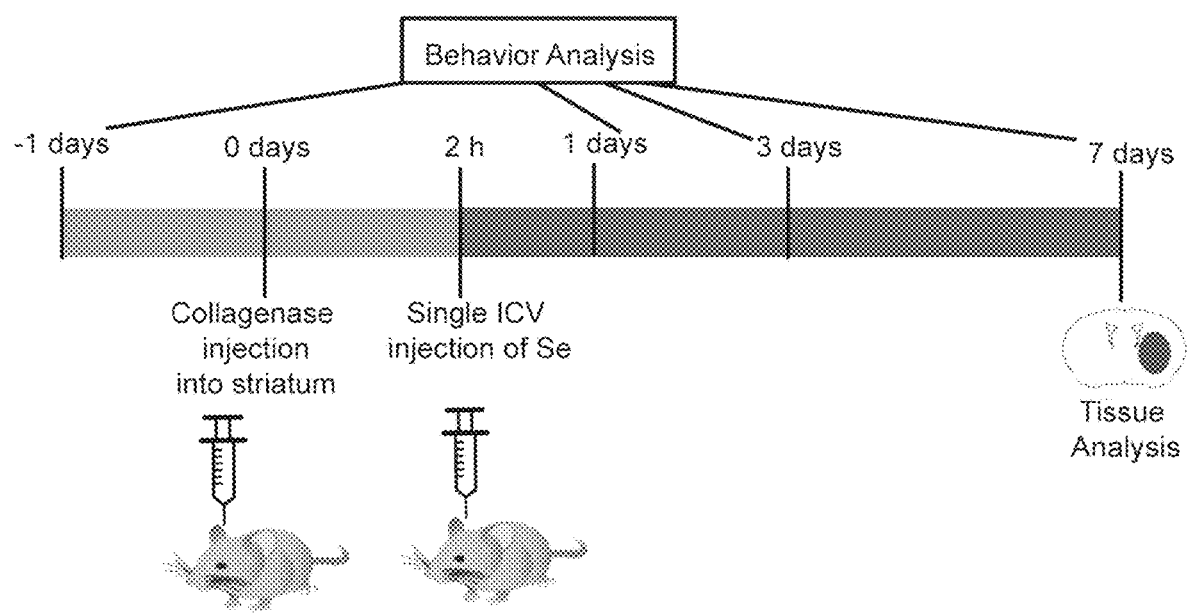
FIG. 5E is a schematic of experimental design where collagenase was injected into the striatum of mice to induce ICH on day 0 followed by a single ICV injection of 2.5 μM Se 2 hours after ICH. Tissue analysis was conducted on day 7, and behavior analysis was conducted on days −1, 1, 3, and 7.
Figure 5F:
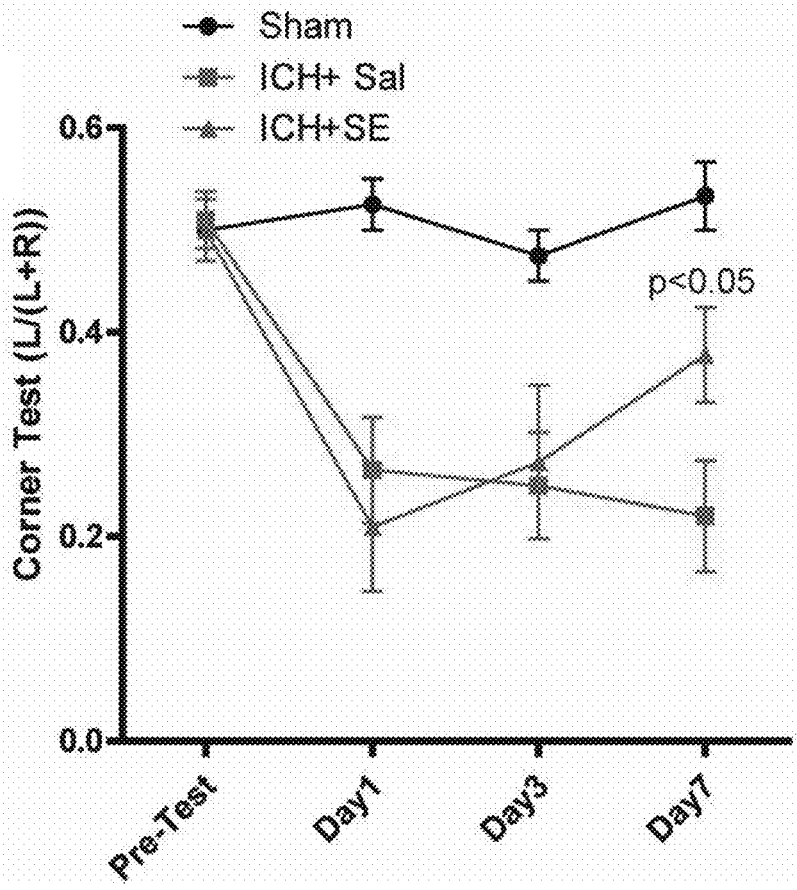
FIG. 5F is a graph of corner test results on different experiment days in sham injected mice and in collagenase injected ICH mice treated with saline or Se (n=12). The results indicate that single Se treatment improved outcomes in the spatial neglect task.
Figure 5G:
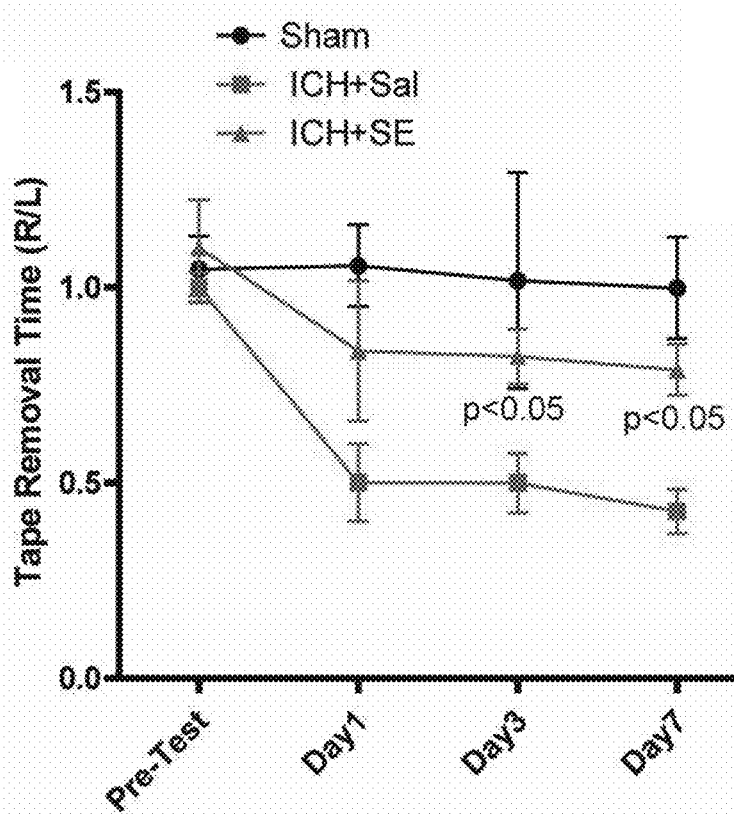
FIG. 5G is a graph of tape removal test results on different experiment days in sham injected mice and in collagenase injected ICH mice treated with saline or 2.5 μM ICV Se (n=12). The results indicate that single Se treatment improved outcomes in the sensory neglect task.
Figure 5H:
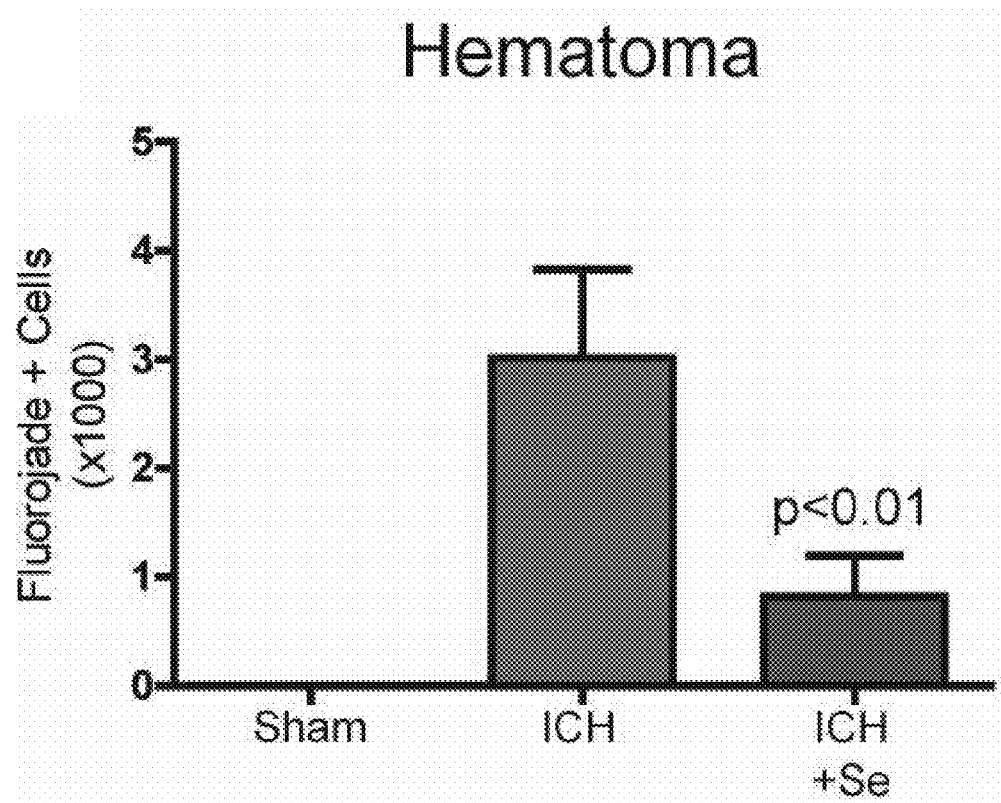
FIG. 5H is a graph showing numbers of fluorojade positive cells in hematomas of sham injected mice and in collagenase injected ICH mice treated with saline or Se.
Figure 5I:
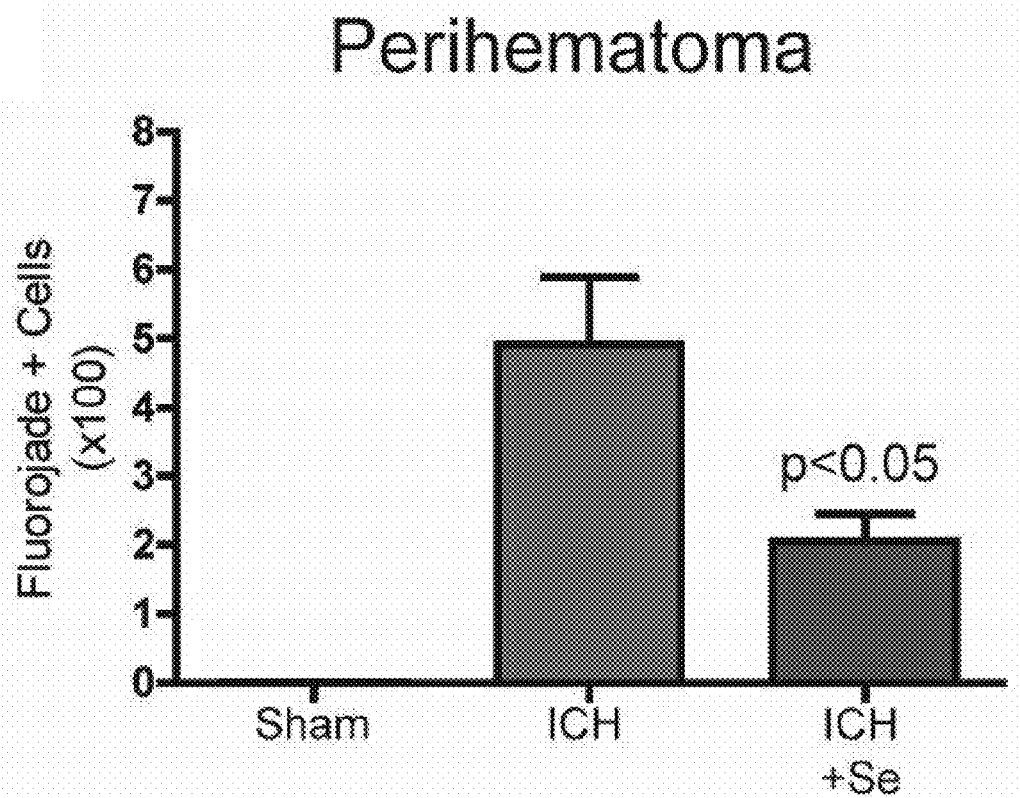
FIG. 5I is a graph showing numbers of fluorojade positive cells in perihematomas of sham injected mice and in collagenase injected ICH mice treated with saline or Se.
Figures 5J, 5K, 5L:
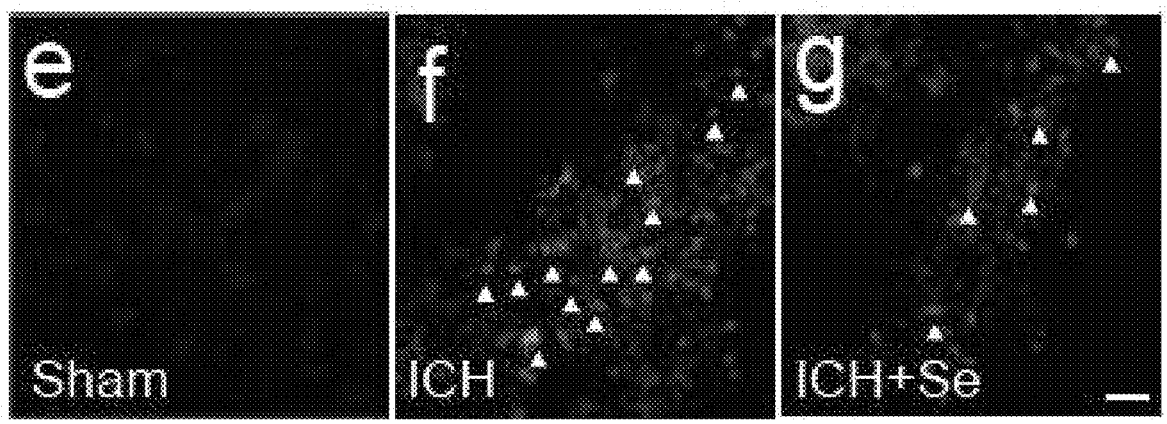
FIGS. 5J-5L are images of fluorojade staining of striatum to indicate degenerating neurons in sham injected mice and in collagenase injected ICH mice treated with saline or Se.
Figure 5M:
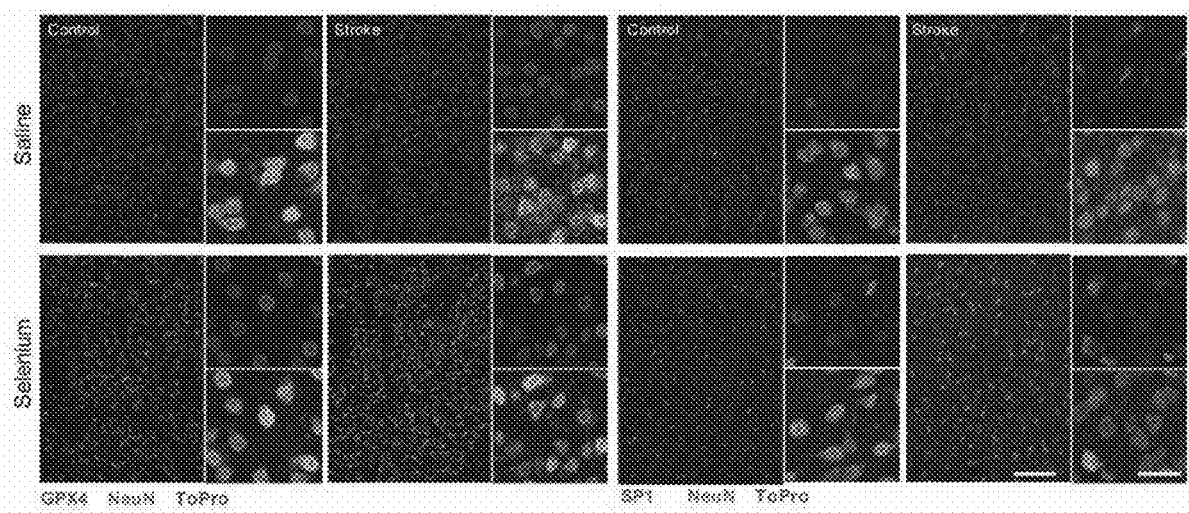
FIG. 5M is a panel of imaging photographs showing that a single dose of 2.5 μM ICV Se increased GPX4 and Sp1 levels in striatal neurons up to 7 days post ICH (n=3). Scale bar=100 μm; insert=25 μm.
Figure 5N:
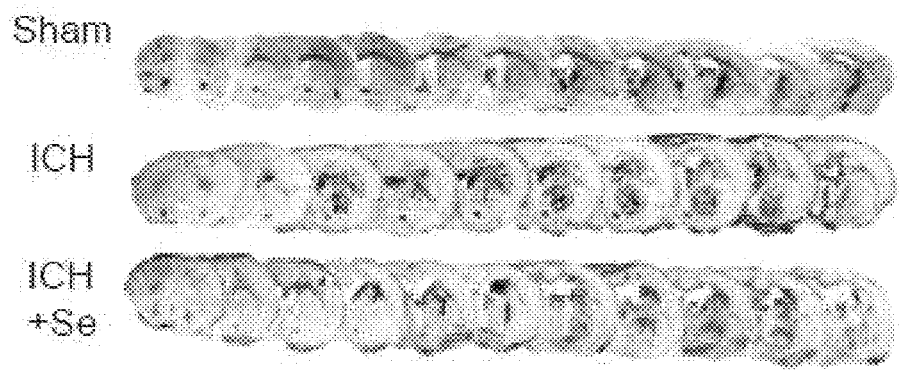
FIG. 5N(a) depicts hematoma volume in sham injected mice and in collagenase injected ICH mice treated with saline or Se.
Figure 5N:
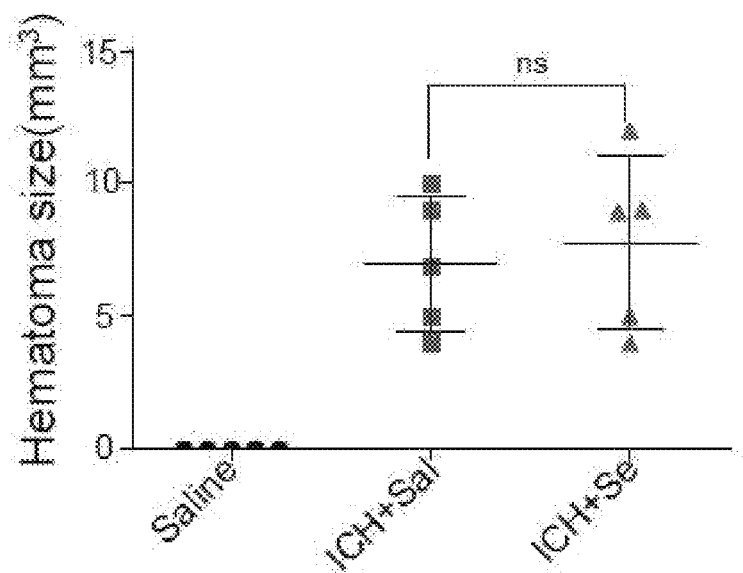

Example 4: Intracerebroventricular Injection of Se Drives Sp1 and GPX4 Expression in Neurons and Improves Functional Recovery FIGS. 5A-5N demonstrate that ICV injection of Se drives GPX4 and transcription factor specificity protein 1 (Sp1) expression and improves recovery. To address whether Se can block ferroptotic death following ICH in vivo, we tested Se in a collagenase mouse model of ICH. Injections in uninjured mice showed that an optimal Se concentration for inducing selenoprotein expression was 2.5 µM (FIGS. 5A-5C). Of note, despite the parabolic response of selenoprotein mRNAs to injected Se, we noted no toxicity or death in mice at any concentration. Intracerebroventricular injection two hours after collagenase-induced striatal ICH resulted in diminished cell death and improved functional recovery at 7 days using a measure of spatial neglect (the corner task), and at 3 and 7 days with a measure of sensory neglect (the tape removal task) (See Schallert et al., Neuropharmacology 39(5): p. 777-87 (2000); Karuppagounder et al., Science Translational Medicine 8(238):328ra29 (2016); and Hua et al., Stroke 33:2478-2484 (2002)) (FIGS. 5D-5L, 48A, and 48B). FIGS. 5H-5L show fluorojade staining for degenerating neurons demonstrated significant reduction in neuronal damage 7 days post ICH and a single dose of 2.5 µM Se (n=5). Because Se injections were performed after the induction of ICH, the reduced cell death and functional improvement is not due to Se inhibiting collagenase activity to inhibit induction of hemorrhage (FIG. 5N). Measurements of tissue selenium levels using inductively coupled plasma mass spectrometry showed that the transcriptional and neuroprotective effects of Se we observe are associated with significant increases in cellular selenium and do not represent a form of nutrient rescue in response to stress-induced selenium depletion in vitro and in vivo (FIGS. 5D and 5M). Immunofluorescence verified that Sp1 and GPX4 protein levels are increased in neurons up to seven days following Se injection (FIGS. 5M, 16A-16C, 17A-17C, and 49). Since our prior studies showed that ICH in vivo induces cell death with features of ferroptosis (See Zille et al., Stroke 48(4): 1033-1043 (2017)), the current study demonstrates that Se derives an adaptive genetic response that reduces ferroptotic cell death and improves functional recovery from ICH.

To address further whether ICH leads to ferroptotic death of neurons in vivo, we examined whether neuron-specific expression of GPX4, a known regulator of ferroptosis in multiple cell types, would, like selenium, result in reduced cell death and improved functional recovery following ICH. Accordingly, we injected an AAV8 viral vector encoding GPX4 under control of the synapsin 1 promoter into the striatum as previously described (Karuppagounder et al., 2016). This protocol resulted in diffuse transduction of predominantly neurons in the mediolateral striatum and expected increases in GPX4 expression (FIG. 68A(a)) (Kugler et al., 2003). As expected, forced GPX4 expression two weeks prior to ICH lead to reductions in cell death (FIGS. 64(Aa) and 68(Bb)) and nearly complete functional recovery following ICH by 14 days in the tests of sensory (FIGS. 64B(b) and 68Dd) or spatial neglect (FIGS. 64B(b) and 68Bb). These beneficial effects were observed without any effect on hematoma size arguing against the unlikely possibility that GPX4 affects collagenase-induced brain bleeding (FIG. 68C(c)). Accordingly, GPX4 is sufficient to prevent cell death following ICH and provide the most definitive molecular evidence to date that neuronal loss following ICH is due to ferroptosis.

Selenium's ability to drive transcriptional expression of GPX4 (and possibility other genes comprising the selenome) to inhibit ferroptosis in vivo makes it an attractive potential therapeutic strategy for ICH. However, intracerebroventricular injection of selenium presents several challenges as a therapeutic strategy. First, intracerebroventricular injection requires insertion of a catheter or needle into the human brain (Ding et al., 2015; Fam et al., 2017), which not only creates risk of infection but also is invasive, and could delay treatment. Second, and more important, in vitro, Se addition to cultured neurons shows a parabolic dose response with a narrow therapeutic window raising concerns about toxicity if doses are not titrated within a narrow range (FIG. 65(Aa)). To overcome these extant challenges, we developed a peptide strategy designed to allow induction of GPX4 and other genes of the selenome with a systemic injection. The peptide contains a transduction domain from the HIV-Tat protein, which is capable of delivering covalently attached cargoes across the BBB into cells of the CNS (Aarts et al., 2002; Cook et al., 2012; Hill et al., 2012). To deliver selenium into cells we utilized amino acids including selenocysteine from the C-terminus of selenoprotein P (SelP) attached to Tat, which we called Tat-SelPep (Tat linked Selenoprotein P Peptide). Full length SeIP is the only selenoprotein that contains a domain containing multiple selenocysteine residues and circulates in the body to distribute selenium (Burk and Hill, 2005).

FIGS. 65A-65K show the Selenoprotein P domain peptide linked to a Tat transduction domain possess a wider therapeutic windo in vitro than Se. Systemic SelPEp treatment improves functional outcomes following ICH via an Sp1 dependent pathway. Exposure of cortical neurons to Tat-SelPep (containing UKUNLN (SEQ ID NO:28) from SeIP), but not Tat-cys (containing 2 cysteine residues without any selenocysteines), or Tat alone lead to concentration dependent protection from hemin-induced ferroptosis with an EC50 of 156 nM, or HCA induced ferroptosis with an EC50 of 91 nM. Tat-cys did result in significant protection until a concentration of 100 μM, more than 100 fold less potent than Tat-SelPep (FIGS. 65(b), and 65(c)). Single cell analysis of cell viability and death confirmed that Tat-SelPep prevented hemin induced ferroptosis and completely preserved cell bodies and neurites of neurons (FIGS. 65D(d) and 69A(a)). Additionally, these studies show that unlike Se exposure, Tat-SelPep has a wide therapeutic window with no apparent toxicity over more than a 3 order of magnitude increase in concentration (FIGS. 65B(b), and 65C(c), suggesting that the Tat-SelPep peptide is as effective as Se supplementation but is more potent and less toxic.

To verify that Tat-SelPep drives GPX4 expression and other genes of the selenome in vitro, we monitored select, candidate RNAs by qPCR. As expected, Tat-SelPep (delivered at an optimally protective dose of 1 μM) induced significant increases in GPX4, SeIP, TXNRD1, GPX3, and SelK (FIG. 65(Ee)). Of note, transcriptional induction of these genes by Tat-SelPep was abrogated by forced expression of mutant Sp1 (FIG. 65E(e)), consistent with our model that Tat-SelPep and Se are affecting neurons by inducing a similar Sp1-dependent transcriptional pathway.

Altogether, these mechanistic and cell biological data in vitro predicted that systemic delivery of Tat-SelPep given after ICH should drive GPX4 expression, abrogate ferroptotic death and stimulate functional recovery in mice. FIG. 68A-68E show overexpression of GPX4 reduces degenerating neurons and improves behavior outcomes following ICH. FIGS. 69A-69F show systemic injection of Tat-SelPep improves behavioral outcomes following ICH; improvement is abrogated by parallel expression of mSp1. As a first step, we used GPX4 expression in distinct organs as a biomarker to define a dose of Tat-SelPep capable of significantly inducing GPX4 mRNA expression in multiple organs including the brain. Intraperitoneal administration of 12 μ☐g/g of Tat-SelPep but not Tat alone induced significant expression of GPX4 in Heart, Liver, Striatum (brain), and cortex (brain) (FIG. 69B(b)). Accordingly, we examined the effect of this dose of Tat-SelPep on cell death and behavioral outcomes when delivered 2 hours post-injury (FIG. 65F(f)). Delivery of Tat-SelPep but not Tat alone reduced cell death (as measured by Fluoro-Jade staining) and improved sensory and spatial neglect beginning at day 3 for sensory and spatial neglect, and reaching statistical significance for both tasks by day 14 following injury (FIGS. 65(Gg), 65(Hh), and 69(Cc-Ff)). As expected from our model, injection of a dominant-negative, mutant form of Sp1 with the DNA binding domain mutated, completed abrogated the cell death reducing and behavioral recovery effects of Tat-SelPep (FIGS. 65(Ii-Kk), 69E(e) and 69(Ff)). These findings are consistent with a scheme where pharmacological selenium can drive the activation of a transcriptional pathway, which is activated, if not sustained by Sp1, leading to the upregulation of anti-ferroptotic GPX4, as well as other genes involved in stress adaptation.

Figure 6A:
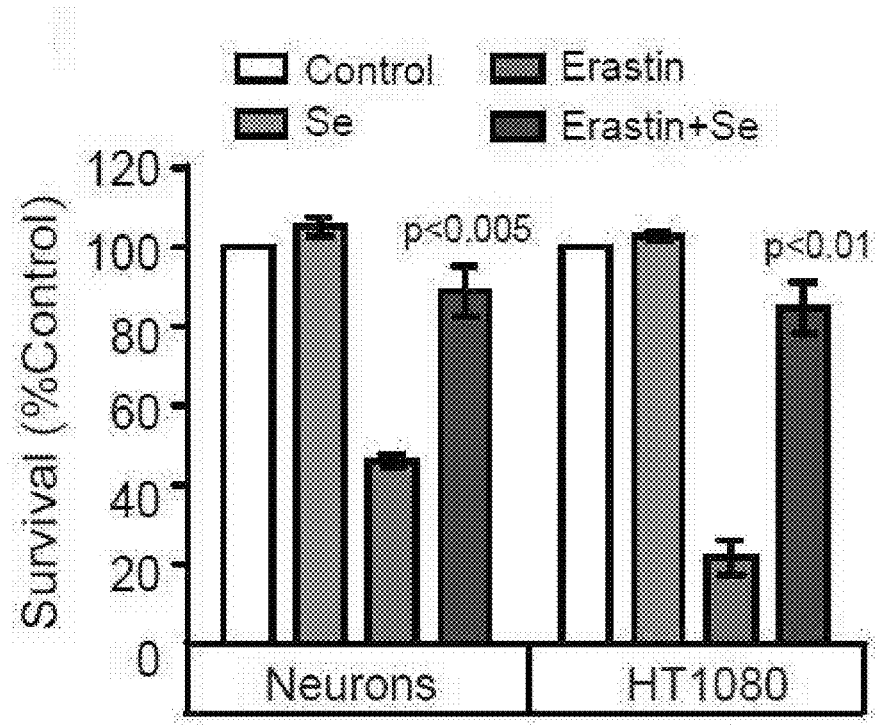
FIG. 6A is a graph of survival rates as measured by MTT assay of neurons and HT1080 cancer cells untreated (control) or treated with erastin, Se, or erastin+Se (1 μM erastin in HT1080 cells; 5 μM erastin in primary neurons; n=4). The results indicate that erastin induced ferroptotic cell death in cancer (HT1080) and neuronal cells, and cell death was blocked by Se treatment.
Figure 6B:
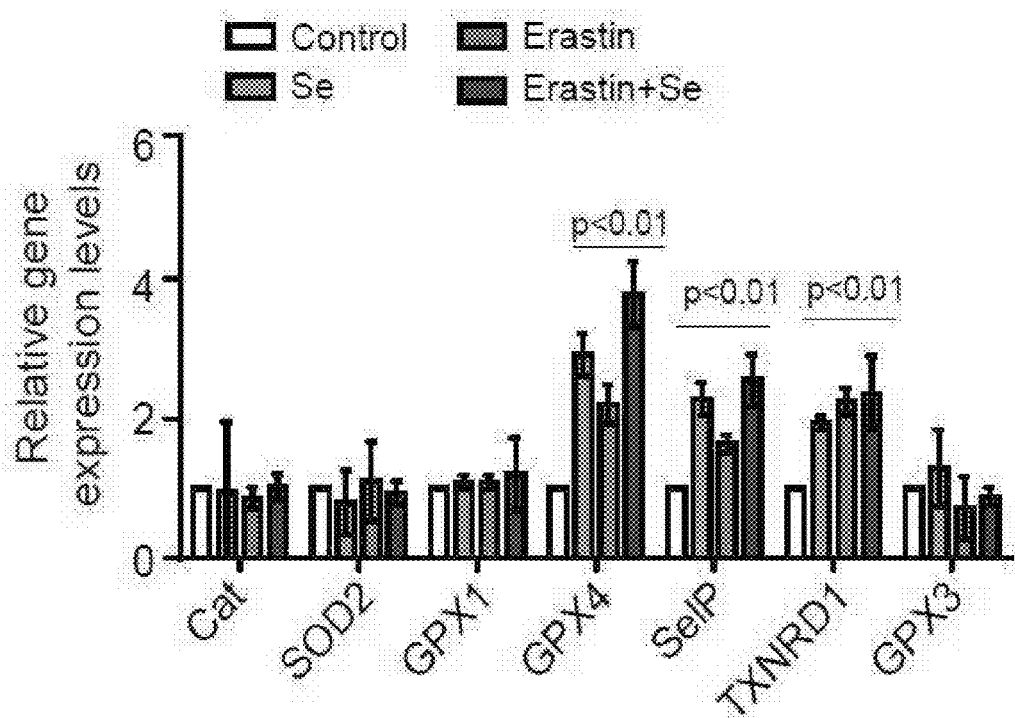
FIG. 6B is a graph of quantitative PCR results showing relative mRNA levels of indicated antioxidant protein genes in HT1080 cancer cells untreated (control) or treated with 1 μM erastin, 1 μM Se, or 1 μM erastin+1 μM Se (n=4).
Figure 6C:
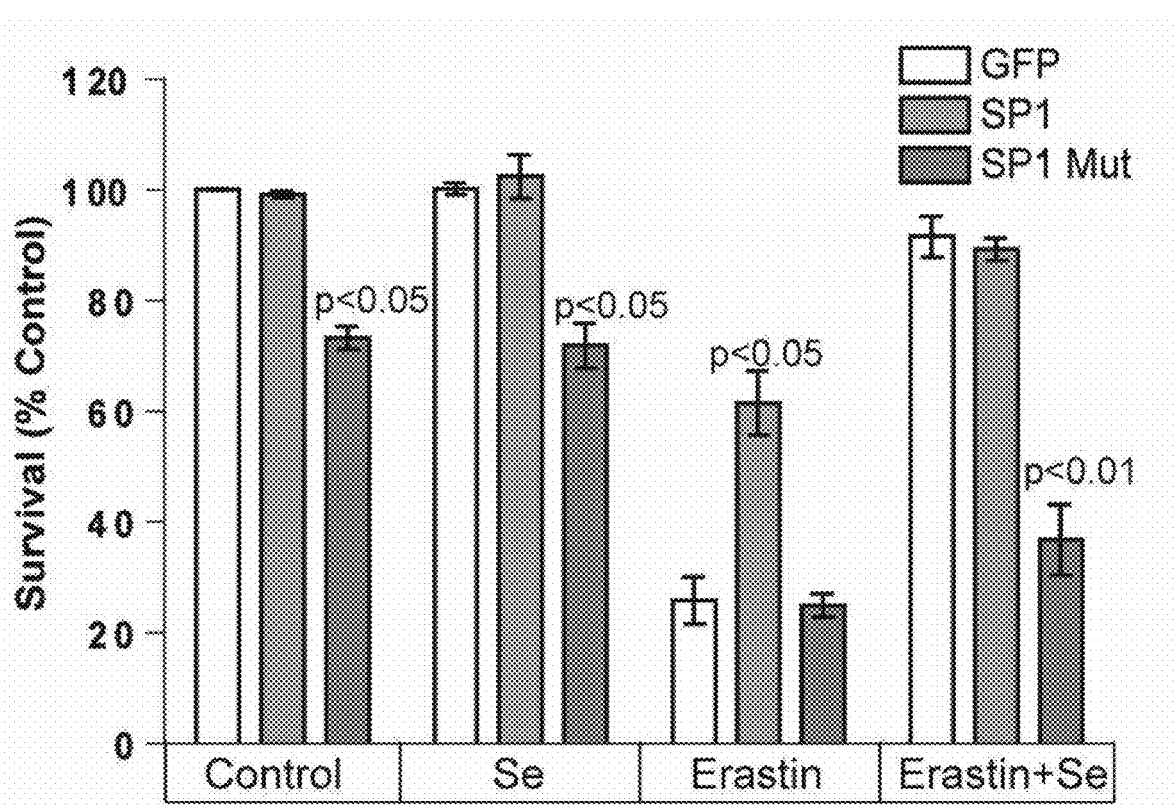
FIG. 6C is a graph of survival rates of HT1080 cells overexpressing GFP, Sp1, or mutant Sp1 (Sp1 Mut) and either untreated (control) or treated with Se, erastin, or erastin+Se. The results indicate that Sp1 overexpression in HT1080 cells protected from erastin treatment, and that mutant Sp1 overexpresion blocked Se dependent protection.
Figure 50:
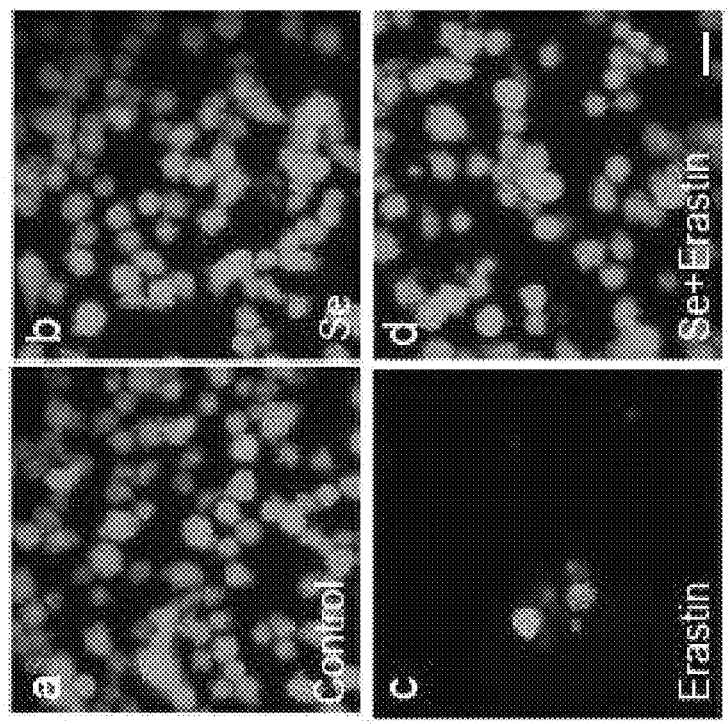
FIG. 50 is a series of images showing live (green)/dead (red) assay results for fibrosarcoma cell line HT1080 after treatment with vehicle or with 1 μM erastin, 1 μM Se, or both (n=3).
Figure 51:
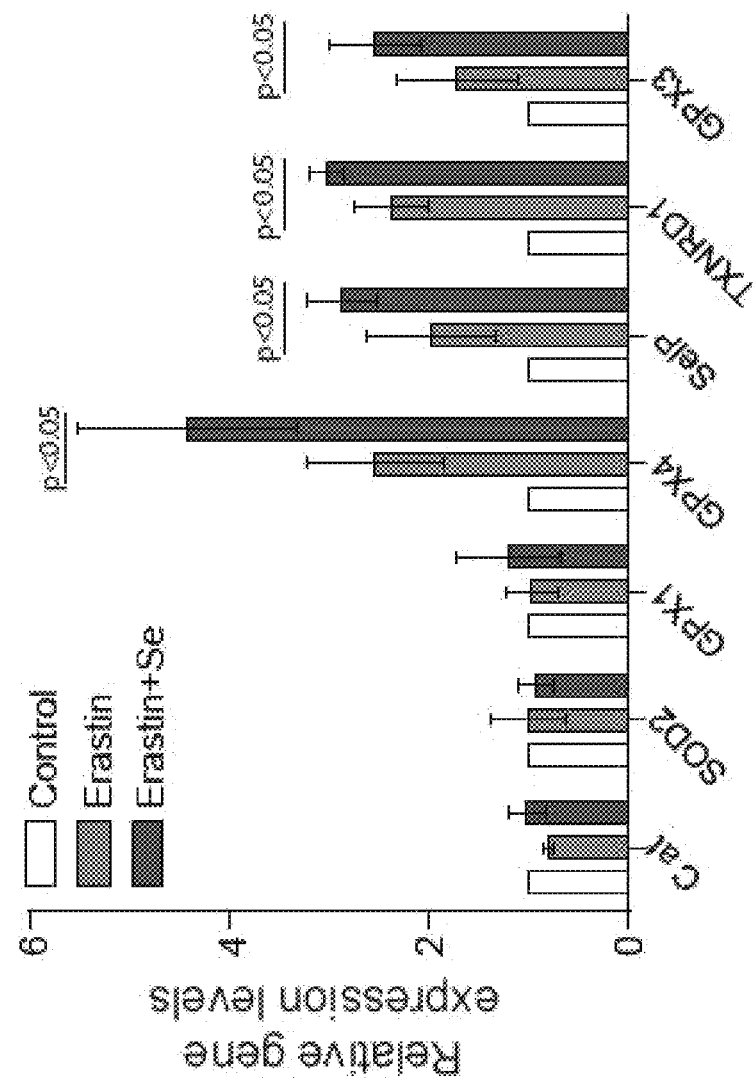
FIG. 51 is a graph showing expression levels as determined by quantitative PCR of antioxidant mRNAs in neurons following six hours of treatment with vehicle (control) or 5 μM erastin ±1 μM Se (n=3).

Example 5: Se Prevents Erastin-Induced Ferroptosis in Cancer Cells and Excitotoxicity and ER Stress Induced Death in Neurons Ferroptosis was originally identified as a mechanism by which the chemotherapeutic agent, erastin, induces death in ras-mutant cancer cells (See Dixon et al., Cell 149(5): 1060-72 (2012)). These seminal studies showed that toxicity by erastin, like glutamate or HCA in cortical neurons, is mediated via inhibition of the $X_c^-$ transporter. Blockade of the $X_c^-$ transporter leads to cellular cysteine starvation, depletion of the antioxidant glutathione, and lipid peroxide-induced ferroptosis (See Dixon et al., supra; Yang et al., Cell 156(1-2): 317-31 (2014)). FIGS. 6A-6C demonstrate that selenite prevents erastin induced ferroptosis, ER stress and glutamate toxicity. Consistent with our findings that Se can block ICH-induced ferroptosis, we found that Se could abrogate erastin-mediated ferroptotic cell death in both in HT-1080 fibrosarcoma cells and primary cortical neurons (FIGS. 6A and 50). Se-induced protection of cancer cells was blocked by the overexpression of a dominant negative Sp1 protein (FIG. 6C). Moreover, Se induced expression of several selenoproteins in erastin-treated cancer cells and neurons (FIGS. 6B and 51). Together these studies demonstrate that Se can drive a transcriptional ferroptosis stress response in transformed and non-transformed cells to prevent cell death.

Figure 52:
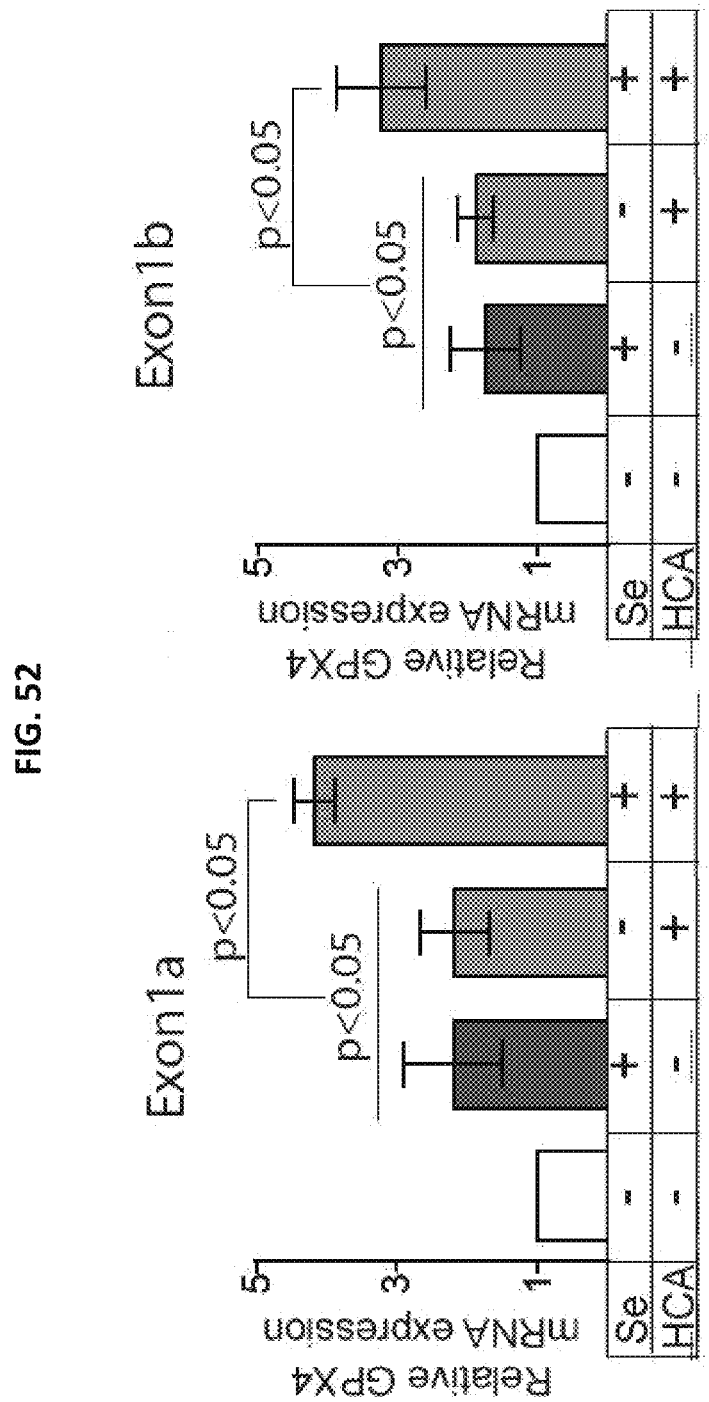
FIG. 52 is a pair of graphs showing GPX4 expression levels as determined by quantitative PCR using primers targeting exon 1a (left) and exon 1b (right) of GPX4 following six hours of treatment with 5 mM HCA, 1 μM Se, or both (n=3).
Figure 52A:
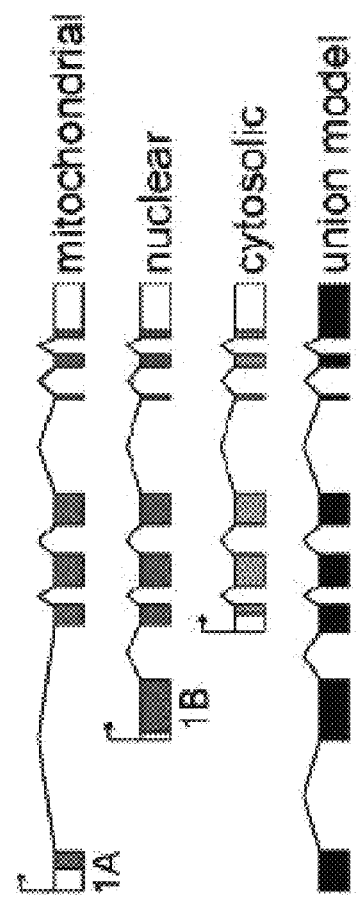
FIG. 52A is a schematic diagram of the GPX4 exon map with various transcript variants and exon union models.
Figure 54A:
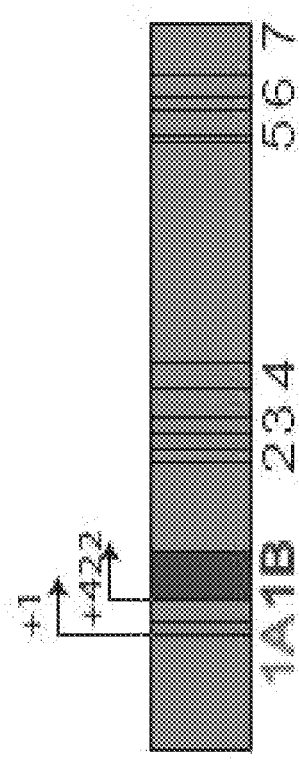
FIG. 54A is a gene map showing changes from RNA sequencing analysis of a mitochondrial GPX4 transcript variant (with exon 1a) and a nuclear GPX4 transsript variant (with exon 1b) (n=4).
Figure 53:
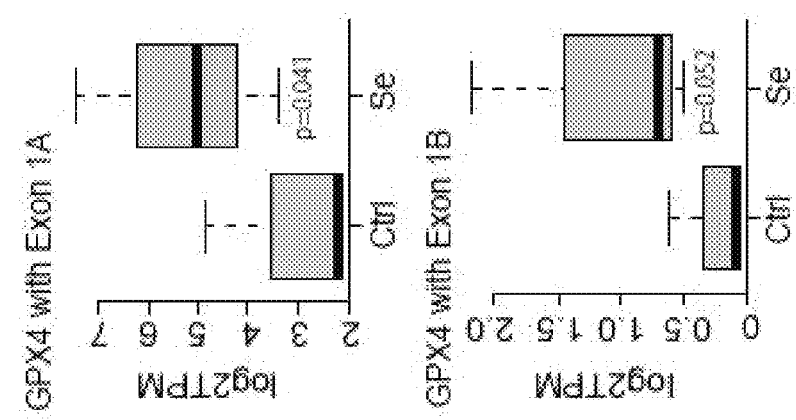
FIG. 53 shows changes in mitochondrial GPX4 transcript variant (with exon 1a) and nuclear GPX4 transcript variant (with exon 1b) from RNA sequencing analysis following 6 h of Se (1 μm) treatment in primary cortical neurons (n=4).
Figure 54B:
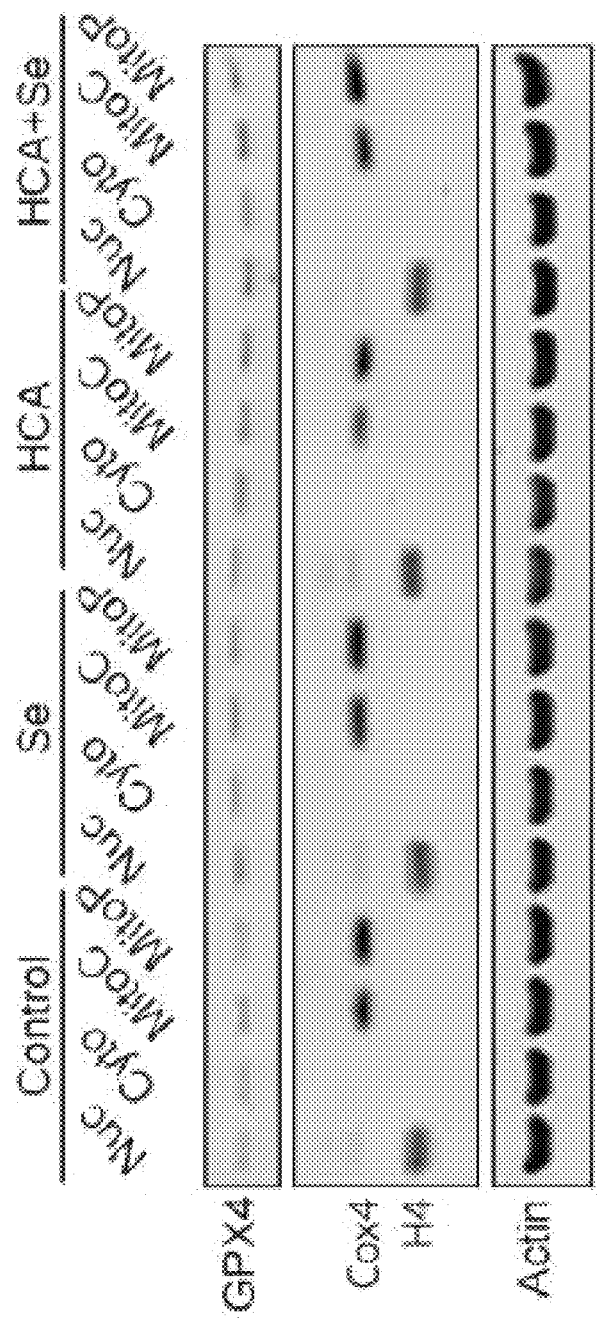
FIG. 54B shows a western blot of GPX4 protein levels in nuclear, cytoplasmic, and mitochondrial (crude and pure) compartments from primary cortical neurons following 8 h treatment with or with Se (1 μM) and HCA (5 mM).
Figure 54C:
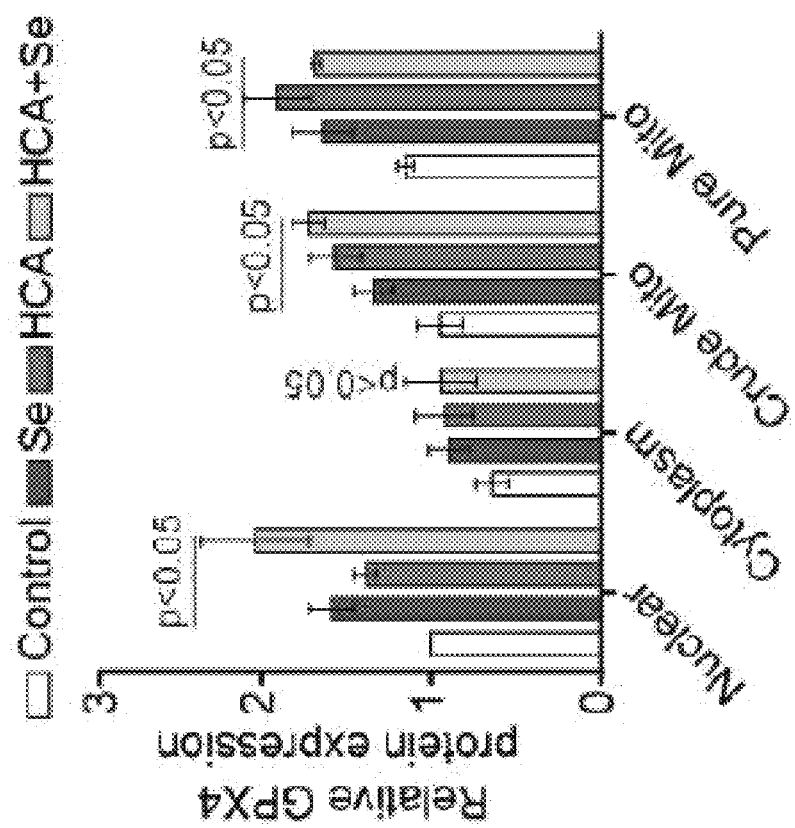
FIG. 54C shows the quantification of GPX4 expression levels from the western blot in FIG. 54B.

The ability of Se to protect multiple cell types from diverse ferroptotic stresses led us to evaluate the systems biology of Se exposure in primary neurons. RNA-seq analysis of primary cortical neurons exposed to protective doses of Se in the presence of ferroptotic stress showed robust upregulation and downregulation of many genes (238 differentially expressed genes). Our bioinformatics programs use an exon union model that scans reads across all exons, and is designated as "full length." Using the exon union model, GPX4 was not differentially expressed between the control and selenium groups. However, consistent with our qPCR data using primers from exon 1a (FIG. 52, left panel), we found that expression of the GPX4 transcript that includes exon 1a was as significantly induced in the RNA sequence analysis by selenium (FIG. 53). The start codon for the mitochondrial form of GPX4, including the mitochondrial targeting sequence, is present in exon 1a (FIG. 54A). As expected, we found increases in GPX4 protein outside the nucleus in hippocampal neuroblasts exposed to selenium (FIG. 14, left panel). Although transcript variants that included exon 1b (which contains the start codon for the nuclear form of GPX4 and its associated nuclear localization sequence) were not significantly upregulated (FIG. 53; $p < 0.052$), qPCR analysis of exon 1b showed that it was significantly induced by Se alone or Se plus a ferroptotic stimulus (FIG. 52, right panel). Immunofluorescence confirmed a significant increase in nuclear GPX4 staining (FIG. 14, left panel). The reason for the discrepancy in detecting significant changes in the "full length" as compared to the mitochondrial and nuclear forms of GPX4 in the RNA sequencing analysis reflects two properties of GPX message: first, mitochondrial and nuclear forms are less abundant RNAs than the cytosolic form so increases in those transcript variants are diluted by less robust changes in the cytosolic form. Second, the full length is upregulated, but not sufficiently to reach statistical significance.

Figure 55:
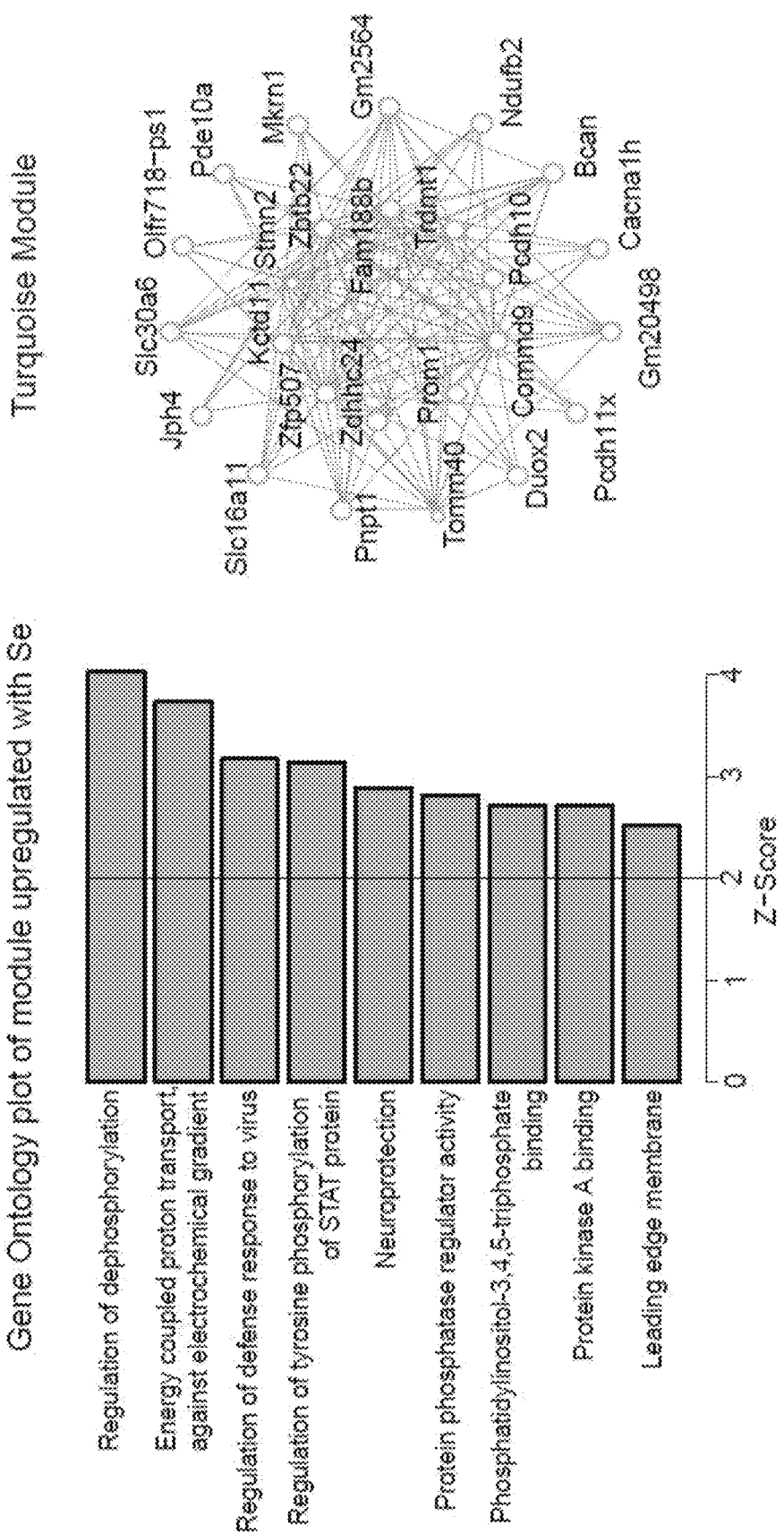
FIG. 55 is a gene ontology (GO) analysis (left) of turquoise module, which was the module most upregulated by Se according to supervised weight gene coexpression network (WGCNA) analysis. Turquoise module hub genes are shown to the right. Hub genes are those genes whose expression values are highly correlated with that of the module's eigengene across samples.
Figure 57:
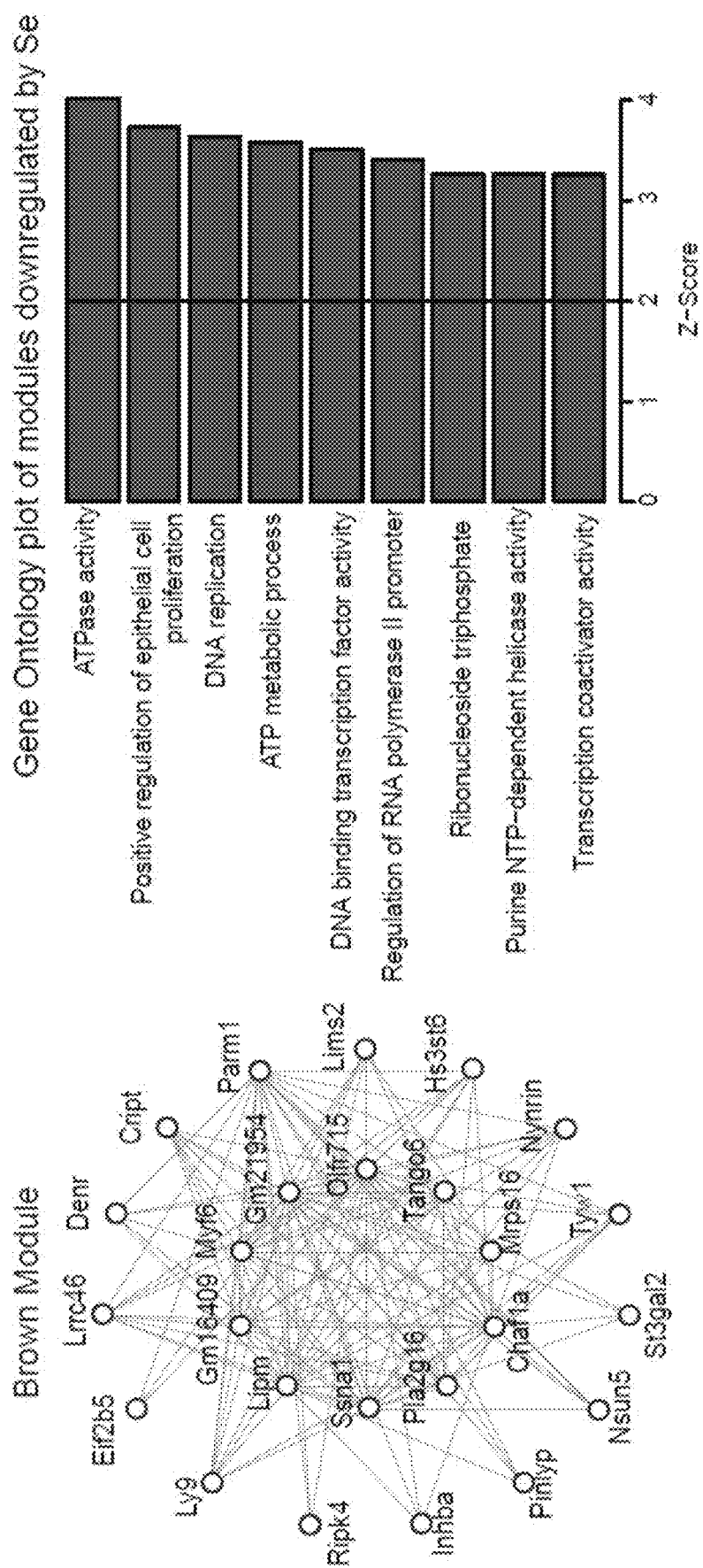
FIG. 57 is a gene ontology (GO) analysis (right) of brown module, which was the module most downregulated by Se according to supervised weight gene coexpression network (WGCNA) analysis. Brown module hub genes are shown to the left. Hub genes are those genes whose expression values are highly correlated with that of the module's eigengene across samples.

To organize the RNA-seq data into biologically coherent networks, we applied a supervised weighted gene-coexpression network analysis (WGCNA) to define networks of genes that are co-regulated with the significantly induced mitochondrial form of GPX4 (exon 1a). This analysis revealed several gene ontology networks that were significantly upregulated (FIGS. 55 and 56: neuroprotection, regulation of defense response to virus, and energy coupled proton transport) and significantly downregulated (FIGS. 57 and 58: ATP metabolism, transcription factor coactivator activity, and DNA replication). The findings are consistent with co-regulation of programs involved in stress response and neuroprotection with the mitochondrial form of GPX4.

Figure 59:
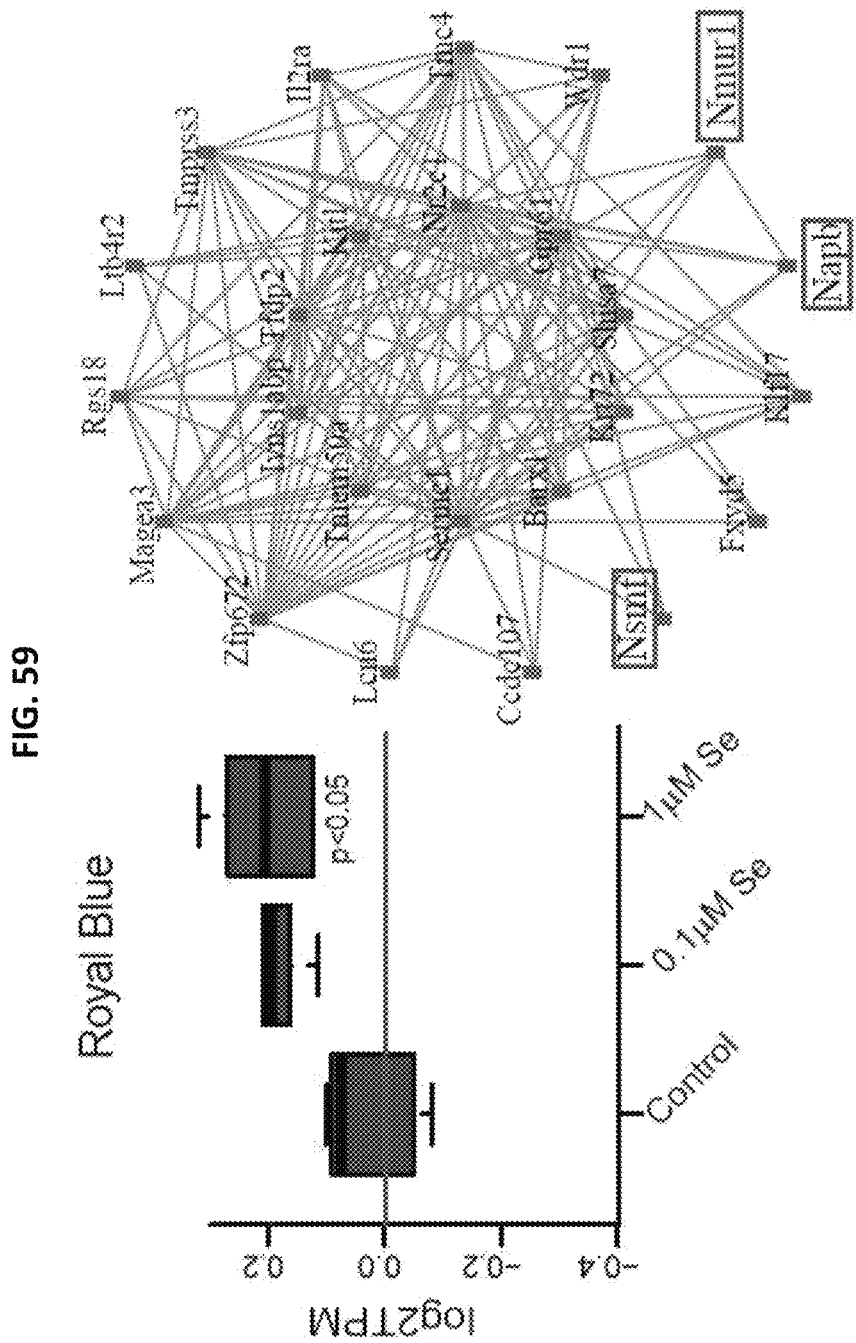
FIG. 59 depicts module eigengene and networks (Royal Blue) significantly upregulated by Se based on unsupervised WGCNA. ER stress and excitotoxicity related genes are highlighted in red (n=4).
Figure 60:
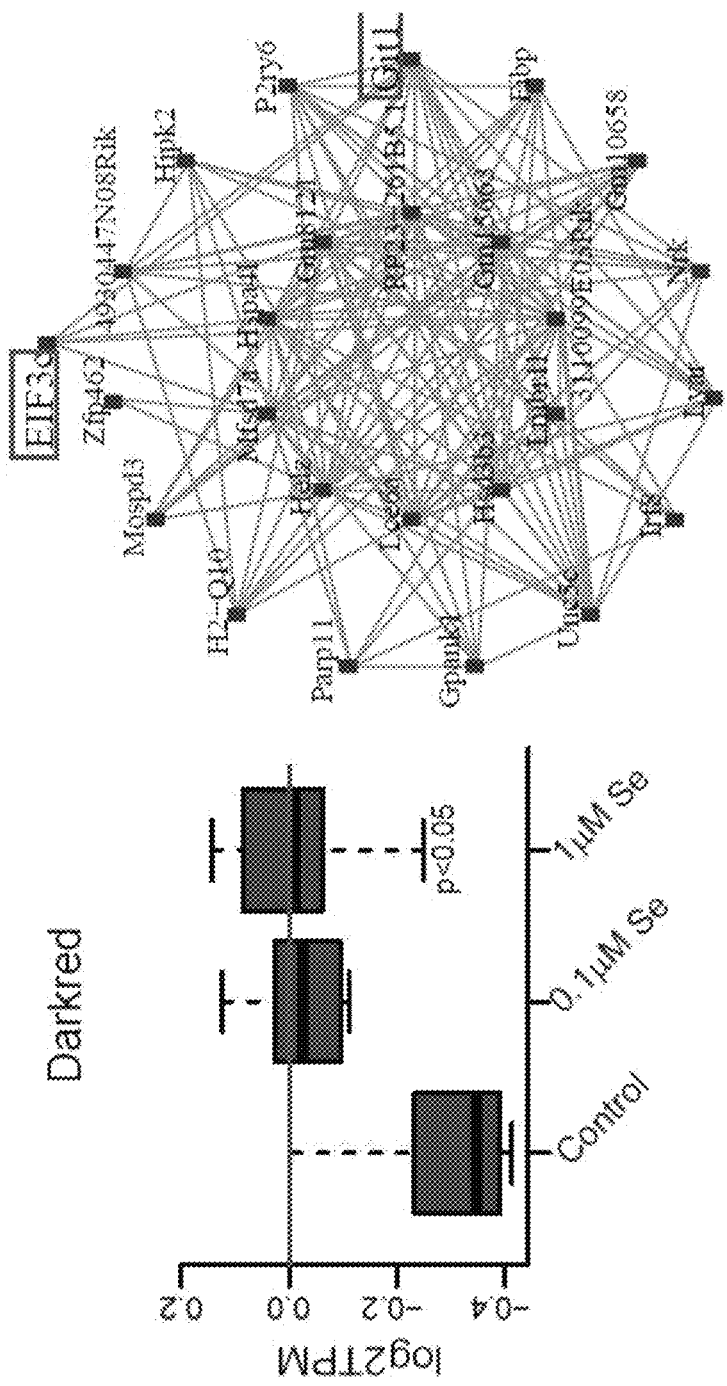
Figure 62A:
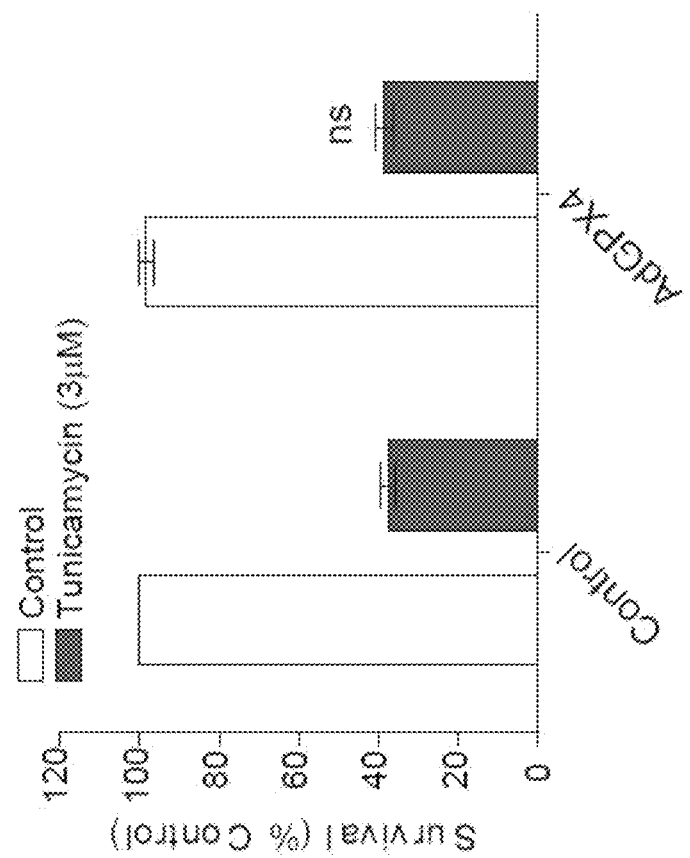
Figure 61:
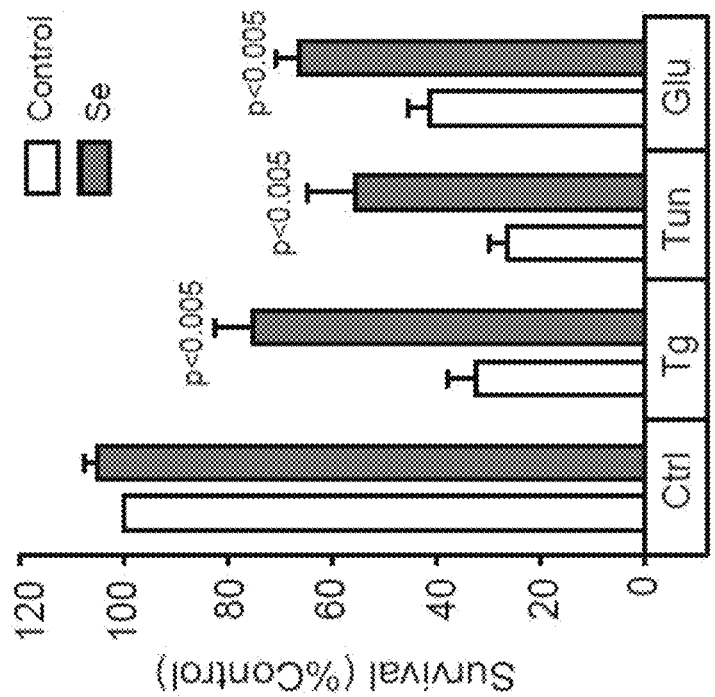
Figure 62B:
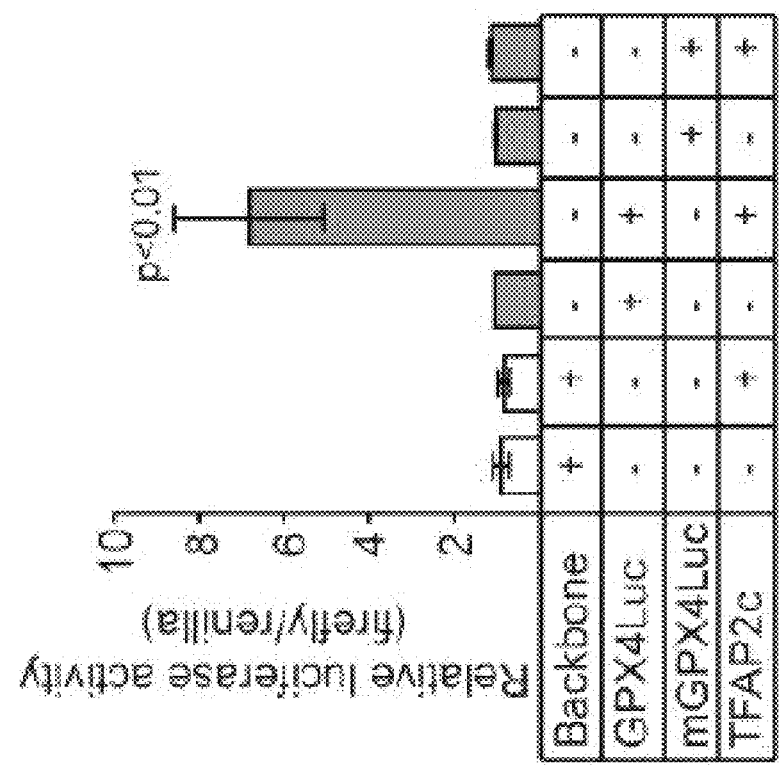
Figure 63:
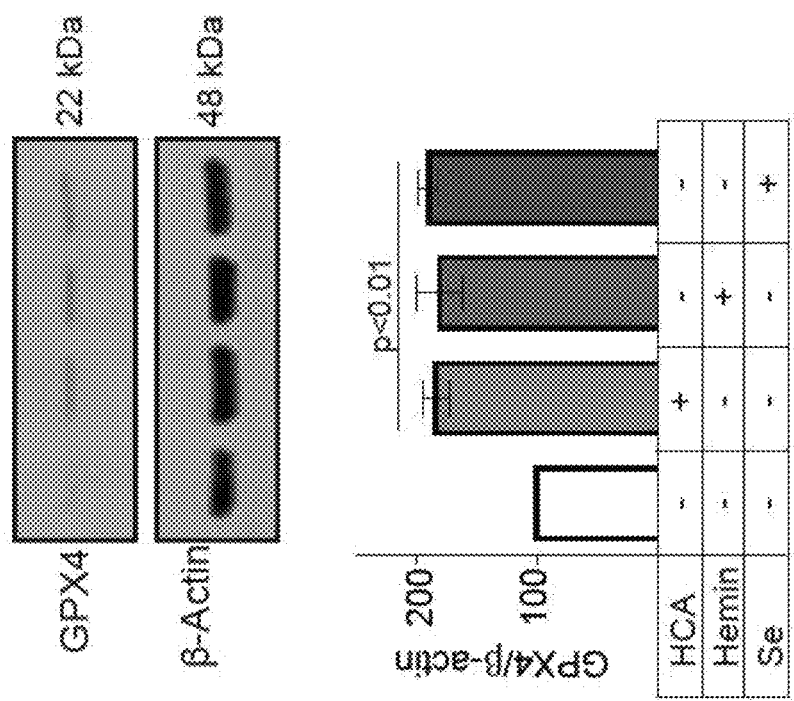

Unsupervised WGCNA identified modules that were upregulated (FIGS. 59 and 60; Royal Blue and Dark Red), containing genes associated with protection from ER stress. These included EIF3c, a component required for stress dependent translation (IRES mediated), especially when stress inhibits cap-dependent translation (See Spriggs et al., Biology of the Cell 100:27-38 (2008)), and Git1, an inhibitor of the IP3 receptor (See Kiviluoto et al., Biochimica et Biophysica Acta 1833:1612-1624 (2013); Zhang et al., J. Biol. Chem. 284:29158-29169 (2009); and Ruiz et al., Cell Calcium 46:273-281 (2009)) that would be expected to diminish ER stress by inhibiting calcium release from the ER. Moreover, Selenoprotein K (SelK), a selenoprotein involved in ER associated degradation of misfolded glycosylated proteins, was also induced by Se (FIG. 32). Accordingly, we find Se significantly inhibited ER stress-induced death induced by thapsigargin or tunicamycin (FIG. 61). Of note, forced expression of GPX4 had no effect on ER stress-induced death, consistent with the notion that other genes that compose the selenome are mediating this protection (FIG. 62A). Additionally, Se protected against excitotoxicity (FIG. 61), where cell death is mediated via multiple stresses including ER stress, supporting the notion that Se can induce broad neuroprotection via activation of many genes, not only GPX4 (FIGS. 59 and 60).

Figure 6D:
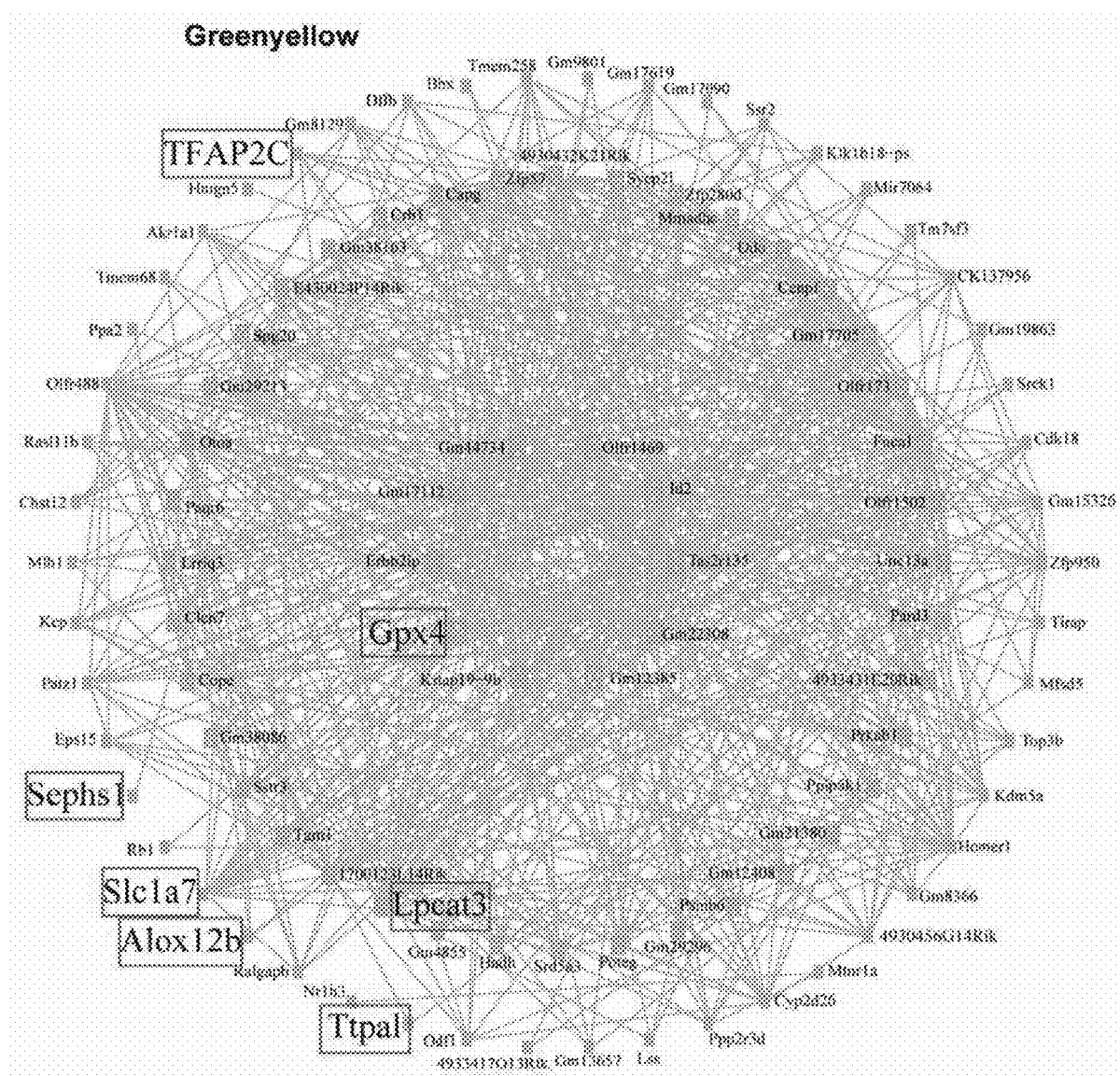
FIG. 6D illustrates a module based on RNA-sequencing, comprising GPX4 as a hub gene and co-regulated ferroptosis associated genes.

Consistent with our findings that GPX4 is a key regulator of ferroptosis (See Dixon et al., Cell 149(5):1060-72 (2012)) (FIGS. 1A-1J and 3A-3U), GPX4 was identified as a hub for the module of genes (yellow-green) with which it is co-regulated (FIG. 6D). Although WGCNA per se does not reveal the specific biological process that links genes within a module, examination of the known genes within the yellow-green module indicates that this module is important for regulating key aspects of ferroptosis. These related genes include: selenophosphate synthetase (SEPHS1), which synthesizes the selenophosphate for selenocysteine tRNA assembly (See Tamura et al., Proc Natl Acad Sci USA 101(46):16162-7 (2004)); TFAP2CTFAP2C, the transcription factor that we empirically found drives GPX4 expression in response to selenium treatment (FIG. 4I); TTPAL (alpha tocopherol transfer protein like), which is critical for the movement of vitamin E (a lipid peroxidation inhibitor (See Khanna et al., J Biol Chem 278(44):43508-15 (2003)) and negative regulator of ferroptosis); and Lysophosphatidylcholine acyltransferase (LPCAT3), which regulates membrane fluidity and phospholipid signaling and has been previously linked to ferroptosis (See Dixon et al., ACS Chem Biol 10(7):1604-9 (2015); Doll et al., Nat Chem Biol 13(1):91-98 (2017)).

Figure 6E:
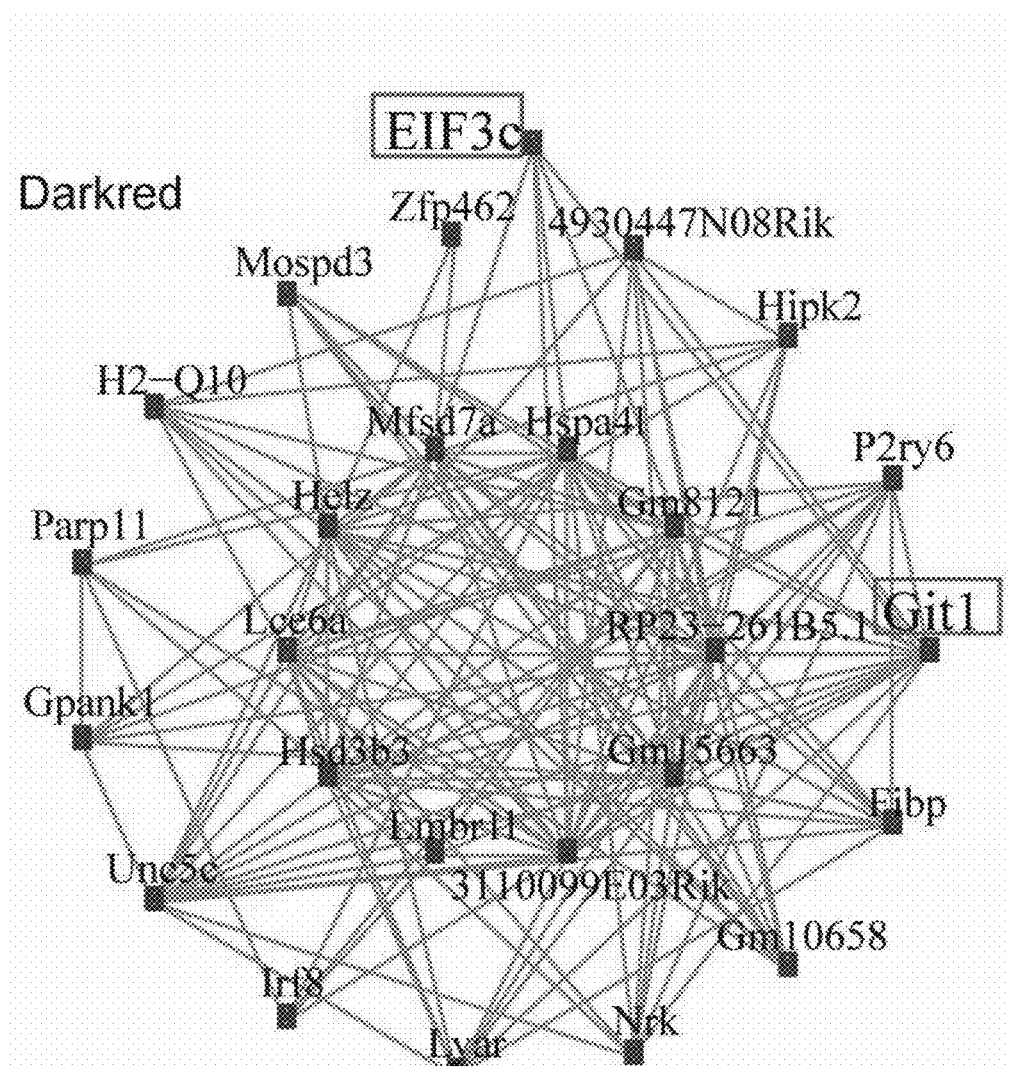
FIGS. 6E and 6F depict modules enriched by the genes most highly regulated with Se and genes associated with ER stress and excitotoxicity inhibition.
Figure 6F:
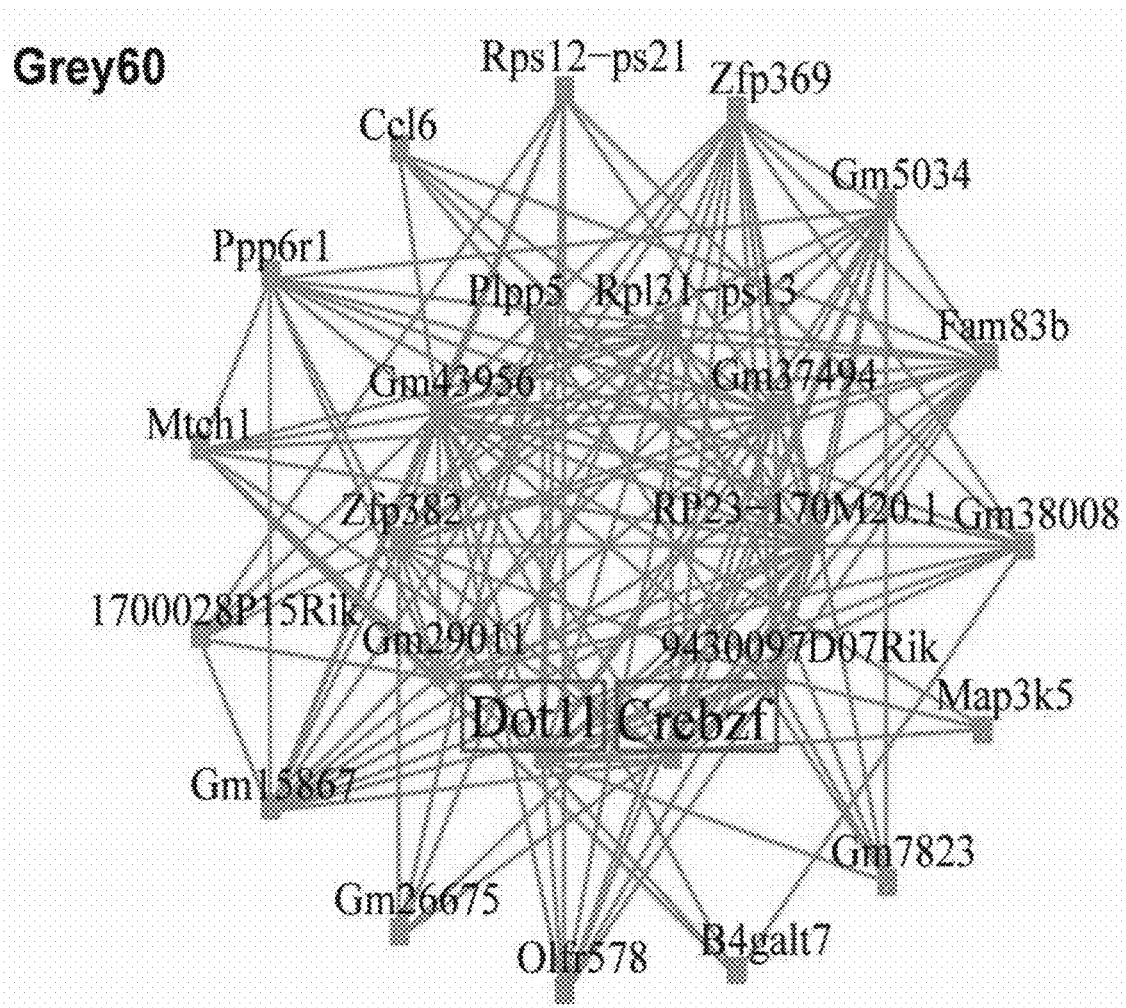
Figure 6G:
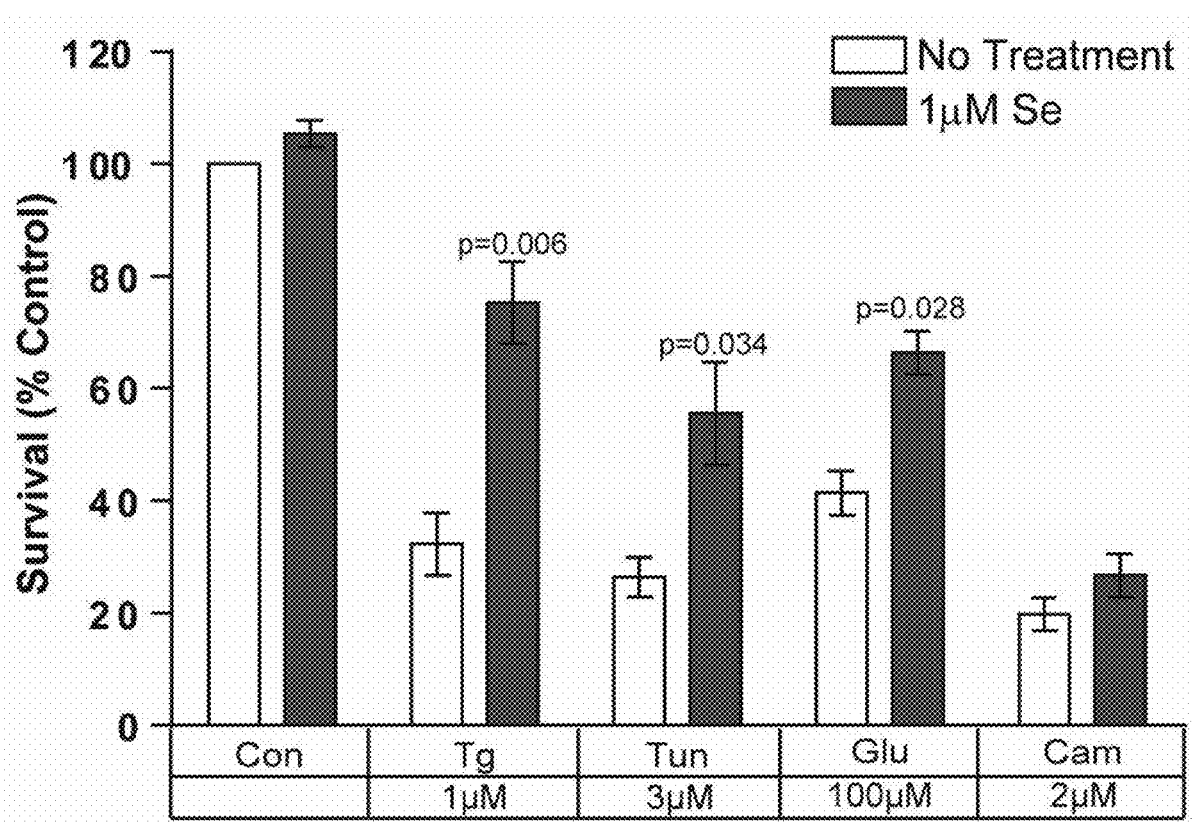
FIG. 6G is a graph of survival rates of neurons untreated or treated with 1 μM Se alone (in the Con group), or treated with 1 μM thapsigargin (Tg), 3 μM tunicamycin (Tun), 100 μM glutamate (Glu), or 2 μM Cam in the absence or presence of co-treatment with 1 μM Se. The results indicate that Se protected against ER stress and glutamate excitotoxicity in neurons.

Two other genes within the yellow-green module were 12-lipoxygenase (Alox12b), a known pro-ferroptotic molecule, and Slc1A7, which is a member of the high affinity glutamate transporter family implicated in ALS (See Lin et al., Neuron 20(3):589-602 (1998)). Since glutamate drives excitotoxicity and 12-lipoxygenase produces toxic lipids in ischemic stroke (See van Leyen et al., Stroke 37(12):3014-8 (2006)), we examined whether Se protects mature cultured neurons against excitotoxicity. We found that 1 µM Se prevented cell death induced by 100 µm glutamate (FIG. 6G). These results suggest that Se can prevent excitotoxic death, in addition to ferroptosis.

Other modules also provide clues to the breadth of Se-induced neuroprotection. In the significantly upregulated grey60 (FIG. 6F) and dark red (FIG. 6E) modules, there are many genes associated with endoplasmic reticulum (ER) stress, which can lead to apoptotic death. These genes include: CREBZF, which dimerizes with ATF4 to inhibit ER stress-induced transcription (See Hogan et al., FEBS Lett 580(1):58-62 (2006); Zhang et al., PLoS One 8(10):e77256 (2013)); Dot1L, a histone methyl transferase that negatively regulates ER stress-induced ATF4 transcription (See Roidl et al., Stem Cells 34(1):233-45 (2016)) (ATF4 can mediate prodeath gene expression) (See Karuppagounder et al., Sci Transl Med 8(328):328ra329 (2016); Lange et al., J Exp Med 205(5):1227-42 (2008)); Git1, an inhibitor of the IP3 receptor (See Kiviluoto et al., Biochim Biophys Acta 1833 (7):1612-24 (2013); Zhang et al., J Biol Chem 284(42): 29158-69 (2009); Ruiz et al., Cell Calcium 46(4):273-81 (2009)) that would be expected to diminish ER stress by inhibiting calcium release from the ER; and EIF3C, a component required for stress dependent translation (IRES mediated), especially when stress inhibits cap-dependent translation (See Spriggs et al., Biol Cell 100(1):27-38 (2008)). To test whether Se can protect against ER stress-induced death, primary neurons were treated with inducers of ER stress-mediated apoptotic cells death, tunicamycin and thapsigargin (FIG. 6G). ER (endoplasmic reticulum) stress occurs due to the cell's inability to manage misfolded proteins. TG (thapsigargin) blocks calcium channels in the ER which are required for protein folding. Tun (tunicamycin) inhibits formation of glycoproteins, a post translational modification. Se was shown to have a protective effect against ER stress-induced death induced by TG or Tun.

This study shows that Se can drive an adaptive gene transcription response that protects neurons from ferroptosis, and indicates that this response can also protect from other cell death mechanisms, such as excitotoxicity and ER stress-induced apoptosis. Our studies with ferroptosis indicate that this protection requires novel transcription of a cassette genes regulated by Se, the selenome. Our findings also show that TFAP2C and Sp1 are important Se-induced regulators of these genes, and this regulation of selenome represents an adaptive transcriptional response to ferroptotic stresses.

Without being bound by theory, it is believed that the protection afforded to neurons in vivo and in vitro by supraphysiological levels of Se is not the result of optimizing nutrient selenium status, but because Se enhances the activity of transcription factors TFAP2C and Sp1 on the promoters of protective genes, such as GPX4. TFAP2C and Sp1 have been separately implicated in selenoprotein transcription (See Kulak et al., Oncogene 32(34):4043-51 (2013); Stoytcheva et al., Biochim Biophys Acta, 1790(11): 1429-40 (2009)), but our studies are the first to show that this regulation occurs in the brain in response to Se exposure, and that it improves functional recovery after hemorrhagic stroke. Achieving pharmacological levels of Se at sites of injury to promote neuronal survival may provide novel therapeutic approaches not only for stroke, Amyotrophic lateral sclerosis, Parkinson's disease and Alzheimer's disease but also protect liver, kidney and the immune system (See Rueli et al., J Alzheimers Dis 55(2):749-762 (2017); Steinbrenner et al., Arch Biochem Biophys 536(2):152-7 (2013); Pillai et al., IUBMB Life 66(4):229-39 (2014)).

While the invention has been described in detail with reference to embodiments for the purposes of making a complete disclosure of the invention, such embodiments are merely exemplary and are not intended to be limiting or represent an exhaustive enumeration of all aspects of the invention. It will be apparent to those of ordinary skill in the art that numerous changes may be made in such details, and the invention is capable of being embodied in other forms, without departing from the spirit, essential characteristics, and principles of the invention. Also, the benefits, advantages, solutions to problems, and any elements that may allow or facilitate any benefit, advantage, or solution are not to be construed as critical, required, or essential to the invention. The scope of the invention is to be limited only by the appended claims.

What is claimed is:

1. A compound comprising:
   (a) a selenium-containing portion, wherein the selenium-containing portion consists of a C-terminus domain selenoprotein P fragment consisting of the sequence UKUNLN (SEQ ID NO:28);
   (b) linked to a Tat transduction domain.

2. The compound of claim 1, further comprising in addition to (a) and (b), a portion (c) which is a sequence fragment selected from the group consisting of NA1, PTP-Sigma, GluR2, SDK-5, and SS31.

3. The compound of claim 1, wherein the compound consists of SEQ ID NO:2.

* * * * *